(12) United States Patent
Davila

(10) Patent No.: US 12,036,273 B2
(45) Date of Patent: Jul. 16, 2024

(54) COMPOSITIONS AND METHODS FOR TARGETING CD99-EXPRESSING CANCERS

(71) Applicant: H. Lee Moffitt Cancer Center and Research Institute, Inc., Tampa, FL (US)

(72) Inventor: Marco L. Davila, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 1007 days.

(21) Appl. No.: 16/960,656

(22) PCT Filed: Jan. 8, 2019

(86) PCT No.: PCT/US2019/012640
§ 371 (c)(1),
(2) Date: Jul. 8, 2020

(87) PCT Pub. No.: WO2019/136419
PCT Pub. Date: Jul. 11, 2019

(65) Prior Publication Data
US 2020/0397882 A1  Dec. 24, 2020

Related U.S. Application Data

(60) Provisional application No. 62/767,867, filed on Nov. 15, 2018, provisional application No. 62/767,864, filed on Nov. 15, 2018, provisional application No. 62/730,397, filed on Sep. 12, 2018, provisional application No. 62/730,374, filed on Sep. 12, 2018, provisional application No. 62/654,617, filed on Apr. 9, 2018, provisional application No. 62/654,625, filed on Apr. 9, 2018, provisional application No. 62/614,779, filed on Jan. 8, 2018.

(51) Int. Cl.
| | |
|---|---|
| *A61K 39/395* | (2006.01) |
| *A61K 39/00* | (2006.01) |
| *A61K 47/65* | (2017.01) |
| *C07K 14/705* | (2006.01) |
| *C07K 14/725* | (2006.01) |
| *C07K 16/08* | (2006.01) |
| *C07K 16/28* | (2006.01) |

(52) U.S. Cl.
CPC .. *A61K 39/001129* (2018.08); *A61K 39/3955* (2013.01); *A61K 47/65* (2017.08); *C07K 14/7051* (2013.01); *C07K 14/70578* (2013.01); *C07K 16/087* (2013.01); *C07K 16/2896* (2013.01); *C07K 2317/56* (2013.01); *C07K 2317/622* (2013.01); *C07K 2319/33* (2013.01)

(58) Field of Classification Search
CPC .... A61K 39/395; C07K 16/28; C07K 14/725; C07K 14/705
See application file for complete search history.

(56) References Cited

U.S. PATENT DOCUMENTS

| | | | |
|---|---|---|---|
| 4,816,567 A | 3/1989 | Cabilly et al. | |
| 6,440,735 B1 | 8/2002 | Gaeta | |
| 6,713,055 B2 | 3/2004 | Schiff | |
| 8,008,449 B2 | 8/2011 | Korman et al. | |
| 8,552,154 B2 | 10/2013 | Freeman et al. | |
| 8,617,546 B2 | 12/2013 | Kang et al. | |
| 10,150,816 B2 * | 12/2018 | Abbot ............... | C07K 16/3061 |
| 2012/0282257 A1 | 11/2012 | Picci et al. | |
| 2014/0086888 A1 | 3/2014 | Heslop et al. | |
| 2016/0168259 A1 | 6/2016 | Kaisha | |
| 2017/0368169 A1 | 12/2017 | Loew et al. | |

FOREIGN PATENT DOCUMENTS

| | | |
|---|---|---|
| JP | 2016-507499 A | 3/2016 |
| JP | 2017-524365 A | 8/2017 |
| WO | 1999057150 A2 | 11/1999 |
| WO | 2014/100385 A1 | 6/2014 |
| WO | 2015039523 A1 | 3/2015 |
| WO | 2015/069935 A1 | 5/2015 |
| WO | 2015/161267 A2 | 10/2015 |
| WO | 2016025454 A2 | 2/2016 |
| WO | 2016/149682 A2 | 9/2016 |

(Continued)

OTHER PUBLICATIONS

Japanese Office Action, Japan Application No. 2020-537629, dated Nov. 22, 2022.
Moricoli, Diego, et al., "Process Development of a Human Recombinant diabody expressed in *E. coli*: engagement of CD99-induced apoptosis for target therapy in Ewing's sarcoma," Appl. Microbiol. Biotechnology, vol. 100 (2016), pp. 3949-3963.
European Search Report, EP App. 19736218.9, issued Feb. 2, 2022 (11 pages).
Chung, Stephen S., et al., "CD99 is a Therapeutic Target on Disease Stem Cells in Myeloid Malignancies," Science Translational Medicine, vol. 9, No. 374 (2017), (13 pages).
Svoldo, et al., "Epstein Barr Virus Specific Cytotoxic T Lymphocytes Expressing the Anti-CD30 Artificial Chimeric T-Cell Receptor for Immunotherapy of Hodgkin Disease," Blood, vol. 110, No. 7 (2007), pp. 2620-2630.

(Continued)

*Primary Examiner* — Xiaozhen Xie
(74) *Attorney, Agent, or Firm* — Thomas | Horstemeyer, LLP

(57) ABSTRACT

Disclosed are compositions and methods for targeted treatment of CD99-expressing cancers. In particular, chimeric antigen receptor (CAR) polypeptides are disclosed that can be used with adoptive cell transfer to target and kill CD99-expressing cancers. Also disclosed are immune effector cells, such as T cells or Natural Killer (NK) cells, that are engineered to express these CARs. Therefore, also disclosed are methods of providing an anti-tumor immunity in a subject with a CD99-expressing cancer that involves adoptive transfer of the disclosed immune effector cells engineered to express the disclosed CARs. Also disclosed are multivalent antibodies are disclosed that are able to engage T-cells to destroy CD99-expressing malignant cells.

17 Claims, 17 Drawing Sheets
Specification includes a Sequence Listing.

(56) References Cited

FOREIGN PATENT DOCUMENTS

| WO | 2017132279 A1 | 8/2017 |
| WO | 2017165464 A1 | 9/2017 |

OTHER PUBLICATIONS

Pasello, Michela, et al., "CD99 at the Crossroads of Physiology and Pathology," Journal of Cell Communication and Signaling, vol. 12, No. 1 (2018), pp. 55-68.
Barker, Juliet N., et al., "Successful treatment of EBV-associated posttransplantation lymphoma after cord blood transplantation using third-party EBV-specific cytotoxic T lymphocytes," Blood, vol. 116, No. 23 (2010), pp. 5045-5049.
Boerner, P., et al., "Production of antigen-specific human monoclonal antibodies from in vitro-primed human splenocytes," The Journal of Immunology, vol. 147 (1991), pp. 86-95.
Doubrovina, Ekaterina, et al., "Adoptive immunotherapy with unselected or EBV-specific T cells for biopsy-proven EBV+ lymphomas after allogeneic hematopoietic cell transplantation," Blood, vol. 119, No. 11 (2012), pp. 2644-2656.
Fauriat, C., et al., "Impaired activating receptor expression pattern in natural killer cells from patients with multiple myeloma," Leukemia, vol. 20 (2006), pp. 732-733.
Fresnak, Andrew D., et al., "Engineered T cells: the promise and challenges of cancer immunotherapy," Nature, vol. 16 (2016), pp. 566-581.
Godfrey, James, et al., "The role of natural killer cells in immunity against multiple myeloma," Leukemia & Lymphoma, vol. 53, No. 9 (2012), pp. 1666-1676.
Holliger, Philipp, et al, "Engineered antibody fragments and the rise of single domains," Nature Biotechnology, vol. 23, No. 9 (2005), pp. 1126-1136.
Hoogenboom, Hennie R., et al., "By-passing Immunisation Human Antibodies from Synthetic Repertoires of Germline Vh Gene Segments Rearranged in Vitro," J. Mol. Biol., vol. 227 (1992), pp. 381-388.
Imai, C., et al., "Chimeric receptors with 4-1BB signaling capacity provoke potent cytotoxicity against acute lymphoblastic leukemia," Leukemia, vol. 18 (2004), pp. 676-684.
Jakobovits, Aya, et al.,, "Germ-line transmission and expression of a human-derived yeast artificial chromosome," Nature, vol. 362 (1993), pp. 255-258.
Jakobovits, Aya, et al., "Analysis of homozygous mutant chimeric mice: Deletion of the immunoglobulin heavy-chain joining region blocks B-cell development and antibody production," Proc. Natl. Acad. Sci., vol. 90 (1993), pp. 2551-2555.
Koehne, Guenther, et al., "Quantitation, selection, and functional characterization of Epstein-Barr virus-specific and alloreactive T cells detected by intracellular interferon-γ production and growth of cytotoxic precursors," Blood, vol. 99, No. 5 (2002), pp. 1730-1740.
Maher, John, et al., "Human T-lymphocyte cytotoxicity and proliferation directed by a single chimeric TCR/CD28 receptor," Nature Biotechnology, vol. 20 (2002), pp. 70-75.
Marks, James D., et al., "By-passing Immunization—Human Antibodies from V-gene Libraries Displayed on Phage," J. Mol. Biol., vol. 222 (1991), pp. 587-597.
Morgan, Richard A., et al., "Case Report of a Serious Adverse Event Following the Administration of T Cells Transduced With a Chimeric Antigen Receptor Recognizing ERBB2," Molecular Therapy, vol. 19, No. 4 (2010), pp. 843-851.
Narni-Mancinelli, Emilie, et al., "The 'T-cell-ness' of NK cells: unexpected similarities between NK cells and T cells," International Immunology, vol. 23, No. 7 (2011), pp. 427-431.
Porter, David L., et al., "Chimeric Antigen Receptor-Modified T Cells in Chronic Lymphoid Leukemia," The New England Journal of Medicine, vol. 365 (2011), pp. 725-733.
Presta, Leonard G., "Antibody engineering," Biotechnology, vol. 3 (1992), pp. 394-398.
Rosenberg, Steven A., et al., "Use of Tumor-Infiltrating Lymphocytes and Interleukin-2 In The Immunotherapy of Patients With Metastatic Melanoma," The New England Journal of Medicine, vol. 319, No. 25 (1988), pp. 1676-1680.
Sadelain, Michel, et al., "Targeting Tumours With Genetically Enhanced T Lympocytes," Nature, vol. 3 (2003), pp. 35-45.
Smith, Corey, et al., "Effective Treatment of Metastatic Forms of Epstein-Barr Virus-Associated Nasopharyngeal Carcinoma with a Novel Adenorvirus-Based Adoptive Immunotherapy," Cancer Research, vol. 72, No. 5 (2012), pp. 1116-1125.
Verhoeyen, Martine, et al., "Reshaping Human Antibodies: Grafting an Antilysozyme Activity," vol. 239 (1988), pp. 1534-1536.
Woof, Jenny M., et al., "Human Antibody-FC Receptor Interactions Illuminated by Crystal Structures," Nature, vol. 4 (2004) (11 pages).
International Search Report issued for PCT/US2019/012640, mailed Apr. 22, 2019.

* cited by examiner

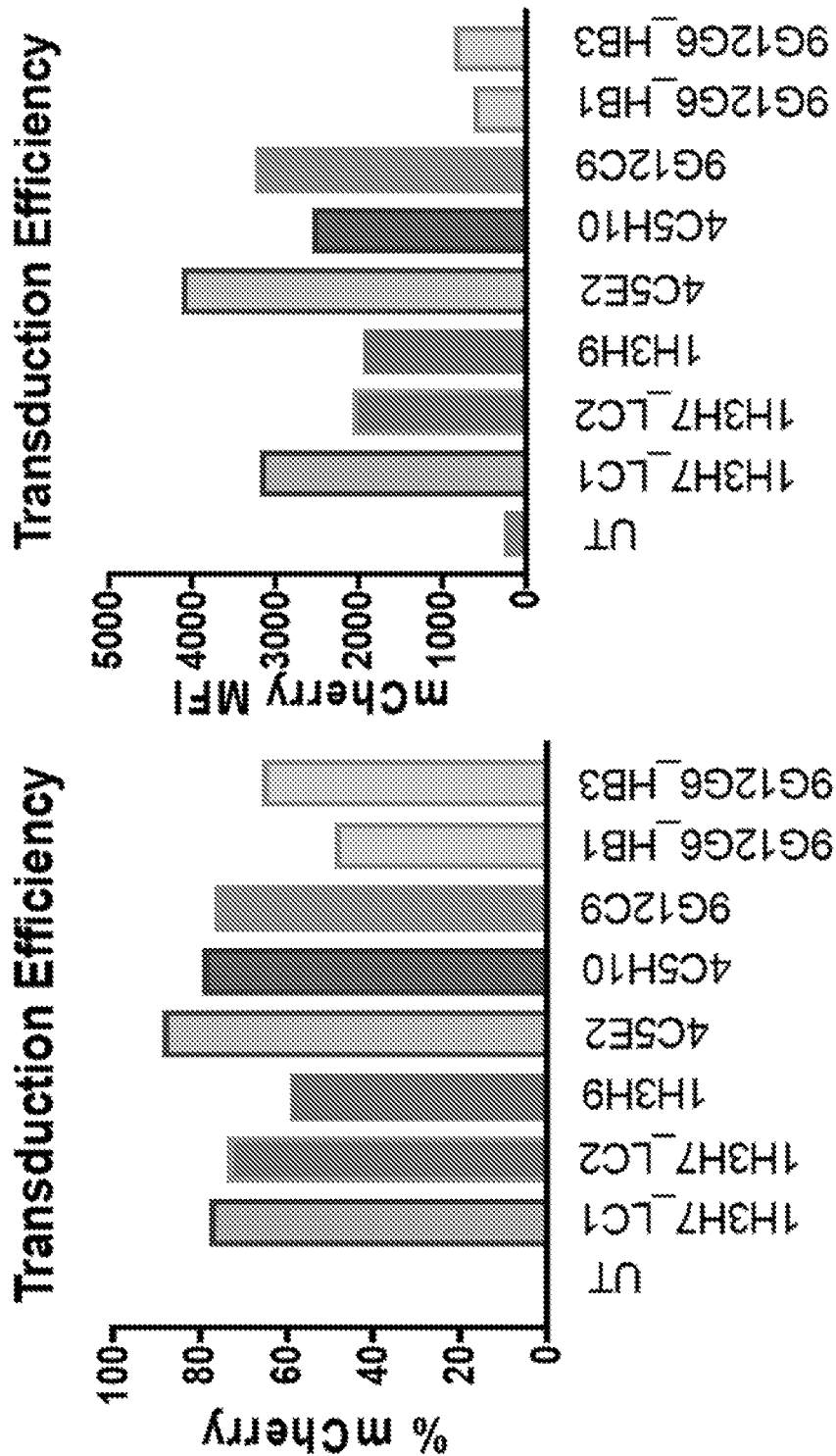

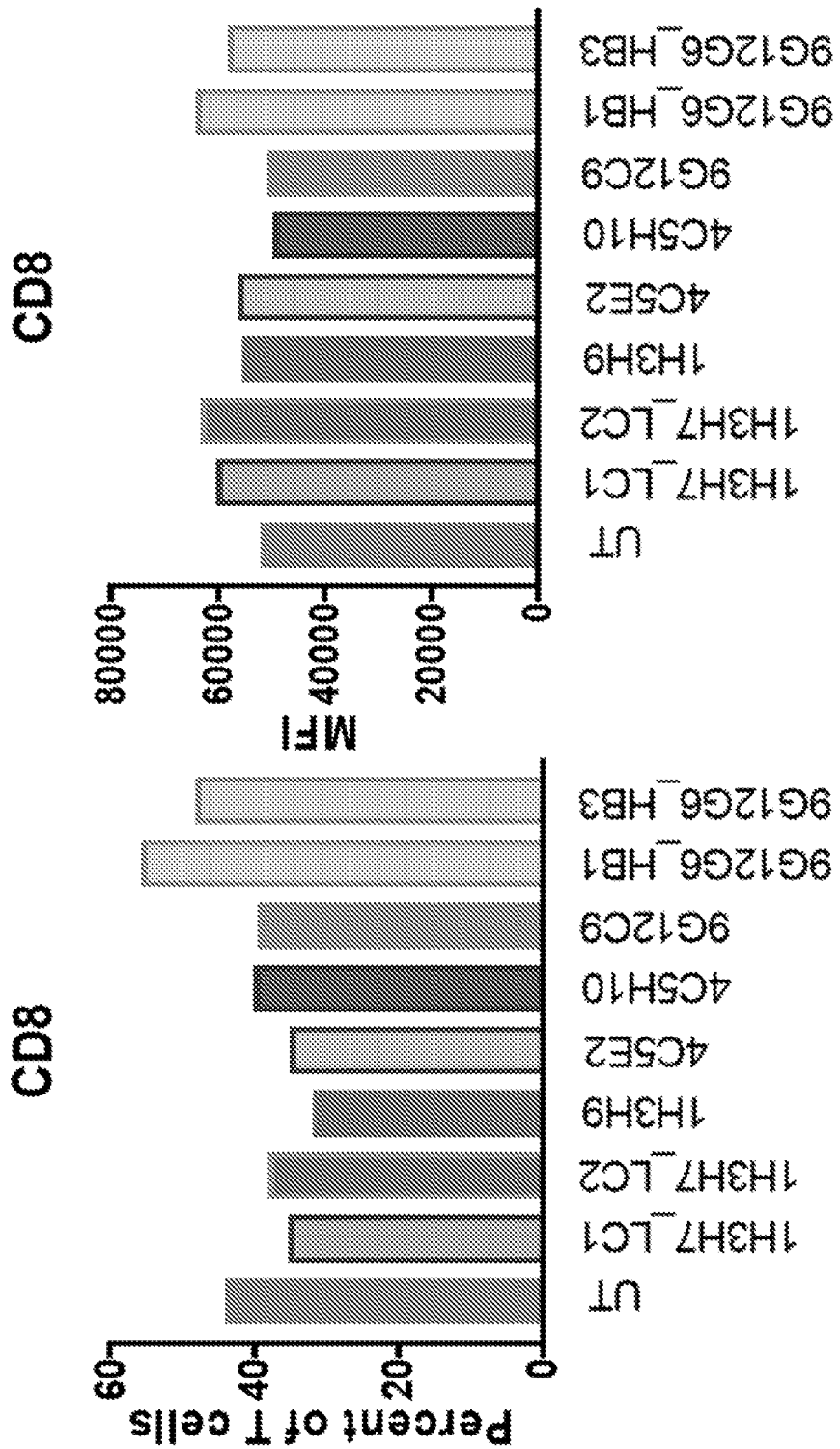

SEQUENCE LISTING

<160> NUMBER OF SEQ ID NOS: 108

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Phe Asp Ile Lys Asp Thr Tyr
1               5

<210> SEQ ID NO 2

```
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Thr Tyr Ala Met Tyr
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct

<400> SEQUENCE: 3

Thr Phe Trp Met
1

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Thr Phe Trp Met Gln
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Construct

<400> SEQUENCE: 5

Ile Asp Pro Ala Asn Gly Asp Thr
1               5

<210> SEQ ID NO 6
<211> LENGTH: 22
<212> TYPE: PRT
<213> ORGANISM: Artificial Sequence
<220> FEATURE:
<223> OTHER INFORMATION: Synthetic Construct

<400> SEQUENCE: 6

Arg Ile Arg Ser Lys Val Asn Asn Tyr Ala Thr Tyr Tyr Ala Asp Ser
1               5                   10                  15

Val Lys Asp Arg Phe Thr
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic Construct

<400> SEQUENCE: 7

Thr Ile Tyr Pro Gly Asp Asp Asp Thr Arg Tyr Thr Gln Lys Phe Lys
1               5                   10                  15
```

```
Gly Arg Ala Thr
        20

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct

<400> SEQUENCE: 8

Ala Arg Arg Gly Gly Leu Ser
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Asp Pro Met Asp Tyr
1               5

<210> SEQ ID NO 10
<211> LENGTH: 12
<212> TYPE: PRT
<213> ORGANISM: Artificial Sequence
<220> FEATURE:
<223> OTHER INFORMATION: Synthetic Construct

<400> SEQUENCE: 10

Ser Gly Tyr Glu Arg Gly Pro Tyr Tyr Phe Asp Ser
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Ser Gly Tyr Glu Arg Gly Pro Tyr Tyr Phe
1               5                   10

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

Gly Asn Ile His Asn Tyr
1               5

<210> SEQ ID NO 13
<211> LENGTH: 16
<212> TYPE: PRT
<213> ORGANISM: Artificial Sequence
<220> FEATURE:
<223> OTHER INFORMATION: Synthetic Construct

<400> SEQUENCE: 13

Gly Ser Ser Lys Ser Leu Leu His Ser Asn Gly Asn Thr Tyr Leu Tyr
```

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Lys Ser Ser Gln Ser Leu Leu Cys Arg Ser Asn Gln Lys Asn Tyr Leu
1               5                   10                  15

Ala

<210> SEQ ID NO 15
<211> LENGTH: 17
<212> TYPE: PRT
<213> ORGANISM: Artificial Sequence
<220> FEATURE:
<223> OTHER INFORMATION: Synthetic Construct

<400> SEQUENCE: 15

Lys Ser Ser Gln Ser Leu Leu Tyr Arg Ser Asn Gln Lys Asn Tyr Leu
1               5                   10                  15

Ala

<210> SEQ ID NO 16
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 16

Asn Ala Lys Xaa
1

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

Arg Val Ser Asn Leu Ala Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Trp Ala Ser Thr Arg Glu Ser
1               5

<210> SEQ ID NO 19
<211> LENGTH: 9
<212> TYPE: PRT

<213> ORGANISM: Artificial Sequence
<220> FEATURE:
<223> OTHER INFORMATION: Synthetic Construct

<400> SEQUENCE: 19

Gln His Phe Trp Ser Thr Pro Trp Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Met Gln His Leu Glu Tyr Pro Tyr Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Gln Gln Tyr Tyr Ser Tyr Pro Leu Thr
1               5

<210> SEQ ID NO 22
<211> LENGTH: 114
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asp Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asp Thr Arg Tyr Asp Pro Glu Phe
    50                  55                  60

Gln Gly Lys Ala Ser Leu Thr Ala Asp Thr Ser Ser Asn Thr Ala Tyr
65                  70                  75                  80

Leu Gln Phe Ser Asn Leu Thr Ser Glu Asp Thr Ala Val Tyr Tyr Cys
                85                  90                  95

Ala Arg Arg Gly Gly Leu Ser Trp Gly Gln Gly Thr Thr Leu Thr Val
                100                 105                 110

Ser Ser

<210> SEQ ID NO 23
<211> LENGTH: 342
<212> TYPE: DNA
<213> ORGANISM: Artificial Sequence
<220> FEATURE:
<223> OTHER INFORMATION: Synthetic Construct

<400> SEQUENCE: 23
gaggttcaac tgcaacagtc tggggcagag cttgtgaagc caggggcctc agtcaagttg      60

-continued

```
tcctgcacag cttctggctt cgacattaaa gacacctata tccactgggt gaaacagagg    120
cctgaacagg gcctggagtg gattggaagg attgatcctg cgaatggtga tactagatat    180
gacccggaat tccagggcaa ggcctctcta acagctgaca catcctccaa tacagcctac    240
ctacaattca gcaacctgac atctgaagac actgccgtct attactgtgc tagaagaggc    300
ggcctctcct ggggccaagg caccactctc acagtctcct ca                      342
```

<210> SEQ ID NO 24
<211> LENGTH: 116
<212> TYPE: PRT
<213> ORGANISM: Artificial Sequence
<220> FEATURE:
<223> OTHER INFORMATION: Synthetic Construct

<400> SEQUENCE: 24

```
Glu Val Gln Leu Glu Glu Ser Gly Gly Gly Leu Val Gln Pro Lys Gly
 1               5                  10                  15

Ser Leu Lys Leu Ser Cys Ala Ala Ser Gly Phe Thr Phe Asn Thr Tyr
            20                  25                  30

Ala Met Tyr Trp Val Cys Gln Ala Pro Gly Lys Gly Leu Lys Trp Val
        35                  40                  45

Ala Arg Ile Arg Ser Lys Val Asn Asn Tyr Ala Thr Tyr Tyr Ala Asp
    50                  55                  60

Ser Val Lys Asp Arg Phe Thr Ile Ser Arg Asp Asp Ser Gln Asn Met
65                  70                  75                  80

Leu Phe Leu His Met Asn Asn Leu Lys Thr Glu Asp Thr Ala Ile Tyr
                85                  90                  95

Phe Cys Val Arg Asp Pro Met Asp Tyr Trp Gly Gln Gly Ile Ser Val
               100                 105                 110

Thr Val Ser Ser
        115
```

<210> SEQ ID NO 25
<211> LENGTH: 348
<212> TYPE: DNA
<213> ORGANISM: Artificial Sequence
<220> FEATURE:
<223> OTHER INFORMATION: Synthetic Construct

<400> SEQUENCE: 25

```
gaggtgcagc tggaggagtc tggtggagga ttggtgcagc ctaaaggatc attgaaactc     60
tcatgtgccg cctccggttt cacctttcaat acctatgcca tgtactgggt ctgccaggct   120
ccaggaaagg gtttgaaatg ggttgctcgc ataagaagta agttaataa ttatgcaaca    180 tattatgccg attcagtgaa agacagattc accatctcca gagatgattc acaaaacatg   240
ctctttctgc acatgaacaa cctgaaaact gaggacactg ccatatattt ctgtgtgaga   300
gatcctatgg actactgggg tcaaggaatc tcagtcaccg tctcctca                 348
```

<210> SEQ ID NO 26
<211> LENGTH: 116
<212> TYPE: PRT
<213> ORGANISM: Artificial Sequence
<220> FEATURE:
<223> OTHER INFORMATION: Synthetic Construct

<400> SEQUENCE: 26

```
Glu Val Gln Leu Val Glu Ser Gly Gly Gly Leu Val Gln Pro Lys Gly
 1               5                  10                  15
```

```
Ser Leu Lys Leu Ser Cys Ala Ala Ser Gly Phe Thr Phe Asn Thr Tyr
            20                  25                  30

Ala Met Tyr Trp Val Cys Gln Ala Pro Gly Lys Gly Leu Lys Trp Val
        35                  40                  45

Ala Arg Ile Arg Ser Lys Val Asn Asn Tyr Ala Thr Tyr Tyr Ala Asp
50                  55                  60

Ser Val Lys Asp Arg Phe Thr Ile Ser Arg Asp Asp Ser Gln Asn Met
65                  70                  75                  80

Leu Phe Leu His Met Asn Asn Leu Lys Thr Glu Asp Thr Ala Ile Tyr
                85                  90                  95

Phe Cys Val Arg Asp Pro Met Asp Tyr Trp Gly Gln Gly Ile Ser Val
            100                 105                 110

Thr Val Ser Ser
        115
```

<210> SEQ ID NO 27
<211> LENGTH: 348
<212> TYPE: DNA
<213> ORGANISM: Artificial Sequence
<220> FEATURE:
<223> OTHER INFORMATION: Synthetic Construct

<400> SEQUENCE: 27

```
gaggtgcagc ttgttgagtc tggtggagga ttggtgcagc ctaaaggatc attgaaactc      60
tcatgtgccg cctccggttt caccttcaat acctatgcca tgtactgggt ctgccaggct     120
ccaggaaagg gtttgaaatg ggttgctcgc ataagaagta agttaataa ttatgcaaca      180 tattatgccg attcagtgaa agacagattc accatctcca gagatgattc acaaaacatg     240
ctctttctgc acatgaacaa cctgaaaact gaggacactg ccatatattt ctgtgtgaga     300
gatcctatgg actactgggg tcaaggaatc tcagtcaccg tctcctca                  348
```

<210> SEQ ID NO 28
<211> LENGTH: 121
<212> TYPE: PRT
<213> ORGANISM: Artificial Sequence
<220> FEATURE:
<223> OTHER INFORMATION: Synthetic Construct

<400> SEQUENCE: 28

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Thr Thr Phe
            20                  25                  30

Trp Met Gln Trp Val Lys Gln Arg Pro Gly Gln Gly Leu Glu Trp Ile
        35                  40                  45

Gly Thr Ile Tyr Pro Gly Asp Asp Thr Arg Tyr Thr Gln Lys Phe
50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser
        115                 120
```

<210> SEQ ID NO 29
<211> LENGTH: 363
<212> TYPE: DNA
<213> ORGANISM: Artificial Sequence
<220> FEATURE:
<223> OTHER INFORMATION: Synthetic Construct

<400> SEQUENCE: 29

```
caggttcagc tccagcagtc tggggctgag ctggcaagac ctggggcttc agtgaagttg      60
tcctgcaagg cttctggcta cacgtttact actttctgga tgcagtgggt aaaacagagg     120
cctggacagg gtctggaatg gattgggact atttatcctg agatgatga tactaggtac      180
actcagaaat tcaagggcag ggccacattg actgcagata atcgtccac cacagcctac      240
atgcaactca gcaacttgtc atctgaggac tctgcggtct attactgtgc aagatcgggg    300
tatgagaggg gcccatacta ctttgactcc tggggccaag gcaccactct cacagtctcc     360
tca                                                                  363
```

<210> SEQ ID NO 30
<211> LENGTH: 121
<212> TYPE: PRT
<213> ORGANISM: Artificial Sequence
<220> FEATURE:
<223> OTHER INFORMATION: Synthetic Construct

<400> SEQUENCE: 30

```
Asp Val Lys Leu Gln Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Arg Val Lys Gln Arg Pro Gly Gln Gly Leu Glu Trp Ile
        35                  40                  45

Gly Thr Ile Tyr Pro Gly Asp Asp Thr Arg Tyr Thr Gln Lys Phe
    50                  55                  60

Lys Gly Arg Ala Thr Leu Thr Ala Asp Lys Ser Ser Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser
        115                 120
```

<210> SEQ ID NO 31
<211> LENGTH: 363
<212> TYPE: DNA
<213> ORGANISM: Artificial Sequence
<220> FEATURE:
<223> OTHER INFORMATION: Synthetic Construct

<400> SEQUENCE: 31

```
gatgtgaagc ttcaggagtc tggggctgag ctggcaagac ctggggcttc agtgaagttg      60
tcctgcaagg cttctggcta cacgtttact actttctgga tgcagcgggt aaaacagagg    120
cctggacagg gtctggaatg gattgggact atttatcctg agatgatga tactaggtac      180
actcagaaat tcaagggcag ggccacattg actgcagata atcgtccac cacagcctac      240
atgcaactca gcaacttgtc atctgaggac tctgcggtct attactgtgc aagatcgggg    300
tatgagaggg gcccatacta ctttgactcc tggggccaag gcaccactct cacagtctcc     360
``` tca                                                                    363

<210> SEQ ID NO 32
<211> LENGTH: 121
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Lys Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Trp Ala Lys Gln Arg Pro Gly Gln Gly Leu Glu Trp Ile
        35                  40                  45

Gly Thr Ile Tyr Pro Gly Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser
        115                 120

<210> SEQ ID NO 33
<211> LENGTH: 363
<212> TYPE: DNA
<213> ORGANISM: Artificial Sequence
<220> FEATURE:
<223> OTHER INFORMATION: Synthetic Construct

<400> SEQUENCE: 33
caggtgcagc tgaaggagtc tggggctgag ctggcaagac ctggggcttc agtgaagttg    60
tcctgcaagg cttctggcta cacgtttact actttctgga tgcagtgggc aaaacagagg   120
cctggacagg gtctggaatg gattgggact atttatcctg gagatgatga tactaggtac   180
actcagaaat tcaagggcag ggccacattg actgcagata aatcgtccac cacagcctac   240
atgcaactca gcaacttgtc atctgaggac tctgcggtct attactgtgc aagatcgggg   300
tatgagaggg gcccatacta ctttgactcc tggggccaag gcaccactct cacagtctcc   360
tca                                                                  363

<210> SEQ ID NO 34
<211> LENGTH: 107
<212> TYPE: PRT
<213> ORGANISM: Artificial Sequence
<220> FEATURE:
<223> OTHER INFORMATION: Synthetic Construct

<400> SEQUENCE: 34

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

```
Tyr Asn Ala Lys Thr Leu Ala Asp Gly Val Pro Ser Arg Phe Ser Gly
 50                  55                  60
Ser Gly Ser Gly Thr Gln Tyr Ser Leu Lys Ile Asn Ser Leu Gln Pro
 65                  70                  75                  80
Glu Asp Phe Gly Ser Tyr Tyr Cys Gln His Phe Trp Ser Thr Pro Trp
                 85                  90                  95
Thr Phe Gly Gly Gly Thr Lys Leu Glu Ile Lys
                100                 105
```

<210> SEQ ID NO 35
<211> LENGTH: 321
<212> TYPE: DNA
<213> ORGANISM: Artificial Sequence
<220> FEATURE:
<223> OTHER INFORMATION: Synthetic Construct

<400> SEQUENCE: 35

```
gacatccaga tgactcagtc tccagcctcc ctatctgcat ctgtgggaga aactgtcacc    60
atcacatgtc gagcaagtgg gaatattcac aattatttag catggtatca gcagaaacag   120
ggaaaatctc ctcagctcct ggtctataat gcaaaaacct tagcagatgg tgtgccatca   180
aggttcagtg gcagtggatc aggaacacaa tattctctca agatcaacag cctgcagcct   240
gaagattttg ggagttatta ctgtcaacat ttttggagta ctccgtggac gttcggtgga   300
ggcaccaagc tggaaatcaa a                                             321
```

<210> SEQ ID NO 36
<211> LENGTH: 112
<212> TYPE: PRT
<213> ORGANISM: Artificial Sequence
<220> FEATURE:
<223> OTHER INFORMATION: Synthetic Construct

<400> SEQUENCE: 36

```
Gly Asn Ser Trp Ser His Ser Leu Arg Ser Leu Ser Val Thr Ile Gly
 1               5                  10                  15
Gln Pro Ala Ser Ile Ser Cys Lys Ser Ser Gln Ser Leu Leu Asp Gly
                20                  25                  30
Asn Gly Lys Thr Tyr Leu Asn Trp Leu Leu Gln Arg Pro Gly Gln Ser
                35                  40                  45
Pro Lys Arg Leu Leu Tyr Leu Val Ser Lys Leu Asp Ser Gly Val Pro
             50                  55                  60
Asp Arg Phe Thr Gly Ser Gly Ser Gly Thr Asp Phe Thr Leu Lys Ile
 65                  70                  75                  80
Ser Arg Val Glu Ala Glu Asp Leu Gly Ile Tyr Tyr Cys Trp Gln Gly
                 85                  90                  95
Thr His Phe Pro Arg Thr Phe Gly Gly Gly Thr Lys Leu Glu Ile Lys
                100                 105                 110
```

<210> SEQ ID NO 37
<211> LENGTH: 112
<212> TYPE: PRT
<213> ORGANISM: Artificial Sequence
<220> FEATURE:
<223> OTHER INFORMATION: Synthetic Construct

<400> SEQUENCE: 37

```
Gly Asn Ser Trp Arg His Ser Pro Arg Ser Leu Ser Val Thr Ile Gly
 1               5                  10                  15
Gln Pro Ala Ser Ile Ser Cys Lys Ser Ser Gln Ser Leu Leu Asp Gly
```

```
                20                  25                  30

Asn Gly Lys Thr Tyr Leu Asn Trp Leu Leu Gln Arg Pro Gly Gln Ser
            35                  40                  45

Pro Lys Arg Leu Leu Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro Arg Thr Phe Gly Gly Gly Thr Lys Leu Glu Ile Lys
            100                 105                 110
```

<210> SEQ ID NO 38
<211> LENGTH: 112
<212> TYPE: PRT
<213> ORGANISM: Artificial Sequence
<220> FEATURE:
<223> OTHER INFORMATION: Synthetic Construct

<400> SEQUENCE: 38

```
Asp Ile Val Met Thr Gln Ala Ala Pro Ser Val Pro Val Thr Pro Gly
1               5                   10                  15

Glu Ser Val Ser Ile Ser Cys Gly Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Val Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Arg Leu Glu Ile Lys
            100                 105                 110
```

<210> SEQ ID NO 39
<211> LENGTH: 336
<212> TYPE: DNA
<213> ORGANISM: Artificial Sequence
<220> FEATURE:
<223> OTHER INFORMATION: Synthetic Construct

<400> SEQUENCE: 39

```
gatattgtga tgactcaggc tgcaccctct gtacctgtca ctcctgggga gtcagtatcc      60
atctcctgcg gctctagtaa gagtctcctg catagtaatg gcaacactta cttgtattgg    120
ttcctgcaga ggccaggcca gtctcctcag ctcctgatat atcgggtgtc caaccttgcc    180
tcaggagtcc cagacaggtt cagtggcagt gggtcaggaa ctgctttcac actgagaatc    240
agtagagtgg aggctgagga tgtgggtgtt tattactgta tgcaacatct agaatatccg    300
tacacgttcg gagggggac caggctggaa ataaaa                              336
```

<210> SEQ ID NO 40
<211> LENGTH: 112
<212> TYPE: PRT
<213> ORGANISM: Artificial Sequence
<220> FEATURE:
<223> OTHER INFORMATION: Synthetic Construct

<400> SEQUENCE: 40

Asp Ile Val Met Thr Gln Ala Ala Pro Ser Val Pro Val Thr Pro Gly
1               5                   10                  15

Glu Ser Val Ser Ile Ser Cys Gly Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Val Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Arg Leu Glu Ile Lys
            100                 105                 110

<210> SEQ ID NO 41
<211> LENGTH: 336
<212> TYPE: DNA
<213> ORGANISM: Artificial Sequence
<220> FEATURE:
<223> OTHER INFORMATION: Synthetic Construct

<400> SEQUENCE: 41
gatattgtga tgactcaggc tgcaccctct gtacctgtca ctcctgggga gtcagtatcc    60
atctcctgcg ggtctagtaa gagtctcctg catagtaatg gcaacactta cttgtattgg   120
ttcctgcaga ggccaggcca gtctcctcag ctcctgatat atcgggtgtc caaccttgcc   180
tcaggagtcc cagacaggtt cagtggcagt gggtcaggaa ctgctttcac actgagaatc   240
agtagagtgg aggctgagga tgtgggtgtt tattactgta tgcaacatct agaatatccg   300
tacacgttcg gaggggggac caggctggaa ataaaa                             336

<210> SEQ ID NO 42
<211> LENGTH: 113
<212> TYPE: PRT
<213> ORGANISM: Artificial Sequence
<220> FEATURE:
<223> OTHER INFORMATION: Synthetic Construct

<400> SEQUENCE: 42

Asp Thr Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Cys Arg
                20                  25                  30

Ser Asn Gln Lys Asn Tyr Leu Ala Trp Tyr Gln Gln Lys Pro Gly Gln
            35                  40                  45

Ser Pro Lys Gln Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 43

<211> LENGTH: 339
<212> TYPE: DNA
<213> ORGANISM: Artificial Sequence
<220> FEATURE:
<223> OTHER INFORMATION: Synthetic Construct

<400> SEQUENCE: 43

```
gacactgtga tgtcacagtc cccatcctcc ctagctgttt cagttggaga aagataact      60
atgagctgca agtccagtca gagtctttta tgtcgtagca atcaaaagaa ctacttggcc    120
tggtaccagc agaaaccagg gcagtctcct aaacagctga tttactgggc atctactagg    180
gaatctgggg tccctgatcg cttcacaggc agtggatctg ggacagattt cactctcacc    240
atcagcagtg tgaaggctga agacctggca gtttattact gtcagcaata ttatagttat    300
ccgctcacgt tcggtgctgg caccaagctg gagctgaaa                           339
```

<210> SEQ ID NO 44
<211> LENGTH: 113
<212> TYPE: PRT
<213> ORGANISM: Artificial Sequence
<220> FEATURE:
<223> OTHER INFORMATION: Synthetic Construct

<400> SEQUENCE: 44

```
Asp Thr Val Met Ser Gln Ser Pro Ser Ser Leu Ala Val Ser Val Gly
1               5                   10                  15
Glu Lys Ile Thr Met Ser Cys Lys Ser Ser Gln Ser Leu Leu Tyr Arg
            20                  25                  30
Ser Asn Gln Lys Asn Tyr Leu Ala Trp Tyr Gln Gln Lys Pro Gly Gln
        35                  40                  45
Ser Pro Lys Gln Leu Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Lys Ala Glu Asp Leu Ala Val Tyr Tyr Cys Gln Gln
                85                  90                  95
Tyr Tyr Ser Tyr Pro Leu Thr Phe Gly Ala Gly Thr Lys Leu Glu Leu
            100                 105                 110
Lys
```

<210> SEQ ID NO 45
<211> LENGTH: 339
<212> TYPE: DNA
<213> ORGANISM: Artificial Sequence
<220> FEATURE:
<223> OTHER INFORMATION: Synthetic Construct

<400> SEQUENCE: 45

```
gacactgtga tgtcacagtc cccatcctcc ctagctgttt cagttggaga aagataact      60
atgagctgca agtccagtca gagtctttta tatcgtagca atcaaaagaa ctacttggcc    120
tggtaccagc agaaaccagg gcagtctcct aaacagctga tttactgggc atctactagg    180
gaatctgggg tccctgatcg cttcacaggc agtggatctg ggacagattt cactctcacc    240
atcagcagtg tgaaggctga agacctggca gtttattact gtcagcaata ttatagttat    300
ccgctcacgt tcggtgctgg caccaagctg gagctgaaa                           339
```

<210> SEQ ID NO 46
<211> LENGTH: 15
<212> TYPE: PRT

<213> ORGANISM: Artificial Sequence
<220> FEATURE:
<223> OTHER INFORMATION: Synthetic Construct

<400> SEQUENCE: 46

Gly Gly Gly Gly Ser Gly Gly Gly Ser Gly Gly Gly Ser
1               5                   10                  15

<210> SEQ ID NO 47
<211> LENGTH: 236
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asp Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asp Thr Arg Tyr Asp Pro Glu Phe
    50                  55                  60

Gln Gly Lys Ala Ser Leu Thr Ala Asp Thr Ser Ser Asn Thr Ala Tyr
65                  70                  75                  80

Leu Gln Phe Ser Asn Leu Thr Ser Glu Asp Thr Ala Val Tyr Tyr Cys
                85                  90                  95

Ala Arg Arg Gly Gly Leu Ser Trp Gly Gln Gly Thr Thr Leu Thr Val
            100                 105                 110

Ser Ser Gly Gly Gly Gly Ser Gly Gly Gly Gly Ser Gly Gly Gly Gly
        115                 120                 125

Ser Asp Ile Gln Met Thr Gln Ser Pro Ala Ser Leu Ser Ala Ser Val
130                 135                 140

Gly Glu Thr Val Thr Ile Thr Cys Arg Ala Ser Gly Asn Ile His Asn
145                 150                 155                 160

Tyr Leu Ala Trp Tyr Gln Gln Lys Gln Gly Lys Ser Pro Gln Leu Leu
                165                 170                 175

Val Tyr Asn Ala Lys Thr Leu Ala Asp Gly Val Pro Ser Arg Phe Ser
            180                 185                 190

Gly Ser Gly Ser Gly Thr Gln Tyr Ser Leu Lys Ile Asn Ser Leu Gln
        195                 200                 205

Pro Glu Asp Phe Gly Ser Tyr Tyr Cys Gln His Phe Trp Ser Thr Pro
    210                 215                 220

Trp Thr Phe Gly Gly Gly Thr Lys Leu Glu Ile Lys
225                 230                 235

<210> SEQ ID NO 48
<211> LENGTH: 241
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asp Ile Lys Asp Thr
            20                  25                  30

Tyr Ile His Trp Val Lys Gln Arg Pro Glu Gln Gly Leu Glu Trp Ile
            35                  40                  45

Gly Arg Ile Asp Pro Ala Asn Gly Asp Thr Arg Tyr Asp Pro Glu Phe
        50                  55                  60

Gln Gly Lys Ala Ser Leu Thr Ala Asp Thr Ser Ser Asn Thr Ala Tyr
65                  70                  75                  80

Leu Gln Phe Ser Asn Leu Thr Ser Glu Asp Thr Ala Val Tyr Tyr Cys
                85                  90                  95

Ala Arg Arg Gly Gly Leu Ser Trp Gly Gln Gly Thr Thr Leu Thr Val
            100                 105                 110

Ser Ser Gly Gly Gly Gly Ser Gly Gly Gly Ser Gly Gly Gly Gly
            115                 120                 125

Ser Gly Asn Ser Trp Ser His Ser Leu Arg Ser Leu Ser Val Thr Ile
        130                 135                 140

Gly Gln Pro Ala Ser Ile Ser Cys Lys Ser Ser Gln Ser Leu Leu Asp
145                 150                 155                 160

Gly Asn Gly Lys Thr Tyr Leu Asn Trp Leu Leu Gln Arg Pro Gly Gln
                165                 170                 175

Ser Pro Lys Arg Leu Leu Tyr Leu Val Ser Lys Leu Asp Ser Gly Val
            180                 185                 190

Pro Asp Arg Phe Thr Gly Ser Gly Ser Gly Thr Asp Phe Thr Leu Lys
        195                 200                 205

Ile Ser Arg Val Glu Ala Glu Asp Leu Gly Ile Tyr Tyr Cys Trp Gln
210                 215                 220

Gly Thr His Phe Pro Arg Thr Phe Gly Gly Thr Lys Leu Glu Ile
225                 230                 235                 240

Lys

<210> SEQ ID NO 49
<211> LENGTH: 241
<212> TYPE: PRT
<213> ORGANISM: Artificial Sequence
<220> FEATURE:
<223> OTHER INFORMATION: Synthetic Construct

<400> SEQUENCE: 49

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asp Ile Lys Asp Thr
            20                  25                  30

Tyr Ile His Trp Val Lys Gln Arg Pro Glu Gln Gly Leu Glu Trp Ile
            35                  40                  45

Gly Arg Ile Asp Pro Ala Asn Gly Asp Thr Arg Tyr Asp Pro Glu Phe
        50                  55                  60

Gln Gly Lys Ala Ser Leu Thr Ala Asp Thr Ser Ser Asn Thr Ala Tyr
65                  70                  75                  80

Leu Gln Phe Ser Asn Leu Thr Ser Glu Asp Thr Ala Val Tyr Tyr Cys
                85                  90                  95

Ala Arg Arg Gly Gly Leu Ser Trp Gly Gln Gly Thr Thr Leu Thr Val
            100                 105                 110

Ser Ser Gly Gly Gly Gly Ser Gly Gly Gly Gly Ser Gly Gly Gly Gly
            115                 120                 125

Ser Gly Asn Ser Trp Arg His Ser Pro Arg Ser Leu Ser Val Thr Ile
        130                 135                 140

Gly Gln Pro Ala Ser Ile Ser Cys Lys Ser Ser Gln Ser Leu Leu Asp
145                 150                 155                 160

Gly Asn Gly Lys Thr Tyr Leu Asn Trp Leu Leu Gln Arg Pro Gly Gln
                165                 170                 175

Ser Pro Lys Arg Leu Leu Tyr Leu Val Ser Lys Leu Asp Ser Gly Val
            180                 185                 190

Pro Asp Arg Phe Thr Gly Ser Gly Ser Gly Thr Asp Phe Thr Leu Lys
        195                 200                 205

Ile Ser Arg Val Glu Ala Glu Asp Leu Gly Ile Tyr Tyr Cys Trp Gln
    210                 215                 220

Gly Thr His Phe Pro Arg Thr Phe Gly Gly Gly Thr Lys Leu Glu Ile
225                 230                 235                 240

Lys

<210> SEQ ID NO 50
<211> LENGTH: 241
<212> TYPE: PRT
<213> ORGANISM: Artificial Sequence
<220> FEATURE:
<223> OTHER INFORMATION: Synthetic Construct

<400> SEQUENCE: 50

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asp Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asp Thr Arg Tyr Asp Pro Glu Phe
    50                  55                  60

Gln Gly Lys Ala Ser Leu Thr Ala Asp Thr Ser Asn Thr Ala Tyr
65                  70                  75                  80

Leu Gln Phe Ser Asn Leu Thr Ser Glu Asp Thr Ala Val Tyr Tyr Cys
                85                  90                  95

Ala Arg Arg Gly Gly Leu Ser Trp Gly Gln Gly Thr Thr Leu Thr Val
            100                 105                 110

Ser Ser Gly Gly Gly Gly Ser Gly Gly Gly Gly Ser Gly Gly Gly Gly
        115                 120                 125

Ser Asp Ile Val Met Thr Gln Ala Ala Pro Ser Val Pro Val Thr Pro
130                 135                 140

Gly Glu Ser Val Ser Ile Ser Cys Gly Ser Ser Lys Ser Leu Leu His
145                 150                 155                 160

Ser Asn Gly Asn Thr Tyr Leu Tyr Trp Phe Leu Gln Arg Pro Gly Gln
                165                 170                 175

Ser Pro Gln Leu Leu Ile Tyr Arg Val Ser Asn Leu Ala Ser Gly Val
            180                 185                 190

Pro Asp Arg Phe Ser Gly Ser Gly Ser Gly Thr Ala Phe Thr Leu Arg
        195                 200                 205

Ile Ser Arg Val Glu Ala Glu Asp Val Gly Val Tyr Tyr Cys Met Gln
    210                 215                 220

His Leu Glu Tyr Pro Tyr Thr Phe Gly Gly Gly Thr Arg Leu Glu Ile
225                 230                 235                 240

Lys

<210> SEQ ID NO 51

<211> LENGTH: 242
<212> TYPE: PRT
<213> ORGANISM: Artificial Sequence
<220> FEATURE:
<223> OTHER INFORMATION: Synthetic Construct

<400> SEQUENCE: 51

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asp Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asp Thr Arg Tyr Asp Pro Glu Phe
    50                  55                  60

Gln Gly Lys Ala Ser Leu Thr Ala Asp Thr Ser Ser Asn Thr Ala Tyr
65                  70                  75                  80

Leu Gln Phe Ser Asn Leu Thr Ser Glu Asp Thr Ala Val Tyr Tyr Cys
                85                  90                  95

Ala Arg Arg Gly Gly Leu Ser Trp Gly Gln Gly Thr Thr Leu Thr Val
            100                 105                 110

Ser Ser Gly Gly Gly Gly Ser Gly Gly Gly Gly Ser Gly Gly Gly Gly
        115                 120                 125

Ser Asp Thr Val Met Ser Gln Ser Pro Ser Ser Leu Ala Val Ser Val
    130                 135                 140

Gly Glu Lys Ile Thr Met Ser Cys Lys Ser Ser Gln Ser Leu Leu Cys
145                 150                 155                 160

Arg Ser Asn Gln Lys Asn Tyr Leu Ala Trp Tyr Gln Gln Lys Pro Gly
                165                 170                 175

Gln Ser Pro Lys Gln Leu Ile Tyr Trp Ala Ser Thr Arg Glu Ser Gly
            180                 185                 190

Val Pro Asp Arg Phe Thr Gly Ser Gly Ser Gly Thr Asp Phe Thr Leu
        195                 200                 205

Thr Ile Ser Ser Val Lys Ala Glu Asp Leu Ala Val Tyr Tyr Cys Gln
    210                 215                 220

Gln Tyr Tyr Ser Tyr Pro Leu Thr Phe Gly Ala Gly Thr Lys Leu Glu
225                 230                 235                 240

Leu Lys
```

<210> SEQ ID NO 52
<211> LENGTH: 242
<212> TYPE: PRT
<213> ORGANISM: Artificial Sequence
<220> FEATURE:
<223> OTHER INFORMATION: Synthetic Construct

<400> SEQUENCE: 52

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asp Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asp Thr Arg Tyr Asp Pro Glu Phe
    50                  55                  60

Gln Gly Lys Ala Ser Leu Thr Ala Asp Thr Ser Ser Asn Thr Ala Tyr
65                  70                  75                  80
```

```
Leu Gln Phe Ser Asn Leu Thr Ser Glu Asp Thr Ala Val Tyr Tyr Cys
                85                  90                  95

Ala Arg Arg Gly Gly Leu Ser Trp Gly Gln Gly Thr Thr Leu Thr Val
            100                 105                 110

Ser Ser Gly Gly Gly Gly Ser Gly Gly Gly Ser Gly Gly Gly Gly
            115                 120                 125

Ser Asp Thr Val Met Ser Gln Ser Pro Ser Ser Leu Ala Val Ser Val
130                 135                 140

Gly Glu Lys Ile Thr Met Ser Cys Lys Ser Ser Gln Ser Leu Leu Tyr
145                 150                 155                 160

Arg Ser Asn Gln Lys Asn Tyr Leu Ala Trp Tyr Gln Gln Lys Pro Gly
                165                 170                 175

Gln Ser Pro Lys Gln Leu Ile Tyr Trp Ala Ser Thr Arg Glu Ser Gly
            180                 185                 190

Val Pro Asp Arg Phe Thr Gly Ser Gly Ser Gly Thr Asp Phe Thr Leu
            195                 200                 205

Thr Ile Ser Ser Val Lys Ala Glu Asp Leu Ala Val Tyr Tyr Cys Gln
    210                 215                 220

Gln Tyr Tyr Ser Tyr Pro Leu Thr Phe Gly Ala Gly Thr Lys Leu Glu
225                 230                 235                 240

Leu Lys

<210> SEQ ID NO 53
<211> LENGTH: 238
<212> TYPE: PRT
<213> ORGANISM: Artificial Sequence
<220> FEATURE:
<223> OTHER INFORMATION: Synthetic Construct

<400> SEQUENCE: 53

Glu Val Gln Leu Glu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Tyr Trp Val Cys Gln Ala Pro Gly Lys Gly Leu Lys Trp Val
        35                  40                  45

Ala Arg Ile Arg Ser Lys Val Asn Asn Tyr Ala Thr Tyr Tyr Ala Asp
50                  55                  60

Ser Val Lys Asp Arg Phe Thr Ile Ser Arg Asp Asp Ser Gln Asn Met
65                  70                  75                  80

Leu Phe Leu His Met Asn Asn Leu Lys Thr Glu Asp Thr Ala Ile Tyr
                85                  90                  95

Phe Cys Val Arg Asp Pro Met Asp Tyr Trp Gly Gln Gly Ile Ser Val
            100                 105                 110

Thr Val Ser Ser Gly Gly Gly Gly Ser Gly Gly Gly Gly Ser Gly Gly
            115                 120                 125

Gly Gly Ser Asp Ile Gln Met Thr Gln Ser Pro Ala Ser Leu Ser Ala
130                 135                 140

Ser Val Gly Glu Thr Val Thr Ile Thr Cys Arg Ala Ser Gly Asn Ile
145                 150                 155                 160

His Asn Tyr Leu Ala Trp Tyr Gln Gln Lys Gln Gly Lys Ser Pro Gln
                165                 170                 175

Leu Leu Val Tyr Asn Ala Lys Thr Leu Ala Asp Gly Val Pro Ser Arg
            180                 185                 190
```

Phe Ser Gly Ser Gly Ser Gly Thr Gln Tyr Ser Leu Lys Ile Asn Ser
              195                 200                 205

Leu Gln Pro Glu Asp Phe Gly Ser Tyr Tyr Cys Gln His Phe Trp Ser
        210                 215                 220

Thr Pro Trp Thr Phe Gly Gly Gly Thr Lys Leu Glu Ile Lys
225                 230                 235

<210> SEQ ID NO 54
<211> LENGTH: 243
<212> TYPE: PRT
<213> ORGANISM: Artificial Sequence
<220> FEATURE:
<223> OTHER INFORMATION: Synthetic Construct

<400> SEQUENCE: 54

Glu Val Gln Leu Glu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Tyr Trp Val Cys Gln Ala Pro Gly Lys Gly Leu Lys Trp Val
        35                  40                  45

Ala Arg Ile Arg Ser Lys Val Asn Asn Tyr Ala Thr Tyr Tyr Ala Asp
    50                  55                  60

Ser Val Lys Asp Arg Phe Thr Ile Ser Arg Asp Asp Ser Gln Asn Met
65                  70                  75                  80

Leu Phe Leu His Met Asn Asn Leu Lys Thr Glu Asp Thr Ala Ile Tyr
                85                  90                  95

Phe Cys Val Arg Asp Pro Met Asp Tyr Trp Gly Gln Gly Ile Ser Val
            100                 105                 110

Thr Val Ser Ser Gly Gly Gly Gly Ser Gly Gly Gly Ser Gly Gly
        115                 120                 125

Gly Gly Ser Gly Asn Ser Trp Ser His Ser Leu Arg Ser Leu Ser Val
    130                 135                 140

Thr Ile Gly Gln Pro Ala Ser Ile Ser Cys Lys Ser Ser Gln Ser Leu
145                 150                 155                 160

Leu Asp Gly Asn Gly Lys Thr Tyr Leu Asn Trp Leu Leu Gln Arg Pro
                165                 170                 175

Gly Gln Ser Pro Lys Arg Leu Leu Tyr Leu Val Ser Lys Leu Asp Ser
            180                 185                 190

Gly Val Pro Asp Arg Phe Thr Gly Ser Gly Ser Gly Thr Asp Phe Thr
        195                 200                 205

Leu Lys Ile Ser Arg Val Glu Ala Glu Asp Leu Gly Ile Tyr Tyr Cys
    210                 215                 220

Trp Gln Gly Thr His Phe Pro Arg Thr Phe Gly Gly Gly Thr Lys Leu
225                 230                 235                 240

Glu Ile Lys

<210> SEQ ID NO 55
<211> LENGTH: 243
<212> TYPE: PRT
<213> ORGANISM: Artificial Sequence
<220> FEATURE:
<223> OTHER INFORMATION: Synthetic Construct

<400> SEQUENCE: 55

Glu Val Gln Leu Glu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Tyr Trp Val Cys Gln Ala Pro Gly Lys Gly Leu Lys Trp Val
            35                  40                  45

Ala Arg Ile Arg Ser Lys Val Asn Asn Tyr Ala Thr Tyr Tyr Ala Asp
        50                  55                  60

Ser Val Lys Asp Arg Phe Thr Ile Ser Arg Asp Asp Ser Gln Asn Met
65                  70                  75                  80

Leu Phe Leu His Met Asn Asn Leu Lys Thr Glu Asp Thr Ala Ile Tyr
                85                  90                  95

Phe Cys Val Arg Asp Pro Met Asp Tyr Trp Gly Gln Gly Ile Ser Val
            100                 105                 110

Thr Val Ser Ser Gly Gly Gly Ser Gly Gly Gly Ser Gly Gly
        115                 120                 125

Gly Gly Ser Gly Asn Ser Trp Arg His Ser Pro Arg Ser Leu Ser Val
        130                 135                 140

Thr Ile Gly Gln Pro Ala Ser Ile Ser Cys Lys Ser Ser Gln Ser Leu
145                 150                 155                 160

Leu Asp Gly Asn Gly Lys Thr Tyr Leu Asn Trp Leu Leu Gln Arg Pro
                165                 170                 175

Gly Gln Ser Pro Lys Arg Leu Leu Tyr Leu Val Ser Lys Leu Asp Ser
            180                 185                 190

Gly Val Pro Asp Arg Phe Thr Gly Ser Gly Ser Gly Thr Asp Phe Thr
        195                 200                 205

Leu Lys Ile Ser Arg Val Glu Ala Glu Asp Leu Gly Ile Tyr Tyr Cys
210                 215                 220

Trp Gln Gly Thr His Phe Pro Arg Thr Phe Gly Gly Gly Thr Lys Leu
225                 230                 235                 240

Glu Ile Lys

<210> SEQ ID NO 56
<211> LENGTH: 243
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Glu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Tyr Trp Val Cys Gln Ala Pro Gly Lys Gly Leu Lys Trp Val
            35                  40                  45

Ala Arg Ile Arg Ser Lys Val Asn Asn Tyr Ala Thr Tyr Tyr Ala Asp
        50                  55                  60

Ser Val Lys Asp Arg Phe Thr Ile Ser Arg Asp Asp Ser Gln Asn Met
65                  70                  75                  80

Leu Phe Leu His Met Asn Asn Leu Lys Thr Glu Asp Thr Ala Ile Tyr
                85                  90                  95

Phe Cys Val Arg Asp Pro Met Asp Tyr Trp Gly Gln Gly Ile Ser Val
            100                 105                 110

Thr Val Ser Ser Gly Gly Gly Ser Gly Gly Gly Ser Gly Gly
        115                 120                 125

Gly Gly Ser Asp Ile Val Met Thr Gln Ala Ala Pro Ser Val Pro Val

```
Thr Pro Gly Glu Ser Val Ser Ile Ser Cys Gly Ser Ser Lys Ser Leu
145                 150                 155                 160

Leu His Ser Asn Gly Asn Thr Tyr Leu Tyr Trp Phe Leu Gln Arg Pro
                165                 170                 175

Gly Gln Ser Pro Gln Leu Leu Ile Tyr Arg Val Ser Asn Leu Ala Ser
            180                 185                 190

Gly Val Pro Asp Arg Phe Ser Gly Ser Gly Ser Gly Thr Ala Phe Thr
        195                 200                 205

Leu Arg Ile Ser Arg Val Glu Ala Glu Asp Val Gly Val Tyr Tyr Cys
    210                 215                 220

Met Gln His Leu Glu Tyr Pro Tyr Thr Phe Gly Gly Gly Thr Arg Leu
225                 230                 235                 240

Glu Ile Lys

<210> SEQ ID NO 57
<211> LENGTH: 244
<212> TYPE: PRT
<213> ORGANISM: Artificial Sequence
<220> FEATURE:
<223> OTHER INFORMATION: Synthetic Construct

<400> SEQUENCE: 57

Glu Val Gln Leu Glu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Tyr Trp Val Cys Gln Ala Pro Gly Lys Gly Leu Lys Trp Val
            35                  40                  45

Ala Arg Ile Arg Ser Lys Val Asn Asn Tyr Ala Thr Tyr Tyr Ala Asp
        50                  55                  60

Ser Val Lys Asp Arg Phe Thr Ile Ser Arg Asp Asp Ser Gln Asn Met
65                  70                  75                  80

Leu Phe Leu His Met Asn Asn Leu Lys Thr Glu Asp Thr Ala Ile Tyr
                85                  90                  95

Phe Cys Val Arg Asp Pro Met Asp Tyr Trp Gly Gln Gly Ile Ser Val
            100                 105                 110

Thr Val Ser Ser Gly Gly Gly Gly Ser Gly Gly Gly Gly Ser Gly Gly
        115                 120                 125

Gly Gly Ser Asp Thr Val Met Ser Gln Ser Pro Ser Ser Leu Ala Val
    130                 135                 140

Ser Val Gly Glu Lys Ile Thr Met Ser Cys Lys Ser Ser Gln Ser Leu
145                 150                 155                 160

Leu Cys Arg Ser Asn Gln Lys Asn Tyr Leu Ala Trp Tyr Gln Gln Lys
                165                 170                 175

Pro Gly Gln Ser Pro Lys Gln Leu Ile Tyr Trp Ala Ser Thr Arg Glu
            180                 185                 190

Ser Gly Val Pro Asp Arg Phe Thr Gly Ser Gly Ser Gly Thr Asp Phe
        195                 200                 205

Thr Leu Thr Ile Ser Ser Val Lys Ala Glu Asp Leu Ala Val Tyr Tyr
    210                 215                 220

Cys Gln Gln Tyr Tyr Ser Tyr Pro Leu Thr Phe Gly Ala Gly Thr Lys
225                 230                 235                 240

Leu Glu Leu Lys
```

```
<210> SEQ ID NO 58
<211> LENGTH: 244
<212> TYPE: PRT
<213> ORGANISM: Artificial Sequence
<220> FEATURE:
<223> OTHER INFORMATION: Synthetic Construct

<400> SEQUENCE: 58

Glu Val Gln Leu Glu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Tyr Trp Val Cys Gln Ala Pro Gly Lys Gly Leu Lys Trp Val
        35                  40                  45

Ala Arg Ile Arg Ser Lys Val Asn Asn Tyr Ala Thr Tyr Tyr Ala Asp
    50                  55                  60

Ser Val Lys Asp Arg Phe Thr Ile Ser Arg Asp Asp Ser Gln Asn Met
65                  70                  75                  80

Leu Phe Leu His Met Asn Asn Leu Lys Thr Glu Asp Thr Ala Ile Tyr
                85                  90                  95

Phe Cys Val Arg Asp Pro Met Asp Tyr Trp Gly Gln Gly Ile Ser Val
            100                 105                 110

Thr Val Ser Ser Gly Gly Gly Gly Ser Gly Gly Gly Ser Gly Gly
        115                 120                 125

Gly Gly Ser Asp Thr Val Met Ser Gln Ser Pro Ser Ser Leu Ala Val
    130                 135                 140

Ser Val Gly Glu Lys Ile Thr Met Ser Cys Lys Ser Ser Gln Ser Leu
145                 150                 155                 160

Leu Tyr Arg Ser Asn Gln Lys Asn Tyr Leu Ala Trp Tyr Gln Gln Lys
                165                 170                 175

Pro Gly Gln Ser Pro Lys Gln Leu Ile Tyr Trp Ala Ser Thr Arg Glu
            180                 185                 190

Ser Gly Val Pro Asp Arg Phe Thr Gly Ser Gly Ser Gly Thr Asp Phe
        195                 200                 205

Thr Leu Thr Ile Ser Ser Val Lys Ala Glu Asp Leu Ala Val Tyr Tyr
    210                 215                 220

Cys Gln Gln Tyr Tyr Ser Tyr Pro Leu Thr Phe Gly Ala Gly Thr Lys
225                 230                 235                 240

Leu Glu Leu Lys

<210> SEQ ID NO 59
<211> LENGTH: 238
<212> TYPE: PRT
<213> ORGANISM: Artificial Sequence
<220> FEATURE:
<223> OTHER INFORMATION: Synthetic Construct

<400> SEQUENCE: 59

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Tyr Trp Val Cys Gln Ala Pro Gly Lys Gly Leu Lys Trp Val
        35                  40                  45

Ala Arg Ile Arg Ser Lys Val Asn Asn Tyr Ala Thr Tyr Tyr Ala Asp
    50                  55                  60
```

```
Ser Val Lys Asp Arg Phe Thr Ile Ser Arg Asp Asp Ser Gln Asn Met
 65                  70                  75                  80

Leu Phe Leu His Met Asn Asn Leu Lys Thr Glu Asp Thr Ala Ile Tyr
                 85                  90                  95

Phe Cys Val Arg Asp Pro Met Asp Tyr Trp Gly Gln Gly Ile Ser Val
            100                 105                 110

Thr Val Ser Ser Gly Gly Gly Gly Ser Gly Gly Gly Ser Gly Gly
        115                 120                 125

Gly Gly Ser Asp Ile Gln Met Thr Gln Ser Pro Ala Ser Leu Ser Ala
    130                 135                 140

Ser Val Gly Glu Thr Val Thr Ile Thr Cys Arg Ala Ser Gly Asn Ile
145                 150                 155                 160

His Asn Tyr Leu Ala Trp Tyr Gln Gln Lys Gln Gly Lys Ser Pro Gln
                165                 170                 175

Leu Leu Val Tyr Asn Ala Lys Thr Leu Ala Asp Gly Val Pro Ser Arg
                180                 185                 190

Phe Ser Gly Ser Gly Ser Gly Thr Gln Tyr Ser Leu Lys Ile Asn Ser
            195                 200                 205

Leu Gln Pro Glu Asp Phe Gly Ser Tyr Tyr Cys Gln His Phe Trp Ser
    210                 215                 220

Thr Pro Trp Thr Phe Gly Gly Gly Thr Lys Leu Glu Ile Lys
225                 230                 235

<210> SEQ ID NO 60
<211> LENGTH: 243
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Tyr Trp Val Cys Gln Ala Pro Gly Lys Gly Leu Lys Trp Val
        35                  40                  45

Ala Arg Ile Arg Ser Lys Val Asn Asn Tyr Ala Thr Tyr Tyr Ala Asp
 50                  55                  60

Ser Val Lys Asp Arg Phe Thr Ile Ser Arg Asp Asp Ser Gln Asn Met
 65                  70                  75                  80

Leu Phe Leu His Met Asn Asn Leu Lys Thr Glu Asp Thr Ala Ile Tyr
                 85                  90                  95

Phe Cys Val Arg Asp Pro Met Asp Tyr Trp Gly Gln Gly Ile Ser Val
            100                 105                 110

Thr Val Ser Ser Gly Gly Gly Gly Ser Gly Gly Gly Ser Gly Gly
        115                 120                 125

Gly Gly Ser Gly Asn Ser Trp Ser His Ser Leu Arg Ser Leu Ser Val
    130                 135                 140

Thr Ile Gly Gln Pro Ala Ser Ile Ser Cys Lys Ser Ser Gln Ser Leu
145                 150                 155                 160

Leu Asp Gly Asn Gly Lys Thr Tyr Leu Asn Trp Leu Leu Gln Arg Pro
                165                 170                 175

Gly Gln Ser Pro Lys Arg Leu Leu Tyr Leu Val Ser Lys Leu Asp Ser
                180                 185                 190
```

```
Gly Val Pro Asp Arg Phe Thr Gly Ser Gly Ser Gly Thr Asp Phe Thr
            195                 200                 205

Leu Lys Ile Ser Arg Val Glu Ala Glu Asp Leu Gly Ile Tyr Tyr Cys
    210                 215                 220

Trp Gln Gly Thr His Phe Pro Arg Thr Phe Gly Gly Gly Thr Lys Leu
225                 230                 235                 240

Glu Ile Lys

<210> SEQ ID NO 61
<211> LENGTH: 243
<212> TYPE: PRT
<213> ORGANISM: Artificial Sequence
<220> FEATURE:
<223> OTHER INFORMATION: Synthetic Construct

<400> SEQUENCE: 61

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Tyr Trp Val Cys Gln Ala Pro Gly Lys Gly Leu Lys Trp Val
        35                  40                  45

Ala Arg Ile Arg Ser Lys Val Asn Asn Tyr Ala Thr Tyr Tyr Ala Asp
    50                  55                  60

Ser Val Lys Asp Arg Phe Thr Ile Ser Arg Asp Ser Gln Asn Met
65                  70                  75                  80

Leu Phe Leu His Met Asn Asn Leu Lys Thr Glu Asp Thr Ala Ile Tyr
                85                  90                  95

Phe Cys Val Arg Asp Pro Met Asp Tyr Trp Gly Gln Gly Ile Ser Val
            100                 105                 110

Thr Val Ser Ser Gly Gly Gly Ser Gly Gly Gly Ser Gly Gly
        115                 120                 125

Gly Gly Ser Gly Asn Ser Trp Arg His Ser Pro Arg Ser Leu Ser Val
    130                 135                 140

Thr Ile Gly Gln Pro Ala Ser Ile Ser Cys Lys Ser Ser Gln Ser Leu
145                 150                 155                 160

Leu Asp Gly Asn Gly Lys Thr Tyr Leu Asn Trp Leu Gln Arg Pro
                165                 170                 175

Gly Gln Ser Pro Lys Arg Leu Leu Tyr Leu Val Ser Lys Leu Asp Ser
            180                 185                 190

Gly Val Pro Asp Arg Phe Thr Gly Ser Gly Ser Gly Thr Asp Phe Thr
        195                 200                 205

Leu Lys Ile Ser Arg Val Glu Ala Glu Asp Leu Gly Ile Tyr Tyr Cys
    210                 215                 220

Trp Gln Gly Thr His Phe Pro Arg Thr Phe Gly Gly Gly Thr Lys Leu
225                 230                 235                 240

Glu Ile Lys

<210> SEQ ID NO 62
<211> LENGTH: 243
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Glu Ser Gly Gly Gly Leu Val Gln Pro Lys Gly
```

```
                1               5                   10                  15
            Ser Leu Lys Leu Ser Cys Ala Ala Ser Gly Phe Thr Phe Asn Thr Tyr
                            20                  25                  30

Ala Met Tyr Trp Val Cys Gln Ala Pro Gly Lys Gly Leu Lys Trp Val
                            35                  40                  45

Ala Arg Ile Arg Ser Lys Val Asn Asn Tyr Ala Thr Tyr Tyr Ala Asp
                            50                  55                  60

Ser Val Lys Asp Arg Phe Thr Ile Ser Arg Asp Asp Ser Gln Asn Met
             65                  70                  75                  80

Leu Phe Leu His Met Asn Asn Leu Lys Thr Glu Asp Thr Ala Ile Tyr
                            85                  90                  95

Phe Cys Val Arg Asp Pro Met Asp Tyr Trp Gly Gln Gly Ile Ser Val
                            100                 105                 110

Thr Val Ser Ser Gly Gly Gly Gly Ser Gly Gly Gly Ser Gly Gly
                            115                 120                 125

Gly Gly Ser Asp Ile Val Met Thr Gln Ala Ala Pro Ser Val Pro Val
                            130                 135                 140

Thr Pro Gly Glu Ser Val Ser Ile Ser Cys Gly Ser Ser Lys Ser Leu
             145                 150                 155                 160

Leu His Ser Asn Gly Asn Thr Tyr Leu Tyr Trp Phe Leu Gln Arg Pro
                            165                 170                 175

Gly Gln Ser Pro Gln Leu Leu Ile Tyr Arg Val Ser Asn Leu Ala Ser
                            180                 185                 190

Gly Val Pro Asp Arg Phe Ser Gly Ser Gly Ser Gly Thr Ala Phe Thr
                            195                 200                 205

Leu Arg Ile Ser Arg Val Glu Ala Glu Asp Val Gly Val Tyr Tyr Cys
                            210                 215                 220

Met Gln His Leu Glu Tyr Pro Tyr Thr Phe Gly Gly Gly Thr Arg Leu
             225                 230                 235                 240

Glu Ile Lys

<210> SEQ ID NO 63
            <211> LENGTH: 244
            <212> TYPE: PRT
            <213> ORGANISM: Artificial Sequence
            <220> FEATURE:
            <223> OTHER INFORMATION: Synthetic Construct

<400> SEQUENCE: 63

Glu Val Gln Leu Val Glu Ser Gly Gly Gly Leu Val Gln Pro Lys Gly
             1                   5                   10                  15

Ser Leu Lys Leu Ser Cys Ala Ala Ser Gly Phe Thr Phe Asn Thr Tyr
                            20                  25                  30

Ala Met Tyr Trp Val Cys Gln Ala Pro Gly Lys Gly Leu Lys Trp Val
                            35                  40                  45

Ala Arg Ile Arg Ser Lys Val Asn Asn Tyr Ala Thr Tyr Tyr Ala Asp
                            50                  55                  60

Ser Val Lys Asp Arg Phe Thr Ile Ser Arg Asp Asp Ser Gln Asn Met
             65                  70                  75                  80

Leu Phe Leu His Met Asn Asn Leu Lys Thr Glu Asp Thr Ala Ile Tyr
                            85                  90                  95

Phe Cys Val Arg Asp Pro Met Asp Tyr Trp Gly Gln Gly Ile Ser Val
                            100                 105                 110

Thr Val Ser Ser Gly Gly Gly Gly Ser Gly Gly Gly Ser Gly Gly
                            115                 120                 125
```

```
Gly Gly Ser Asp Thr Val Met Ser Gln Ser Pro Ser Ser Leu Ala Val
            130                 135                 140

Ser Val Gly Glu Lys Ile Thr Met Ser Cys Lys Ser Ser Gln Ser Leu
145                 150                 155                 160

Leu Cys Arg Ser Asn Gln Lys Asn Tyr Leu Ala Trp Tyr Gln Gln Lys
                165                 170                 175

Pro Gly Gln Ser Pro Lys Gln Leu Ile Tyr Trp Ala Ser Thr Arg Glu
                180                 185                 190

Ser Gly Val Pro Asp Arg Phe Thr Gly Ser Gly Ser Gly Thr Asp Phe
                195                 200                 205

Thr Leu Thr Ile Ser Ser Val Lys Ala Glu Asp Leu Ala Val Tyr Tyr
            210                 215                 220

Cys Gln Gln Tyr Tyr Ser Tyr Pro Leu Thr Phe Gly Ala Gly Thr Lys
225                 230                 235                 240

Leu Glu Leu Lys
```

<210> SEQ ID NO 64
<211> LENGTH: 244
<212> TYPE: PRT
<213> ORGANISM: Artificial Sequence
<220> FEATURE:
<223> OTHER INFORMATION: Synthetic Construct

<400> SEQUENCE: 64

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Tyr Trp Val Cys Gln Ala Pro Gly Lys Gly Leu Lys Trp Val
            35                  40                  45

Ala Arg Ile Arg Ser Lys Val Asn Asn Tyr Ala Thr Tyr Tyr Ala Asp
        50                  55                  60

Ser Val Lys Asp Arg Phe Thr Ile Ser Arg Asp Asp Ser Gln Asn Met
65                  70                  75                  80

Leu Phe Leu His Met Asn Asn Leu Lys Thr Glu Asp Thr Ala Ile Tyr
                85                  90                  95

Phe Cys Val Arg Asp Pro Met Asp Tyr Trp Gly Gln Gly Ile Ser Val
            100                 105                 110

Thr Val Ser Ser Gly Gly Gly Gly Ser Gly Gly Gly Gly Ser Gly Gly
        115                 120                 125

Gly Gly Ser Asp Thr Val Met Ser Gln Ser Pro Ser Ser Leu Ala Val
            130                 135                 140

Ser Val Gly Glu Lys Ile Thr Met Ser Cys Lys Ser Ser Gln Ser Leu
145                 150                 155                 160

Leu Tyr Arg Ser Asn Gln Lys Asn Tyr Leu Ala Trp Tyr Gln Gln Lys
                165                 170                 175

Pro Gly Gln Ser Pro Lys Gln Leu Ile Tyr Trp Ala Ser Thr Arg Glu
                180                 185                 190

Ser Gly Val Pro Asp Arg Phe Thr Gly Ser Gly Ser Gly Thr Asp Phe
                195                 200                 205

Thr Leu Thr Ile Ser Ser Val Lys Ala Glu Asp Leu Ala Val Tyr Tyr
            210                 215                 220

Cys Gln Gln Tyr Tyr Ser Tyr Pro Leu Thr Phe Gly Ala Gly Thr Lys
225                 230                 235                 240
```

Leu Glu Leu Lys

<210> SEQ ID NO 65
<211> LENGTH: 243
<212> TYPE: PRT
<213> ORGANISM: Artificial Sequence
<220> FEATURE:
<223> OTHER INFORMATION: Synthetic Construct

<400> SEQUENCE: 65

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Trp Val Lys Gln Arg Pro Gly Gln Gly Leu Glu Trp Ile
        35                  40                  45

Gly Thr Ile Tyr Pro Gly Asp Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Gly Gly Gly Gly Ser Gly Gly
            115                 120                 125

Gly Gly Ser Gly Gly Gly Ser Asp Ile Gln Met Thr Gln Ser Pro
    130                 135                 140

Ala Ser Leu Ser Ala Ser Val Gly Glu Thr Val Thr Ile Thr Cys Arg
145                 150                 155                 160

Ala Ser Gly Asn Ile His Asn Tyr Leu Ala Trp Tyr Gln Gln Lys Gln
                165                 170                 175

Gly Lys Ser Pro Gln Leu Leu Val Tyr Asn Ala Lys Thr Leu Ala Asp
            180                 185                 190

Gly Val Pro Ser Arg Phe Ser Gly Ser Gly Ser Gly Thr Gln Tyr Ser
        195                 200                 205

Leu Lys Ile Asn Ser Leu Gln Pro Glu Asp Phe Gly Ser Tyr Tyr Cys
    210                 215                 220

Gln His Phe Trp Ser Thr Pro Trp Thr Phe Gly Gly Gly Thr Lys Leu
225                 230                 235                 240

Glu Ile Lys

<210> SEQ ID NO 66
<211> LENGTH: 248
<212> TYPE: PRT
<213> ORGANISM: Artificial Sequence
<220> FEATURE:
<223> OTHER INFORMATION: Synthetic Construct

<400> SEQUENCE: 66

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Trp Val Lys Gln Arg Pro Gly Gln Gly Leu Glu Trp Ile
        35                  40                  45

Gly Thr Ile Tyr Pro Gly Asp Asp Asp Thr Arg Tyr Thr Gln Lys Phe

```
            50                  55                  60
Lys Gly Arg Ala Thr Leu Thr Ala Asp Lys Ser Ser Thr Thr Ala Tyr
 65                  70                  75                  80

Met Gln Leu Ser Asn Leu Ser Ser Glu Asp Ser Ala Val Tyr Tyr Cys
                 85                  90                  95

Ala Arg Ser Gly Tyr Glu Arg Gly Pro Tyr Tyr Phe Asp Ser Trp Gly
                100                 105                 110

Gln Gly Thr Thr Leu Thr Val Ser Ser Gly Gly Gly Ser Gly Gly
                115                 120                 125

Gly Gly Ser Gly Gly Gly Ser Gly Asn Ser Trp Ser His Ser Leu
130                 135                 140

Arg Ser Leu Ser Val Thr Ile Gly Gln Pro Ala Ser Ile Ser Cys Lys
145                 150                 155                 160

Ser Ser Gln Ser Leu Leu Asp Gly Asn Gly Lys Thr Tyr Leu Asn Trp
                165                 170                 175

Leu Leu Gln Arg Pro Gly Gln Ser Pro Lys Arg Leu Leu Tyr Leu Val
                180                 185                 190

Ser Lys Leu Asp Ser Gly Val Pro Asp Arg Phe Thr Gly Ser Gly Ser
                195                 200                 205

Gly Thr Asp Phe Thr Leu Lys Ile Ser Arg Val Glu Ala Glu Asp Leu
                210                 215                 220

Gly Ile Tyr Tyr Cys Trp Gln Gly Thr His Phe Pro Arg Thr Phe Gly
225                 230                 235                 240

Gly Gly Thr Lys Leu Glu Ile Lys
                245

<210> SEQ ID NO 67
<211> LENGTH: 248
<212> TYPE: PRT
<213> ORGANISM: Artificial Sequence
<220> FEATURE:
<223> OTHER INFORMATION: Synthetic Construct

<400> SEQUENCE: 67

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Thr Phe
                20                  25                  30

Trp Met Gln Trp Val Lys Gln Arg Pro Gly Gln Gly Leu Glu Trp Ile
             35                  40                  45

Gly Thr Ile Tyr Pro Gly Asp Asp Asp Thr Arg Tyr Thr Gln Lys Phe
 50                  55                  60

Lys Gly Arg Ala Thr Leu Thr Ala Asp Lys Ser Ser Thr Thr Ala Tyr
 65                  70                  75                  80

Met Gln Leu Ser Asn Leu Ser Ser Glu Asp Ser Ala Val Tyr Tyr Cys
                 85                  90                  95

Ala Arg Ser Gly Tyr Glu Arg Gly Pro Tyr Tyr Phe Asp Ser Trp Gly
                100                 105                 110

Gln Gly Thr Thr Leu Thr Val Ser Ser Gly Gly Gly Ser Gly Gly
                115                 120                 125

Gly Gly Ser Gly Gly Gly Ser Gly Asn Ser Trp Arg His Ser Pro
130                 135                 140

Arg Ser Leu Ser Val Thr Ile Gly Gln Pro Ala Ser Ile Ser Cys Lys
145                 150                 155                 160

Ser Ser Gln Ser Leu Leu Asp Gly Asn Gly Lys Thr Tyr Leu Asn Trp
```

165                 170                 175

Leu Leu Gln Arg Pro Gly Gln Ser Pro Lys Arg Leu Leu Tyr Leu Val
            180                 185                 190

Ser Lys Leu Asp Ser Gly Val Pro Asp Arg Phe Thr Gly Ser Gly Ser
            195                 200                 205

Gly Thr Asp Phe Thr Leu Lys Ile Ser Arg Val Glu Ala Glu Asp Leu
            210                 215                 220

Gly Ile Tyr Tyr Cys Trp Gln Gly Thr His Phe Pro Arg Thr Phe Gly
225                 230                 235                 240

Gly Gly Thr Lys Leu Glu Ile Lys
                245

<210> SEQ ID NO 68
<211> LENGTH: 248
<212> TYPE: PRT
<213> ORGANISM: Artificial Sequence
<220> FEATURE:
<223> OTHER INFORMATION: Synthetic Construct

<400> SEQUENCE: 68

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Trp Val Lys Gln Arg Pro Gly Gln Gly Leu Glu Trp Ile
        35                  40                  45

Gly Thr Ile Tyr Pro Gly Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser Gly Gly Gly Ser Gly Gly
        115                 120                 125

Gly Gly Ser Gly Gly Gly Ser Asp Ile Val Met Thr Gln Ala Ala
    130                 135                 140

Pro Ser Val Pro Val Thr Pro Gly Glu Ser Val Ser Ile Ser Cys Gly
145                 150                 155                 160

Ser Ser Lys Ser Leu Leu His Ser Asn Gly Asn Thr Tyr Leu Tyr Trp
                165                 170                 175

Phe Leu Gln Arg Pro Gly Gln Ser Pro Gln Leu Leu Ile Tyr Arg Val
            180                 185                 190

Ser Asn Leu Ala Ser Gly Val Pro Asp Arg Phe Ser Gly Ser Gly Ser
            195                 200                 205

Gly Thr Ala Phe Thr Leu Arg Ile Ser Arg Val Glu Ala Glu Asp Val
        210                 215                 220

Gly Val Tyr Tyr Cys Met Gln His Leu Glu Tyr Pro Tyr Thr Phe Gly
225                 230                 235                 240

Gly Gly Thr Arg Leu Glu Ile Lys
                245

<210> SEQ ID NO 69
<211> LENGTH: 249
<212> TYPE: PRT

<213> ORGANISM: Artificial Sequence
<220> FEATURE:
<223> OTHER INFORMATION: Synthetic Construct

<400> SEQUENCE: 69

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Trp Val Lys Gln Arg Pro Gly Gln Gly Leu Glu Trp Ile
        35                  40                  45

Gly Thr Ile Tyr Pro Gly Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Gly Gly Gly Gly Ser Gly Gly
        115                 120                 125

Gly Gly Ser Gly Gly Gly Ser Asp Thr Val Met Ser Gln Ser Pro
    130                 135                 140

Ser Ser Leu Ala Val Ser Val Gly Glu Lys Ile Thr Met Ser Cys Lys
145                 150                 155                 160

Ser Ser Gln Ser Leu Leu Cys Arg Ser Asn Gln Lys Asn Tyr Leu Ala
                165                 170                 175

Trp Tyr Gln Gln Lys Pro Gly Gln Ser Pro Lys Gln Leu Ile Tyr Trp
            180                 185                 190

Ala Ser Thr Arg Glu Ser Gly Val Pro Asp Arg Phe Thr Gly Ser Gly
        195                 200                 205

Ser Gly Thr Asp Phe Thr Leu Thr Ile Ser Ser Val Lys Ala Glu Asp
    210                 215                 220

Leu Ala Val Tyr Tyr Cys Gln Gln Tyr Tyr Ser Tyr Pro Leu Thr Phe
225                 230                 235                 240

Gly Ala Gly Thr Lys Leu Glu Leu Lys
                245
```

<210> SEQ ID NO 70
<211> LENGTH: 249
<212> TYPE: PRT
<213> ORGANISM: Artificial Sequence
<220> FEATURE:
<223> OTHER INFORMATION: Synthetic Construct

<400> SEQUENCE: 70

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Trp Val Lys Gln Arg Pro Gly Gln Gly Leu Glu Trp Ile
        35                  40                  45

Gly Thr Ile Tyr Pro Gly Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80
```

```
Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser Gly Gly Gly Ser Gly Gly
        115                 120                 125

Gly Gly Ser Gly Gly Gly Ser Asp Thr Val Met Ser Gln Ser Pro
    130                 135                 140

Ser Ser Leu Ala Val Ser Val Gly Glu Lys Ile Thr Met Ser Cys Lys
145             150                 155                 160

Ser Ser Gln Ser Leu Leu Tyr Arg Ser Asn Gln Lys Asn Tyr Leu Ala
            165                 170                 175

Trp Tyr Gln Gln Lys Pro Gly Gln Ser Pro Lys Gln Leu Ile Tyr Trp
            180                 185                 190

Ala Ser Thr Arg Glu Ser Gly Val Pro Asp Arg Phe Thr Gly Ser Gly
            195                 200                 205

Ser Gly Thr Asp Phe Thr Leu Thr Ile Ser Ser Val Lys Ala Glu Asp
        210                 215                 220

Leu Ala Val Tyr Tyr Cys Gln Gln Tyr Tyr Ser Tyr Pro Leu Thr Phe
225                 230                 235                 240

Gly Ala Gly Thr Lys Leu Glu Leu Lys
                245

<210> SEQ ID NO 71
<211> LENGTH: 243
<212> TYPE: PRT
<213> ORGANISM: Artificial Sequence
<220> FEATURE:
<223> OTHER INFORMATION: Synthetic Construct

<400> SEQUENCE: 71

Asp Val Lys Leu Gln Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Arg Val Lys Gln Arg Pro Gly Gln Gly Leu Glu Trp Ile
        35                  40                  45

Gly Thr Ile Tyr Pro Gly Asp Asp Asp Thr Arg Tyr Thr Gln Lys Phe
    50                  55                  60

Lys Gly Arg Ala Thr Leu Thr Ala Asp Lys Ser Ser Thr Thr Ala Tyr
65              70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ala Ser Leu Ser Ala Ser Val Gly Glu Thr Val Thr Ile Thr Cys Arg
145             150                 155                 160

Ala Ser Gly Asn Ile His Asn Tyr Leu Ala Trp Tyr Gln Gln Lys Gln
            165                 170                 175

Gly Lys Ser Pro Gln Leu Leu Val Tyr Asn Ala Lys Thr Leu Ala Asp
            180                 185                 190
```

```
Gly Val Pro Ser Arg Phe Ser Gly Ser Gly Ser Gly Thr Gln Tyr Ser
            195                 200                 205

Leu Lys Ile Asn Ser Leu Gln Pro Glu Asp Phe Gly Ser Tyr Tyr Cys
        210                 215                 220

Gln His Phe Trp Ser Thr Pro Trp Thr Phe Gly Gly Gly Thr Lys Leu
225                 230                 235                 240

Glu Ile Lys

<210> SEQ ID NO 72
<211> LENGTH: 248
<212> TYPE: PRT
<213> ORGANISM: Artificial Sequence
<220> FEATURE:
<223> OTHER INFORMATION: Synthetic Construct

<400> SEQUENCE: 72

Asp Val Lys Leu Gln Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Arg Val Lys Gln Arg Pro Gly Gln Gly Leu Glu Trp Ile
        35                  40                  45

Gly Thr Ile Tyr Pro Gly Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser Gly Gly Gly Ser Gly Gly
            115                 120                 125

Gly Gly Ser Gly Gly Gly Ser Gly Asn Ser Trp Ser His Ser Leu
        130                 135                 140

Arg Ser Leu Ser Val Thr Ile Gly Gln Pro Ala Ser Ile Ser Cys Lys
145                 150                 155                 160

Ser Ser Gln Ser Leu Leu Asp Gly Asn Gly Lys Thr Tyr Leu Asn Trp
                165                 170                 175

Leu Leu Gln Arg Pro Gly Gln Ser Pro Lys Arg Leu Leu Tyr Leu Val
            180                 185                 190

Ser Lys Leu Asp Ser Gly Val Pro Asp Arg Phe Thr Gly Ser Gly Ser
        195                 200                 205

Gly Thr Asp Phe Thr Leu Lys Ile Ser Arg Val Glu Ala Glu Asp Leu
    210                 215                 220

Gly Ile Tyr Tyr Cys Trp Gln Gly Thr His Phe Pro Arg Thr Phe Gly
225                 230                 235                 240

Gly Gly Thr Lys Leu Glu Ile Lys
                245

<210> SEQ ID NO 73
<211> LENGTH: 248
<212> TYPE: PRT
<213> ORGANISM: Artificial Sequence
<220> FEATURE:
<223> OTHER INFORMATION: Synthetic Construct

<400> SEQUENCE: 73
```

Asp Val Lys Leu Gln Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Arg Val Lys Gln Arg Pro Gly Gln Gly Leu Glu Trp Ile
        35                  40                  45

Gly Thr Ile Tyr Pro Gly Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser Gly Gly Gly Ser Gly Gly
            115                 120                 125

Gly Gly Ser Gly Gly Gly Ser Gly Asn Ser Trp Arg His Ser Pro
            130                 135                 140

Arg Ser Leu Ser Val Thr Ile Gly Gln Pro Ala Ser Ile Ser Cys Lys
145                 150                 155                 160

Ser Ser Gln Ser Leu Leu Asp Gly Asn Gly Lys Thr Tyr Leu Asn Trp
                165                 170                 175

Leu Leu Gln Arg Pro Gly Gln Ser Pro Lys Arg Leu Leu Tyr Leu Val
            180                 185                 190

Ser Lys Leu Asp Ser Gly Val Pro Asp Arg Phe Thr Gly Ser Gly Ser
            195                 200                 205

Gly Thr Asp Phe Thr Leu Lys Ile Ser Arg Val Glu Ala Glu Asp Leu
210                 215                 220

Gly Ile Tyr Tyr Cys Trp Gln Gly Thr His Phe Pro Arg Thr Phe Gly
225                 230                 235                 240

Gly Gly Thr Lys Leu Glu Ile Lys
            245

<210> SEQ ID NO 74
<211> LENGTH: 248
<212> TYPE: PRT
<213> ORGANISM: Artificial Sequence
<220> FEATURE:
<223> OTHER INFORMATION: Synthetic Construct

<400> SEQUENCE: 74

Asp Val Lys Leu Gln Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Arg Val Lys Gln Arg Pro Gly Gln Gly Leu Glu Trp Ile
        35                  40                  45

Gly Thr Ile Tyr Pro Gly Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser Gly Gly Ser Gly Gly
            115                 120                 125

Gly Gly Ser Gly Gly Gly Ser Asp Ile Val Met Thr Gln Ala Ala
        130                 135                 140

Pro Ser Val Pro Val Thr Pro Gly Glu Ser Val Ser Ile Ser Cys Gly
145                 150                 155                 160

Ser Ser Lys Ser Leu Leu His Ser Asn Gly Asn Thr Tyr Leu Tyr Trp
                165                 170                 175

Phe Leu Gln Arg Pro Gly Gln Ser Pro Gln Leu Leu Ile Tyr Arg Val
            180                 185                 190

Ser Asn Leu Ala Ser Gly Val Pro Asp Arg Phe Ser Gly Ser Gly Ser
        195                 200                 205

Gly Thr Ala Phe Thr Leu Arg Ile Ser Arg Val Glu Ala Glu Asp Val
    210                 215                 220

Gly Val Tyr Tyr Cys Met Gln His Leu Glu Tyr Pro Tyr Thr Phe Gly
225                 230                 235                 240

Gly Gly Thr Arg Leu Glu Ile Lys
                245

<210> SEQ ID NO 75
<211> LENGTH: 248
<212> TYPE: PRT
<213> ORGANISM: Artificial Sequence
<220> FEATURE:
<223> OTHER INFORMATION: Synthetic Construct

<400> SEQUENCE: 75

Asp Val Lys Leu Gln Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Arg Val Lys Gln Arg Pro Gly Gln Gly Leu Glu Trp Ile
        35                  40                  45

Gly Thr Ile Tyr Pro Gly Asp Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser Gly Gly Ser Gly Gly
            115                 120                 125

Gly Gly Ser Gly Gly Gly Ser Asp Ile Val Met Thr Gln Ala Ala
        130                 135                 140

Pro Ser Val Pro Val Thr Pro Gly Glu Ser Val Ser Ile Ser Cys Gly
145                 150                 155                 160

Ser Ser Lys Ser Leu Leu His Ser Asn Gly Asn Thr Tyr Leu Tyr Trp
                165                 170                 175

Phe Leu Gln Arg Pro Gly Gln Ser Pro Gln Leu Leu Ile Tyr Arg Val
            180                 185                 190

Ser Asn Leu Ala Ser Gly Val Pro Asp Arg Phe Ser Gly Ser Gly Ser
        195                 200                 205

Gly Thr Ala Phe Thr Leu Arg Ile Ser Arg Val Glu Ala Glu Asp Val
    210                 215                 220

Gly Val Tyr Tyr Cys Met Gln His Leu Glu Pro Tyr Thr Phe Gly
225                 230                 235                 240

Gly Gly Thr Arg Leu Glu Ile Lys
                245

<210> SEQ ID NO 76
<211> LENGTH: 249
<212> TYPE: PRT
<213> ORGANISM: Artificial Sequence
<220> FEATURE:
<223> OTHER INFORMATION: Synthetic Construct

<400> SEQUENCE: 76

Asp Val Lys Leu Gln Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Arg Val Lys Gln Arg Pro Gly Gln Gly Leu Glu Trp Ile
        35                  40                  45

Gly Thr Ile Tyr Pro Gly Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Gly Gly Gly Ser Gly Gly
        115                 120                 125

Gly Gly Ser Gly Gly Gly Ser Asp Thr Val Met Ser Gln Ser Pro
    130                 135                 140

Ser Ser Leu Ala Val Ser Val Gly Glu Lys Ile Thr Met Ser Cys Lys
145                 150                 155                 160

Ser Ser Gln Ser Leu Leu Cys Arg Ser Asn Gln Lys Asn Tyr Leu Ala
                165                 170                 175

Trp Tyr Gln Gln Lys Pro Gly Gln Ser Pro Lys Gln Leu Ile Tyr Trp
            180                 185                 190

Ala Ser Thr Arg Glu Ser Gly Val Pro Asp Arg Phe Thr Gly Ser Gly
        195                 200                 205

Ser Gly Thr Asp Phe Thr Leu Thr Ile Ser Ser Val Lys Ala Glu Asp
    210                 215                 220

Leu Ala Val Tyr Tyr Cys Gln Gln Tyr Tyr Ser Tyr Pro Leu Thr Phe
225                 230                 235                 240

Gly Ala Gly Thr Lys Leu Glu Leu Lys
                245

<210> SEQ ID NO 77
<211> LENGTH: 249
<212> TYPE: PRT
<213> ORGANISM: Artificial Sequence
<220> FEATURE:
<223> OTHER INFORMATION: Synthetic Construct

<400> SEQUENCE: 77

Asp Val Lys Leu Gln Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Arg Val Lys Gln Arg Pro Gly Gln Gly Leu Glu Trp Ile
            35                  40                  45

Gly Thr Ile Tyr Pro Gly Asp Asp Thr Arg Tyr Thr Gln Lys Phe
        50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
                100                 105                 110

Gln Gly Thr Thr Leu Thr Val Ser Ser Gly Gly Gly Ser Gly Gly
            115                 120                 125

Gly Gly Ser Gly Gly Gly Ser Asp Thr Val Met Ser Gln Ser Pro
        130                 135                 140

Ser Ser Leu Ala Val Ser Val Gly Glu Lys Ile Thr Met Ser Cys Lys
145                 150                 155                 160

Ser Ser Gln Ser Leu Leu Tyr Arg Ser Asn Gln Lys Asn Tyr Leu Ala
                165                 170                 175

Trp Tyr Gln Gln Lys Pro Gly Gln Ser Pro Lys Gln Leu Ile Tyr Trp
                180                 185                 190

Ala Ser Thr Arg Glu Ser Gly Val Pro Asp Arg Phe Thr Gly Ser Gly
                195                 200                 205

Ser Gly Thr Asp Phe Thr Leu Thr Ile Ser Ser Val Lys Ala Glu Asp
        210                 215                 220

Leu Ala Val Tyr Tyr Cys Gln Gln Tyr Tyr Ser Tyr Pro Leu Thr Phe
225                 230                 235                 240

Gly Ala Gly Thr Lys Leu Glu Leu Lys
                245

<210> SEQ ID NO 78
<211> LENGTH: 243
<212> TYPE: PRT
<213> ORGANISM: Artificial Sequence
<220> FEATURE:
<223> OTHER INFORMATION: Synthetic Construct

<400> SEQUENCE: 78

Gln Val Gln Leu Lys Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
                20                  25                  30

Trp Met Gln Trp Ala Lys Gln Arg Pro Gly Gln Gly Leu Glu Trp Ile
            35                  40                  45

Gly Thr Ile Tyr Pro Gly Asp Asp Thr Arg Tyr Thr Gln Lys Phe
        50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
                100                 105                 110

Gln Gly Thr Thr Leu Thr Val Ser Ser Gly Gly Gly Ser Gly Gly
            115                 120                 125

Gly Gly Ser Gly Gly Gly Ser Asp Ile Gln Met Thr Gln Ser Pro
        130                 135                 140

```
Ala Ser Leu Ser Ala Ser Val Gly Glu Thr Val Thr Ile Thr Cys Arg
145                 150                 155                 160

Ala Ser Gly Asn Ile His Asn Tyr Leu Ala Trp Tyr Gln Gln Lys Gln
            165                 170                 175

Gly Lys Ser Pro Gln Leu Leu Val Tyr Asn Ala Lys Thr Leu Ala Asp
        180                 185                 190

Gly Val Pro Ser Arg Phe Ser Gly Ser Gly Ser Gly Thr Gln Tyr Ser
        195                 200                 205

Leu Lys Ile Asn Ser Leu Gln Pro Glu Asp Phe Gly Ser Tyr Tyr Cys
    210                 215                 220

Gln His Phe Trp Ser Thr Pro Trp Thr Phe Gly Gly Gly Thr Lys Leu
225                 230                 235                 240

Glu Ile Lys

<210> SEQ ID NO 79
<211> LENGTH: 248
<212> TYPE: PRT
<213> ORGANISM: Artificial Sequence
<220> FEATURE:
<223> OTHER INFORMATION: Synthetic Construct

<400> SEQUENCE: 79

Gln Val Gln Leu Lys Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Trp Ala Lys Gln Arg Pro Gly Gln Gly Leu Glu Trp Ile
        35                  40                  45

Gly Thr Ile Tyr Pro Gly Asp Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser Gly Gly Gly Ser Gly Gly
        115                 120                 125

Gly Gly Ser Gly Gly Gly Ser Gly Asn Ser Trp Ser His Ser Leu
    130                 135                 140

Arg Ser Leu Ser Val Thr Ile Gly Gln Pro Ala Ser Ile Ser Cys Lys
145                 150                 155                 160

Ser Ser Gln Ser Leu Leu Asp Gly Asn Gly Lys Thr Tyr Leu Asn Trp
                165                 170                 175

Leu Leu Gln Arg Pro Gly Gln Ser Pro Lys Arg Leu Leu Tyr Leu Val
            180                 185                 190

Ser Lys Leu Asp Ser Gly Val Pro Asp Arg Phe Thr Gly Ser Gly Ser
        195                 200                 205

Gly Thr Asp Phe Thr Leu Lys Ile Ser Arg Val Glu Ala Glu Asp Leu
    210                 215                 220

Gly Ile Tyr Tyr Cys Trp Gln Gly Thr His Phe Pro Arg Thr Phe Gly
225                 230                 235                 240

Gly Gly Thr Lys Leu Glu Ile Lys
                245
```

```
<210> SEQ ID NO 80
<211> LENGTH: 248
<212> TYPE: PRT
<213> ORGANISM: Artificial Sequence
<220> FEATURE:
<223> OTHER INFORMATION: Synthetic Construct

<400> SEQUENCE: 80

Gln Val Gln Leu Lys Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Trp Ala Lys Gln Arg Pro Gly Gln Gly Leu Glu Trp Ile
        35                  40                  45

Gly Thr Ile Tyr Pro Gly Asp Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser Gly Gly Gly Ser Gly Gly
        115                 120                 125

Gly Gly Ser Gly Gly Gly Ser Gly Asn Ser Trp Arg His Ser Pro
    130                 135                 140

Arg Ser Leu Ser Val Thr Ile Gly Gln Pro Ala Ser Ile Ser Cys Lys
145                 150                 155                 160

Ser Ser Gln Ser Leu Leu Asp Gly Asn Gly Lys Thr Tyr Leu Asn Trp
                165                 170                 175

Leu Leu Gln Arg Pro Gly Gln Ser Pro Lys Arg Leu Leu Tyr Leu Val
            180                 185                 190

Ser Lys Leu Asp Ser Gly Val Pro Asp Arg Phe Thr Gly Ser Gly Ser
        195                 200                 205

Gly Thr Asp Phe Thr Leu Lys Ile Ser Arg Val Glu Ala Glu Asp Leu
    210                 215                 220

Gly Ile Tyr Tyr Cys Trp Gln Gly Thr His Phe Pro Arg Thr Phe Gly
225                 230                 235                 240

Gly Gly Thr Lys Leu Glu Ile Lys
                245

<210> SEQ ID NO 81
<211> LENGTH: 248
<212> TYPE: PRT
<213> ORGANISM: Artificial Sequence
<220> FEATURE:
<223> OTHER INFORMATION: Synthetic Construct

<400> SEQUENCE: 81

Gln Val Gln Leu Lys Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Trp Ala Lys Gln Arg Pro Gly Gln Gly Leu Glu Trp Ile
        35                  40                  45

Gly Thr Ile Tyr Pro Gly Asp Asp Asp Thr Arg Tyr Thr Gln Lys Phe
    50                  55                  60
```

```
Lys Gly Arg Ala Thr Leu Thr Ala Asp Lys Ser Ser Thr Ala Tyr
 65                  70                  75                  80

Met Gln Leu Ser Asn Leu Ser Ser Glu Asp Ser Ala Val Tyr Tyr Cys
                 85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser Gly Gly Gly Ser Gly Gly
            115                 120                 125

Gly Gly Ser Gly Gly Gly Ser Asp Ile Val Met Thr Gln Ala Ala
        130                 135                 140

Pro Ser Val Pro Val Thr Pro Gly Glu Ser Val Ser Ile Ser Cys Gly
145                 150                 155                 160

Ser Ser Lys Ser Leu Leu His Ser Asn Gly Asn Thr Tyr Leu Tyr Trp
                165                 170                 175

Phe Leu Gln Arg Pro Gly Gln Ser Pro Gln Leu Leu Ile Tyr Arg Val
            180                 185                 190

Ser Asn Leu Ala Ser Gly Val Pro Asp Arg Phe Ser Gly Ser Gly Ser
            195                 200                 205

Gly Thr Ala Phe Thr Leu Arg Ile Ser Arg Val Glu Ala Glu Asp Val
210                 215                 220

Gly Val Tyr Tyr Cys Met Gln His Leu Glu Tyr Pro Tyr Thr Phe Gly
225                 230                 235                 240

Gly Gly Thr Arg Leu Glu Ile Lys
                245

<210> SEQ ID NO 82
<211> LENGTH: 248
<212> TYPE: PRT
<213> ORGANISM: Artificial Sequence
<220> FEATURE:
<223> OTHER INFORMATION: Synthetic Construct

<400> SEQUENCE: 82

Gln Val Gln Leu Lys Glu Ser Gly Ala Glu Leu Ala Arg Pro Gly Ala
  1               5                  10                  15

Ser Val Lys Leu Ser Cys Lys Ala Ser Gly Tyr Thr Phe Thr Thr Phe
                 20                  25                  30

Trp Met Gln Trp Ala Lys Gln Arg Pro Gly Gln Gly Leu Glu Trp Ile
             35                  40                  45

Gly Thr Ile Tyr Pro Gly Asp Asp Asp Thr Arg Tyr Thr Gln Lys Phe
         50                  55                  60

Lys Gly Arg Ala Thr Leu Thr Ala Asp Lys Ser Ser Thr Ala Tyr
 65                  70                  75                  80

Met Gln Leu Ser Asn Leu Ser Ser Glu Asp Ser Ala Val Tyr Tyr Cys
                 85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser Gly Gly Gly Ser Gly Gly
            115                 120                 125

Gly Gly Ser Gly Gly Gly Ser Asp Ile Val Met Thr Gln Ala Ala
        130                 135                 140

Pro Ser Val Pro Val Thr Pro Gly Glu Ser Val Ser Ile Ser Cys Gly
145                 150                 155                 160

Ser Ser Lys Ser Leu Leu His Ser Asn Gly Asn Thr Tyr Leu Tyr Trp
                165                 170                 175
```

-continued

```
Phe Leu Gln Arg Pro Gly Gln Ser Pro Gln Leu Leu Ile Tyr Arg Val
                180                 185                 190

Ser Asn Leu Ala Ser Gly Val Pro Asp Arg Phe Ser Gly Ser Gly Ser
            195                 200                 205

Gly Thr Ala Phe Thr Leu Arg Ile Ser Arg Val Glu Ala Glu Asp Val
210                 215                 220

Gly Val Tyr Tyr Cys Met Gln His Leu Glu Tyr Pro Tyr Thr Phe Gly
225                 230                 235                 240

Gly Gly Thr Arg Leu Glu Ile Lys
                245

<210> SEQ ID NO 83
<211> LENGTH: 249
<212> TYPE: PRT
<213> ORGANISM: Artificial Sequence
<220> FEATURE:
<223> OTHER INFORMATION: Synthetic Construct

<400> SEQUENCE: 83

Gln Val Gln Leu Lys Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Trp Ala Lys Gln Arg Pro Gly Gln Gly Leu Glu Trp Ile
        35                  40                  45

Gly Thr Ile Tyr Pro Gly Asp Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Ser Gly Gly Gly Ser Gly Gly
        115                 120                 125

Gly Gly Ser Gly Gly Gly Ser Asp Thr Val Met Ser Gln Ser Pro
    130                 135                 140

Ser Ser Leu Ala Val Ser Val Gly Glu Lys Ile Thr Met Ser Cys Lys
145                 150                 155                 160

Ser Ser Gln Ser Leu Leu Cys Arg Ser Asn Gln Lys Asn Tyr Leu Ala
                165                 170                 175

Trp Tyr Gln Gln Lys Pro Gly Gln Ser Pro Lys Gln Leu Ile Tyr Trp
            180                 185                 190

Ala Ser Thr Arg Glu Ser Gly Val Pro Asp Arg Phe Thr Gly Ser Gly
        195                 200                 205

Ser Gly Thr Asp Phe Thr Leu Thr Ile Ser Ser Val Lys Ala Glu Asp
    210                 215                 220

Leu Ala Val Tyr Tyr Cys Gln Gln Tyr Tyr Ser Tyr Pro Leu Thr Phe
225                 230                 235                 240

Gly Ala Gly Thr Lys Leu Glu Leu Lys
                245

<210> SEQ ID NO 84
<211> LENGTH: 249
<212> TYPE: PRT
<213> ORGANISM: Artificial Sequence
```

```
<220> FEATURE:
<223> OTHER INFORMATION: Synthetic Construct

<400> SEQUENCE: 84

Gln Val Gln Leu Lys Glu Ser Gly Ala Glu Leu Ala Arg Pro Gly Ala
1               5                   10                  15

Ser Val Lys Leu Ser Cys Lys Ala Ser Gly Tyr Thr Phe Thr Thr Phe
            20                  25                  30

Trp Met Gln Trp Ala Lys Gln Arg Pro Gly Gln Gly Leu Glu Trp Ile
        35                  40                  45

Gly Thr Ile Tyr Pro Gly Asp Asp Thr Arg Tyr Thr Gln Lys Phe
    50                  55                  60

Lys Gly Arg Ala Thr Leu Thr Ala Asp Lys Ser Ser Thr Thr Ala Tyr
65                  70                  75                  80

Met Gln Leu Ser Asn Leu Ser Ser Glu Asp Ser Ala Val Tyr Tyr Cys
                85                  90                  95

Ala Arg Ser Gly Tyr Glu Arg Gly Pro Tyr Tyr Phe Asp Ser Trp Gly
            100                 105                 110

Gln Gly Thr Thr Leu Thr Val Ser Gly Gly Gly Ser Gly Gly
            115                 120                 125

Gly Gly Ser Gly Gly Gly Ser Asp Thr Val Met Ser Gln Ser Pro
    130                 135                 140

Ser Ser Leu Ala Val Ser Val Gly Glu Lys Ile Thr Met Ser Cys Lys
145                 150                 155                 160

Ser Ser Gln Ser Leu Leu Tyr Arg Ser Asn Gln Lys Asn Tyr Leu Ala
                165                 170                 175

Trp Tyr Gln Gln Lys Pro Gly Gln Ser Pro Lys Gln Leu Ile Tyr Trp
            180                 185                 190

Ala Ser Thr Arg Glu Ser Gly Val Pro Asp Arg Phe Thr Gly Ser Gly
            195                 200                 205

Ser Gly Thr Asp Phe Thr Leu Thr Ile Ser Ser Val Lys Ala Glu Asp
    210                 215                 220

Leu Ala Val Tyr Tyr Cys Gln Gln Tyr Tyr Ser Tyr Pro Leu Thr Phe
225                 230                 235                 240

Gly Ala Gly Thr Lys Leu Glu Leu Lys
                245

<210> SEQ ID NO 85
<211> LENGTH: 236
<212> TYPE: PRT
<213> ORGANISM: Artificial Sequence
<220> FEATURE:
<223> OTHER INFORMATION: Synthetic Construct

<400> SEQUENCE: 85

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
```

```
                      85                  90                  95
Thr Phe Gly Gly Gly Thr Lys Leu Glu Ile Lys Gly Gly Gly Ser
                    100                 105                 110

Gly Gly Gly Gly Ser Gly Gly Gly Ser Glu Val Gln Leu Gln Gln
                    115                 120                 125

Ser Gly Ala Glu Leu Val Lys Pro Gly Ala Ser Val Lys Leu Ser Cys
    130                 135                 140

Thr Ala Ser Gly Phe Asp Ile Lys Asp Thr Tyr Ile His Trp Val Lys
145                 150                 155                 160

Gln Arg Pro Glu Gln Gly Leu Glu Trp Ile Gly Arg Ile Asp Pro Ala
                    165                 170                 175

Asn Gly Asp Thr Arg Tyr Asp Pro Glu Phe Gln Gly Lys Ala Ser Leu
                    180                 185                 190

Thr Ala Asp Thr Ser Ser Asn Thr Ala Tyr Leu Gln Phe Ser Asn Leu
                195                 200                 205

Thr Ser Glu Asp Thr Ala Val Tyr Tyr Cys Ala Arg Arg Gly Gly Leu
            210                 215                 220

Ser Trp Gly Gln Gly Thr Thr Leu Thr Val Ser Ser
225                 230                 235
```

<210> SEQ ID NO 86
<211> LENGTH: 238
<212> TYPE: PRT
<213> ORGANISM: Artificial Sequence
<220> FEATURE:
<223> OTHER INFORMATION: Synthetic Construct

<400> SEQUENCE: 86

```
Asp Ile Gln Met Thr Gln Ser Pro Ala Ser Leu Ser Ala Ser Val Gly
1               5                  10                  15

Glu Thr Val Thr Ile Thr Cys Arg Ala Ser Gly Asn Ile His Asn Tyr
                 20                  25                  30

Leu Ala Trp Tyr Gln Gln Lys Gln Gly Lys Ser Pro Gln Leu Leu Val
             35                  40                  45

Tyr Asn Ala Lys Thr Leu Ala Asp Gly Val Pro Ser Arg Phe Ser Gly
50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                 85                  90                  95

Thr Phe Gly Gly Gly Thr Lys Leu Glu Ile Lys Gly Gly Gly Gly Ser
                100                 105                 110

Gly Gly Gly Gly Ser Gly Gly Gly Ser Glu Val Gln Leu Glu Glu
                115                 120                 125

Ser Gly Gly Gly Leu Val Gln Pro Lys Gly Ser Leu Lys Leu Ser Cys
    130                 135                 140

Ala Ala Ser Gly Phe Thr Phe Asn Thr Tyr Ala Met Tyr Trp Val Cys
145                 150                 155                 160

Gln Ala Pro Gly Lys Gly Leu Lys Trp Val Ala Arg Ile Arg Ser Lys
                165                 170                 175

Val Asn Asn Tyr Ala Thr Tyr Tyr Ala Asp Ser Val Lys Asp Arg Phe
                180                 185                 190

Thr Ile Ser Arg Asp Asp Ser Gln Asn Met Leu Phe Leu His Met Asn
            195                 200                 205

Asn Leu Lys Thr Glu Asp Thr Ala Ile Tyr Phe Cys Val Arg Asp Pro
```

```
                210                 215                 220
Met Asp Tyr Trp Gly Gln Gly Ile Ser Val Thr Val Ser Ser
225                 230                 235

<210> SEQ ID NO 87
<211> LENGTH: 238
<212> TYPE: PRT
<213> ORGANISM: Artificial Sequence
<220> FEATURE:
<223> OTHER INFORMATION: Synthetic Construct

<400> SEQUENCE: 87

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Lys Gly Ser Leu Lys Leu Ser Cys
130                 135                 140

Ala Ala Ser Gly Phe Thr Phe Asn Thr Tyr Ala Met Tyr Trp Val Cys
145                 150                 155                 160

Gln Ala Pro Gly Lys Gly Leu Lys Trp Val Ala Arg Ile Arg Ser Lys
                165                 170                 175

Val Asn Asn Tyr Ala Thr Tyr Tyr Ala Asp Ser Val Lys Asp Arg Phe
            180                 185                 190

Thr Ile Ser Arg Asp Asp Ser Gln Asn Met Leu Phe Leu His Met Asn
        195                 200                 205

Asn Leu Lys Thr Glu Asp Thr Ala Ile Tyr Phe Cys Val Arg Asp Pro
210                 215                 220

Met Asp Tyr Trp Gly Gln Gly Ile Ser Val Thr Val Ser Ser
225                 230                 235

<210> SEQ ID NO 88
<211> LENGTH: 243
<212> TYPE: PRT
<213> ORGANISM: Artificial Sequence
<220> FEATURE:
<223> OTHER INFORMATION: Synthetic Construct

<400> SEQUENCE: 88

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45
```

Tyr Asn Ala Lys Thr Leu Ala Asp Gly Val Pro Ser Arg Phe Ser Gly
                50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys Gly Gly Gly Gly Ser
                100                 105                 110

Gly Gly Gly Gly Ser Gly Gly Gly Ser Gln Val Gln Leu Gln Gln
                115                 120                 125

Ser Gly Ala Glu Leu Ala Arg Pro Gly Ala Ser Val Lys Leu Ser Cys
130                 135                 140

Lys Ala Ser Gly Tyr Thr Phe Thr Thr Phe Trp Met Gln Trp Val Lys
145                 150                 155                 160

Gln Arg Pro Gly Gln Gly Leu Glu Trp Ile Gly Thr Ile Tyr Pro Gly
                165                 170                 175

Asp Asp Asp Thr Arg Tyr Thr Gln Lys Phe Lys Gly Arg Ala Thr Leu
                180                 185                 190

Thr Ala Asp Lys Ser Ser Thr Thr Ala Tyr Met Gln Leu Ser Asn Leu
                195                 200                 205

Ser Ser Glu Asp Ser Ala Val Tyr Tyr Cys Ala Arg Ser Gly Tyr Glu
                210                 215                 220

Arg Gly Pro Tyr Tyr Phe Asp Ser Trp Gly Gln Gly Thr Thr Leu Thr
225                 230                 235                 240

Val Ser Ser

<210> SEQ ID NO 89
<211> LENGTH: 243
<212> TYPE: PRT
<213> ORGANISM: Artificial Sequence
<220> FEATURE:
<223> OTHER INFORMATION: Synthetic Construct

<400> SEQUENCE: 89

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ala Trp Tyr Gln Gln Lys Gln Gly Lys Ser Pro Gln Leu Leu Val
                35                  40                  45

Tyr Asn Ala Lys Thr Leu Ala Asp Gly Val Pro Ser Arg Phe Ser Gly
                50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys Gly Gly Gly Gly Ser
                100                 105                 110

Gly Gly Gly Gly Ser Gly Gly Gly Ser Asp Val Lys Leu Gln Glu
                115                 120                 125

Ser Gly Ala Glu Leu Ala Arg Pro Gly Ala Ser Val Lys Leu Ser Cys
130                 135                 140

Lys Ala Ser Gly Tyr Thr Phe Thr Thr Phe Trp Met Gln Arg Val Lys
145                 150                 155                 160

Gln Arg Pro Gly Gln Gly Leu Glu Trp Ile Gly Thr Ile Tyr Pro Gly

```
                        165                 170                 175
Asp Asp Asp Thr Arg Tyr Thr Gln Lys Phe Lys Gly Arg Ala Thr Leu
                    180                 185                 190

Thr Ala Asp Lys Ser Ser Thr Thr Ala Tyr Met Gln Leu Ser Asn Leu
                195                 200                 205

Ser Ser Glu Asp Ser Ala Val Tyr Tyr Cys Ala Arg Ser Gly Tyr Glu
            210                 215                 220

Arg Gly Pro Tyr Tyr Phe Asp Ser Trp Gly Gln Gly Thr Thr Leu Thr
225                 230                 235                 240

Val Ser Ser

<210> SEQ ID NO 90
<211> LENGTH: 243
<212> TYPE: PRT
<213> ORGANISM: Artificial Sequence
<220> FEATURE:
<223> OTHER INFORMATION: Synthetic Construct

<400> SEQUENCE: 90

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys Gly Gly Gly Gly Ser
                100                 105                 110

Gly Gly Gly Gly Ser Gly Gly Gly Ser Gln Val Gln Leu Lys Glu
            115                 120                 125

Ser Gly Ala Glu Leu Ala Arg Pro Gly Ala Ser Val Lys Leu Ser Cys
    130                 135                 140

Lys Ala Ser Gly Tyr Thr Phe Thr Thr Phe Trp Met Gln Trp Ala Lys
145                 150                 155                 160

Gln Arg Pro Gly Gln Gly Leu Glu Trp Ile Gly Thr Ile Tyr Pro Gly
                165                 170                 175

Asp Asp Asp Thr Arg Tyr Thr Gln Lys Phe Lys Gly Arg Ala Thr Leu
                    180                 185                 190

Thr Ala Asp Lys Ser Ser Thr Thr Ala Tyr Met Gln Leu Ser Asn Leu
                195                 200                 205

Ser Ser Glu Asp Ser Ala Val Tyr Tyr Cys Ala Arg Ser Gly Tyr Glu
            210                 215                 220

Arg Gly Pro Tyr Tyr Phe Asp Ser Trp Gly Gln Gly Thr Thr Leu Thr
225                 230                 235                 240

Val Ser Ser

<210> SEQ ID NO 91
<211> LENGTH: 241
<212> TYPE: PRT
<213> ORGANISM: Artificial Sequence
<220> FEATURE:
```

<223> OTHER INFORMATION: Synthetic Construct

<400> SEQUENCE: 91

Asp Ile Val Met Thr Gln Ala Ala Pro Ser Val Pro Val Thr Pro Gly
1               5                   10                  15

Glu Ser Val Ser Ile Ser Cys Gly Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Arg Leu Glu Ile Lys
            100                 105                 110

Gly Gly Gly Gly Ser Gly Gly Gly Gly Ser Gly Gly Gly Gly Ser Glu
        115                 120                 125

Val Gln Leu Gln Gln Ser Gly Ala Glu Leu Val Lys Pro Gly Ala Ser
    130                 135                 140

Val Lys Leu Ser Cys Thr Ala Ser Gly Phe Asp Ile Lys Asp Thr Tyr
145                 150                 155                 160

Ile His Trp Val Lys Gln Arg Pro Glu Gln Gly Leu Glu Trp Ile Gly
                165                 170                 175

Arg Ile Asp Pro Ala Asn Gly Asp Thr Arg Tyr Asp Pro Glu Phe Gln
            180                 185                 190

Gly Lys Ala Ser Leu Thr Ala Asp Thr Ser Ser Asn Thr Ala Tyr Leu
        195                 200                 205

Gln Phe Ser Asn Leu Thr Ser Glu Asp Thr Ala Val Tyr Tyr Cys Ala
    210                 215                 220

Arg Arg Gly Gly Leu Ser Trp Gly Gln Gly Thr Thr Leu Thr Val Ser
225                 230                 235                 240

Ser

<210> SEQ ID NO 92
<211> LENGTH: 243
<212> TYPE: PRT
<213> ORGANISM: Artificial Sequence
<220> FEATURE:
<223> OTHER INFORMATION: Synthetic Construct

<400> SEQUENCE: 92

Asp Ile Val Met Thr Gln Ala Ala Pro Ser Val Pro Val Thr Pro Gly
1               5                   10                  15

Glu Ser Val Ser Ile Ser Cys Gly Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

```
Leu Glu Tyr Pro Tyr Thr Phe Gly Gly Gly Thr Arg Leu Glu Ile Lys
                100                 105                 110

Gly Gly Gly Gly Ser Gly Gly Gly Ser Gly Gly Gly Ser Glu
            115                 120                 125

Val Gln Leu Glu Glu Ser Gly Gly Gly Leu Val Gln Pro Lys Gly Ser
        130                 135                 140

Leu Lys Leu Ser Cys Ala Ala Ser Gly Phe Thr Phe Asn Thr Tyr Ala
145                 150                 155                 160

Met Tyr Trp Val Cys Gln Ala Pro Gly Lys Gly Leu Lys Trp Val Ala
                165                 170                 175

Arg Ile Arg Ser Lys Val Asn Asn Tyr Ala Thr Tyr Tyr Ala Asp Ser
                180                 185                 190

Val Lys Asp Arg Phe Thr Ile Ser Arg Asp Asp Ser Gln Asn Met Leu
        195                 200                 205

Phe Leu His Met Asn Asn Leu Lys Thr Glu Asp Thr Ala Ile Tyr Phe
        210                 215                 220

Cys Val Arg Asp Pro Met Asp Tyr Trp Gly Gln Gly Ile Ser Val Thr
225                 230                 235                 240

Val Ser Ser

<210> SEQ ID NO 93
<211> LENGTH: 243
<212> TYPE: PRT
<213> ORGANISM: Artificial Sequence
<220> FEATURE:
<223> OTHER INFORMATION: Synthetic Construct

<400> SEQUENCE: 93

Asp Ile Val Met Thr Gln Ala Ala Pro Ser Val Pro Val Thr Pro Gly
1               5                   10                  15

Glu Ser Val Ser Ile Ser Cys Gly Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Arg Leu Glu Ile Lys
                100                 105                 110

Gly Gly Gly Gly Ser Gly Gly Gly Ser Gly Gly Gly Ser Glu
            115                 120                 125

Val Gln Leu Val Glu Ser Gly Gly Gly Leu Val Gln Pro Lys Gly Ser
        130                 135                 140

Leu Lys Leu Ser Cys Ala Ala Ser Gly Phe Thr Phe Asn Thr Tyr Ala
145                 150                 155                 160

Met Tyr Trp Val Cys Gln Ala Pro Gly Lys Gly Leu Lys Trp Val Ala
                165                 170                 175

Arg Ile Arg Ser Lys Val Asn Asn Tyr Ala Thr Tyr Tyr Ala Asp Ser
                180                 185                 190

Val Lys Asp Arg Phe Thr Ile Ser Arg Asp Asp Ser Gln Asn Met Leu
        195                 200                 205

Phe Leu His Met Asn Asn Leu Lys Thr Glu Asp Thr Ala Ile Tyr Phe
```

-continued

```
                210                 215                 220
Cys Val Arg Asp Pro Met Asp Tyr Trp Gly Gln Gly Ile Ser Val Thr
225                 230                 235                 240

Val Ser Ser
```

<210> SEQ ID NO 94
<211> LENGTH: 248
<212> TYPE: PRT
<213> ORGANISM: Artificial Sequence
<220> FEATURE:
<223> OTHER INFORMATION: Synthetic Construct

<400> SEQUENCE: 94

```
Asp Ile Val Met Thr Gln Ala Ala Pro Ser Val Pro Val Thr Pro Gly
1               5                   10                  15

Glu Ser Val Ser Ile Ser Cys Gly Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Arg Leu Glu Ile Lys
            100                 105                 110

Gly Gly Gly Gly Ser Gly Gly Gly Ser Gly Gly Gly Gly Ser Gln
        115                 120                 125

Val Gln Leu Gln Gln Ser Gly Ala Glu Leu Ala Arg Pro Gly Ala Ser
    130                 135                 140

Val Lys Leu Ser Cys Lys Ala Ser Gly Tyr Thr Phe Thr Thr Phe Trp
145                 150                 155                 160

Met Gln Trp Val Lys Gln Arg Pro Gly Gln Gly Leu Glu Trp Ile Gly
                165                 170                 175

Thr Ile Tyr Pro Gly Asp Asp Asp Thr Arg Tyr Thr Gln Lys Phe Lys
            180                 185                 190

Gly Arg Ala Thr Leu Thr Ala Asp Lys Ser Ser Thr Thr Ala Tyr Met
        195                 200                 205

Gln Leu Ser Asn Leu Ser Ser Glu Asp Ser Ala Val Tyr Tyr Cys Ala
    210                 215                 220

Arg Ser Gly Tyr Glu Arg Gly Pro Tyr Tyr Phe Asp Ser Trp Gly Gln
225                 230                 235                 240

Gly Thr Thr Leu Thr Val Ser Ser
                245
```

<210> SEQ ID NO 95
<211> LENGTH: 248
<212> TYPE: PRT
<213> ORGANISM: Artificial Sequence
<220> FEATURE:
<223> OTHER INFORMATION: Synthetic Construct

<400> SEQUENCE: 95

```
Asp Ile Val Met Thr Gln Ala Ala Pro Ser Val Pro Val Thr Pro Gly
1               5                   10                  15

Glu Ser Val Ser Ile Ser Cys Gly Ser Ser Lys Ser Leu Leu His Ser
```

Asn Gly Asn Thr Tyr Leu Tyr Trp Phe Leu Gln Arg Pro Gly Gln Ser
            35                  40                  45

Pro Gln Leu Leu Ile Tyr Arg Val Ser Asn Leu Ala Ser Gly Val Pro
        50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Arg Leu Glu Ile Lys
                100                 105                 110

Gly Gly Gly Gly Ser Gly Gly Gly Ser Gly Gly Gly Gly Ser Asp
            115                 120                 125

Val Lys Leu Gln Glu Ser Gly Ala Glu Leu Ala Arg Pro Gly Ala Ser
    130                 135                 140

Val Lys Leu Ser Cys Lys Ala Ser Gly Tyr Thr Phe Thr Thr Phe Trp
145                 150                 155                 160

Met Gln Arg Val Lys Gln Arg Pro Gly Gln Gly Leu Glu Trp Ile Gly
                165                 170                 175

Thr Ile Tyr Pro Gly Asp Asp Asp Thr Arg Tyr Thr Gln Lys Phe Lys
                180                 185                 190

Gly Arg Ala Thr Leu Thr Ala Asp Lys Ser Ser Thr Thr Ala Tyr Met
            195                 200                 205

Gln Leu Ser Asn Leu Ser Ser Glu Asp Ser Ala Val Tyr Tyr Cys Ala
        210                 215                 220

Arg Ser Gly Tyr Glu Arg Gly Pro Tyr Tyr Phe Asp Ser Trp Gly Gln
225                 230                 235                 240

Gly Thr Thr Leu Thr Val Ser Ser
                245

<210> SEQ ID NO 96
<211> LENGTH: 248
<212> TYPE: PRT
<213> ORGANISM: Artificial Sequence
<220> FEATURE:
<223> OTHER INFORMATION: Synthetic Construct

<400> SEQUENCE: 96

Asp Ile Val Met Thr Gln Ala Ala Pro Ser Val Pro Val Thr Pro Gly
 1               5                  10                  15

Glu Ser Val Ser Ile Ser Cys Gly Ser Ser Lys Ser Leu Leu His Ser
            20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Val Ser Asn Leu Ala Ser Gly Val Pro
        50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Arg Leu Glu Ile Lys
                100                 105                 110

Gly Gly Gly Gly Ser Gly Gly Gly Ser Gly Gly Gly Gly Ser Gln
            115                 120                 125

Val Gln Leu Lys Glu Ser Gly Ala Glu Leu Ala Arg Pro Gly Ala Ser

```
                130             135             140
Val Lys Leu Ser Cys Lys Ala Ser Gly Tyr Thr Phe Thr Thr Phe Trp
145                 150                 155                 160

Met Gln Trp Ala Lys Gln Arg Pro Gly Gln Gly Leu Glu Trp Ile Gly
                165                 170                 175

Thr Ile Tyr Pro Gly Asp Asp Thr Arg Tyr Thr Gln Lys Phe Lys
                180                 185                 190

Gly Arg Ala Thr Leu Thr Ala Asp Lys Ser Ser Thr Ala Tyr Met
                195                 200                 205

Gln Leu Ser Asn Leu Ser Ser Glu Asp Ser Ala Val Tyr Tyr Cys Ala
                210                 215                 220

Arg Ser Gly Tyr Glu Arg Gly Pro Tyr Tyr Phe Asp Ser Trp Gly Gln
225                 230                 235                 240

Gly Thr Thr Leu Thr Val Ser Ser
                245
```

<210> SEQ ID NO 97
<211> LENGTH: 242
<212> TYPE: PRT
<213> ORGANISM: Artificial Sequence
<220> FEATURE:
<223> OTHER INFORMATION: Synthetic Construct

<400> SEQUENCE: 97

```
Asp Thr Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Cys Arg
                20                  25                  30

Ser Asn Gln Lys Asn Tyr Leu Ala Trp Tyr Gln Gln Lys Pro Gly Gln
            35                  40                  45

Ser Pro Lys Gln Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
                100                 105                 110

Lys Gly Gly Gly Gly Ser Gly Gly Gly Gly Ser Gly Gly Gly Gly Ser
                115                 120                 125

Glu Val Gln Leu Gln Gln Ser Gly Ala Glu Leu Val Lys Pro Gly Ala
                130                 135                 140

Ser Val Lys Leu Ser Cys Thr Ala Ser Gly Phe Asp Ile Lys Asp Thr
145                 150                 155                 160

Tyr Ile His Trp Val Lys Gln Arg Pro Glu Gln Gly Leu Glu Trp Ile
                165                 170                 175

Gly Arg Ile Asp Pro Ala Asn Gly Asp Thr Arg Tyr Asp Pro Glu Phe
                180                 185                 190

Gln Gly Lys Ala Ser Leu Thr Ala Asp Thr Ser Ser Asn Thr Ala Tyr
                195                 200                 205

Leu Gln Phe Ser Asn Leu Thr Ser Glu Asp Thr Ala Val Tyr Tyr Cys
                210                 215                 220

Ala Arg Arg Gly Gly Leu Ser Trp Gly Gln Gly Thr Thr Leu Thr Val
225                 230                 235                 240

Ser Ser
```

<210> SEQ ID NO 98
<211> LENGTH: 244
<212> TYPE: PRT
<213> ORGANISM: Artificial Sequence
<220> FEATURE:
<223> OTHER INFORMATION: Synthetic Construct

<400> SEQUENCE: 98

```
Asp Thr Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Cys Arg
            20                  25                  30

Ser Asn Gln Lys Asn Tyr Leu Ala Trp Tyr Gln Gln Lys Pro Gly Gln
        35                  40                  45

Ser Pro Lys Gln Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys Gly Gly Gly Gly Ser Gly Gly Gly Ser Gly Gly Gly Gly Ser
        115                 120                 125

Glu Val Gln Leu Glu Glu Ser Gly Gly Gly Leu Val Gln Pro Lys Gly
    130                 135                 140

Ser Leu Lys Leu Ser Cys Ala Ala Ser Gly Phe Thr Phe Asn Thr Tyr
145                 150                 155                 160

Ala Met Tyr Trp Val Cys Gln Ala Pro Gly Lys Gly Leu Lys Trp Val
                165                 170                 175

Ala Arg Ile Arg Ser Lys Val Asn Asn Tyr Ala Thr Tyr Tyr Ala Asp
            180                 185                 190

Ser Val Lys Asp Arg Phe Thr Ile Ser Arg Asp Asp Ser Gln Asn Met
        195                 200                 205

Leu Phe Leu His Met Asn Asn Leu Lys Thr Glu Asp Thr Ala Ile Tyr
    210                 215                 220

Phe Cys Val Arg Asp Pro Met Asp Tyr Trp Gly Gln Gly Ile Ser Val
225                 230                 235                 240

Thr Val Ser Ser
```

<210> SEQ ID NO 99
<211> LENGTH: 244
<212> TYPE: PRT
<213> ORGANISM: Artificial Sequence
<220> FEATURE:
<223> OTHER INFORMATION: Synthetic Construct

<400> SEQUENCE: 99

```
Asp Thr Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Cys Arg
            20                  25                  30

Ser Asn Gln Lys Asn Tyr Leu Ala Trp Tyr Gln Gln Lys Pro Gly Gln
        35                  40                  45

Ser Pro Lys Gln Leu Ile Tyr Trp Ala Ser Thr Arg Glu Ser Gly Val
    50                  55                  60
```

-continued

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys Gly Gly Gly Gly Ser Gly Gly Gly Ser Gly Gly Gly Gly Ser
            115                 120                 125

Glu Val Gln Leu Val Glu Ser Gly Gly Leu Val Gln Pro Lys Gly
130                 135                 140

Ser Leu Lys Leu Ser Cys Ala Ala Ser Gly Phe Thr Phe Asn Thr Tyr
145                 150                 155                 160

Ala Met Tyr Trp Val Cys Gln Ala Pro Gly Lys Gly Leu Lys Trp Val
            165                 170                 175

Ala Arg Ile Arg Ser Lys Val Asn Asn Tyr Ala Thr Tyr Tyr Ala Asp
            180                 185                 190

Ser Val Lys Asp Arg Phe Thr Ile Ser Arg Asp Asp Ser Gln Asn Met
            195                 200                 205

Leu Phe Leu His Met Asn Asn Leu Lys Thr Glu Asp Thr Ala Ile Tyr
210                 215                 220

Phe Cys Val Arg Asp Pro Met Asp Tyr Trp Gly Gln Gly Ile Ser Val
225                 230                 235                 240

Thr Val Ser Ser

<210> SEQ ID NO 100
<211> LENGTH: 249
<212> TYPE: PRT
<213> ORGANISM: Artificial Sequence
<220> FEATURE:
<223> OTHER INFORMATION: Synthetic Construct

<400> SEQUENCE: 100

Asp Thr Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Cys Arg
            20                  25                  30

Ser Asn Gln Lys Asn Tyr Leu Ala Trp Tyr Gln Gln Lys Pro Gly Gln
        35                  40                  45

Ser Pro Lys Gln Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys Gly Gly Gly Gly Ser Gly Gly Gly Ser Gly Gly Gly Gly Ser
            115                 120                 125

Gln Val Gln Leu Gln Gln Ser Gly Ala Glu Leu Ala Arg Pro Gly Ala
130                 135                 140

Ser Val Lys Leu Ser Cys Lys Ala Ser Gly Tyr Thr Phe Thr Thr Phe
145                 150                 155                 160

Trp Met Gln Trp Val Lys Gln Arg Pro Gly Gln Gly Leu Glu Trp Ile
            165                 170                 175

-continued

```
Gly Thr Ile Tyr Pro Gly Asp Asp Thr Arg Tyr Thr Gln Lys Phe
                180                 185                 190

Lys Gly Arg Ala Thr Leu Thr Ala Asp Lys Ser Ser Thr Thr Ala Tyr
            195                 200                 205

Met Gln Leu Ser Asn Leu Ser Ser Glu Asp Ser Ala Val Tyr Tyr Cys
        210                 215                 220

Ala Arg Ser Gly Tyr Glu Arg Gly Pro Tyr Tyr Phe Asp Ser Trp Gly
225                 230                 235                 240

Gln Gly Thr Thr Leu Thr Val Ser Ser
                245
```

<210> SEQ ID NO 101
<211> LENGTH: 249
<212> TYPE: PRT
<213> ORGANISM: Artificial Sequence
<220> FEATURE:
<223> OTHER INFORMATION: Synthetic Construct

<400> SEQUENCE: 101

```
Asp Thr Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Cys Arg
            20                  25                  30

Ser Asn Gln Lys Asn Tyr Leu Ala Trp Tyr Gln Gln Lys Pro Gly Gln
        35                  40                  45

Ser Pro Lys Gln Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys Gly Gly Gly Gly Ser Gly Gly Gly Gly Ser Gly Gly Gly Gly Ser
        115                 120                 125

Asp Val Lys Leu Gln Glu Ser Gly Ala Glu Leu Ala Arg Pro Gly Ala
    130                 135                 140

Ser Val Lys Leu Ser Cys Lys Ala Ser Gly Tyr Thr Phe Thr Thr Phe
145                 150                 155                 160

Trp Met Gln Arg Val Lys Gln Arg Pro Gly Gln Gly Leu Glu Trp Ile
                165                 170                 175

Gly Thr Ile Tyr Pro Gly Asp Asp Thr Arg Tyr Thr Gln Lys Phe
                180                 185                 190

Lys Gly Arg Ala Thr Leu Thr Ala Asp Lys Ser Ser Thr Thr Ala Tyr
            195                 200                 205

Met Gln Leu Ser Asn Leu Ser Ser Glu Asp Ser Ala Val Tyr Tyr Cys
        210                 215                 220

Ala Arg Ser Gly Tyr Glu Arg Gly Pro Tyr Tyr Phe Asp Ser Trp Gly
225                 230                 235                 240

Gln Gly Thr Thr Leu Thr Val Ser Ser
                245
```

<210> SEQ ID NO 102
<211> LENGTH: 249
<212> TYPE: PRT
<213> ORGANISM: Artificial Sequence
<220> FEATURE:

<223> OTHER INFORMATION: Synthetic Construct

<400> SEQUENCE: 102

```
Asp Thr Val Met Ser Gln Ser Pro Ser Ser Leu Ala Val Ser Val Gly
1               5                   10                  15

Glu Lys Ile Thr Met Ser Cys Lys Ser Gln Ser Leu Leu Cys Arg
                20                  25                  30

Ser Asn Gln Lys Asn Tyr Leu Ala Trp Tyr Gln Gln Lys Pro Gly Gln
            35                  40                  45

Ser Pro Lys Gln Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
                100                 105                 110

Lys Gly Gly Gly Gly Ser Gly Gly Gly Gly Ser Gly Gly Gly Gly Ser
            115                 120                 125

Gln Val Gln Leu Lys Glu Ser Gly Ala Glu Leu Ala Arg Pro Gly Ala
        130                 135                 140

Ser Val Lys Leu Ser Cys Lys Ala Ser Gly Tyr Thr Phe Thr Thr Phe
145                 150                 155                 160

Trp Met Gln Trp Ala Lys Gln Arg Pro Gly Gln Gly Leu Glu Trp Ile
                165                 170                 175

Gly Thr Ile Tyr Pro Gly Asp Asp Thr Arg Tyr Thr Gln Lys Phe
                180                 185                 190

Lys Gly Arg Ala Thr Leu Thr Ala Asp Lys Ser Ser Thr Thr Ala Tyr
            195                 200                 205

Met Gln Leu Ser Asn Leu Ser Ser Glu Asp Ser Ala Val Tyr Tyr Cys
        210                 215                 220

Ala Arg Ser Gly Tyr Glu Arg Gly Pro Tyr Tyr Phe Asp Ser Trp Gly
225                 230                 235                 240

Gln Gly Thr Thr Leu Thr Val Ser Ser
                245
```

<210> SEQ ID NO 103
<211> LENGTH: 242
<212> TYPE: PRT
<213> ORGANISM: Artificial Sequence
<220> FEATURE:
<223> OTHER INFORMATION: Synthetic Construct

<400> SEQUENCE: 103

```
Asp Thr Val Met Ser Gln Ser Pro Ser Ser Leu Ala Val Ser Val Gly
1               5                   10                  15

Glu Lys Ile Thr Met Ser Cys Lys Ser Gln Ser Leu Leu Tyr Arg
                20                  25                  30

Ser Asn Gln Lys Asn Tyr Leu Ala Trp Tyr Gln Gln Lys Pro Gly Gln
            35                  40                  45

Ser Pro Lys Gln Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95
```

Tyr Tyr Ser Tyr Pro Leu Thr Phe Gly Ala Gly Thr Lys Leu Glu Leu
            100                 105                 110

Lys Gly Gly Gly Ser Gly Gly Gly Ser Gly Gly Gly Ser
            115                 120                 125

Glu Val Gln Leu Gln Gln Ser Gly Ala Glu Leu Val Lys Pro Gly Ala
            130                 135                 140

Ser Val Lys Leu Ser Cys Thr Ala Ser Gly Phe Asp Ile Lys Asp Thr
145                 150                 155                 160

Tyr Ile His Trp Val Lys Gln Arg Pro Glu Gln Gly Leu Glu Trp Ile
                165                 170                 175

Gly Arg Ile Asp Pro Ala Asn Gly Asp Thr Arg Tyr Asp Pro Glu Phe
            180                 185                 190

Gln Gly Lys Ala Ser Leu Thr Ala Asp Thr Ser Ser Asn Thr Ala Tyr
            195                 200                 205

Leu Gln Phe Ser Asn Leu Thr Ser Glu Asp Thr Ala Val Tyr Tyr Cys
            210                 215                 220

Ala Arg Arg Gly Gly Leu Ser Trp Gly Gln Gly Thr Thr Leu Thr Val
225                 230                 235                 240

Ser Ser

<210> SEQ ID NO 104
<211> LENGTH: 244
<212> TYPE: PRT
<213> ORGANISM: Artificial Sequence
<220> FEATURE:
<223> OTHER INFORMATION: Synthetic Construct

<400> SEQUENCE: 104

Asp Thr Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Tyr Arg
            20                  25                  30

Ser Asn Gln Lys Asn Tyr Leu Ala Trp Tyr Gln Gln Lys Pro Gly Gln
            35                  40                  45

Ser Pro Lys Gln Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys Gly Gly Gly Ser Gly Gly Gly Ser Gly Gly Gly Ser
            115                 120                 125

Glu Val Gln Leu Glu Glu Ser Gly Gly Gly Leu Val Gln Pro Lys Gly
            130                 135                 140

Ser Leu Lys Leu Ser Cys Ala Ala Ser Gly Phe Thr Phe Asn Thr Tyr
145                 150                 155                 160

Ala Met Tyr Trp Val Cys Gln Ala Pro Gly Lys Gly Leu Lys Trp Val
                165                 170                 175

Ala Arg Ile Arg Ser Lys Val Asn Asn Tyr Ala Thr Tyr Tyr Ala Asp
            180                 185                 190

Ser Val Lys Asp Arg Phe Thr Ile Ser Arg Asp Asp Ser Gln Asn Met
            195                 200                 205

Leu Phe Leu His Met Asn Asn Leu Lys Thr Glu Asp Thr Ala Ile Tyr
210                 215                 220

Phe Cys Val Arg Asp Pro Met Asp Tyr Trp Gly Gln Gly Ile Ser Val
225                 230                 235                 240

Thr Val Ser Ser

<210> SEQ ID NO 105
<211> LENGTH: 244
<212> TYPE: PRT
<213> ORGANISM: Artificial Sequence
<220> FEATURE:
<223> OTHER INFORMATION: Synthetic Construct

<400> SEQUENCE: 105

Asp Thr Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Tyr Arg
                20                  25                  30

Ser Asn Gln Lys Asn Tyr Leu Ala Trp Tyr Gln Lys Pro Gly Gln
        35                  40                  45

Ser Pro Lys Gln Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
                100                 105                 110

Lys Gly Gly Gly Gly Ser Gly Gly Gly Ser Gly Gly Gly Gly Ser
            115                 120                 125

Glu Val Gln Leu Val Glu Ser Gly Gly Gly Leu Val Gln Pro Lys Gly
            130                 135                 140

Ser Leu Lys Leu Ser Cys Ala Ala Ser Gly Phe Thr Phe Asn Thr Tyr
145                 150                 155                 160

Ala Met Tyr Trp Val Cys Gln Ala Pro Gly Lys Gly Leu Lys Trp Val
                165                 170                 175

Ala Arg Ile Arg Ser Lys Val Asn Asn Tyr Ala Thr Tyr Tyr Ala Asp
                180                 185                 190

Ser Val Lys Asp Arg Phe Thr Ile Ser Arg Asp Asp Ser Gln Asn Met
            195                 200                 205

Leu Phe Leu His Met Asn Asn Leu Lys Thr Glu Asp Thr Ala Ile Tyr
210                 215                 220

Phe Cys Val Arg Asp Pro Met Asp Tyr Trp Gly Gln Gly Ile Ser Val
225                 230                 235                 240

Thr Val Ser Ser

<210> SEQ ID NO 106
<211> LENGTH: 249
<212> TYPE: PRT
<213> ORGANISM: Artificial Sequence
<220> FEATURE:
<223> OTHER INFORMATION: Synthetic Construct

<400> SEQUENCE: 106

Asp Thr Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Tyr Arg

```
            20                  25                  30
Ser Asn Gln Lys Asn Tyr Leu Ala Trp Tyr Gln Gln Lys Pro Gly Gln
        35                  40                  45

Ser Pro Lys Gln Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys Gly Gly Gly Gly Ser Gly Gly Gly Gly Ser Gly Gly Gly Gly Ser
        115                 120                 125

Gln Val Gln Leu Gln Gln Ser Gly Ala Glu Leu Ala Arg Pro Gly Ala
    130                 135                 140

Ser Val Lys Leu Ser Cys Lys Ala Ser Gly Tyr Thr Phe Thr Thr Phe
145                 150                 155                 160

Trp Met Gln Trp Val Lys Gln Arg Pro Gly Gln Gly Leu Glu Trp Ile
                165                 170                 175

Gly Thr Ile Tyr Pro Gly Asp Asp Thr Arg Tyr Thr Gln Lys Phe
            180                 185                 190

Lys Gly Arg Ala Thr Leu Thr Ala Asp Lys Ser Ser Thr Thr Ala Tyr
        195                 200                 205

Met Gln Leu Ser Asn Leu Ser Ser Glu Asp Ser Ala Val Tyr Tyr Cys
    210                 215                 220

Ala Arg Ser Gly Tyr Glu Arg Gly Pro Tyr Tyr Phe Asp Ser Trp Gly
225                 230                 235                 240

Gln Gly Thr Thr Leu Thr Val Ser Ser
                245

<210> SEQ ID NO 107
<211> LENGTH: 249
<212> TYPE: PRT
<213> ORGANISM: Artificial Sequence
<220> FEATURE:
<223> OTHER INFORMATION: Synthetic Construct

<400> SEQUENCE: 107

Asp Thr Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Tyr Arg
            20                  25                  30

Ser Asn Gln Lys Asn Tyr Leu Ala Trp Tyr Gln Gln Lys Pro Gly Gln
        35                  40                  45

Ser Pro Lys Gln Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys Gly Gly Gly Gly Ser Gly Gly Gly Gly Ser Gly Gly Gly Gly Ser
        115                 120                 125

Asp Val Lys Leu Gln Glu Ser Gly Ala Glu Leu Ala Arg Pro Gly Ala
```

```
            130                 135                 140

Ser Val Lys Leu Ser Cys Lys Ala Ser Gly Tyr Thr Phe Thr Thr Phe
145                 150                 155                 160

Trp Met Gln Arg Val Lys Gln Arg Pro Gly Gln Gly Leu Glu Trp Ile
                165                 170                 175

Gly Thr Ile Tyr Pro Gly Asp Asp Thr Arg Tyr Thr Gln Lys Phe
            180                 185                 190

Lys Gly Arg Ala Thr Leu Thr Ala Asp Lys Ser Ser Thr Thr Ala Tyr
            195                 200                 205

Met Gln Leu Ser Asn Leu Ser Ser Glu Asp Ser Ala Val Tyr Tyr Cys
            210                 215                 220

Ala Arg Ser Gly Tyr Glu Arg Gly Pro Tyr Tyr Phe Asp Ser Trp Gly
225                 230                 235                 240

Gln Gly Thr Thr Leu Thr Val Ser Ser
                245

<210> SEQ ID NO 108
<211> LENGTH: 249
<212> TYPE: PRT
<213> ORGANISM: Artificial Sequence
<220> FEATURE:
<223> OTHER INFORMATION: Synthetic Construct

<400> SEQUENCE: 108

Asp Thr Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Tyr Arg
                20                  25                  30

Ser Asn Gln Lys Asn Tyr Leu Ala Trp Tyr Gln Gln Lys Pro Gly Gln
            35                  40                  45

Ser Pro Lys Gln Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
                100                 105                 110

Lys Gly Gly Gly Gly Ser Gly Gly Gly Gly Ser Gly Gly Gly Gly Ser
            115                 120                 125

Gln Val Gln Leu Lys Glu Ser Gly Ala Glu Leu Ala Arg Pro Gly Ala
            130                 135                 140

Ser Val Lys Leu Ser Cys Lys Ala Ser Gly Tyr Thr Phe Thr Thr Phe
145                 150                 155                 160

Trp Met Gln Trp Ala Lys Gln Arg Pro Gly Gln Gly Leu Glu Trp Ile
                165                 170                 175

Gly Thr Ile Tyr Pro Gly Asp Asp Thr Arg Tyr Thr Gln Lys Phe
            180                 185                 190

Lys Gly Arg Ala Thr Leu Thr Ala Asp Lys Ser Ser Thr Thr Ala Tyr
            195                 200                 205

Met Gln Leu Ser Asn Leu Ser Ser Glu Asp Ser Ala Val Tyr Tyr Cys
            210                 215                 220
```

```
Ala Arg Ser Gly Tyr Glu Arg Gly Pro Tyr Tyr Phe Asp Ser Trp Gly
225                 230                 235                 240

Gln Gly Thr Thr Leu Thr Val Ser Ser
                245
```

COMPOSITIONS AND METHODS FOR TARGETING CD99-EXPRESSING CANCERS

CROSS-REFERENCE TO RELATED APPLICATIONS

This application is a National Stage of International Application No. PCT/US2019/012640, filed Jan. 8, 2019, which claims benefit of U.S. Provisional Application Ser. No. 62/614,779, filed Jan. 8, 2018, Application Ser. No. 62/654,617, filed Apr. 9, 2018, Application Ser. No. 62/654,625, filed Apr. 9, 2018, Application Ser. No. 62/730,374, filed Sep. 12, 2018, Application Ser. No. 62/730,397, filed Sep. 12, 2018, Application Ser. No. 62/767,864, filed Nov. 15, 2018, and Application Ser. No. 62/767,867, filed Nov. 15, 2018, which are all hereby incorporated herein by reference in their entirety.

SEQUENCE LISTING

This application contains a sequence listing filed in electronic form as an ASCII.txt file entitled "320103-2030 Sequence Listing_ST25" created on Jan. 6, 2019. The content of the sequence listing is incorporated herein in its entirety.

BACKGROUND

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are properly harnessed.

SUMMARY

Compositions and methods for targeted treatment of CD99-expressing cancers are disclosed. For example, anti-CD99 monoclonal antibodies from hybridomas 1H3, 4C5, 9G12, 3C7, 2F11, 4D5, 4F4, and 6A10 are provided herein. For example, antibodies from the hybridoma clones 1H3H7, 1H3E9, 4C5E2, 4C5H10, 9G12C9, and 9G12G6, demonstrated particularly good binding to CD99. Also disclosed are recombinant, humanized, and/or chimeric antibodies comprising at least the antigen binding regions of one or more of these antibodies.

Also disclosed herein are multispecific, multivalent antibodies that are able to engage T-cells to destroy CD99-expressing malignant cells. For example, the antibody can be a bi-specific T-cell engager. The antibodies can be engineered from fusion polypeptides, such as fusion polypeptides having the following formula:

$V_L I—V_H I—V_L T—V_H T$, $V_L T—V_H T—V_L I—V_H I$, $V_H T—V_L T—V_H I—V_L I$, $V_H I—V_L I—V_H T—V_L T$, $V_L I—V_H I—V_H T—V_L T$, $V_L T—V_H T—V_H I—V_L I$, wherein "$V_L I$" is a light chain variable domain specific for an immune cell antigen;

wherein "$V_H T$" is a heavy chain variable domain specific for CD99;

wherein "$V_L T$" is a light chain variable domain specific for CD99;

wherein "$V_H I$" is a heavy chain variable domain specific for the immune cell antigen; and wherein "-" consists of a peptide linker or a peptide bond.

The immune cell antigen can be a cell surface molecule that is expressed on human NK cells, T cells, monocytes, macrophages or granulocytes. For example, the cell surface molecule can be antigen CD2, CD3, CD16, CD64, CD89; NKp30, NKp44, NKp46, NKp80 (KLR-F1), NKG2C or NKG2D.

Also disclosed is an isolated nucleic acid encoding the disclosed fusion polypeptide, as well as nucleic acid vectors containing this isolated nucleic acid operably linked to an expression control sequence. Also disclosed are cells transfected with these vectors and the use of these cells to produce the disclosed fusion polypeptides.

Also disclosed is a pharmaceutical composition comprising a molecule disclosed herein in a pharmaceutically acceptable carrier. Also disclosed is a method for treating cancer in a subject that involves administering to the subject a therapeutically effective amount of a disclosed pharmaceutical composition. In some cases, the cancer can be any CD99-expressing malignancy. In some cases, the cancer comprises a myelodysplastic syndrome, acute myeloid leukemia, or bi-phenotypic leukemia.

Also disclosed are chimeric antigen receptor (CAR) polypeptides that can be used with adoptive cell transfer to target and kill CD99-expressing cancers. The disclosed CAR polypeptides contain in an ectodomain an anti-CD99 binding agent that can bind CD99-expressing cancer cells. Also disclosed is an immune effector cell genetically modified to express the disclosed CAR polypeptide.

The anti-CD99 binding agent is in some embodiments an antibody fragment that specifically binds CD99. For example, the antigen binding domain can be a Fab or a single-chain variable fragment (scFv) of an antibody that specifically binds CD99. The anti-CD99 binding agent is in some embodiments an aptamer that specifically binds CD99. For example, the anti-CD99 binding agent can be a peptide aptamer selected from a random sequence pool based on its ability to bind CD99. The anti-CD99 binding agent can also be a natural ligand of CD99, or a variant and/or fragment thereof capable of binding CD99.

In some embodiments, the anti-CD99 region of the disclosed antibody or CAR is derived from hybridoma 1H3, 4C5, 9G12, 3C7, 2F11, 4D5, 4F4, 6A10, or combinations thereof. In some embodiments, the anti-CD99 region (e.g. scFv) can comprise a variable heavy ($V_H$) domain having CDR1, CDR2 and CDR3 sequences and a variable light ($V_L$) domain having CDR1, CDR2 and CDR3 sequences.

In some embodiments, the CDR1 sequence of the $V_H$ domain comprises the amino acid sequence GFDIKDTY (SEQ ID NO:1), TYAMY (SEQ ID NO:2), TFWM (SEQ ID NO:3), or TFWMQ (SEQ ID NO:4); the CDR2 sequence of the $V_H$ domain comprises the amino acid sequence IDPANGDT (SEQ ID NO:5), RIRSKVNNYATYY-ADSVKDRFT (SEQ ID NO:6), or TIYPGDDDTRYTQKFKGRAT (SEQ ID NO:7); the CDR3 sequence of the $V_H$ domain comprises the amino acid sequence ARRGGLS (SEQ ID NO:8), DPMDY (SEQ ID NO:9), or SGYERGPYYFDS (SEQ ID NO:10), or SGYERGPYYF (SEQ ID NO: 11); the CDR1 sequence of the $V_L$ comprises the amino acid sequence GNIHNY (SEQ ID NO:12), GSSKSLLHSNGNTYLY (SEQ ID NO:13), KSSQSLLCRSNQKNYLA (SEQ ID NO:14), or KSSQSLLYRSNQKNYLA (SEQ ID NO:15); the CDR2 sequence of the $V_L$ domain comprises the amino acid sequence NAKX (SEQ ID NO:16), RVSNLAS (SEQ ID NO:17), or WASTRES (SEQ ID NO:18); and the CDR3 sequence of the $V_L$ domain comprises the amino acid sequence QHFWSTPWT (SEQ ID NO:19), MQHLEYPYT (SEQ ID NO:20), or QQYYSYPLT (SEQ ID NO:21).

Therefore, in some embodiments, the anti-CD99 $V_H$ domain comprises the amino acid sequence (SEQ ID NO: 22, 1H3H7)
EVQLQQSGAELVKPGASVKLSCTASGFDIKDTYIHWVKQRPEQGLEWIGR

IDPANGDTRYDPEFQGKASLTADTSSNTAYLQFSNLTSEDTAVYYCARRG

GLSWGQGTTLTVSS.

Therefore, in some embodiments, the anti-CD99 heavy chain is encoded by the nucleic acid sequence (SEQ ID NO: 23, 1H3H7)
GAGGTTCAACTGCAACAGTCTGGGGCAGAGCTTGTGAAGCCAGGGGCCTC

AGTCAAGTTGTCCTGCACAGCTTCTGGCTTCGACATTAAAGACACCTATA

TCCACTGGGTGAAACAGAGGCCTGAACAGGGCCTGGAGTGGATTGGAAGG

ATTGATCCTGCGAATGGTGATACTAGATATGACCCGGAATTCCAGGGCAA

GGCCTCTCTAACAGCTGACACATCCTCCAATACAGCCTACCTACAATTCA

GCAACCTGACATCTGAAGACACTGCCGTCTATTACTGTGCTAGAAGAGGC

GGCCTCTCCTGGGGCCAAGGCACCACTCTCACAGTCTCCTCA.

Therefore, in some embodiments, the anti-CD99 $V_H$ domain comprises the amino acid sequence (SEQ ID NO: 24, 4C5E2)
EVQLEESGGGLVQPKGSLKLSCAASGFTFNTYAMYVWCQAPGKGLKWVAR

IRSKVNNYATYYADSVKDRFTISRDDSQNMLFLHMNNLKTEDTAIYFCVR

DPMDYWGQGISVTVSS.

Therefore, in some embodiments, the anti-CD99 heavy chain is encoded by the nucleic acid sequence (SEQ ID NO: 25, 4C5E2)
GAGGTGCAGCTGGAGGAGTCTGGTGGAGGATTGGTGCAGCCTAAAGGATC

ATTGAAACTCTCATGTGCCGCCTCCGGTTTCACCTTCAATACCTATGCCA

TGTACTGGGTCTGCCAGGCTCCAGGAAAGGGTTTGAAATGGGTTGCTCGC

ATAAGAAGTAAAGTTAATAATTATGCAACATATTATGCCGATTCAGTGAA

AGACAGATTCACCATCTCCAGAGATGATTCACAAAACATGCTCTTTCTGC

ACATGAACAACCTGAAAACTGAGGACACTGCCATATATTTCTGTGTGAGA

GATCCTATGGACTACTGGGGTCAAGGAATCTCAGTCACCGTCTCCTCA.

Therefore, in some embodiments, the anti-CD99 $V_H$ domain comprises the amino acid sequence (SEQ ID NO: 26, 4C5H10)
EVQLVESGGGLVQPKGSLKLSCAASGFTFNTYAMYWVCQAPGKGLKWVAR

IRSKVNNYATYYADSVKDRFTISRDDSQNMLFLHMNNLKTEDTAIYFCVR

DPMDYWGQGISVTVSS.

Therefore, in some embodiments, the anti-CD99 heavy chain is encoded by the nucleic acid sequence (SEQ ID NO: 27, 4C5H10)
GAGGTGCAGCTTGTTGAGTCTGGTGGAGGATTGGTGCAGCCTAAAGGATC

ATTGAAACTCTCATGTGCCGCCTCCGGTTTCACCTTCAATACCTATGCCA

TGTACTGGGTCTGCCAGGCTCCAGGAAAGGGTTTGAAATGGGTTGCTCGC

ATAAGAAGTAAAGTTAATAATTATGCAACATATTATGCCGATTCAGTGAA

AGACAGATTCACCATCTCCAGAGATGATTCACAAAACATGCTCTTTCTGC

ACATGAACAACCTGAAAACTGAGGACACTGCCATATATTTCTGTGTGAGA

GATCCTATGGACTACTGGGGTCAAGGAATCTCAGTCACCGTCTCCTCA.

Therefore, in some embodiments, the anti-CD99 $V_H$ domain comprises the (SEQ ID NO: 28, 9G12C9)
QVQLQQSGAELARPGASVKLSCKASGYTFTTFWMQWVKQRPGQGLEWIGT

IYPGDDDTRYTQKFKGRATLTADKSSTTAYMQLSNLSSEDSAVYYCARSG

YERGPYYFDSWGQGTTLTVSS.

amino acid sequence (SEQ ID NO: 29, 9G12C9)
CAGGTTCAGCTCCAGCAGTCTGGGGCTGAGCTGGCAAGACCTGGGGCTTC

AGTGAAGTTGTCCTGCAAGGCTTCTGGCTACACGTTTACTACTTTCTGGA

TGCAGTGGGTAAAACAGAGGCCTGGACAGGGTCTGGAATGGATTGGGACT

ATTTATCCTGGAGATGATGATACTAGGTACACTCAGAAATTCAAGGGCAG

GGCCACATTGACTGCAGATAAATCGTCCACCACAGCCTACATGCAACTCA

GCAACTTGTCATCTGAGGACTCTGCGGTCTATTACTGTGCAAGATCGGGG

TATGAGAGGGCCCATACTACTTTGACTCCTGGGGCCAAGGCACCACTCT

CACAGTCTCCTCA.

Therefore, in some embodiments, the anti-CD99 heavy chain is encoded by the nucleic acid sequence (SEQ ID NO: 30, 9G12G6 HB1)
DVKLQESGAELARPGASVKLSCKASGYTFTTFWMQRVKQRPGQGLEWIGT

IYPGDDDTRYTQKFKGRATLTADKSSTTAYMQLSNLSSEDSAVYYCARSG

YERGPYYFDSWGQGTTLTVSS.

Therefore, in some embodiments, the anti-CD99 $V_H$ domain comprises the amino acid sequence Therefore, in some embodiments, the anti-CD99 heavy chain is encoded by the nucleic acid sequence (SEQ ID NO: 31, 9G12G6 HB1)
GATGTGAAGCTTCAGGAGTCTGGGGCTGAGCTGGCAAGACCTGGGGCTTC

AGTGAAGTTGTCCTGCAAGGCTTCTGGCTACACGTTTACTACTTTCTGGA

TGCAGCGGGTAAAACAGAGGCCTGGACAGGGTCTGGAATGGATTGGGACT

ATTTATCCTGGAGATGATGATACTAGGTACACTCAGAAATTCAAGGGCAG

GGCCACATTGACTGCAGATAAATCGTCCACCACAGCCTACATGCAACTCA

GCAACTTGTCATCTGAGGACTCTGCGGTCTATTACTGTGCAAGATCGGGG

TATGAGAGGGGCCCATACTACTTTGACTCCTGGGGCCAAGGCACCACTCT

CACAGTCTCCTCA.

In some embodiments, the anti-CD99 $V_H$ domain comprises the amino acid sequence (SEQ ID NO: 32, 9G12G6 HB3)
QVQLKESGAELARPGASVKLSCKASGYTFTTFWMQWAKQRPGQGLEWIGT

IYPGDDDTRYTQKFKGRATLTADKSSTTAYMQLSNLSSEDSAVYYCARSG

YERGPYYFDSWGQGTTLTVSS.

Therefore, in some embodiments, the anti-CD99 heavy chain is encoded by the nucleic acid sequence (SEQ ID NO: 33, 9G12G6HB3)
CAGGTGCAGCTGAAGGAGTCTGGGGCTGAGCTGGCAAGACCTGGGGCTTC

AGTGAAGTTGTCCTGCAAGGCTTCTGGCTACACGTTTACTACTTTCTGGA

TGCAGTGGGCAAAACAGAGGCCTGGACAGGGTCTGGAATGGATTGGGACT

ATTTATCCTGGAGATGATGATACTAGGTACACTCAGAAATTCAAGCCCAG

GGCCACATTGACTGCAGATAAATCGTCCACCACAGCCTACATGCAACTCA

GCAACTTGTCATCTGAGGACTCTGCGGTCTATTACTGTGCAAGATCGGGG

TATGAGAGGGGCCCATACTACTTTGACTCCTGGGGCCAAGGCACCACTCT

CACAGTCTCCTCA.

In some embodiments, the anti-CD99 $V_L$ domain comprises the amino acid sequence (SEQ ID NO: 34, 1H3H9)
DIQMTQSPASLSASVGETVTITCRASGNIHNYLAWYQQKQGKSPQLLVYN

AKTLADGVPSRFSGSGSGTQYSLKINSLQPEDFGSYYCQHFWSTPWTFGG

GTKLEIK.

Therefore, in some embodiments, the anti-CD99 light chain is encoded by the nucleic acid sequence (SEQ ID NO: 35, 1H3H9)
GACATCCAGATGACTCAGTCTCCAGCCTCCCTATCTGCATCTGTGGGAGA

AACTGTCACCATCACATGTCGAGCAAGTGGGAATATTCACAATTATTTAG

CATGGTATCAGCAGAAACAGGGAAAATCTCCTCAGCTCCTGGTCTATAAT

GCAAAAACCTTAGCAGATGGTGTGCCATCAAGGTTCAGTGGCAGTGGATC

AGGAACACAATATTCTCTCAAGATCAACAGCCTGCAGCCTGAAGATTTTG

GGAGTTATTACTGTCAACATTTTTGGAGTACTCCGTGGACGTTCGGTGGA

GGCACCAAGCTGGAAATCAAA.

In some embodiments, the anti-CD99 $V_L$ domain comprises the amino acid sequence (SEQ ID NO: 36, 1H3H7 LC1)
GNSWSHSLRSLSVTIGQPASISCKSSQSLLDGNGKTYLNWLLQRPGQSPK

RLLYLVSKLDSGVPDRFTGSGSGTDFTLKISRVEAEDLGIYYCWQGTHFP

RTFGGGTKLEIK.

In some embodiments, the anti-CD99 $V_L$ domain comprises the amino acid sequence (SEQ ID NO: 37, 1H3H7 LC2)
GNSWRHSPRSLSVTIGQPASISCKSSQSLLDGNGKTYLNWLLQRPGQSPK

RLLYLVSKLDSGVPDRFTGSGSGTDFTLKISRVEAEDLGIYYCWQGTHFP

RTFGGGTKLEIK.

In some embodiments, the anti-CD99 $V_L$ domain comprises the amino acid sequence (SEQ ID NO: 38, 4C5E2)
DIVMTQAAPSVPVTPGESVSISCGSSKSLLHSNGNTYLYWFLQRPGQSPQ

LLIYRVSNLASGVPDRFSGSGSGTAFTLRISRVEAEDVGVYYCMQHLEYP

YTFGGGTRLEIK.

Therefore, in some embodiments, the anti-CD99 light chain is encoded by the nucleic acid sequence (SEQ ID NO: 39, 4C5E2)
GATATTGTGATGACTCAGGCTGCACCCTCTGTACCTGTCACTCCTGGGGA

GTCAGTATCCATCTCCTGCGGGTCTAGTAAGAGTCTCCTGCATAGTAATG

GCAACACTTACTTGTATTGGTTCCTGCAGAGGCCAGGCCAGTCTCCTCAG

CTCCTGATATATCGGGTGTCCAACCTTGCCTCAGGAGTCCCAGACAGGTT

CAGTGGCAGTGGGTCAGGAACTGCTTTCACACTGAGAATCAGTAGAGTGG

AGGCTGAGGATGTGGGTGTTTATTACTGTATGCAACATCTAGAATATCCG

TACACGTTCGGAGGGGGGACCAGGCTGGAAATAAAA.

In some embodiments, the anti-CD99 $V_L$ domain comprises the amino acid sequence (SEQ ID NO: 40, 4C5H10)
DIVMTQAAPSVPVTPGESVSISCGSSKSLLHSNGNTYLYWFLQRPGQSPQ

LLIYRVSNLASGVPDRFSGSGSGTAFTLRISRVEAEDVGVYYCMQHLEYP

YTFGGGTRLEIK.

Therefore, in some embodiments, the anti-CD99 light chain is encoded by the nucleic acid sequence (SEQ ID NO: 41, 4C5H10)
GATATTGTGATGACTCAGGCTGCACCCTCTGTACCTGTCACTCCTGGGGA

GTCAGTATCCATCTCCTGCGGGTCTAGTAAGAGTCTCCTGCATAGTAATG

GCAACACTTACTTGTATTGGTTCCTGCAGAGGCCAGGCCAGTCTCCTCAG

CTCCTGATATATCGGGTGTCCAACCTTGCCTCAGGAGTCCCAGACAGGTT

CAGTGGCAGTGGGTCAGGAACTGCTTTCACACTGAGAATCAGTAGAGTGG

-continued
AGGCTGAGGATGTGGGTGTTTATTACTGTATGCAACATCTAGAATATCCG

TACACGTTCGGAGGGGGACCAGGCTGGAAATAAAA.

In some embodiments, the anti-CD99 $V_L$ domain comprises the amino acid sequence (SEQ ID NO: 42, 9G12C9)
DTVMSQSPSSLAVSVGEKITMSCKSSQSLLCRSNQKNYLAWYQQKPGQSP

KQUYWASTRESGVPDRFTGSGSGTDFTLTISSVKAEDLAVYYCQQYYSYP

LTFGAGTKLELK.

Therefore, in some embodiments, the anti-CD99 light chain is encoded by the nucleic acid sequence (SEQ ID NO: 43, 9G12C9)
GACACTGTGATGTCACAGTCCCCATCCTCCCTAGCTGTTTCAGTTGGAGA

GAAGATAACTATGAGCTGCAAGTCCAGTCAGAGTCTTTTATGTCGTAGCA

ATCAAAAGAACTACTTGGCCTGGTACCAGCAGAAACCAGGGCAGTCTCCT

AAACAGCTGATTTACTGGGCATCTACTAGGGAATCTGGGGTCCCTGATCG

CTTCACAGGCAGTGGATCTGGGACAGATTTCACTCTCACCATCAGCAGTG

TGAAGGCTGAAGACCTGGCAGTTTATTACTGTCAGCAATATTATAGTTAT

CCGCTCACGTTCGGTGCTGGCACCAAGCTGGAGCTGAAA.

In some embodiments, the anti-CD99 $V_L$ domain comprises the amino acid sequence (SEQ ID NO: 44, 9G12G6)
DTVMSQSPSSLAVSVGEKITMSCKSSQSLLYRSNQKNYLAWYQQKPGQSP

KQLIYWASTRESGVPDRFTGSGSGTDFTLTISSVKAEDLAVYYCQQYYSY

PLTFGAGTKLELK.

Therefore, in some embodiments, the anti-CD99 light chain is encoded by the nucleic acid sequence (SEQ ID NO: 45, 9G12G6)
GACACTGTGATGTCACAGTCCCCATCCTCCCTAGCTGTTTCAGTTGGAGA

GAAGATAACTATGAGCTGCAAGTCCAGTCAGAGTCTTTTATATCGTAGCA

ATCAAAAGAACTACTTGGCCTGGTACCAGCAGAAACCAGGGCAGTCTCCT

AAACAGCTGATTTACTGGGCATCTACTAGGGAATCTGGGGTCCCTGATCG

CTTCACAGGCAGTGGATCTGGGACAGATTTCACTCTCACCATCAGCAGTG

TGAAGGCTGAAGACCTGGCAGTTTATTACTGTCAGCAATATTATAGTTAT

CCGCTCACGTTCGGTGCTGGCACCAAGCTGGAGCTGAAA.

The heavy and light chains are preferably separated by a linker. Suitable linkers for scFv antibodies are known in the art. In some embodiments, the linker comprises the amino acid sequence GGGGSGGGGSGGGGS (SEQ ID NO:46). The scFv can have the formula $NH_3$—$V_H$-linker—$V_L$—COOH or $NH_3$—$V_L$-linker-$V_H$—COOH.

In some embodiments, the anti-CD99 scFv comprises an amino acid sequence:

(SEQ ID NO: 47)
EVQLQQSGAELVKPGASVKLSCTASGFDIKDTYIHWVKQRPEQGLEWIGR

IDPANGDTRYDPEFQGKASLTADTSSNTAYLQFSNLTSEDTAVYYCARRG

GLSWGQGTTLTVSSGGGGSGGGGSGGGGSDIQMTQSPASLSASVGETVTI

TCRASGNIHNYLAWYQQKQGKSPQLLVYNAKTLADGVPSRFSGSGSGTQY

SLKINSLQPEDFGSYYCQHFWSTPWTTFGGGTKLEIK.

In some embodiments, the anti-CD99 scFv comprises an amino acid sequence:

(SEQ ID NO: 48)
EVQLQQSGAELVKPGASVKLSCTASGFDIKDTYIHWVKQRPEQGLEWIGR

IDPANGDTRYDPEFQGKASLTADTSSNTAYLQFSNLTSEDTAVYYCARRG

GLSWGQGTTLTVSSGGGGSGGGGSGGGGSGNSWSHSLRSLSVTIGQPASI

SCKSSQSLLDGNGKTYLNWLLQRPGQSPKRLLYLVSKLDSGVPDRFTGSG

SGTDFTLKISRVEAEDLGIYYCWQGTHFPRTFGGGTKLEIK.

In some embodiments, the anti-CD99 scFv comprises an amino acid sequence:

(SEQ ID NO: 49)
EVQLQQSGAELVKPGASVKLSCTASGFDIKDTYIHWVKQRPEQGLEWIGRI

DPANGDTRYDPEFQGKASLTADTSSNTAYLQFSNLTSEDTAVYYCARRGGL

SWGQGTTLTVSSGGGGSGGGGSGGGGSGNSWRHSPRSLSVTIGQPASISCK

SSQSLLDGNGKTYLNWLLQRPGQSPKRLLYLVSKLDSGVPDRFTGSGSGTD

FTLKISRVEAEDLGIYYCWQGTHFPRTFGGGTKLEIK.

In some embodiments, the anti-CD99 scFv comprises an amino acid sequence:

(SEQ ID NO: 50)
EVQLQQSGAELVKPGASVKLSCTASGFDIKDTYIHWVKQRPEQGLEWIGRI

DPANGDTRYDPEFQGKASLTADTSSNTAYLQFSNLTSEDTAVYYCARRGGL

SWGQGTTLTVSSGGGGSGGGGSGGGGSDIVMTQAAPSVPVTPGESVSISCG

SSKSLLHSNGNTYLYWFLQRPGQSPQLLIYRVSNLASGVPDRFSGSGSGTA

FTLRISRVEAEDVGVYYCMQHLEYPYTFGGGTRLEIK.

In some embodiments, the anti-CD99 scFv comprises an amino acid sequence:

(SEQ ID NO: 51)
EVQLQQSGAELVKPGASVKLSCTASGFDIKDTYIHWVKQRPEQGLEWIGRI

DPANGDTRYDPEFQGKASLTADTSSNTAYLQFSNLTSEDTAVYYCARRGGL

SWGQGTTLTVSSGGGGSGGGGSGGGGSDTVMSQSPSSLAVSVGEKITMSCK

SSQSLLCRSNQKNYLAWYQQKPGQSPKQLIYWASTRESGVPDRFTGSGSGT

DFTLTISSVKAEDLAVYYCQQYYSYPLTFGAGTKLELK.

In some embodiments, the anti-CD99 scFv comprises an amino acid sequence:

(SEQ ID NO: 52)
EVQLQQSGAELVKPGASVKLSCTASGFDIKDTYIHWVKQRPEQGLEWIGRI
DPANGDTRYDPEFQGKASLTADTSSNTAYLQFSNLTSEDTAVYYCARRGGL
SWGQGTTLTVSSGGGGSGGGGSGGGGSDTVMSQSPSSLAVSVGEKITMSCK
SSQSLLYRSNQKNYLAWYQQKPGQSPKQLIYWASTRESGVPDRFTGSGSGT
DFTLTISSVKAEDLAVYYCQQYYSYPLTFGAGTKLELK.

In some embodiments, the anti-CD99 scFv comprises an amino acid sequence:

(SEQ ID NO: 53)
EVQLEESGGGLVQPKGSLKLSCAASGFTFNTYAMYWVCQAPGKGLKWVARI
RSKVNNYATYYADSVKDRFTISRDDSQNMLFLHMNNLKTEDTAIYFCVRDP
MDYWGQGISVTVSSGGGGSGGGGSGGGGSDIQMTQSPASLSASVGETVTIT
CRASGNIHNYLAWYQQKQGKSPQLLVYNAKTLADGVPSRFSGSGSGTQYSL
KINSLQPEDFGSYYCQHFWSTPWTFGGGTKLEIK.

In some embodiments, the anti-CD99 scFv comprises an amino acid sequence:

(SEQ ID NO: 54)
EVQLEESGGGLVQPKGSLKLSCAASGFTFNTYAMYWVCQAPGKGLKMARIR
SKVNNYATYYADSVKDRFTISRDDSQNMLFLHMNNLKTEDTAIYFCVRDPM
DYWGQGISVTVSSGGGGSGGGGSGGGGSGNSWSHSLRSLSVTIGQPASISC
KSSQSLLDGNGKTYLNWLLQRPGQSPKRLLYLVSKLDSGVPDRFTGSGSGT
DFTLKISRVEAEDLGIYYCWQGTHFPRTFGGGTKLEIK.

In some embodiments, the anti-CD99 scFv comprises an amino acid sequence:

(SEQ ID NO: 55)
EVQLEESGGGLVQPKGSLKLSCAASGFTFNTYAMYWVCQAPGKGLKWVARI
RSKVNNYATYYADSVKDRFTISRDDSQNMLFLHMNNLKTEDTAIYFCVRDP
MDYWGQGISVTVSSGGGGSGGGGSGGGGSGNSWRHSPRSLSVTIGQPASIS
CKSSQSLLDGNGKTYLNWLLQRPGQSPKRLLYLVSKLDSGVPDRFTGSGSG
TDFTLKISRVEAEDLGIYYCWQGTHFPRTFGGGTKLEIK.

In some embodiments, the anti-CD99 scFv comprises an amino acid sequence:

(SEQ ID NO: 56)
EVQLEESGGGLVQPKGSLKLSCAASGFTFNTYAMYWVCQAPGKGLKWVARI
RSKVNNYATYYADSVKDRFTISRDDSQNMLFLHMNNLKTEDTAIYFCVRDP
MDYWGQGISVTVSSGGGGSGGGGSGGGGSDIVMTQAAPSVPVTPGESVSIS
CGSSKSLLHSNGNTYLYWFLQRPGQSPQLLIYRVSNLASGVPDRFSGSGSG
TAFTLRISRVEAEDVGVYYCMQHLEYPYTFGGGTRLEIK.

In some embodiments, the anti-CD99 scFv comprises an amino acid sequence:

(SEQ ID NO: 57)
EVQLEESGGGLVQPKGSLKLSCAASGFTFNTYAMYWVCQAPGKGLKWVARI
RSKVNNYATYYADSVKDRFTISRDDSQNMLFLHMNNLKTEDTAIYFCVRDP
MDYWGQGISVTVSSGGGGSGGGGSGGGGSDTVMSQSPSSLAVSVGEKITMS
CKSSQSLLCRSNQKNYLAWYQQKPGQSPKQLIYWASTRESGVPDRFTGSGS
GTDFTLTISSVKAEDLAVYYCQQYYSYPLTFGAGTKLELK.

In some embodiments, the anti-CD99 scFv comprises an amino acid sequence:

(SEQ ID NO: 58)
EVQLEESGGGLVQPKGSLKLSCAASGFTFNTYAMYWVCQAPGKGLKWVARI
RSKVNNYATYYADSVKDRFTISRDDSQNMLFLHMNNLKTEDTAIYFCVRDP
MDYWGQGISVTVSSGGGGSGGGGSGGGGSDTVMSQSPSSLAVSVGEKITMS
CKSSQSLLYRSNQKNYLAWYQQKPGQSPKQLIYWASTRESGVPDRFTGSGS
GTDFTLTISSVKAEDLAVYYCQQYYSYPLTFGAGTKLELK.

In some embodiments, the anti-CD99 scFv comprises an amino acid sequence:

(SEQ ID NO: 59)
EVQLVESGGGLVQPKGSLKLSCAASGFTFNTYAMYWVCQAPGKGLKWVARI
RSKVNNYATYYADSVKDRFTISRDDSQNMLFLHMNNLKTEDTAIYFCVRDP
MDYWGQGISVTVSSGGGGSGGGGSGGGGSDIQMTQSPASLSASVGETVTIT
CRASGNIHNYLAWYQQKQGKSPQLLVYNAKTLADGVPSRFSGSGSGTQYSL
KINSLQPEDFGSYYCQHFWSTPWTFGGGTKLEIK.

In some embodiments, the anti-CD99 scFv comprises an amino acid sequence:

(SEQ ID NO: 60)
EVQLVESGGGLVQPKGSLKLSCAASGFTFNTYAMYWVCQAPGKGLKWVARI
RSKVNNYATYYADSVKDRFTISRDDSQNMLFLHMNNLKTEDTAIYFCVRDP
MDYWGQGISVTVSSGGGGSGGGGSGGGGSGNSWSHSLRSLSVTIGQPASIS
CKSSQSLLDGNGKTYLNWLLQRPGQSPKRLLYLVSKLDSGVPDRFTGSGSG
TDFTLKISRVEAEDLGIYYCWQGTHFPRTFGGGTKLEIK.

In some embodiments, the anti-CD99 scFv comprises an amino acid sequence:

(SEQ ID NO: 61)
EVQLVESGGGLVQPKGSLKLSCAASGFTFNTYAMYWVCQAPGKGLKWVARI
RSKVNNYATYYADSVKDRFTISRDDSQNMLFLHMNNLKTEDTAIYFCVRDP
MDYWGQGISVTVSSGGGGSGGGGSGGGGSGNSWRHSPRSLSVTIGQPASIS
CKSSQSLLDGNGKTYLNWLLQRPGQSPKRLLYLVSKLDSGVPDRFTGSGSG
TDFTLKISRVEAEDLGIYYCWQGTHFPRTFGGGTKLEIK.

In some embodiments, the anti-CD99 scFv comprises an amino acid sequence:

(SEQ ID NO: 62)
EVQLVESGGGLVQPKGSLKLSCAASGFTFNTYAMYWVCQAPGKGLKWVARI
RSKVNNYATYYADSVKDRFTISRDDSQNMLFLHMNNLKTEDTAIYFCVRDP
MDYWGQGISVTVSSGGGGSGGGGSGGGGSDIVMTQAAPSVPVTPGESVSIS
CGSSKSLLHSNGNTYLYWFLQRPGQSPQLLIYRVSNLASGVPDRFSGSGSG
TAFTLRISRVEAEDVGVYYCMQHLEYPYTFGGGTRLEIK.

In some embodiments, the anti-CD99 scFv comprises an amino acid sequence:

(SEQ ID NO: 63)
EVQLVESGGGLVQPKGSLKLSCAASGFTFNTYAMYWVCQAPGKGLKWVARI
RSKVNNYATYYADSVKDRFTISRDDSQNMLFLHMNNLKTEDTAIYFCVRDP
MDYWGQGISVTVSSGGGGSGGGGSGGGGSDTVMSQSPSSLAVSVGEKITMS
CKSSQSLLCRSNQKNYLAWYQQKPGQSPKQLIYWASTRESGVPDRFTGSGS
GTDFTLTISSVKAEDLAVYYCQQYYSYPLTFGAGTKLELK.

In some embodiments, the anti-CD99 scFv comprises an amino acid sequence:

(SEQ ID NO: 64)
EVQLVESGGGLVQPKGSLKLSCAASGFTFNTYAMYWVCQAPGKGLKWVARI
RSKVNNYATYYADSVKDRFTISRDDSQNMLFLHMNNLKTEDTAIYFCVRDP
MDYWGQGISVTVSSGGGGSGGGGSGGGGSDTVMSQSPSSLAVSVGEKITMS
CKSSQSLLYRSNQKNYLAWYQQKPGQSPKQLIYWASTRESGVPDRFTGSGS
GTDFTLTISSVKAEDLAVYYCQQYYSYPLTFGAGTKLELK.

In some embodiments, the anti-CD99 scFv comprises an amino acid sequence:

(SEQ ID NO: 65)
QVQLQQSGAELARPGASVKLSCKASGYTFTTFWMQWVKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSDIQMTQSPASLSASVGE
TVTITCRASGNIHNYLAWYQQKQGKSPQLLVYNAKTLADGVPSRFSGSGSG
TQYSLKINSLQPEDFGSYYCQHFWSTPWTFGGGTKLEIK.

In some embodiments, the anti-CD99 scFv comprises an amino acid sequence:

(SEQ ID NO: 66)
QVQLQQSGAELARPGASVKLSCKASGYTFTTFWMQWVKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSGNSWSHSLRSLSVTIGQ
PASISCKSSQSLLDGNGKTYLNWLLQRPGQSPKRLLYLVSKLDSGVPDRFT
GSGSGTDFTLKISRVEAEDLGIYYCWQGTHFPRTFGGGTKLEIK.

In some embodiments, the anti-CD99 scFv comprises an amino acid sequence:

(SEQ ID NO: 67)
QVQLQQSGAELARPGASVKLSCKASGYTFTTFWMQWVKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSGNSWRHSPRSLSVTIGQ
PASISCKSSQSLLDGNGKTYLNWLLQRPGQSPKRLLYLVSKLDSGVPDRFT
GSGSGTDFTLKISRVEAEDLGIYYCWQGTHFPRTFGGGTKLEIK.

In some embodiments, the anti-CD99 scFv comprises an amino acid sequence:

(SEQ ID NO: 68)
QVQLQQSGAELARPGASVKLSCKASGYTFTTFWMQWVKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSDIVMTQAAPSVPVTPGE
SVSISCGSSKSLLHSNGNTYLYWFLQRPGQSPQLLIYRVSNLASGVPDRFS
GSGSGTAFTLRISRVEAEDVGVYYCMQHLEYPYTFGGGTRLEIK.

In some embodiments, the anti-CD99 scFv comprises an amino acid sequence:

(SEQ ID NO: 69)
QVQLQQSGAELARPGASVKLSCKASGYTFTTFWMQWVKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSDTVMSQSPSSLAVSVGE
KITMSCKSSQSLLCRSNQKNYLAWYQQKPGQSPKQLIYWASTRESGVPDRF
TGSGSGTDFTLTISSVKAEDLAVYYCQQYYSYPLTFGAGTKLELK.

In some embodiments, the anti-CD99 scFv comprises an amino acid sequence:

(SEQ ID NO: 70)
QVQLQQSGAELARPGASVKLSCKASGYTFTTFWMQWVKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSDTVMSQSPSSLAVSVGE
KITMSCKSSQSLLYRSNQKNYLAWYQQKPGQSPKQUYWASTRESGVPDRFT
GSGSGTDFTLTISSVKAEDLAVYYCQQYYSYPLTFGAGTKLELK.

In some embodiments, the anti-CD99 scFv comprises an amino acid sequence:

(SEQ ID NO: 71)
DVKLQESGAELARPGASVKLSCKASGYTFTTFWMQRVKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSDIQMTQSPASLSASVGE
TVTITCRASGNIHNYLAWYQQKQGKSPQLLVYNAKTLADGVPSRFSGSGSG
TQYSLKINSLQPEDFGSYYCQHFWSTPWTFGGGTKLEIK.

In some embodiments, the anti-CD99 scFv comprises an amino acid sequence:

(SEQ ID NO: 72)
DVKLQESGAELARPGASVKLSCKASGYTFTTFWMQRVKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSGNSWSHSLRSLSVTIGQ
PASISCKSSQSLLDGNGKTYLNWLLQRPGQSPKRLLYLVSKLDSGVPDRFT
GSGSGTDFTLKISRVEAEDLGIYYCWQGTHFPRTFGGGTKLEIK.

In some embodiments, the anti-CD99 scFv comprises an amino acid sequence:

(SEQ ID NO: 73)
DVKLQESGAELARPGASVKLSCKASGYTFTTFWMQRVKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSGNSWRHSPRSLSVTIGQ
PASISCKSSQSLLDGNGKTYLNWLLQRPGQSPKRLLYLVSKLDSGVPDRFT
GSGSGTDFTLKISRVEAEDLGIYYCWQGTHFPRTFGGGTKLEIK.

In some embodiments, the anti-CD99 scFv comprises an amino acid sequence:

(SEQ ID NO: 74)
DVKLQESGAELARPGASVKLSCKASGYTFTTFWMQRVKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSDIVMTQAAPSVPVTPGE
SVSISCGSSKSLLHSNGNTYLYWFLQRPGQSPQLLIYRVSNLASGVPDRFS
GSGSGTAFTLRISRVEAEDVGVYYCMQHLEYPYTFGGGTRLEIK.

In some embodiments, the anti-CD99 scFv comprises an amino acid sequence:

(SEQ ID NO: 75)
DVKLQESGAELARPGASVKLSCKASGYTFTTFWMQRVKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSDIVMTQAAPSVPVTPGE
SVSISCGSSKSLLHSNGNTYLYWFLQRPGQSPQLLIYRVSNLASGVPDRFS
GSGSGTAFTLRISRVEAEDVGVYYCMQHLEYPYTFGGGTRLEIK.

In some embodiments, the anti-CD99 scFv comprises an amino acid sequence:

(SEQ ID NO: 76)
DVKLQESGAELARPGASVKLSCKASGYTFTTFWMQRVKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSDTVMSQSPSSLAVSVGE
KITMSCKSSQSLLCRSNQKNYLAWYQQKPGQSPKQUYWASTRESGVPDRFT
GSGSGTDFTLTISSVKAEDLAVYYCQQYYSYPLTFGAGTKLELK.

In some embodiments, the anti-CD99 scFv comprises an amino acid sequence:

(SEQ ID NO: 77)
DVKLQESGAELARPGASVKLSCKASGYTFTTFWMQRVKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSDTVMSQSPSSLAVSVGE
KITMSCKSSQSLLYRSNQKNYLAWYQQKPGQSPKQUYWASTRESGVPDRFT
GSGSGTDFTLTISSVKAEDLAVYYCQQYYSYPLTFGAGTKLELK.

In some embodiments, the anti-CD99 scFv comprises an amino acid sequence:

(SEQ ID NO: 78)
QVQLKESGAELARPGASVKLSCKASGYTFTTFWMQWAKQRPGQGLEWIGTI
YPGDDDTRYTQKFKGRATLTADKSSTTAYMQLSNLSSEDSAVYYCARSGYE
RGPYYFDSWGQGTTLTVSSGGGGSGGGGSGGGGSDIQMTQSPASLSASVGE
TVTITCRASGNIHNYLAWYQQKQGKSPQLLVYNAKTLADGVPSRFSGSGSG
TQYSLKINSLQPEDFGSYYCQHFWSTPWTTFGGGTKLEIK.

In some embodiments, the anti-CD99 scFv comprises an amino acid sequence:

(SEQ ID NO: 79)
QVQLKESGAELARPGASVKLSCKASGYTFTTFWMQWAKQRPGQGLEWIGT
IYPGDDDTRYTQKFKGRATLTADKSSTTAYMQLSNLSSEDSAVYYCARSG
YERGPYYFDSWGQGTTLTVSSGGGGSGGGGSGGGGSGNSWSHSLRSLSVT
IGQPASISCKSSQSLLDGNGKTYLNWLLQRPGQSPKRLLYLVSKLDSGVP
DRFTGSGSGTDFTLKISRVEAEDLGIYYCWQGTHFPRTFGGGTKLEIK.

In some embodiments, the anti-CD99 scFv comprises an amino acid sequence:

(SEQ ID NO: 80)
QVQLKESGAELARPGASVKLSCKASGYTFTTFWMQWAKQRPGQGLEWIGT
IYPGDDDTRYTQKFKGRATLTADKSSTTAYMQLSNLSSEDSAVYYCARSG
YERGPYYFDSWGQGTTLTVSSGGGGSGGGGSGGGGSGNSWRHSPRSLSVT
IGQPASISCKSSQSLLDGNGKTYLNWLLQRPGQSPKRLLYLVSKLDSGVP
DRFTGSGSGTDFTLKISRVEAEDLGIYYCWQGTHFPRTFGGGTKLEIK.

In some embodiments, the anti-CD99 scFv comprises an amino acid sequence:

(SEQ ID NO: 81)
QVQLKESGAELARPGASVKLSCKASGYTFTTFWMQWAKQRPGQGLEWIGT
IYPGDDDTRYTQKFKGRATLTADKSSTTAYMQLSNLSSEDSAVYYCARSG
YERGPYYFDSWGQGTTLTVSSGGGGSGGGGSGGGGSDIVMTQAAPSVPVT
PGESVSISCGSSKSLLHSNGNTYLYWFLQRPGQSPQLLIYRVSNLASGVP
DRFSGSGSGTAFTLRISRVEAEDVGVYYCMQHLEYPYTFGGGTRLEIK.

In some embodiments, the anti-CD99 scFv comprises an amino acid sequence:

(SEQ ID NO: 82)
QVQLKESGAELARPGASVKLSCKASGYTFTTFWMQWAKQRPGQGLEWIGT
IYPGDDDTRYTQKFKGRATLTADKSSTTAYMQLSNLSSEDSAVYYCARSG
YERGPYYFDSWGQGTTLTVSSGGGGSGGGGSGGGGSDIVMTQAAPSVPVT
PGESVSISCGSSKSLLHSNGNTYLYWFLQRPGQSPQLLIYRVSNLASGVP
DRFSGSGSGTAFTLRISRVEAEDVGVYYCMQHLEYPYTFGGGTRLEIK.

In some embodiments, the anti-CD99 scFv comprises an amino acid sequence:

(SEQ ID NO: 83)
QVQLKESGAELARPGASVKLSCKASGYTFTTFWMQWAKQRPGQGLEWIGT
IYPGDDDTRYTQKFKGRATLTADKSSTTAYMQLSNLSSEDSAVYYCARSG
YERGPYYFDSWGQGTTLTVSSGGGGSGGGGSGGGGSDTVMSQSPSSLAVS
VGEKITMSCKSSQSLLCRSNQKNYLAWYQQKPGQSPKQLIYWASTRESGV
PDRFTGSGSGTDFTLTISSVKAEDLAVYYCQQYYSYPLTFGAGTKLELK.

In some embodiments, the anti-CD99 scFv comprises an amino acid sequence:

(SEQ ID NO: 84)
QVQLKESGAELARPGASVKLSCKASGYTFTTFWMQWAKQRPGQGLEWIGT
IYPGDDDTRYTQKFKGRATLTADKSSTTAYMQLSNLSSEDSAVYYCARSG
YERGPYYFDSWGQGTTLTVSSGGGGSGGGGSGGGGSDTVMSQSPSSLAVS
VGEKITMSCKSSQSLLYRSNQKNYLAWYQQKPGQSPKQLIYWASTRESGV
PDRFTGSGSGTDFTLTISSVKAEDLAVYYCQQYYSYPLTFGAGTKLELK.

In some embodiments, the anti-CD99 scFv comprises an amino acid sequence:

(SEQ ID NO: 85)
DIQMTQSPASLSASVGETVTITCRASGNIHNYLAWYQQKQGKSPQLLVYN
AKTLADGVPSRFSGSGSGTQYSLKINSLQPEDFGSYYCQHFWSTPWTFGG
GTKLEIKGGGGSGGGGSGGGGSEVQLQQSGAELVKPGASVKLSCTASGFD
IKDTYIHWVKQRPEQGLEWIGRIDPANGDTRYDPEFQGKASLTADTSSNT
AYLQFSNLTSEDTAVYYCARRGGLSWGQGTTLTVSS.

In some embodiments, the anti-CD99 scFv comprises an amino acid sequence:

(SEQ ID NO: 86)
DIQMTQSPASLSASVGETVTITCRASGNIHNYLAWYQQKQGKSPQLLVYN
AKTLADGVPSRFSGSGSGTQYSLKINSLQPEDFGSYYCQHFWSTPWTFGG
GTKLEIKGGGGSGGGGSGGGGSEVQLEESGGGLVQPKGSLKLSCAASGFT
FNTYAMYWVCQAPGKGLKWVARIRSKVNNYATYYADSVKDRFTISRDDSQ
NMLFLHMNNLKTEDTAIYFCVRDPMDYWGQGISVTVSS.

In some embodiments, the anti-CD99 scFv comprises an amino acid sequence:

(SEQ ID NO: 87)
DIQMTQSPASLSASVGETVTITCRASGNIHNYLAWYQQKQGKSPQLLVYN
AKTLADGVPSRFSGSGSGTQYSLKINSLQPEDFGSYYCQHFWSTPWTFGG
GTKLEIKGGGGSGGGGSGGGGSEVQLVESGGGLVQPKGSLKLSCAASGFT
FNTYAMYWVCQAPGKGLKWVARIRSKVNNYATYYADSVKDRFTISRDDSQ
NMLFLHMNNLKTEDTAIYFCVRDPMDYWGQGISVTVSS.

In some embodiments, the anti-CD99 scFv comprises an amino acid sequence:

(SEQ ID NO: 88)
DIQMTQSPASLSASVGETVTITCRASGNIHNYLAWYQQKQGKSPQLLVYN
AKTLADGVPSRFSGSGSGTQYSLKINSLQPEDFGSYYCQHFWSTPWTFGG
GTKLEIKGGGGSGGGGSGGGGSQVQLQQSGAELARPGASVKLSCKASGYT
FTTFWMQWVKQRPGQGLEWIGTIYPGDDDTRYTQKFKGRATLTADKSSTT
AYMQLSNLSSEDSAVYYCARSGYERGPYYFDSWGQGTTLTVSS.

In some embodiments, the anti-CD99 scFv comprises an amino acid sequence:

(SEQ ID NO: 89)
DIQMTQSPASLSASVGETVTITCRASGNIHNYLAWYQQKQGKSPQLLVYN
AKTLADGVPSRFSGSGSGTQYSLKINSLQPEDFGSYYCQHFWSTPWTFGG
GTKLEIKGGGGSGGGGSGGGGSDVKLQESGAELARPGASVKLSCKASGYT
FTTFWMQRVKQRPGQGLEWIGTIYPGDDDTRYTQKFKGRATLTADKSSTT
AYMQLSNLSSEDSAVYYCARSGYERGPYYFDSWGQGTTLTVSS.

In some embodiments, the anti-CD99 scFv comprises an amino acid sequence:

(SEQ ID NO: 90)
DIQMTQSPASLSASVGETVTITCRASGNIHNYLAWYQQKQGKSPQLLVYN
AKTLADGVPSRFSGSGSGTQYSLKINSLQPEDFGSYYCQHFWSTPWTFGG
GTKLEIKGGGGSGGGGSGGGGSQVQLKESGAELARPGASVKLSCKASGYT
FTTFWMQWAKQRPGQGLEWIGTIYPGDDDTRYTQKFKGRATLTADKSSTT
AYMQLSNLSSEDSAVYYCARSGYERGPYYFDSWGQGTTLTVSS.

In some embodiments, the anti-CD99 scFv comprises an amino acid sequence:

(SEQ ID NO: 91)
DIVMTQAAPSVPVTPGESVSISCGSSKSLLHSNGNTYLYWFLQRPGQSPQ
LLIYRVSNLASGVPDRFSGSGSGTAFTLRISRVEAEDVGVYYCMQHLEYP
YTFGGGTRLEIKGGGGSGGGGSGGGGSEVQLQQSGAELVKPGASVKLSCT
ASGFDIKDTYIHWVKQRPEQGLEWIGRIDPANGDTRYDPEFQGKASLTAD
TSSNTAYLQFSNLTSEDTAVYYCARRGGLSWGQGTTLTVSS.

In some embodiments, the anti-CD99 scFv comprises an amino sequence:

(SEQ ID NO: 92)
DIVMTQAAPSVPVTPGESVSISCGSSKSLLHSNGNTYLYWFLQRPGQSPQ
LLIYRVSNLASGVPDRFSGSGSGTAFTLRISRVEAEDVGVYYCMQHLEYP

In some embodiments, the anti-CD99 scFv comprises an amino acid sequence:

(SEQ ID NO: 93)
DIVMTQAAPSVPVTPGESVSISCGSSKSLLHSNGNTYLYWFLQRPGQSPQ

LLIYRVSNLASGVPDRFSGSGSGTAFTLRISRVEAEDVGVYYCMQHLEYP

YTFGGGTRLEIKGGGGSGGGGSGGGGSEVQLEESGGGLVQPKGSLKLSCA

ASGFTFNTYAMYWVCQAPGKGLKWVARIRSKVNNYATYYADSVKDRFTIS

RDDSQNMLFLHMNNLKTEDTAIYFCVRDPMDYWGQGISVTVSS.

In some embodiments, the anti-CD99 scFv comprises an amino acid sequence:

(SEQ ID NO: 94)
DIVMTQAAPSVPVTPGESVSISCGSSKSLLHSNGNTYLYWFLQRPGQSPQ

LLIYRVSNLASGVPDRFSGSGSGTAFTLRISRVEAEDVGVYYCMQHLEYP

YTFGGGTRLEIKGGGGSGGGGSGGGGSQVQLQQSGAELARPGASVKLSCK

ASGYTFTTFWMQVWKQRPGQGLEWIGTIYPGDDDTRYTQKFKGRATLTAD

KSSTTAYMQLSNLSSEDSAVYYCARSGYERGPYYFDSWGQGTTLTVSS.

In some embodiments, the anti-CD99 scFv comprises an amino acid sequence:

(SEQ ID NO: 95)
DIVMTQAAPSVPVTPGESVSISCGSSKSLLHSNGNTYLYWFLQRPGQSPQ

LLIYRVSNLASGVPDRFSGSGSGTAFTLRISRVEAEDVGVYYCMQHLEYP

YTFGGGTRLEIKGGGGSGGGGSGGGGSDVKLQESGAELARPGASVKLSCK

ASGYTFTTFWMQRVKQRPGQGLEWIGTIYPGDDDTRYTQKFKGRATLTAD

KSSTTAYMQLSNLSSEDSAVYYCARSGYERGPYYFDSWGQGTTLTVSS.

In some embodiments, the anti-CD99 scFv comprises an amino acid sequence:

(SEQ ID NO: 96)
DIVMTQAAPSVPVTPGESVSISCGSSKSLLHSNGNTYLYWFLQRPGQSPQ

LLIYRVSNLASGVPDRFSGSGSGTAFTLRISRVEAEDVGVYYCMQHLEYP

YTFGGGTRLEIKGGGGSGGGGSGGGGSQVQLKESGAELARPGASVKLSCK

ASGYTFTTFWMQWAKQRPGQGLEWIGTIYPGDDDTRYTQKFKGRATLTAD

KSSTTAYMQLSNLSSEDSAVYYCARSGYERGPYYFDSWGQGTTLTVSS.

In some embodiments, the anti-CD99 scFv comprises an amino acid sequence:

(SEQ ID NO: 97)
DTVMSQSPSSLAVSVGEKITMSCKSSQSLLCRSNQKNYLAWYQQKPGQSP

KQLIYWASTRESGVPDRFTGSGSGTDFTLTISSVKAEDLAVYYCQQYYSY

PLTFGAGTKLELKGGGGSGGGGSGGGGSEVQLQQSGAELVKPGASVKLSC

TASGFDIKDTYIHWVKQRPEQGLEWIGRIDPANGDTRYDPEFQGKASLTA

DTSSNTAYLQFSNLTSEDTAVYYCARRGGLSWGQGTTLTVSS.

In some embodiments, the anti-CD99 scFv comprises an amino acid sequence:

(SEQ ID NO: 98)
DTVMSQSPSSLAVSVGEKITMSCKSSQSLLCRSNQKNYLAWYQQKPGQSP

KQLIYWASTRESGVPDRFTGSGSGTDFTLTISSVKAEDLAVYYCQQYYSY

PLTFGAGTKLELKGGGGSGGGGSGGGGSEVQLEESGGGLVQPKGSLKLSC

AASGFTFNTYAMYWVCQAPGKGLKWVARIRSKVNNYATYYADSVKDRFTI

SRDDSQNMLFLHMNNLKTEDTAIYFCVRDPMDYWGQGISVTVSS.

In some embodiments, the anti-CD99 scFv comprises an amino acid sequence:

(SEQ ID NO: 99)
DTVMSQSPSSLAVSVGEKITMSCKSSQSLLCRSNQKNYLAWYQQKPGQSP

KQLIYWASTRESGVPDRFTGSGSGTDFTLTISSVKAEDLAVYYCQQYYSY

PLTFGAGTKLELKGGGGSGGGGSGGGGSEVQLVESGGGLVQPKGSLKLSC

AASGFTFNTYAMYWVCQAPGKGLKWVARIRSKVNNYATYYADSVKDRFTI

SRDDSQNMLFLHMNNLKTEDTAIYFCVRDPMDYWGQGISVTVSS.

In some embodiments, the anti-CD99 scFv comprises an amino acid sequence:

(SEQ ID NO: 100)
DTVMSQSPSSLAVSVGEKITMSCKSSQSLLCRSNQKNYLAWYQQKPGQSP

KQLIYWASTRESGVPDRFTGSGSGTDFTLTISSVKAEDLAVYYCQQYYSY

PLTFGAGTKLELKGGGGSGGGGSGGGGSQVQLQQSGAELARPGASVKLSC

KASGYTFTTFWMQVKQRPGQGLEWIGTIYPGDDDTRYTQKFKGRATLTA

DKSSTTAYMQLSNLSSEDSAVYYCARSGYERGPYYFDSWGQGTTLTVSS.

In some embodiments, the anti-CD99 scFv comprises an amino acid sequence:

(SEQ ID NO: 101)
DTVMSQSPSSLAVSVGEKITMSCKSSQSLLCRSNQKNYLAWYQQKPGQSP

KQLIYWASTRESGVPDRFTGSGSGTDFTLTISSVKAEDLAVYYCQQYYSY

PLTFGAGTKLELKGGGGSGGGGSGGGGSDVKLQESGAELARPGASVKLSC

KASGYTFTTFWMQRVKQRPGQGLEWIGTIYPGDDDTRYTQKFKGRATLTA

DKSSTTAYMQLSNLSSEDSAVYYCARSGYERGPYYFDSWGQGTTLTVSS.

In some embodiments, the anti-CD99 scFv comprises an amino acid sequence:

(SEQ ID NO: 102)
DTVMSQSPSSLAVSVGEKITMSCKSSQSLLCRSNQKNYLAWYQQKPGQSP

KQLIYWASTRESGVPDRFTGSGSGTDFTLTISSVKAEDLAVYYCQQYYSY

PLTFGAGTKLELKGGGGSGGGGSGGGGSQVQLKESGAELARPGASVKLSC

KASGYTFTTFWMQWAKQRPGQGLEWIGTIYPGDDDTRYTQKFKGRATLTA

DKSSTTAYMQLSNLSSEDSAVYYCARSGYERGPYYFDSWGQGTTLTVSS.

In some embodiments, the anti-CD99 scFv comprises an amino acid sequence:

(SEQ ID NO: 103)
DTVMSQSPSSLAVSVGEKITMSCKSSQSLLYRSNQKNYLAWYQQKPGQSP

KQLIYWASTRESGVPDRFTGSGSGTDFTLTISSVKAEDLAVYYCQQYYSY

PLTFGAGTKLELKGGGGSGGGGSGGGGSEVQLQQSGAELVKPGASVKLSC

TASGFDIKDTYIHWVKQRPEQGLEWIGRIDPANGDTRYDPEFQGKASLTA

DTSSNTAYLQFSNLTSEDTAVYYCARRGGLSWGQGTTLTVSS.

In some embodiments, the anti-CD99 scFv comprises an amino acid sequence:

(SEQ ID NO: 104)
DTVMSQSPSSLAVSVGEKITMSCKSSQSLLYRSNQKNYLAWYQQKPGQSP

KQLIYWASTRESGVPDRFTGSGSGTDFTLTISSVKAEDLAVYYCQQYYSY

PLTFGAGTKLELKGGGGSGGGGSGGGGSEVQLEESGGGLVQPKGSLKLSC

AASGFTFNTYAMYWVCQAPGKGLKWVARIRSKVNNYATYYADSVKDRFTI

SRDDSQNMLFLHMNNLKTEDTAIYFCVRDPMDYWGQGISVTVSS.

In some embodiments, the anti-CD99 scFv comprises an amino acid sequence:

(SEQ ID NO: 105)
DTVMSQSPSSLAVSVGEKITMSCKSSQSLLYRSNQKNYLAWYQQKPGQSP

KQLIYWASTRESGVPDRFTGSGSGTDFTLTISSVKAEDLAVYYCQQYYSY

PLTFGAGTKLELKGGGGSGGGGSGGGGSEVQLVESGGGLVQPKGSLKLSC

AASGFTFNTYAMYWVCQAPGKGLKWVARIRSKVNNYATYYADSVKDRFTI

SRDDSQNMLFLHMNNLKTEDTAIYFCVRDPMDYWGQGISVTVSS.

In some embodiments, the anti-CD99 scFv comprises an amino acid sequence:

(SEQ ID NO: 106)
DTVMSQSPSSLAVSVGEKITMSCKSSQSLLYRSNQKNYLAWYQQKPGQSP

KQLIYWASTRESGVPDRFTGSGSGTDFTLTISSVKAEDLAVYYCQQYYSY

PLTFGAGTKLELKGGGGSGGGGSGGGGSQVQLQQSGAELARPGASVKLSC

KASGYTFTTFWMQWVKQRPGQGLEWIGTIYPGDDDTRYTQKFKGRATLTA

DKSSTTAYMQLSNLSSEDSAVYYCARSGYERGPYYFDSWGQGTTLTVSS.

In some embodiments, the anti-CD99 scFv comprises an amino acid sequence:

(SEQ ID NO: 107)
DTVMSQSPSSLAVSVGEKITMSCKSSQSLLYRSNQKNYLAWYQQKPGQSP

KQLIYWASTRESGVPDRFTGSGSGTDFTLTISSVKAEDLAVYYCQQYYSY

PLTFGAGTKLELKGGGGSGGGGSGGGGSDVKLQESGAELARPGASVKLSC

KASGYTFTTFWMQRVKQRPGQGLEWIGTIYPGDDDTRYTQKFKGRATLTA

DKSSTTAYMQLSNLSSEDSAVYYCARSGYERGPYYFDSWGQGTTLTVSS.

In some embodiments, the anti-CD99 scFv comprises an amino acid sequence:

(SEQ ID NO: 108)
DTVMSQSPSSLAVSVGEKITMSCKSSQSLLYRSNQKNYLAWYQQKPGQSP

KQLIYWASTRESGVPDRFTGSGSGTDFTLTISSVKAEDLAVYYCQQYYSY

PLTFGAGTKLELKGGGGSGGGGSGGGGSQVQLKESGAELARPGASVKLSC

KASGYTFTTFWMQWAKQRPGQGLEWIGTIYPGDDDTRYTQKFKGRATLTA

DKSSTTAYMQLSNLSSEDSAVYYCARSGYERGPYYFDSWGQGTTLTVSS.

As with other CARs, the disclosed polypeptides can also contain a transmembrane domain and an endodomain capable of activating an immune effector cell. For example, the endodomain can contain a signaling domain and one or more co-stimulatory signaling regions.

In some embodiments, the intracellular signaling domain is a CD3 zeta (CD3ζ signaling domain. In some embodiments, the costimulatory signaling region comprises the cytoplasmic domain of CD28, 4-1BB, or a combination thereof. In some cases, the costimulatory signaling region contains 1, 2, 3, or 4 cytoplasmic domains of one or more intracellular signaling and/or costimulatory molecules. In some embodiments, the co-stimulatory signaling region contains one or more mutations in the cytoplasmic domains of CD28 and/or 4-1BB that enhance signaling.

In some embodiments, the CAR polypeptide contains an incomplete endodomain. For example, the CAR polypeptide can contain only an intracellular signaling domain or a co-stimulatory domain, but not both. In these embodiments, the immune effector cell is not activated unless it and a second CAR polypeptide (or endogenous T-cell receptor) that contains the missing domain both bind their respective antigens. Therefore, in some embodiments, the CAR polypeptide contains a CD3 zeta (CD3ζ signaling domain but does not contain a costimulatory signaling region (CSR). In other embodiments, the CAR polypeptide contains the cytoplasmic domain of CD28, 4-1BB, or a combination thereof, but does not contain a CD3 zeta (CD3ζ signaling domain (SD).

Also disclosed are isolated nucleic acid sequences encoding the disclosed CAR polypeptides, vectors comprising these isolated nucleic acids, and cells containing these vectors. For example, the cell can be an immune effector cell selected from the group consisting of an alpha-beta T cells, a gamma-delta T cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, and a regulatory T cell.

In some embodiments, the cell exhibits an anti-tumor immunity when the antigen binding domain of the CAR binds to CD99.

Also disclosed is a method of providing an anti-tumor immunity in a subject with a CD99-expressing cancer that involves administering to the subject an effective amount of an immune effector cell genetically modified with a disclosed CD99-specific CAR.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 8A to 8I show immunephenotype of anti-CD99 CARs. Healthy T cells isolated from PBMCs were transduced with anti-CD99 CARs. Following 1-week of culturing without antigen stimulation, cells were stained for CD3, CD4, CD8, PD1, CCR7, and CD45RA, and data were collected on a flow cytometer. Transduction efficiency was determined based on mCherry expression (FIGS. 8A and 8B). Live, CAR positive T cells were analyzed for CD4, CD8, and PD1 expression (FIGS. 8C-8H). T cells subsets were also analyzed based on CCR7 and CD45RA expression (FIG. 8I). EFF=effector, EM=effector memory, CM=central memory, N=Naïve.

DETAILED DESCRIPTION

Figure 1:
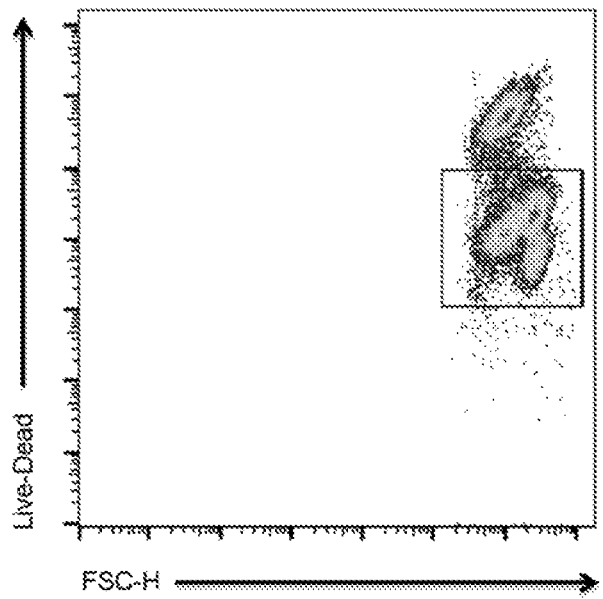
FIG. 1 contains a flow cytometry plot showing gate used for live cells in CD99-PE analysis.

Disclosed herein are bispecific antibodies and chimeric antigen receptors (CAR), that can specifically recognize tumor-associated antigens (TAA) on CD99-expressing cancers. Also disclosed are immune effector cells, such as T cells or Natural Killer (NK) cells, that are engineered to express these CARs. Therefore, also disclosed are methods for providing an anti-tumor immunity in a subject with CD99-expressing cancers using the disclosed antibodies and immune effector cells.

Antibodies

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)).

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327

(1988); and Presta, Curr. Op. Struct. Biol., 2:593-596 (1992)) Methods for humanizing non-human antibodies are well known in the art.

Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, a humanized form of a non human antibody (or a fragment thereof) is a chimeric antibody or fragment (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two $V_H$ and two $V_L$ regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target.

Still shorter linkers (one or two amino acids) lead to the formation of trimers (triabodies or tribodies). Tetrabodies have also been produced. They exhibit an even higher affinity to their targets than diabodies.

A bi-specific antibody designed to selectively bind CD3 and CD99 would trigger non-specific T-cell activation & cytokine storm. A bi-specific diabody designed to selectively bind CD3 and CD99 would have a molecular weight (55-60 kD) less than the renal clearance threshold, which would result in rapid elimination. As such, diabodies must be administered by a continuous infusion. The disclosed tetravalent, bi-specific antibody can have a molecular weight (e.g., 105-110 kD) greater than the renal filtration threshold with markedly extended PK.

Provided are fusion polypeptides capable of forming a multivalent engineered antibody that is able to engage T-cells to destroy CD99-expressing malignant cells. The engineered antibody may comprise for example, at least one scFv, at least one Fab fragment, at least one Fv fragment, etc. It may be bivalent, trivalent, tetravalent, etc. The multivalent antibodies is multispecific, e.g., bispecific, trispecific, tetraspecific, etc. The multivalent antibodies may be in any form, such as a diabody, triabody, tetrabody, etc.

Bivalent and bispecific antibodies can be constructed using only antibody variable domains. A fairly efficient and relatively simple method is to make the linker sequence between the $V_H$ and $V_L$ domains so short that they cannot fold over and bind one another. Reduction of the linker length to 3-12 residues prevents the monomeric configuration of the scFv molecule and favors intermolecular VH-VL pairings with formation of a 60 kDa non-covalent scFv dimer "diabody". The diabody format can also be used for generation of recombinant bis-pecific antibodies, which are obtained by the noncovalent association of two single-chain fusion products, consisting of the VH domain from one antibody connected by a short linker to the VL domain of another antibody. Reducing the linker length still further below three residues can result in the formation of trimers ("triabody", about 90 kDa) or tetramers ("tetrabody", about 120 kDa). For a review of engineered antibodies, particularly single domain fragments, see Holliger and Hudson, 2005, Nature Biotechnology, 23:1126-1136. All of such engineered antibodies may be used in the fusion polypeptides provided herein. Tetravalent Tandab® may be prepared substantially as described in WO 1999057150 A3 or US20060233787, which are incorporated by reference for the teaching of methods of making Tandab® molecules.

The antigen recognition sites or entire variable regions of the engineered antibodies may be derived from one or more parental antibodies directed against any antigen of interest (e.g., CD99). The parental antibodies can include naturally occurring antibodies or antibody fragments, antibodies or antibody fragments adapted from naturally occurring antibodies, antibodies constructed de novo using sequences of antibodies or antibody fragments known to be specific for an antigen of interest. Sequences that may be derived from parental antibodies include heavy and/or light chain variable regions and/or CDRs, framework regions or other portions thereof.

Multivalent, multispecific antibodies may contain a heavy chain comprising two or more variable regions and/or a light chain comprising one or more variable regions wherein at least two of the variable regions recognize different epitopes on the same antigen.

Candidate engineered antibodies for inclusion in the fusion polypeptides, or the fusion polypeptides themselves, may be screened for activity using a variety of known assays. For example, screening assays to determine binding specificity are well known and routinely practiced in the art. For a comprehensive discussion of such assays, see Harlow et al. (Eds.), ANTIBODIES: A LABORATORY MANUAL; Cold Spring Harbor Laboratory; Cold Spring Harbor, N.Y., 1988, Chapter 6.

Pharmaceutical Composition

Also disclosed is a pharmaceutical composition comprising a disclosed molecule in a pharmaceutically acceptable carrier. Pharmaceutical carriers are known to those skilled in the art. These most typically would be standard carriers for administration of drugs to humans, including solutions such as sterile water, saline, and buffered solutions at physiological pH. For example, suitable carriers and their formulations are described in Remington: The Science and Practice of Pharmacy (21 ed.) ed. PP. Gerbino, Lippincott Williams & Wilkins, Philadelphia, P A. 2005. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. The solution should be RNAse free.

Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base- addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Methods of Treatment

Also disclosed is a method for treating a CD99-expressing cancer in a subject by administering to the subject a therapeutically effective amount of the disclosed pharmaceutical composition. The method can further involve administering to the subject a chemotherapy such as fludarabine, cytarabine, cyclophosphamide, idarubicin, daunorubicin, or a targeted inhibitor such as imbruvica, midostaurin, idelalisib, or an immune agents such as PD1 or PDL1 inhibitors.

The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for a CD99-expressing cancer. Thus, the method can further comprise identifying a subject at risk for a CD99-expressing cancer prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical daily dosage of the disclosed composition used alone might range from about 1 µg/kg to up to 100 mg/kg of body weight or more per day, depending on the factors mentioned above.

In some embodiments, the molecule is administered in a dose equivalent to parenteral administration of about 0.1 ng to about 100 g per kg of body weight, about 10 ng to about 50 g per kg of body weight, about 100 ng to about 1 g per kg of body weight, from about 1µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of molecule containing lenalidomide administered to achieve a therapeutic effective dose is about 0.1 ng, 1 ng, 10 ng, 100 ng, 1 pg, 10 pg, 100 pg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

CD99-specific chimeric antigen receptors (CAR) CARs generally incorporate an antigen recognition domain from the single-chain variable fragments (scFv) of a monoclonal antibody (mAb) with transmembrane signaling motifs involved in lymphocyte activation (Sadelain M, et al. Nat Rev Cancer 2003 3:35-45). Disclosed herein is a CD99-specific chimeric antigen receptor (CAR) that can be that can be expressed in immune effector cells to enhance antitumor activity against CD99-specific CARs.

The disclosed CAR is generally made up of three domains: an ectodomain, a transmembrane domain, and an endodomain. The ectodomain comprises the CD99-binding region and is responsible for antigen recognition. It also optionally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain a signaling domain (ISD) and a co-stimulatory signaling region (CSR).

A "signaling domain (SD)" generally contains immunoreceptor tyrosine-based activation motifs (ITAMs) that activate a signaling cascade when the ITAM is phosphorylated. The term "co-stimulatory signaling region (CSR)" refers to intracellular signaling domains from costimulatory protein receptors, such as CD28, 41BB, and ICOS, that are able to enhance T-cell activation by T-cell receptors.

In some embodiments, the endodomain contains an SD or a CSR, but not both. In these embodiments, an immune effector cell containing the disclosed CAR is only activated if another CAR (or a T-cell receptor) containing the missing domain also binds its respective antigen.

In some embodiments, the disclosed CAR is defined by the formula:

SP—CD99—HG—TM—CSR—SD; or

SP—CD99—HG—TM—SD—CSR;

wherein "SP" represents an optional signal peptide,
wherein "CD99" represents a CD99-binding region,
wherein "HG" represents an optional hinge domain,
wherein "TM" represents a transmembrane domain,
wherein "CSR" represents one or more co-stimulatory signaling regions,
wherein "SD" represents a signaling domain, and
wherein "-" represents a peptide bond or linker.

Additional CAR constructs are described, for example, in Fresnak AD, et al.

Engineered T cells: the promise and challenges of cancer immunotherapy. Nat Rev Cancer. 2016 Aug. 23; 16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

TRUCKs (T cells redirected for universal cytokine killing) co-express a chimeric antigen receptor (CAR) and an antitumor cytokine. Cytokine expression may be constitutive or induced by T cell activation. Targeted by CAR specificity, localized production of pro-inflammatory cytokines recruits endogenous immune cells to tumor sites and may potentiate an antitumor response.

Universal, allogeneic CAR T cells are engineered to no longer express endogenous T cell receptor (TCR) and/or major histocompatibility complex (MHC) molecules, thereby preventing graft-versus-host disease (GVHD) or rejection, respectively.

Self-driving CARs co-express a CAR and a chemokine receptor, which binds to a tumor ligand, thereby enhancing tumor homing.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

Marked CAR T cells express a CAR plus a tumor epitope to which an existing monoclonal antibody agent binds. In the setting of intolerable adverse effects, administration of the monoclonal antibody clears the CAR T cells and alleviates symptoms with no additional off-tumor effects.

A tandem CAR (TanCAR) T cell expresses a single CAR consisting of two linked single-chain variable fragments (scFvs) that have different affinities fused to intracellular co-stimulatory domain(s) and a CD3 domain. TanCAR T cell activation is achieved only when target cells co-express both targets.

A dual CAR T cell expresses two separate CARs with different ligand binding targets; one CAR includes only the CD3 domain and the other CAR includes only the co-stimulatory domain(s). Dual CAR T cell activation requires co-expression of both targets on the tumor.

A safety CAR (sCAR) consists of an extracellular scFv fused to an intracellular inhibitory domain. sCAR T cells co-expressing a standard CAR become activated only when encountering target cells that possess the standard CAR target but lack the sCAR target.

The antigen recognition domain of the disclosed CAR is usually an scFv. There are however many alternatives. An antigen recognition domain from native T-cell receptor (TCR) alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from CD8, CD3ζ(CD3ō, CD3γ, CD3ε, CD32 (Fc gamma RIIa), DAP10, DAP12, CD79a, CD79b, FcγRIy, Fcγ RIIIy , Fcε RIβ (FCERIB), and FcεRIγ (FCERIG).

In particular embodiments, the intracellular signaling domain is derived from CD3 zeta (CD3ζ) (TCR zeta, GenBank accno. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3 (chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. Preclinical studies have indicated that the second generation of CAR designs improves the antitumor activity of T cells. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3ζ signaling domain by itself or combined with any other desired cytoplasmic domain(s) useful in the context of the CAR of the invention. For example, the cytoplasmic domain of the CAR can comprise a CD3ζ(chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD83, CD8, CD4, b2c, CD80, CD86, DAP10, DAP12, MyD88, BTNL3, and NKG2D. Thus, while the CAR is exemplified primarily with CD28 as the co-stimulatory signaling element, other costimulatory elements can be used alone or in combination with other co-stimulatory signaling elements.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety (e.g., anti-CD99 scFv) and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

Tables 1, 2, and 3 below provide some example combinations of CD99-binding region, co-stimulatory signaling regions, and intracellular signaling domain that can occur in the disclosed CARs.

TABLE 1

First Generation CARs

| ScFv | Signal Domain |
|------|---------------|
| CD99 | CD8 |
| CD99 | CD3ζ |
| CD99 | CD3δ |
| CD99 | CD3γ |
| CD99 | CD3ε |
| CD99 | FcγRI-γ |
| CD99 | FcγRIII-γ |
| CD99 | FcεRIβ |

TABLE 1-continued

First Generation CARs

| ScFv | Signal Domain |
|---|---|
| CD99 | FcεRIγ |
| CD99 | DAP10 |
| CD99 | DAP12 |
| CD99 | CD32 |
| CD99 | CD79a |

TABLE 2

Second Generation CARs

| ScFv | Co-stimulatory Signal | Signal Domain | ScFv | Co-stimulatory Signal | Signal Domain |
|---|---|---|---|---|---|
| CD99 | CD28 | CD8 | CD99 | CD80 | FcεRIβ |
| CD99 | CD28 | CD3ζ | CD99 | CD80 | FcεRIγ |
| CD99 | CD28 | CD3δ | CD99 | CD80 | DAP10 |
| CD99 | CD28 | CD3γ | CD99 | CD80 | DAP12 |
| CD99 | CD28 | CD3ε | CD99 | CD80 | CD32 |
| CD99 | CD28 | FcγRI-γ | CD99 | CD80 | CD79a |
| CD99 | CD28 | FcγRIII-γ | CD99 | CD80 | CD79b |
| CD99 | CD28 | FcεRIβ | CD99 | CD86 | CD8 |
| CD99 | CD28 | FcεRIγ | CD99 | CD86 | CD3ζ |
| CD99 | CD28 | DAP10 | CD99 | CD86 | CD3δ |
| CD99 | CD28 | DAP12 | CD99 | CD86 | CD3γ |
| CD99 | CD28 | CD32 | CD99 | CD86 | CD3ε |
| CD99 | CD28 | CD79a | CD99 | CD86 | FcγRI-γ |
| CD99 | CD28 | CD79b | CD99 | CD86 | FcγRIII-γ |
| CD99 | CD8 | CD8 | CD99 | CD86 | FcεRIβ |
| CD99 | CD8 | CD3ζ | CD99 | CD86 | FcεRIγ |
| CD99 | CD8 | CD3δ | CD99 | CD86 | DAP10 |
| CD99 | CD8 | CD3γ | CD99 | CD86 | DAP12 |
| CD99 | CD8 | CD3ε | CD99 | CD86 | CD32 |
| CD99 | CD8 | FcγRI-γ | CD99 | CD86 | CD79a |
| CD99 | CD8 | FcγRIII-γ | CD99 | CD86 | CD79b |
| CD99 | CD8 | FcεRIβ | CD99 | OX40 | CD8 |
| CD99 | CD8 | FcεRIγ | CD99 | OX40 | CD3ζ |
| CD99 | CD8 | DAP10 | CD99 | OX40 | CD3δ |
| CD99 | CD8 | DAP12 | CD99 | OX40 | CD3γ |
| CD99 | CD8 | CD32 | CD99 | OX40 | CD3ε |
| CD99 | CD8 | CD79a | CD99 | OX40 | FcγRI-γ |
| CD99 | CD8 | CD79b | CD99 | OX40 | FcγRIII-γ |
| CD99 | CD4 | CD8 | CD99 | OX40 | FcεRIβ |
| CD99 | CD4 | CD3ζ | CD99 | OX40 | FcεRIγ |
| CD99 | CD4 | CD3δ | CD99 | OX40 | DAP10 |
| CD99 | CD4 | CD3γ | CD99 | OX40 | DAP12 |
| CD99 | CD4 | CD3ε | CD99 | OX40 | CD32 |
| CD99 | CD4 | FcγRI-γ | CD99 | OX40 | CD79a |
| CD99 | CD4 | FcγRIII-γ | CD99 | OX40 | CD79b |
| CD99 | CD4 | FcεRIβ | CD99 | DAP10 | CD8 |
| CD99 | CD4 | FcεRIγ | CD99 | DAP10 | CD3ζ |
| CD99 | CD4 | DAP10 | CD99 | DAP10 | CD3δ |
| CD99 | CD4 | DAP12 | CD99 | DAP10 | CD3γ |
| CD99 | CD4 | CD32 | CD99 | DAP10 | CD3ε |
| CD99 | CD4 | CD79a | CD99 | DAP10 | FcγRI-γ |
| CD99 | CD4 | CD79b | CD99 | DAP10 | FcγRIII-γ |
| CD99 | b2c | CD8 | CD99 | DAP10 | FcεRIβ |
| CD99 | b2c | CD3ζ | CD99 | DAP10 | FcεRIγ |
| CD99 | b2c | CD3δ | CD99 | DAP10 | DAP10 |
| CD99 | b2c | CD3γ | CD99 | DAP10 | DAP12 |
| CD99 | b2c | CD3ε | CD99 | DAP10 | CD32 |
| CD99 | b2c | FcγRI-γ | CD99 | DAP10 | CD79a |
| CD99 | b2c | FcγRIII-γ | CD99 | DAP10 | CD79b |
| CD99 | b2c | FcεRIβ | CD99 | DAP12 | CD8 |
| CD99 | b2c | FcεRIγ | CD99 | DAP12 | CD3ζ |
| CD99 | b2c | DAP10 | CD99 | DAP12 | CD3δ |
| CD99 | b2c | DAP12 | CD99 | DAP12 | CD3γ |
| CD99 | b2c | CD32 | CD99 | DAP12 | CD3ε |
| CD99 | b2c | CD79a | CD99 | DAP12 | FcγRI-γ |
| CD99 | b2c | CD79b | CD99 | DAP12 | FcγRIII-γ |
| CD99 | CD137/41BB | CD8 | CD99 | DAP12 | FcεRIβ |
| CD99 | CD137/41BB | CD3ζ | CD99 | DAP12 | FcεRIγ |
| CD99 | CD137/41BB | CD3δ | CD99 | DAP12 | DAP10 |
| CD99 | CD137/41BB | CD3γ | CD99 | DAP12 | DAP12 |
| CD99 | CD137/41BB | CD3ε | CD99 | DAP12 | CD32 |
| CD99 | CD137/41BB | FcγRI-γ | CD99 | DAP12 | CD79a |
| CD99 | CD137/41BB | FcγRIII-γ | CD99 | DAP12 | CD79b |
| CD99 | CD137/41BB | FcεRIβ | CD99 | MyD88 | CD8 |
| CD99 | CD137/41BB | FcεRIγ | CD99 | MyD88 | CD3ζ |
| CD99 | CD137/41BB | DAP10 | CD99 | MyD88 | CD3δ |
| CD99 | CD137/41BB | DAP12 | CD99 | MyD88 | CD3γ |
| CD99 | CD137/41BB | CD32 | CD99 | MyD88 | CD3ε |
| CD99 | CD137/41BB | CD79a | CD99 | MyD88 | FcγRI-γ |
| CD99 | CD137/41BB | CD79b | CD99 | MyD88 | FcγRIII-γ |
| CD99 | ICOS | CD8 | CD99 | MyD88 | FcεRIβ |
| CD99 | ICOS | CD3ζ | CD99 | MyD88 | FcεRIγ |
| CD99 | ICOS | CD3δ | CD99 | MyD88 | DAP10 |
| CD99 | ICOS | CD3γ | CD99 | MyD88 | DAP12 |
| CD99 | ICOS | CD3ε | CD99 | MyD88 | CD32 |
| CD99 | ICOS | FcγRI-γ | CD99 | MyD88 | CD79a |
| CD99 | ICOS | FcγRIII-γ | CD99 | MyD88 | CD79b |
| CD99 | ICOS | FcεRIβ | CD99 | CD7 | CD8 |
| CD99 | ICOS | FcεRIγ | CD99 | CD7 | CD3ζ |
| CD99 | ICOS | DAP10 | CD99 | CD7 | CD3δ |
| CD99 | ICOS | DAP12 | CD99 | CD7 | CD3γ |
| CD99 | ICOS | CD32 | CD99 | CD7 | CD3ε |
| CD99 | ICOS | CD79a | CD99 | CD7 | FcγRI-γ |
| CD99 | ICOS | CD79b | CD99 | CD7 | FcγRIII-γ |
| CD99 | CD27 | CD8 | CD99 | CD7 | FcεRIβ |
| CD99 | CD27 | CD3ζ | CD99 | CD7 | FcεRIγ |
| CD99 | CD27 | CD3δ | CD99 | CD7 | DAP10 |
| CD99 | CD27 | CD3γ | CD99 | CD7 | DAP12 |
| CD99 | CD27 | CD3ε | CD99 | CD7 | CD32 |
| CD99 | CD27 | FcγRI-γ | CD99 | CD7 | CD79a |
| CD99 | CD27 | FcγRIII-γ | CD99 | CD7 | CD79b |
| CD99 | CD27 | FcεRIβ | CD99 | BTNL3 | CD8 |
| CD99 | CD27 | FcεRIγ | CD99 | BTNL3 | CD3ζ |
| CD99 | CD27 | DAP10 | CD99 | BTNL3 | CD3δ |
| CD99 | CD27 | DAP12 | CD99 | BTNL3 | CD3γ |
| CD99 | CD27 | CD32 | CD99 | BTNL3 | CD3ε |
| CD99 | CD27 | CD79a | CD99 | BTNL3 | FcγRI-γ |
| CD99 | CD27 | CD79b | CD99 | BTNL3 | FcγRIII-γ |
| CD99 | CD28δ | CD8 | CD99 | BTNL3 | FcεRIβ |
| CD99 | CD28δ | CD3ζ | CD99 | BTNL3 | FcεRIγ |
| CD99 | CD28δ | CD3δ | CD99 | BTNL3 | DAP10 |
| CD99 | CD28δ | CD3γ | CD99 | BTNL3 | DAP12 |
| CD99 | CD28δ | CD3ε | CD99 | BTNL3 | CD32 |
| CD99 | CD28δ | FcγRI-γ | CD99 | BTNL3 | CD79a |
| CD99 | CD28δ | FcγRIII-γ | CD99 | BTNL3 | CD79b |
| CD99 | CD28δ | FcεRIβ | CD99 | NKG2D | CD8 |
| CD99 | CD28δ | FcεRIγ | CD99 | NKG2D | CD3ζ |
| CD99 | CD28δ | DAP10 | CD99 | NKG2D | CD3δ |
| CD99 | CD28δ | DAP12 | CD99 | NKG2D | CD3γ |
| CD99 | CD28δ | CD32 | CD99 | NKG2D | CD3ε |
| CD99 | CD28δ | CD79a | CD99 | NKG2D | FcγRI-γ |
| CD99 | CD28δ | CD79b | CD99 | NKG2D | FcγRIII-γ |
| CD99 | CD80 | CD8 | CD99 | NKG2D | FcεRIβ |
| CD99 | CD80 | CD3ζ | CD99 | NKG2D | FcεRIγ |
| CD99 | CD80 | CD3δ | CD99 | NKG2D | DAP10 |
| CD99 | CD80 | CD3γ | CD99 | NKG2D | DAP12 |
| CD99 | CD80 | CD3ε | CD99 | NKG2D | CD32 |
| CD99 | CD80 | FcγRI-γ | CD99 | NKG2D | CD79a |
| CD99 | CD80 | FcγRIII-γ | CD99 | NKG2D | CD79b |

TABLE 3

Third Generation CARs

| ScFv | Co-stimulatory Signal | Co-stimulatory Signal | Signal Domain |
|---|---|---|---|
| CD99 | CD28 | CD28 | CD8 |
| CD99 | CD28 | CD28 | CD3ζ |
| CD99 | CD28 | CD28 | CD3δ |

TABLE 3-continued

Third Generation CARs

| ScFv | Co-stimulatory Signal | Co-stimulatory Signal | Signal Domain |
|---|---|---|---|
| CD99 | CD28 | CD28 | CD3γ |
| CD99 | CD28 | CD28 | CD3ε |
| CD99 | CD28 | CD28 | FcγRI-γ |
| CD99 | CD28 | CD28 | FcγRIII-γ |
| CD99 | CD28 | CD28 | FcεRIβ |
| CD99 | CD28 | CD28 | FcεRIγ |
| CD99 | CD28 | CD28 | DAP10 |
| CD99 | CD28 | CD28 | DAP12 |
| CD99 | CD28 | CD28 | CD32 |
| CD99 | CD28 | CD28 | CD79a |
| CD99 | CD28 | CD28 | CD79b |
| CD99 | CD28 | CD8 | CD8 |
| CD99 | CD28 | CD8 | CD3ζ |
| CD99 | CD28 | CD8 | CD3δ |
| CD99 | CD28 | CD8 | CD3γ |
| CD99 | CD28 | CD8 | CD3ε |
| CD99 | CD28 | CD8 | FcγRI-γ |
| CD99 | CD28 | CD8 | FcγRIII-γ |
| CD99 | CD28 | CD8 | FcεRIβ |
| CD99 | CD28 | CD8 | FcεRIγ |
| CD99 | CD28 | CD8 | DAP10 |
| CD99 | CD28 | CD8 | DAP12 |
| CD99 | CD28 | CD8 | CD32 |
| CD99 | CD28 | CD8 | CD79a |
| CD99 | CD28 | CD8 | CD79b |
| CD99 | CD28 | CD4 | CD8 |
| CD99 | CD28 | CD4 | CD3ζ |
| CD99 | CD28 | CD4 | CD3δ |
| CD99 | CD28 | CD4 | CD3γ |
| CD99 | CD28 | CD4 | CD3ε |
| CD99 | CD28 | CD4 | FcγRI-γ |
| CD99 | CD28 | CD4 | FcγRIII-γ |
| CD99 | CD28 | CD4 | FcεRIβ |
| CD99 | CD28 | CD4 | FcεRIγ |
| CD99 | CD28 | CD4 | DAP10 |
| CD99 | CD28 | CD4 | DAP12 |
| CD99 | CD28 | CD4 | CD32 |
| CD99 | CD28 | CD4 | CD79a |
| CD99 | CD28 | CD4 | CD79b |
| CD99 | CD28 | b2c | CD8 |
| CD99 | CD28 | b2c | CD3ζ |
| CD99 | CD28 | b2c | CD3δ |
| CD99 | CD28 | b2c | CD3γ |
| CD99 | CD28 | b2c | CD3ε |
| CD99 | CD28 | b2c | FcγRI-γ |
| CD99 | CD28 | b2c | FcγRIII-γ |
| CD99 | CD28 | b2c | FcεRIβ |
| CD99 | CD28 | b2c | FcεRIγ |
| CD99 | CD28 | b2c | DAP10 |
| CD99 | CD28 | b2c | DAP12 |
| CD99 | CD28 | b2c | CD32 |
| CD99 | CD28 | b2c | CD79a |
| CD99 | CD28 | b2c | CD79b |
| CD99 | CD28 | CD137/41BB | CD8 |
| CD99 | CD28 | CD137/41BB | CD3ζ |
| CD99 | CD28 | CD137/41BB | CD3δ |
| CD99 | CD28 | CD137/41BB | CD3γ |
| CD99 | CD28 | CD137/41BB | CD3ε |
| CD99 | CD28 | CD137/41BB | FcγRI-γ |
| CD99 | CD28 | CD137/41BB | FcγRIII-γ |
| CD99 | CD28 | CD137/41BB | FcεRIβ |
| CD99 | CD28 | CD137/41BB | FcεRIγ |
| CD99 | CD28 | CD137/41BB | DAP10 |
| CD99 | CD28 | CD137/41BB | DAP12 |
| CD99 | CD28 | CD137/41BB | CD32 |
| CD99 | CD28 | CD137/41BB | CD79a |
| CD99 | CD28 | CD137/41BB | CD79b |
| CD99 | CD28 | ICOS | CD8 |
| CD99 | CD28 | ICOS | CD3ζ |
| CD99 | CD28 | ICOS | CD3δ |
| CD99 | CD28 | ICOS | CD3γ |
| CD99 | CD28 | ICOS | CD3ε |
| CD99 | CD28 | ICOS | FcγRI-γ |
| CD99 | CD28 | ICOS | FcγRIII-γ |
| CD99 | CD28 | ICOS | FcεRIβ |
| CD99 | CD28 | ICOS | FcεRIγ |
| CD99 | CD28 | ICOS | DAP10 |
| CD99 | CD28 | ICOS | DAP12 |
| CD99 | CD28 | ICOS | CD32 |
| CD99 | CD28 | ICOS | CD79a |
| CD99 | CD28 | ICOS | CD79b |
| CD99 | CD28 | CD27 | CD8 |
| CD99 | CD28 | CD27 | CD3ζ |
| CD99 | CD28 | CD27 | CD3δ |
| CD99 | CD28 | CD27 | CD3γ |
| CD99 | CD28 | CD27 | CD3ε |
| CD99 | CD28 | CD27 | FcγRI-γ |
| CD99 | CD28 | CD27 | FcγRIII-γ |
| CD99 | CD28 | CD27 | FcεRIβ |
| CD99 | CD28 | CD27 | FcεRIγ |
| CD99 | CD28 | CD27 | DAP10 |
| CD99 | CD28 | CD27 | DAP12 |
| CD99 | CD28 | CD27 | CD32 |
| CD99 | CD28 | CD27 | CD79a |
| CD99 | CD28 | CD27 | CD79b |
| CD99 | CD28 | CD28δ | CD8 |
| CD99 | CD28 | CD28δ | CD3ζ |
| CD99 | CD28 | CD28δ | CD3δ |
| CD99 | CD28 | CD28δ | CD3γ |
| CD99 | CD28 | CD28δ | CD3ε |
| CD99 | CD28 | CD28δ | FcγRI-γ |
| CD99 | CD28 | CD28δ | FcγRIII-γ |
| CD99 | CD28 | CD28δ | FcεRIβ |
| CD99 | CD28 | CD28δ | FcεRIγ |
| CD99 | CD28 | CD28δ | DAP10 |
| CD99 | CD28 | CD28δ | DAP12 |
| CD99 | CD28 | CD28δ | CD32 |
| CD99 | CD28 | CD28δ | CD79a |
| CD99 | CD28 | CD28δ | CD79b |
| CD99 | CD28 | CD80 | CD8 |
| CD99 | CD28 | CD80 | CD3ζ |
| CD99 | CD28 | CD80 | CD3δ |
| CD99 | CD28 | CD80 | CD3γ |
| CD99 | CD28 | CD80 | CD3ε |
| CD99 | CD28 | CD80 | FcγRI-γ |
| CD99 | CD28 | CD80 | FcγRIII-γ |
| CD99 | CD28 | CD80 | FcεRIβ |
| CD99 | CD28 | CD80 | FcεRIγ |
| CD99 | CD28 | CD80 | DAP10 |
| CD99 | CD28 | CD80 | DAP12 |
| CD99 | CD28 | CD80 | CD32 |
| CD99 | CD28 | CD80 | CD79a |
| CD99 | CD28 | CD80 | CD79b |
| CD99 | CD28 | CD86 | CD8 |
| CD99 | CD28 | CD86 | CD3ζ |
| CD99 | CD28 | CD86 | CD3δ |
| CD99 | CD28 | CD86 | CD3γ |
| CD99 | CD28 | CD86 | CD3ε |
| CD99 | CD28 | CD86 | FcγRI-γ |
| CD99 | CD28 | CD86 | FcγRIII-γ |
| CD99 | CD28 | CD86 | FcεRIβ |
| CD99 | CD28 | CD86 | FcεRIγ |
| CD99 | CD28 | CD86 | DAP10 |
| CD99 | CD28 | CD86 | DAP12 |
| CD99 | CD28 | CD86 | CD32 |
| CD99 | CD28 | CD86 | CD79a |
| CD99 | CD28 | CD86 | CD79b |
| CD99 | CD28 | OX40 | CD8 |
| CD99 | CD28 | OX40 | CD3ζ |
| CD99 | CD28 | OX40 | CD3δ |
| CD99 | CD28 | OX40 | CD3γ |
| CD99 | CD28 | OX40 | CD3ε |
| CD99 | CD28 | OX40 | FcγRI-γ |
| CD99 | CD28 | OX40 | FcγRIII-γ |
| CD99 | CD28 | OX40 | FcεRIβ |
| CD99 | CD28 | OX40 | FcεRIγ |
| CD99 | CD28 | OX40 | DAP10 |
| CD99 | CD28 | OX40 | DAP12 |
| CD99 | CD28 | OX40 | CD32 |
| CD99 | CD28 | OX40 | CD79a |

TABLE 3-continued

Third Generation CARs

| ScFv | Co-stimulatory Signal | Co-stimulatory Signal | Signal Domain |
|---|---|---|---|
| CD99 | CD28 | OX40 | CD79b |
| CD99 | CD28 | DAP10 | CD8 |
| CD99 | CD28 | DAP10 | CD3ζ |
| CD99 | CD28 | DAP10 | CD3δ |
| CD99 | CD28 | DAP10 | CD3γ |
| CD99 | CD28 | DAP10 | CD3ε |
| CD99 | CD28 | DAP10 | FcγRI-γ |
| CD99 | CD28 | DAP10 | FcγRIII-γ |
| CD99 | CD28 | DAP10 | FcεRIβ |
| CD99 | CD28 | DAP10 | FcεRIγ |
| CD99 | CD28 | DAP10 | DAP10 |
| CD99 | CD28 | DAP10 | DAP12 |
| CD99 | CD28 | DAP10 | CD32 |
| CD99 | CD28 | DAP10 | CD79a |
| CD99 | CD28 | DAP10 | CD79b |
| CD99 | CD28 | DAP12 | CD8 |
| CD99 | CD28 | DAP12 | CD3ζ |
| CD99 | CD28 | DAP12 | CD3δ |
| CD99 | CD28 | DAP12 | CD3γ |
| CD99 | CD28 | DAP12 | CD3ε |
| CD99 | CD28 | DAP12 | FcγRI-γ |
| CD99 | CD28 | DAP12 | FcγRIII-γ |
| CD99 | CD28 | DAP12 | FcεRIβ |
| CD99 | CD28 | DAP12 | FcεRIγ |
| CD99 | CD28 | DAP12 | DAP10 |
| CD99 | CD28 | DAP12 | DAP12 |
| CD99 | CD28 | DAP12 | CD32 |
| CD99 | CD28 | DAP12 | CD79a |
| CD99 | CD28 | DAP12 | CD79b |
| CD99 | CD28 | MyD88 | CD8 |
| CD99 | CD28 | MyD88 | CD3ζ |
| CD99 | CD28 | MyD88 | CD3δ |
| CD99 | CD28 | MyD88 | CD3γ |
| CD99 | CD28 | MyD88 | CD3ε |
| CD99 | CD28 | MyD88 | FcγRI-γ |
| CD99 | CD28 | MyD88 | FcγRIII-γ |
| CD99 | CD28 | MyD88 | FcεRIβ |
| CD99 | CD28 | MyD88 | FcεRIγ |
| CD99 | CD28 | MyD88 | DAP10 |
| CD99 | CD28 | MyD88 | DAP12 |
| CD99 | CD28 | MyD88 | CD32 |
| CD99 | CD28 | MyD88 | CD79a |
| CD99 | CD28 | MyD88 | CD79b |
| CD99 | CD28 | CD7 | CD8 |
| CD99 | CD28 | CD7 | CD3ζ |
| CD99 | CD28 | CD7 | CD3δ |
| CD99 | CD28 | CD7 | CD3γ |
| CD99 | CD28 | CD7 | CD3ε |
| CD99 | CD28 | CD7 | FcγRI-γ |
| CD99 | CD28 | CD7 | FcγRIII-γ |
| CD99 | CD28 | CD7 | FcεRIβ |
| CD99 | CD28 | CD7 | FcεRIγ |
| CD99 | CD28 | CD7 | DAP10 |
| CD99 | CD28 | CD7 | DAP12 |
| CD99 | CD28 | CD7 | CD32 |
| CD99 | CD28 | CD7 | CD79a |
| CD99 | CD28 | CD7 | CD79b |
| CD99 | CD28 | BTNL3 | CD8 |
| CD99 | CD28 | BTNL3 | CD3ζ |
| CD99 | CD28 | BTNL3 | CD3δ |
| CD99 | CD28 | BTNL3 | CD3γ |
| CD99 | CD28 | BTNL3 | CD3ε |
| CD99 | CD28 | BTNL3 | FcγRI-γ |
| CD99 | CD28 | BTNL3 | FcγRIII-γ |
| CD99 | CD28 | BTNL3 | FcεRIβ |
| CD99 | CD28 | BTNL3 | FcεRIγ |
| CD99 | CD28 | BTNL3 | DAP10 |
| CD99 | CD28 | BTNL3 | DAP12 |
| CD99 | CD28 | BTNL3 | CD32 |
| CD99 | CD28 | BTNL3 | CD79a |
| CD99 | CD28 | BTNL3 | CD79b |
| CD99 | CD28 | NKG2D | CD8 |
| CD99 | CD28 | NKG2D | CD3ζ |
| CD99 | CD28 | NKG2D | CD3δ |
| CD99 | CD28 | NKG2D | CD3γ |
| CD99 | CD28 | NKG2D | CD3ε |
| CD99 | CD28 | NKG2D | FcγRI-γ |
| CD99 | CD28 | NKG2D | FcγRIII-γ |
| CD99 | CD28 | NKG2D | FcεRIβ |
| CD99 | CD28 | NKG2D | FcεRIγ |
| CD99 | CD28 | NKG2D | DAP10 |
| CD99 | CD28 | NKG2D | DAP12 |
| CD99 | CD28 | NKG2D | CD32 |
| CD99 | CD28 | NKG2D | CD79a |
| CD99 | CD28 | NKG2D | CD79b |
| CD99 | CD8 | CD28 | CD8 |
| CD99 | CD8 | CD28 | CD3ζ |
| CD99 | CD8 | CD28 | CD3δ |
| CD99 | CD8 | CD28 | CD3γ |
| CD99 | CD8 | CD28 | CD3ε |
| CD99 | CD8 | CD28 | FcγRI-γ |
| CD99 | CD8 | CD28 | FcγRIII-γ |
| CD99 | CD8 | CD28 | FcεRIβ |
| CD99 | CD8 | CD28 | FcεRIγ |
| CD99 | CD8 | CD28 | DAP10 |
| CD99 | CD8 | CD28 | DAP12 |
| CD99 | CD8 | CD28 | CD32 |
| CD99 | CD8 | CD28 | CD79a |
| CD99 | CD8 | CD28 | CD79b |
| CD99 | CD8 | CD8 | CD8 |
| CD99 | CD8 | CD8 | CD3ζ |
| CD99 | CD8 | CD8 | CD3δ |
| CD99 | CD8 | CD8 | CD3γ |
| CD99 | CD8 | CD8 | CD3ε |
| CD99 | CD8 | CD8 | FcγRI-γ |
| CD99 | CD8 | CD8 | FcγRIII-γ |
| CD99 | CD8 | CD8 | FcεRIβ |
| CD99 | CD8 | CD8 | FcεRIγ |
| CD99 | CD8 | CD8 | DAP10 |
| CD99 | CD8 | CD8 | DAP12 |
| CD99 | CD8 | CD8 | CD32 |
| CD99 | CD8 | CD8 | CD79a |
| CD99 | CD8 | CD8 | CD79b |
| CD99 | CD8 | CD4 | CD8 |
| CD99 | CD8 | CD4 | CD3ζ |
| CD99 | CD8 | CD4 | CD3δ |
| CD99 | CD8 | CD4 | CD3γ |
| CD99 | CD8 | CD4 | CD3ε |
| CD99 | CD8 | CD4 | FcγRI-γ |
| CD99 | CD8 | CD4 | FcγRIII-γ |
| CD99 | CD8 | CD4 | FcεRIβ |
| CD99 | CD8 | CD4 | FcεRIγ |
| CD99 | CD8 | CD4 | DAP10 |
| CD99 | CD8 | CD4 | DAP12 |
| CD99 | CD8 | CD4 | CD32 |
| CD99 | CD8 | CD4 | CD79a |
| CD99 | CD8 | CD4 | CD79b |
| CD99 | CD8 | b2c | CD8 |
| CD99 | CD8 | b2c | CD3ζ |
| CD99 | CD8 | b2c | CD3δ |
| CD99 | CD8 | b2c | CD3γ |
| CD99 | CD8 | b2c | CD3ε |
| CD99 | CD8 | b2c | FcγRI-γ |
| CD99 | CD8 | b2c | FcγRIII-γ |
| CD99 | CD8 | b2c | FcεRIβ |
| CD99 | CD8 | b2c | FcεRIγ |
| CD99 | CD8 | b2c | DAP10 |
| CD99 | CD8 | b2c | DAP12 |
| CD99 | CD8 | b2c | CD32 |
| CD99 | CD8 | b2c | CD79a |
| CD99 | CD8 | b2c | CD79b |
| CD99 | CD8 | CD137/41BB | CD8 |
| CD99 | CD8 | CD137/41BB | CD3ζ |
| CD99 | CD8 | CD137/41BB | CD3δ |
| CD99 | CD8 | CD137/41BB | CD3γ |
| CD99 | CD8 | CD137/41BB | CD3ε |
| CD99 | CD8 | CD137/41BB | FcγRI-γ |
| CD99 | CD8 | CD137/41BB | FcγRIII-γ |
| CD99 | CD8 | CD137/41BB | FcεRIβ |
| CD99 | CD8 | CD137/41BB | FcεRIγ |

TABLE 3-continued

Third Generation CARs

| ScFv | Co-stimulatory Signal | Co-stimulatory Signal | Signal Domain |
|---|---|---|---|
| CD99 | CD8 | CD137/41BB | DAP10 |
| CD99 | CD8 | CD137/41BB | DAP12 |
| CD99 | CD8 | CD137/41BB | CD32 |
| CD99 | CD8 | CD137/41BB | CD79a |
| CD99 | CD8 | CD137/41BB | CD79b |
| CD99 | CD8 | ICOS | CD8 |
| CD99 | CD8 | ICOS | CD3ζ |
| CD99 | CD8 | ICOS | CD3δ |
| CD99 | CD8 | ICOS | CD3γ |
| CD99 | CD8 | ICOS | CD3ε |
| CD99 | CD8 | ICOS | FcγRI-γ |
| CD99 | CD8 | ICOS | FcγRIII-γ |
| CD99 | CD8 | ICOS | FcεRIβ |
| CD99 | CD8 | ICOS | FcεRIγ |
| CD99 | CD8 | ICOS | DAP10 |
| CD99 | CD8 | ICOS | DAP12 |
| CD99 | CD8 | ICOS | CD32 |
| CD99 | CD8 | ICOS | CD79a |
| CD99 | CD8 | ICOS | CD79b |
| CD99 | CD8 | CD27 | CD8 |
| CD99 | CD8 | CD27 | CD3ζ |
| CD99 | CD8 | CD27 | CD3δ |
| CD99 | CD8 | CD27 | CD3γ |
| CD99 | CD8 | CD27 | CD3ε |
| CD99 | CD8 | CD27 | FcγRI-γ |
| CD99 | CD8 | CD27 | FcγRIII-γ |
| CD99 | CD8 | CD27 | FcεRIβ |
| CD99 | CD8 | CD27 | FcεRIγ |
| CD99 | CD8 | CD27 | DAP10 |
| CD99 | CD8 | CD27 | DAP12 |
| CD99 | CD8 | CD27 | CD32 |
| CD99 | CD8 | CD27 | CD79a |
| CD99 | CD8 | CD27 | CD79b |
| CD99 | CD8 | CD28δ | CD8 |
| CD99 | CD8 | CD28δ | CD3ζ |
| CD99 | CD8 | CD28δ | CD3δ |
| CD99 | CD8 | CD28δ | CD3γ |
| CD99 | CD8 | CD28δ | CD3ε |
| CD99 | CD8 | CD28δ | FcγRI-γ |
| CD99 | CD8 | CD28δ | FcγRIII-γ |
| CD99 | CD8 | CD28δ | FcεRIβ |
| CD99 | CD8 | CD28δ | FcεRIγ |
| CD99 | CD8 | CD28δ | DAP10 |
| CD99 | CD8 | CD28δ | DAP12 |
| CD99 | CD8 | CD28δ | CD32 |
| CD99 | CD8 | CD28δ | CD79a |
| CD99 | CD8 | CD28δ | CD79b |
| CD99 | CD8 | CD80 | CD8 |
| CD99 | CD8 | CD80 | CD3ζ |
| CD99 | CD8 | CD80 | CD3δ |
| CD99 | CD8 | CD80 | CD3γ |
| CD99 | CD8 | CD80 | CD3ε |
| CD99 | CD8 | CD80 | FcγRI-γ |
| CD99 | CD8 | CD80 | FcγRIII-γ |
| CD99 | CD8 | CD80 | FcεRIβ |
| CD99 | CD8 | CD80 | FcεRIγ |
| CD99 | CD8 | CD80 | DAP10 |
| CD99 | CD8 | CD80 | DAP12 |
| CD99 | CD8 | CD80 | CD32 |
| CD99 | CD8 | CD80 | CD79a |
| CD99 | CD8 | CD80 | CD79b |
| CD99 | CD8 | CD86 | CD8 |
| CD99 | CD8 | CD86 | CD3ζ |
| CD99 | CD8 | CD86 | CD3δ |
| CD99 | CD8 | CD86 | CD3γ |
| CD99 | CD8 | CD86 | CD3ε |
| CD99 | CD8 | CD86 | FcγRI-γ |
| CD99 | CD8 | CD86 | FcγRIII-γ |
| CD99 | CD8 | CD86 | FcεRIβ |
| CD99 | CD8 | CD86 | FcεRIγ |
| CD99 | CD8 | CD86 | DAP10 |
| CD99 | CD8 | CD86 | DAP12 |
| CD99 | CD8 | CD86 | CD32 |
| CD99 | CD8 | CD86 | CD79a |
| CD99 | CD8 | CD86 | CD79b |
| CD99 | CD8 | OX40 | CD8 |
| CD99 | CD8 | OX40 | CD3ζ |
| CD99 | CD8 | OX40 | CD3δ |
| CD99 | CD8 | OX40 | CD3γ |
| CD99 | CD8 | OX40 | CD3ε |
| CD99 | CD8 | OX40 | FcγRI-γ |
| CD99 | CD8 | OX40 | FcγRIII-γ |
| CD99 | CD8 | OX40 | FcεRIβ |
| CD99 | CD8 | OX40 | FcεRIγ |
| CD99 | CD8 | OX40 | DAP10 |
| CD99 | CD8 | OX40 | DAP12 |
| CD99 | CD8 | OX40 | CD32 |
| CD99 | CD8 | OX40 | CD79a |
| CD99 | CD8 | OX40 | CD79b |
| CD99 | CD8 | DAP10 | CD8 |
| CD99 | CD8 | DAP10 | CD3ζ |
| CD99 | CD8 | DAP10 | CD3δ |
| CD99 | CD8 | DAP10 | CD3γ |
| CD99 | CD8 | DAP10 | CD3ε |
| CD99 | CD8 | DAP10 | FcγRI-γ |
| CD99 | CD8 | DAP10 | FcγRIII-γ |
| CD99 | CD8 | DAP10 | FcεRIβ |
| CD99 | CD8 | DAP10 | FcεRIγ |
| CD99 | CD8 | DAP10 | DAP10 |
| CD99 | CD8 | DAP10 | DAP12 |
| CD99 | CD8 | DAP10 | CD32 |
| CD99 | CD8 | DAP10 | CD79a |
| CD99 | CD8 | DAP10 | CD79b |
| CD99 | CD8 | DAP12 | CD8 |
| CD99 | CD8 | DAP12 | CD3ζ |
| CD99 | CD8 | DAP12 | CD3δ |
| CD99 | CD8 | DAP12 | CD3γ |
| CD99 | CD8 | DAP12 | CD3ε |
| CD99 | CD8 | DAP12 | FcγRI-γ |
| CD99 | CD8 | DAP12 | FcγRIII-γ |
| CD99 | CD8 | DAP12 | FcεRIβ |
| CD99 | CD8 | DAP12 | FcεRIγ |
| CD99 | CD8 | DAP12 | DAP10 |
| CD99 | CD8 | DAP12 | DAP12 |
| CD99 | CD8 | DAP12 | CD32 |
| CD99 | CD8 | DAP12 | CD79a |
| CD99 | CD8 | DAP12 | CD79b |
| CD99 | CD8 | MyD88 | CD8 |
| CD99 | CD8 | MyD88 | CD3ζ |
| CD99 | CD8 | MyD88 | CD3δ |
| CD99 | CD8 | MyD88 | CD3γ |
| CD99 | CD8 | MyD88 | CD3ε |
| CD99 | CD8 | MyD88 | FcγRI-γ |
| CD99 | CD8 | MyD88 | FcγRIII-γ |
| CD99 | CD8 | MyD88 | FcεRIβ |
| CD99 | CD8 | MyD88 | FcεRIγ |
| CD99 | CD8 | MyD88 | DAP10 |
| CD99 | CD8 | MyD88 | DAP12 |
| CD99 | CD8 | MyD88 | CD32 |
| CD99 | CD8 | MyD88 | CD79a |
| CD99 | CD8 | MyD88 | CD79b |
| CD99 | CD8 | CD7 | CD8 |
| CD99 | CD8 | CD7 | CD3ζ |
| CD99 | CD8 | CD7 | CD3δ |
| CD99 | CD8 | CD7 | CD3γ |
| CD99 | CD8 | CD7 | CD3ε |
| CD99 | CD8 | CD7 | FcγRI-γ |
| CD99 | CD8 | CD7 | FcγRIII-γ |
| CD99 | CD8 | CD7 | FcεRIβ |
| CD99 | CD8 | CD7 | FcεRIγ |
| CD99 | CD8 | CD7 | DAP10 |
| CD99 | CD8 | CD7 | DAP12 |
| CD99 | CD8 | CD7 | CD32 |
| CD99 | CD8 | CD7 | CD79a |
| CD99 | CD8 | CD7 | CD79b |
| CD99 | CD8 | BTNL3 | CD8 |
| CD99 | CD8 | BTNL3 | CD3ζ |
| CD99 | CD8 | BTNL3 | CD3δ |
| CD99 | CD8 | BTNL3 | CD3γ |
| CD99 | CD8 | BTNL3 | CD3ε |

TABLE 3-continued

Third Generation CARs

| ScFv | Co-stimulatory Signal | Co-stimulatory Signal | Signal Domain |
|---|---|---|---|
| CD99 | CD8 | BTNL3 | FcγRI-γ |
| CD99 | CD8 | BTNL3 | FcγRIII-γ |
| CD99 | CD8 | BTNL3 | FcεRIβ |
| CD99 | CD8 | BTNL3 | FcεRIγ |
| CD99 | CD8 | BTNL3 | DAP10 |
| CD99 | CD8 | BTNL3 | DAP12 |
| CD99 | CD8 | BTNL3 | CD32 |
| CD99 | CD8 | BTNL3 | CD79a |
| CD99 | CD8 | BTNL3 | CD79b |
| CD99 | CD8 | NKG2D | CD8 |
| CD99 | CD8 | NKG2D | CD3ζ |
| CD99 | CD8 | NKG2D | CD3δ |
| CD99 | CD8 | NKG2D | CD3γ |
| CD99 | CD8 | NKG2D | CD3ε |
| CD99 | CD8 | NKG2D | FcγRI-γ |
| CD99 | CD8 | NKG2D | FcγRIII-γ |
| CD99 | CD8 | NKG2D | FcεRIβ |
| CD99 | CD8 | NKG2D | FcεRIγ |
| CD99 | CD8 | NKG2D | DAP10 |
| CD99 | CD8 | NKG2D | DAP12 |
| CD99 | CD8 | NKG2D | CD32 |
| CD99 | CD8 | NKG2D | CD79a |
| CD99 | CD8 | NKG2D | CD79b |
| CD99 | CD4 | CD28 | CD8 |
| CD99 | CD4 | CD28 | CD3ζ |
| CD99 | CD4 | CD28 | CD3δ |
| CD99 | CD4 | CD28 | CD3γ |
| CD99 | CD4 | CD28 | CD3ε |
| CD99 | CD4 | CD28 | FcγRI-γ |
| CD99 | CD4 | CD28 | FcγRIII-γ |
| CD99 | CD4 | CD28 | FcεRIβ |
| CD99 | CD4 | CD28 | FcεRIγ |
| CD99 | CD4 | CD28 | DAP10 |
| CD99 | CD4 | CD28 | DAP12 |
| CD99 | CD4 | CD28 | CD32 |
| CD99 | CD4 | CD28 | CD79a |
| CD99 | CD4 | CD28 | CD79b |
| CD99 | CD4 | CD8 | CD8 |
| CD99 | CD4 | CD8 | CD3ζ |
| CD99 | CD4 | CD8 | CD3δ |
| CD99 | CD4 | CD8 | CD3γ |
| CD99 | CD4 | CD8 | CD3ε |
| CD99 | CD4 | CD8 | FcγRI-γ |
| CD99 | CD4 | CD8 | FcγRIII-γ |
| CD99 | CD4 | CD8 | FcεRIβ |
| CD99 | CD4 | CD8 | FcεRIγ |
| CD99 | CD4 | CD8 | DAP10 |
| CD99 | CD4 | CD8 | DAP12 |
| CD99 | CD4 | CD8 | CD32 |
| CD99 | CD4 | CD8 | CD79a |
| CD99 | CD4 | CD8 | CD79b |
| CD99 | CD4 | CD4 | CD8 |
| CD99 | CD4 | CD4 | CD3ζ |
| CD99 | CD4 | CD4 | CD3δ |
| CD99 | CD4 | CD4 | CD3γ |
| CD99 | CD4 | CD4 | CD3ε |
| CD99 | CD4 | CD4 | FcγRI-γ |
| CD99 | CD4 | CD4 | FcγRIII-γ |
| CD99 | CD4 | CD4 | FcεRIβ |
| CD99 | CD4 | CD4 | FcεRIγ |
| CD99 | CD4 | CD4 | DAP10 |
| CD99 | CD4 | CD4 | DAP12 |
| CD99 | CD4 | CD4 | CD32 |
| CD99 | CD4 | CD4 | CD79a |
| CD99 | CD4 | CD4 | CD79b |
| CD99 | CD4 | b2c | CD8 |
| CD99 | CD4 | b2c | CD3ζ |
| CD99 | CD4 | b2c | CD3δ |
| CD99 | CD4 | b2c | CD3γ |
| CD99 | CD4 | b2c | CD3ε |
| CD99 | CD4 | b2c | FcγRI-γ |
| CD99 | CD4 | b2c | FcγRIII-γ |
| CD99 | CD4 | b2c | FcεRIβ |
| CD99 | CD4 | b2c | FcεRIγ |
| CD99 | CD4 | b2c | DAP10 |
| CD99 | CD4 | b2c | DAP12 |
| CD99 | CD4 | b2c | CD32 |
| CD99 | CD4 | b2c | CD79a |
| CD99 | CD4 | b2c | CD79b |
| CD99 | CD4 | CD137/41BB | CD8 |
| CD99 | CD4 | CD137/41BB | CD3ζ |
| CD99 | CD4 | CD137/41BB | CD3δ |
| CD99 | CD4 | CD137/41BB | CD3γ |
| CD99 | CD4 | CD137/41BB | CD3ε |
| CD99 | CD4 | CD137/41BB | FcγRI-γ |
| CD99 | CD4 | CD137/41BB | FcγRIII-γ |
| CD99 | CD4 | CD137/41BB | FcεRIβ |
| CD99 | CD4 | CD137/41BB | FcεRIγ |
| CD99 | CD4 | CD137/41BB | DAP10 |
| CD99 | CD4 | CD137/41BB | DAP12 |
| CD99 | CD4 | CD137/41BB | CD32 |
| CD99 | CD4 | CD137/41BB | CD79a |
| CD99 | CD4 | CD137/41BB | CD79b |
| CD99 | CD4 | ICOS | CD8 |
| CD99 | CD4 | ICOS | CD3ζ |
| CD99 | CD4 | ICOS | CD3δ |
| CD99 | CD4 | ICOS | CD3γ |
| CD99 | CD4 | ICOS | CD3ε |
| CD99 | CD4 | ICOS | FcγRI-γ |
| CD99 | CD4 | ICOS | FcγRIII-γ |
| CD99 | CD4 | ICOS | FcεRIβ |
| CD99 | CD4 | ICOS | FcεRIγ |
| CD99 | CD4 | ICOS | DAP10 |
| CD99 | CD4 | ICOS | DAP12 |
| CD99 | CD4 | ICOS | CD32 |
| CD99 | CD4 | ICOS | CD79a |
| CD99 | CD4 | ICOS | CD79b |
| CD99 | CD4 | CD27 | CD8 |
| CD99 | CD4 | CD27 | CD3ζ |
| CD99 | CD4 | CD27 | CD3δ |
| CD99 | CD4 | CD27 | CD3γ |
| CD99 | CD4 | CD27 | CD3ε |
| CD99 | CD4 | CD27 | FcγRI-γ |
| CD99 | CD4 | CD27 | FcγRIII-γ |
| CD99 | CD4 | CD27 | FcεRIβ |
| CD99 | CD4 | CD27 | FcεRIγ |
| CD99 | CD4 | CD27 | DAP10 |
| CD99 | CD4 | CD27 | DAP12 |
| CD99 | CD4 | CD27 | CD32 |
| CD99 | CD4 | CD27 | CD79a |
| CD99 | CD4 | CD27 | CD79b |
| CD99 | CD4 | CD28δ | CD8 |
| CD99 | CD4 | CD28δ | CD3ζ |
| CD99 | CD4 | CD28δ | CD3δ |
| CD99 | CD4 | CD28δ | CD3γ |
| CD99 | CD4 | CD28δ | CD3ε |
| CD99 | CD4 | CD28δ | FcγRI-γ |
| CD99 | CD4 | CD28δ | FcγRIII-γ |
| CD99 | CD4 | CD28δ | FcεRIβ |
| CD99 | CD4 | CD28δ | FcεRIγ |
| CD99 | CD4 | CD28δ | DAP10 |
| CD99 | CD4 | CD28δ | DAP12 |
| CD99 | CD4 | CD28δ | CD32 |
| CD99 | CD4 | CD28δ | CD79a |
| CD99 | CD4 | CD28δ | CD79b |
| CD99 | CD4 | CD80 | CD8 |
| CD99 | CD4 | CD80 | CD3ζ |
| CD99 | CD4 | CD80 | CD3δ |
| CD99 | CD4 | CD80 | CD3γ |
| CD99 | CD4 | CD80 | CD3ε |
| CD99 | CD4 | CD80 | FcγRI-γ |
| CD99 | CD4 | CD80 | FcγRIII-γ |
| CD99 | CD4 | CD80 | FcεRIβ |
| CD99 | CD4 | CD80 | FcεRIγ |
| CD99 | CD4 | CD80 | DAP10 |
| CD99 | CD4 | CD80 | DAP12 |
| CD99 | CD4 | CD80 | CD32 |
| CD99 | CD4 | CD80 | CD79a |
| CD99 | CD4 | CD80 | CD79b |
| CD99 | CD4 | CD86 | CD8 |

TABLE 3-continued

Third Generation CARs

| ScFv | Co-stimulatory Signal | Co-stimulatory Signal | Signal Domain |
|---|---|---|---|
| CD99 | CD4 | CD86 | CD3ζ |
| CD99 | CD4 | CD86 | CD3δ |
| CD99 | CD4 | CD86 | CD3γ |
| CD99 | CD4 | CD86 | CD3ε |
| CD99 | CD4 | CD86 | FcγRI-γ |
| CD99 | CD4 | CD86 | FcγRIII-γ |
| CD99 | CD4 | CD86 | FcεRIβ |
| CD99 | CD4 | CD86 | FcεRIγ |
| CD99 | CD4 | CD86 | DAP10 |
| CD99 | CD4 | CD86 | DAP12 |
| CD99 | CD4 | CD86 | CD32 |
| CD99 | CD4 | CD86 | CD79a |
| CD99 | CD4 | CD86 | CD79b |
| CD99 | CD4 | OX40 | CD8 |
| CD99 | CD4 | OX40 | CD3ζ |
| CD99 | CD4 | OX40 | CD3δ |
| CD99 | CD4 | OX40 | CD3γ |
| CD99 | CD4 | OX40 | CD3ε |
| CD99 | CD4 | OX40 | FcγRI-γ |
| CD99 | CD4 | OX40 | FcγRIII-γ |
| CD99 | CD4 | OX40 | FcεRIβ |
| CD99 | CD4 | OX40 | FcεRIγ |
| CD99 | CD4 | OX40 | DAP10 |
| CD99 | CD4 | OX40 | DAP12 |
| CD99 | CD4 | OX40 | CD32 |
| CD99 | CD4 | OX40 | CD79a |
| CD99 | CD4 | OX40 | CD79b |
| CD99 | CD4 | DAP10 | CD8 |
| CD99 | CD4 | DAP10 | CD3ζ |
| CD99 | CD4 | DAP10 | CD3δ |
| CD99 | CD4 | DAP10 | CD3γ |
| CD99 | CD4 | DAP10 | CD3ε |
| CD99 | CD4 | DAP10 | FcγRI-γ |
| CD99 | CD4 | DAP10 | FcγRIII-γ |
| CD99 | CD4 | DAP10 | FcεRIβ |
| CD99 | CD4 | DAP10 | FcεRIγ |
| CD99 | CD4 | DAP10 | DAP10 |
| CD99 | CD4 | DAP10 | DAP12 |
| CD99 | CD4 | DAP10 | CD32 |
| CD99 | CD4 | DAP10 | CD79a |
| CD99 | CD4 | DAP10 | CD79b |
| CD99 | CD4 | DAP12 | CD8 |
| CD99 | CD4 | DAP12 | CD3ζ |
| CD99 | CD4 | DAP12 | CD3δ |
| CD99 | CD4 | DAP12 | CD3γ |
| CD99 | CD4 | DAP12 | CD3ε |
| CD99 | CD4 | DAP12 | FcγRI-γ |
| CD99 | CD4 | DAP12 | FcγRIII-γ |
| CD99 | CD4 | DAP12 | FcεRIβ |
| CD99 | CD4 | DAP12 | FcεRIγ |
| CD99 | CD4 | DAP12 | DAP10 |
| CD99 | CD4 | DAP12 | DAP12 |
| CD99 | CD4 | DAP12 | CD32 |
| CD99 | CD4 | DAP12 | CD79a |
| CD99 | CD4 | DAP12 | CD79b |
| CD99 | CD4 | MyD88 | CD8 |
| CD99 | CD4 | MyD88 | CD3ζ |
| CD99 | CD4 | MyD88 | CD3δ |
| CD99 | CD4 | MyD88 | CD3γ |
| CD99 | CD4 | MyD88 | CD3ε |
| CD99 | CD4 | MyD88 | FcγRI-γ |
| CD99 | CD4 | MyD88 | FcγRIII-γ |
| CD99 | CD4 | MyD88 | FcεRIβ |
| CD99 | CD4 | MyD88 | FcεRIγ |
| CD99 | CD4 | MyD88 | DAP10 |
| CD99 | CD4 | MyD88 | DAP12 |
| CD99 | CD4 | MyD88 | CD32 |
| CD99 | CD4 | MyD88 | CD79a |
| CD99 | CD4 | MyD88 | CD79b |
| CD99 | CD4 | CD7 | CD8 |
| CD99 | CD4 | CD7 | CD3ζ |
| CD99 | CD4 | CD7 | CD3δ |
| CD99 | CD4 | CD7 | CD3γ |
| CD99 | CD4 | CD7 | CD3ε |
| CD99 | CD4 | CD7 | FcγRI-γ |
| CD99 | CD4 | CD7 | FcγRIII-γ |
| CD99 | CD4 | CD7 | FcεRIβ |
| CD99 | CD4 | CD7 | FcεRIγ |
| CD99 | CD4 | CD7 | DAP10 |
| CD99 | CD4 | CD7 | DAP12 |
| CD99 | CD4 | CD7 | CD32 |
| CD99 | CD4 | CD7 | CD79a |
| CD99 | CD4 | CD7 | CD79b |
| CD99 | CD4 | BTNL3 | CD8 |
| CD99 | CD4 | BTNL3 | CD3ζ |
| CD99 | CD4 | BTNL3 | CD3δ |
| CD99 | CD4 | BTNL3 | CD3γ |
| CD99 | CD4 | BTNL3 | CD3ε |
| CD99 | CD4 | BTNL3 | FcγRI-γ |
| CD99 | CD4 | BTNL3 | FcγRIII-γ |
| CD99 | CD4 | BTNL3 | FcεRIβ |
| CD99 | CD4 | BTNL3 | FcεRIγ |
| CD99 | CD4 | BTNL3 | DAP10 |
| CD99 | CD4 | BTNL3 | DAP12 |
| CD99 | CD4 | BTNL3 | CD32 |
| CD99 | CD4 | BTNL3 | CD79a |
| CD99 | CD4 | BTNL3 | CD79b |
| CD99 | CD4 | NKG2D | CD8 |
| CD99 | CD4 | NKG2D | CD3ζ |
| CD99 | CD4 | NKG2D | CD3δ |
| CD99 | CD4 | NKG2D | CD3γ |
| CD99 | CD4 | NKG2D | CD3ε |
| CD99 | CD4 | NKG2D | FcγRI-γ |
| CD99 | CD4 | NKG2D | FcγRIII-γ |
| CD99 | CD4 | NKG2D | FcεRIβ |
| CD99 | CD4 | NKG2D | FcεRIγ |
| CD99 | CD4 | NKG2D | DAP10 |
| CD99 | CD4 | NKG2D | DAP12 |
| CD99 | CD4 | NKG2D | CD32 |
| CD99 | CD4 | NKG2D | CD79a |
| CD99 | CD4 | NKG2D | CD79b |
| CD99 | b2c | CD28 | CD8 |
| CD99 | b2c | CD28 | CD3ζ |
| CD99 | b2c | CD28 | CD3δ |
| CD99 | b2c | CD28 | CD3γ |
| CD99 | b2c | CD28 | CD3ε |
| CD99 | b2c | CD28 | FcγRI-γ |
| CD99 | b2c | CD28 | FcγRIII-γ |
| CD99 | b2c | CD28 | FcεRIβ |
| CD99 | b2c | CD28 | FcεRIγ |
| CD99 | b2c | CD28 | DAP10 |
| CD99 | b2c | CD28 | DAP12 |
| CD99 | b2c | CD28 | CD32 |
| CD99 | b2c | CD28 | CD79a |
| CD99 | b2c | CD28 | CD79b |
| CD99 | b2c | CD8 | CD8 |
| CD99 | b2c | CD8 | CD3ζ |
| CD99 | b2c | CD8 | CD3δ |
| CD99 | b2c | CD8 | CD3γ |
| CD99 | b2c | CD8 | CD3ε |
| CD99 | b2c | CD8 | FcγRI-γ |
| CD99 | b2c | CD8 | FcγRIII-γ |
| CD99 | b2c | CD8 | FcεRIβ |
| CD99 | b2c | CD8 | FcεRIγ |
| CD99 | b2c | CD8 | DAP10 |
| CD99 | b2c | CD8 | DAP12 |
| CD99 | b2c | CD8 | CD32 |
| CD99 | b2c | CD8 | CD79a |
| CD99 | b2c | CD8 | CD79b |
| CD99 | b2c | CD4 | CD8 |
| CD99 | b2c | CD4 | CD3ζ |
| CD99 | b2c | CD4 | CD3δ |
| CD99 | b2c | CD4 | CD3γ |
| CD99 | b2c | CD4 | CD3ε |
| CD99 | b2c | CD4 | FcγRI-γ |
| CD99 | b2c | CD4 | FcγRIII-γ |
| CD99 | b2c | CD4 | FcεRIβ |
| CD99 | b2c | CD4 | FcεRIγ |
| CD99 | b2c | CD4 | DAP10 |
| CD99 | b2c | CD4 | DAP12 |

TABLE 3-continued

Third Generation CARs

| ScFv | Co-stimulatory Signal | Co-stimulatory Signal | Signal Domain |
|---|---|---|---|
| CD99 | b2c | CD4 | CD32 |
| CD99 | b2c | CD4 | CD79a |
| CD99 | b2c | CD4 | CD79b |
| CD99 | b2c | b2c | CD8 |
| CD99 | b2c | b2c | CD3ζ |
| CD99 | b2c | b2c | CD3δ |
| CD99 | b2c | b2c | CD3γ |
| CD99 | b2c | b2c | CD3ε |
| CD99 | b2c | b2c | FcγRI-γ |
| CD99 | b2c | b2c | FcγRIII-γ |
| CD99 | b2c | b2c | FcεRIβ |
| CD99 | b2c | b2c | FcεRIγ |
| CD99 | b2c | b2c | DAP10 |
| CD99 | b2c | b2c | DAP12 |
| CD99 | b2c | b2c | CD32 |
| CD99 | b2c | b2c | CD79a |
| CD99 | b2c | b2c | CD79b |
| CD99 | b2c | CD137/41BB | CD8 |
| CD99 | b2c | CD137/41BB | CD3ζ |
| CD99 | b2c | CD137/41BB | CD3δ |
| CD99 | b2c | CD137/41BB | CD3γ |
| CD99 | b2c | CD137/41BB | CD3ε |
| CD99 | b2c | CD137/41BB | FcγRI-γ |
| CD99 | b2c | CD137/41BB | FcγRIII-γ |
| CD99 | b2c | CD137/41BB | FcεRIβ |
| CD99 | b2c | CD137/41BB | FcεRIγ |
| CD99 | b2c | CD137/41BB | DAP10 |
| CD99 | b2c | CD137/41BB | DAP12 |
| CD99 | b2c | CD137/41BB | CD32 |
| CD99 | b2c | CD137/41BB | CD79a |
| CD99 | b2c | CD137/41BB | CD79b |
| CD99 | b2c | ICOS | CD8 |
| CD99 | b2c | ICOS | CD3ζ |
| CD99 | b2c | ICOS | CD3δ |
| CD99 | b2c | ICOS | CD3γ |
| CD99 | b2c | ICOS | CD3ε |
| CD99 | b2c | ICOS | FcγRI-γ |
| CD99 | b2c | ICOS | FcγRIII-γ |
| CD99 | b2c | ICOS | FcεRIβ |
| CD99 | b2c | ICOS | FcεRIγ |
| CD99 | b2c | ICOS | DAP10 |
| CD99 | b2c | ICOS | DAP12 |
| CD99 | b2c | ICOS | CD32 |
| CD99 | b2c | ICOS | CD79a |
| CD99 | b2c | ICOS | CD79b |
| CD99 | b2c | CD27 | CD8 |
| CD99 | b2c | CD27 | CD3ζ |
| CD99 | b2c | CD27 | CD3δ |
| CD99 | b2c | CD27 | CD3γ |
| CD99 | b2c | CD27 | CD3ε |
| CD99 | b2c | CD27 | FcγRI-γ |
| CD99 | b2c | CD27 | FcγRIII-γ |
| CD99 | b2c | CD27 | FcεRIβ |
| CD99 | b2c | CD27 | FcεRIγ |
| CD99 | b2c | CD27 | DAP10 |
| CD99 | b2c | CD27 | DAP12 |
| CD99 | b2c | CD27 | CD32 |
| CD99 | b2c | CD27 | CD79a |
| CD99 | b2c | CD27 | CD79b |
| CD99 | b2c | CD28δ | CD8 |
| CD99 | b2c | CD28δ | CD3ζ |
| CD99 | b2c | CD28δ | CD3δ |
| CD99 | b2c | CD28δ | CD3γ |
| CD99 | b2c | CD28δ | CD3ε |
| CD99 | b2c | CD28δ | FcγRI-γ |
| CD99 | b2c | CD28δ | FcγRIII-γ |
| CD99 | b2c | CD28δ | FcεRIβ |
| CD99 | b2c | CD28δ | FcεRIγ |
| CD99 | b2c | CD28δ | DAP10 |
| CD99 | b2c | CD28δ | DAP12 |
| CD99 | b2c | CD28δ | CD32 |
| CD99 | b2c | CD28δ | CD79a |
| CD99 | b2c | CD28δ | CD79b |
| CD99 | b2c | CD80 | CD8 |
| CD99 | b2c | CD80 | CD3ζ |
| CD99 | b2c | CD80 | CD3δ |
| CD99 | b2c | CD80 | CD3γ |
| CD99 | b2c | CD80 | CD3ε |
| CD99 | b2c | CD80 | FcγRI-γ |
| CD99 | b2c | CD80 | FcγRIII-γ |
| CD99 | b2c | CD80 | FcεRIβ |
| CD99 | b2c | CD80 | FcεRIγ |
| CD99 | b2c | CD80 | DAP10 |
| CD99 | b2c | CD80 | DAP12 |
| CD99 | b2c | CD80 | CD32 |
| CD99 | b2c | CD80 | CD79a |
| CD99 | b2c | CD80 | CD79b |
| CD99 | b2c | CD86 | CD8 |
| CD99 | b2c | CD86 | CD3ζ |
| CD99 | b2c | CD86 | CD3δ |
| CD99 | b2c | CD86 | CD3γ |
| CD99 | b2c | CD86 | CD3ε |
| CD99 | b2c | CD86 | FcγRI-γ |
| CD99 | b2c | CD86 | FcγRIII-γ |
| CD99 | b2c | CD86 | FcεRIβ |
| CD99 | b2c | CD86 | FcεRIγ |
| CD99 | b2c | CD86 | DAP10 |
| CD99 | b2c | CD86 | DAP12 |
| CD99 | b2c | CD86 | CD32 |
| CD99 | b2c | CD86 | CD79a |
| CD99 | b2c | CD86 | CD79b |
| CD99 | b2c | OX40 | CD8 |
| CD99 | b2c | OX40 | CD3ζ |
| CD99 | b2c | OX40 | CD3δ |
| CD99 | b2c | OX40 | CD3γ |
| CD99 | b2c | OX40 | CD3ε |
| CD99 | b2c | OX40 | FcγRI-γ |
| CD99 | b2c | OX40 | FcγRIII-γ |
| CD99 | b2c | OX40 | FcεRIβ |
| CD99 | b2c | OX40 | FcεRIγ |
| CD99 | b2c | OX40 | DAP10 |
| CD99 | b2c | OX40 | DAP12 |
| CD99 | b2c | OX40 | CD32 |
| CD99 | b2c | OX40 | CD79a |
| CD99 | b2c | OX40 | CD79b |
| CD99 | b2c | DAP10 | CD8 |
| CD99 | b2c | DAP10 | CD3ζ |
| CD99 | b2c | DAP10 | CD3δ |
| CD99 | b2c | DAP10 | CD3γ |
| CD99 | b2c | DAP10 | CD3ε |
| CD99 | b2c | DAP10 | FcγRI-γ |
| CD99 | b2c | DAP10 | FcγRIII-γ |
| CD99 | b2c | DAP10 | FcεRIβ |
| CD99 | b2c | DAP10 | FcεRIγ |
| CD99 | b2c | DAP10 | DAP10 |
| CD99 | b2c | DAP10 | DAP12 |
| CD99 | b2c | DAP10 | CD32 |
| CD99 | b2c | DAP10 | CD79a |
| CD99 | b2c | DAP10 | CD79b |
| CD99 | b2c | DAP12 | CD8 |
| CD99 | b2c | DAP12 | CD3ζ |
| CD99 | b2c | DAP12 | CD3δ |
| CD99 | b2c | DAP12 | CD3γ |
| CD99 | b2c | DAP12 | CD3ε |
| CD99 | b2c | DAP12 | FcγRI-γ |
| CD99 | b2c | DAP12 | FcγRIII-γ |
| CD99 | b2c | DAP12 | FcεRIβ |
| CD99 | b2c | DAP12 | FcεRIγ |
| CD99 | b2c | DAP12 | DAP10 |
| CD99 | b2c | DAP12 | DAP12 |
| CD99 | b2c | DAP12 | CD32 |
| CD99 | b2c | DAP12 | CD79a |
| CD99 | b2c | DAP12 | CD79b |
| CD99 | b2c | MyD88 | CD8 |
| CD99 | b2c | MyD88 | CD3ζ |
| CD99 | b2c | MyD88 | CD3δ |
| CD99 | b2c | MyD88 | CD3γ |
| CD99 | b2c | MyD88 | CD3ε |
| CD99 | b2c | MyD88 | FcγRI-γ |
| CD99 | b2c | MyD88 | FcγRIII-γ |

TABLE 3-continued

Third Generation CARs

| ScFv | Co-stimulatory Signal | Co-stimulatory Signal | Signal Domain |
|---|---|---|---|
| CD99 | b2c | MyD88 | FcεRIβ |
| CD99 | b2c | MyD88 | FcεRIγ |
| CD99 | b2c | MyD88 | DAP10 |
| CD99 | b2c | MyD88 | DAP12 |
| CD99 | b2c | MyD88 | CD32 |
| CD99 | b2c | MyD88 | CD79a |
| CD99 | b2c | MyD88 | CD79b |
| CD99 | b2c | CD7 | CD8 |
| CD99 | b2c | CD7 | CD3ζ |
| CD99 | b2c | CD7 | CD3δ |
| CD99 | b2c | CD7 | CD3γ |
| CD99 | b2c | CD7 | CD3ε |
| CD99 | b2c | CD7 | FcγRI-γ |
| CD99 | b2c | CD7 | FcγRIII-γ |
| CD99 | b2c | CD7 | FcεRIβ |
| CD99 | b2c | CD7 | FcεRIγ |
| CD99 | b2c | CD7 | DAP10 |
| CD99 | b2c | CD7 | DAP12 |
| CD99 | b2c | CD7 | CD32 |
| CD99 | b2c | CD7 | CD79a |
| CD99 | b2c | CD7 | CD79b |
| CD99 | b2c | BTNL3 | CD8 |
| CD99 | b2c | BTNL3 | CD3ζ |
| CD99 | b2c | BTNL3 | CD3δ |
| CD99 | b2c | BTNL3 | CD3γ |
| CD99 | b2c | BTNL3 | CD3ε |
| CD99 | b2c | BTNL3 | FcγRI-γ |
| CD99 | b2c | BTNL3 | FcγRIII-γ |
| CD99 | b2c | BTNL3 | FcεRIβ |
| CD99 | b2c | BTNL3 | FcεRIγ |
| CD99 | b2c | BTNL3 | DAP10 |
| CD99 | b2c | BTNL3 | DAP12 |
| CD99 | b2c | BTNL3 | CD32 |
| CD99 | b2c | BTNL3 | CD79a |
| CD99 | b2c | BTNL3 | CD79b |
| CD99 | b2c | NKG2D | CD8 |
| CD99 | b2c | NKG2D | CD3ζ |
| CD99 | b2c | NKG2D | CD3δ |
| CD99 | b2c | NKG2D | CD3γ |
| CD99 | b2c | NKG2D | CD3ε |
| CD99 | b2c | NKG2D | FcγRI-γ |
| CD99 | b2c | NKG2D | FcγRIII-γ |
| CD99 | b2c | NKG2D | FcεRIβ |
| CD99 | b2c | NKG2D | FcεRIγ |
| CD99 | b2c | NKG2D | DAP10 |
| CD99 | b2c | NKG2D | DAP12 |
| CD99 | b2c | NKG2D | CD32 |
| CD99 | b2c | NKG2D | CD79a |
| CD99 | b2c | NKG2D | CD79b |
| CD99 | CD137/41BB | CD28 | CD8 |
| CD99 | CD137/41BB | CD28 | CD3ζ |
| CD99 | CD137/41BB | CD28 | CD3δ |
| CD99 | CD137/41BB | CD28 | CD3γ |
| CD99 | CD137/41BB | CD28 | CD3ε |
| CD99 | CD137/41BB | CD28 | FcγRI-γ |
| CD99 | CD137/41BB | CD28 | FcγRIII-γ |
| CD99 | CD137/41BB | CD28 | FcεRIβ |
| CD99 | CD137/41BB | CD28 | FcεRIγ |
| CD99 | CD137/41BB | CD28 | DAP10 |
| CD99 | CD137/41BB | CD28 | DAP12 |
| CD99 | CD137/41BB | CD28 | CD32 |
| CD99 | CD137/41BB | CD28 | CD79a |
| CD99 | CD137/41BB | CD28 | CD79b |
| CD99 | CD137/41BB | CD8 | CD8 |
| CD99 | CD137/41BB | CD8 | CD3ζ |
| CD99 | CD137/41BB | CD8 | CD3δ |
| CD99 | CD137/41BB | CD8 | CD3γ |
| CD99 | CD137/41BB | CD8 | CD3ε |
| CD99 | CD137/41BB | CD8 | FcγRI-γ |
| CD99 | CD137/41BB | CD8 | FcγRIII-γ |
| CD99 | CD137/41BB | CD8 | FcεRIβ |
| CD99 | CD137/41BB | CD8 | FcεRIγ |
| CD99 | CD137/41BB | CD8 | DAP10 |
| CD99 | CD137/41BB | CD8 | DAP12 |
| CD99 | CD137/41BB | CD8 | CD32 |
| CD99 | CD137/41BB | CD8 | CD79a |
| CD99 | CD137/41BB | CD8 | CD79b |
| CD99 | CD137/41BB | CD4 | CD8 |
| CD99 | CD137/41BB | CD4 | CD3ζ |
| CD99 | CD137/41BB | CD4 | CD3δ |
| CD99 | CD137/41BB | CD4 | CD3γ |
| CD99 | CD137/41BB | CD4 | CD3ε |
| CD99 | CD137/41BB | CD4 | FcγRI-γ |
| CD99 | CD137/41BB | CD4 | FcγRIII-γ |
| CD99 | CD137/41BB | CD4 | FcεRIβ |
| CD99 | CD137/41BB | CD4 | FcεRIγ |
| CD99 | CD137/41BB | CD4 | DAP10 |
| CD99 | CD137/41BB | CD4 | DAP12 |
| CD99 | CD137/41BB | CD4 | CD32 |
| CD99 | CD137/41BB | CD4 | CD79a |
| CD99 | CD137/41BB | CD4 | CD79b |
| CD99 | CD137/41BB | b2c | CD8 |
| CD99 | CD137/41BB | b2c | CD3ζ |
| CD99 | CD137/41BB | b2c | CD3δ |
| CD99 | CD137/41BB | b2c | CD3γ |
| CD99 | CD137/41BB | b2c | CD3ε |
| CD99 | CD137/41BB | b2c | FcγRI-γ |
| CD99 | CD137/41BB | b2c | FcγRIII-γ |
| CD99 | CD137/41BB | b2c | FcεRIβ |
| CD99 | CD137/41BB | b2c | FcεRIγ |
| CD99 | CD137/41BB | b2c | DAP10 |
| CD99 | CD137/41BB | b2c | DAP12 |
| CD99 | CD137/41BB | b2c | CD32 |
| CD99 | CD137/41BB | b2c | CD79a |
| CD99 | CD137/41BB | b2c | CD79b |
| CD99 | CD137/41BB | CD137/41BB | CD8 |
| CD99 | CD137/41BB | CD137/41BB | CD3ζ |
| CD99 | CD137/41BB | CD137/41BB | CD3δ |
| CD99 | CD137/41BB | CD137/41BB | CD3γ |
| CD99 | CD137/41BB | CD137/41BB | CD3ε |
| CD99 | CD137/41BB | CD137/41BB | FcγRI-γ |
| CD99 | CD137/41BB | CD137/41BB | FcγRIII-γ |
| CD99 | CD137/41BB | CD137/41BB | FcεRIβ |
| CD99 | CD137/41BB | CD137/41BB | FcεRIγ |
| CD99 | CD137/41BB | CD137/41BB | DAP10 |
| CD99 | CD137/41BB | CD137/41BB | DAP12 |
| CD99 | CD137/41BB | CD137/41BB | CD32 |
| CD99 | CD137/41BB | CD137/41BB | CD79a |
| CD99 | CD137/41BB | CD137/41BB | CD79b |
| CD99 | CD137/41BB | ICOS | CD8 |
| CD99 | CD137/41BB | ICOS | CD3ζ |
| CD99 | CD137/41BB | ICOS | CD3δ |
| CD99 | CD137/41BB | ICOS | CD3γ |
| CD99 | CD137/41BB | ICOS | CD3ε |
| CD99 | CD137/41BB | ICOS | FcγRI-γ |
| CD99 | CD137/41BB | ICOS | FcγRIII-γ |
| CD99 | CD137/41BB | ICOS | FcεRIβ |
| CD99 | CD137/41BB | ICOS | FcεRIγ |
| CD99 | CD137/41BB | ICOS | DAP10 |
| CD99 | CD137/41BB | ICOS | DAP12 |
| CD99 | CD137/41BB | ICOS | CD32 |
| CD99 | CD137/41BB | ICOS | CD79a |
| CD99 | CD137/41BB | ICOS | CD79b |
| CD99 | CD137/41BB | CD27 | CD8 |
| CD99 | CD137/41BB | CD27 | CD3ζ |
| CD99 | CD137/41BB | CD27 | CD3δ |
| CD99 | CD137/41BB | CD27 | CD3γ |
| CD99 | CD137/41BB | CD27 | CD3ε |
| CD99 | CD137/41BB | CD27 | FcγRI-γ |
| CD99 | CD137/41BB | CD27 | FcγRIII-γ |
| CD99 | CD137/41BB | CD27 | FcεRIβ |
| CD99 | CD137/41BB | CD27 | FcεRIγ |
| CD99 | CD137/41BB | CD27 | DAP10 |
| CD99 | CD137/41BB | CD27 | DAP12 |
| CD99 | CD137/41BB | CD27 | CD32 |
| CD99 | CD137/41BB | CD27 | CD79a |
| CD99 | CD137/41BB | CD27 | CD79b |
| CD99 | CD137/41BB | CD28δ | CD8 |
| CD99 | CD137/41BB | CD28δ | CD3ζ |
| CD99 | CD137/41BB | CD28δ | CD3δ |

TABLE 3-continued

Third Generation CARs

| ScFv | Co-stimulatory Signal | Co-stimulatory Signal | Signal Domain |
|---|---|---|---|
| CD99 | CD137/41BB | CD28δ | CD3γ |
| CD99 | CD137/41BB | CD28δ | CD3ε |
| CD99 | CD137/41BB | CD28δ | FcγRI-γ |
| CD99 | CD137/41BB | CD28δ | FcγRIII-γ |
| CD99 | CD137/41BB | CD28δ | FcεRIβ |
| CD99 | CD137/41BB | CD28δ | FcεRIγ |
| CD99 | CD137/41BB | CD28δ | DAP10 |
| CD99 | CD137/41BB | CD28δ | DAP12 |
| CD99 | CD137/41BB | CD28δ | CD32 |
| CD99 | CD137/41BB | CD28δ | CD79a |
| CD99 | CD137/41BB | CD28δ | CD79b |
| CD99 | CD137/41BB | CD80 | CD8 |
| CD99 | CD137/41BB | CD80 | CD3ζ |
| CD99 | CD137/41BB | CD80 | CD3δ |
| CD99 | CD137/41BB | CD80 | CD3γ |
| CD99 | CD137/41BB | CD80 | CD3ε |
| CD99 | CD137/41BB | CD80 | FcγRI-γ |
| CD99 | CD137/41BB | CD80 | FcγRIII-γ |
| CD99 | CD137/41BB | CD80 | FcεRIβ |
| CD99 | CD137/41BB | CD80 | FcεRIγ |
| CD99 | CD137/41BB | CD80 | DAP10 |
| CD99 | CD137/41BB | CD80 | DAP12 |
| CD99 | CD137/41BB | CD80 | CD32 |
| CD99 | CD137/41BB | CD80 | CD79a |
| CD99 | CD137/41BB | CD80 | CD79b |
| CD99 | CD137/41BB | CD86 | CD8 |
| CD99 | CD137/41BB | CD86 | CD3ζ |
| CD99 | CD137/41BB | CD86 | CD3δ |
| CD99 | CD137/41BB | CD86 | CD3γ |
| CD99 | CD137/41BB | CD86 | CD3ε |
| CD99 | CD137/41BB | CD86 | FcγRI-γ |
| CD99 | CD137/41BB | CD86 | FcγRIII-γ |
| CD99 | CD137/41BB | CD86 | FcεRIβ |
| CD99 | CD137/41BB | CD86 | FcεRIγ |
| CD99 | CD137/41BB | CD86 | DAP10 |
| CD99 | CD137/41BB | CD86 | DAP12 |
| CD99 | CD137/41BB | CD86 | CD32 |
| CD99 | CD137/41BB | CD86 | CD79a |
| CD99 | CD137/41BB | CD86 | CD79b |
| CD99 | CD137/41BB | OX40 | CD8 |
| CD99 | CD137/41BB | OX40 | CD3ζ |
| CD99 | CD137/41BB | OX40 | CD3δ |
| CD99 | CD137/41BB | OX40 | CD3γ |
| CD99 | CD137/41BB | OX40 | CD3ε |
| CD99 | CD137/41BB | OX40 | FcγRI-γ |
| CD99 | CD137/41BB | OX40 | FcγRIII-γ |
| CD99 | CD137/41BB | OX40 | FcεRIβ |
| CD99 | CD137/41BB | OX40 | FcεRIγ |
| CD99 | CD137/41BB | OX40 | DAP10 |
| CD99 | CD137/41BB | OX40 | DAP12 |
| CD99 | CD137/41BB | OX40 | CD32 |
| CD99 | CD137/41BB | OX40 | CD79a |
| CD99 | CD137/41BB | OX40 | CD79b |
| CD99 | CD137/41BB | DAP10 | CD8 |
| CD99 | CD137/41BB | DAP10 | CD3ζ |
| CD99 | CD137/41BB | DAP10 | CD3δ |
| CD99 | CD137/41BB | DAP10 | CD3γ |
| CD99 | CD137/41BB | DAP10 | CD3ε |
| CD99 | CD137/41BB | DAP10 | FcγRI-γ |
| CD99 | CD137/41BB | DAP10 | FcγRIII-γ |
| CD99 | CD137/41BB | DAP10 | FcεRIβ |
| CD99 | CD137/41BB | DAP10 | FcεRIγ |
| CD99 | CD137/41BB | DAP10 | DAP10 |
| CD99 | CD137/41BB | DAP10 | DAP12 |
| CD99 | CD137/41BB | DAP10 | CD32 |
| CD99 | CD137/41BB | DAP10 | CD79a |
| CD99 | CD137/41BB | DAP10 | CD79b |
| CD99 | CD137/41BB | DAP12 | CD8 |
| CD99 | CD137/41BB | DAP12 | CD3ζ |
| CD99 | CD137/41BB | DAP12 | CD3δ |
| CD99 | CD137/41BB | DAP12 | CD3γ |
| CD99 | CD137/41BB | DAP12 | CD3ε |
| CD99 | CD137/41BB | DAP12 | FcγRI-γ |
| CD99 | CD137/41BB | DAP12 | FcγRIII-γ |
| CD99 | CD137/41BB | DAP12 | FcεRIβ |
| CD99 | CD137/41BB | DAP12 | FcεRIγ |
| CD99 | CD137/41BB | DAP12 | DAP10 |
| CD99 | CD137/41BB | DAP12 | DAP12 |
| CD99 | CD137/41BB | DAP12 | CD32 |
| CD99 | CD137/41BB | DAP12 | CD79a |
| CD99 | CD137/41BB | DAP12 | CD79b |
| CD99 | CD137/41BB | MyD88 | CD8 |
| CD99 | CD137/41BB | MyD88 | CD3ζ |
| CD99 | CD137/41BB | MyD88 | CD3δ |
| CD99 | CD137/41BB | MyD88 | CD3γ |
| CD99 | CD137/41BB | MyD88 | CD3ε |
| CD99 | CD137/41BB | MyD88 | FcγRI-γ |
| CD99 | CD137/41BB | MyD88 | FcγRIII-γ |
| CD99 | CD137/41BB | MyD88 | FcεRIβ |
| CD99 | CD137/41BB | MyD88 | FcεRIγ |
| CD99 | CD137/41BB | MyD88 | DAP10 |
| CD99 | CD137/41BB | MyD88 | DAP12 |
| CD99 | CD137/41BB | MyD88 | CD32 |
| CD99 | CD137/41BB | MyD88 | CD79a |
| CD99 | CD137/41BB | MyD88 | CD79b |
| CD99 | CD137/41BB | CD7 | CD8 |
| CD99 | CD137/41BB | CD7 | CD3ζ |
| CD99 | CD137/41BB | CD7 | CD3δ |
| CD99 | CD137/41BB | CD7 | CD3γ |
| CD99 | CD137/41BB | CD7 | CD3ε |
| CD99 | CD137/41BB | CD7 | FcγRI-γ |
| CD99 | CD137/41BB | CD7 | FcγRIII-γ |
| CD99 | CD137/41BB | CD7 | FcεRIβ |
| CD99 | CD137/41BB | CD7 | FcεRIγ |
| CD99 | CD137/41BB | CD7 | DAP10 |
| CD99 | CD137/41BB | CD7 | DAP12 |
| CD99 | CD137/41BB | CD7 | CD32 |
| CD99 | CD137/41BB | CD7 | CD79a |
| CD99 | CD137/41BB | CD7 | CD79b |
| CD99 | CD137/41BB | BTNL3 | CD8 |
| CD99 | CD137/41BB | BTNL3 | CD3ζ |
| CD99 | CD137/41BB | BTNL3 | CD3δ |
| CD99 | CD137/41BB | BTNL3 | CD3γ |
| CD99 | CD137/41BB | BTNL3 | CD3ε |
| CD99 | CD137/41BB | BTNL3 | FcγRI-γ |
| CD99 | CD137/41BB | BTNL3 | FcγRIII-γ |
| CD99 | CD137/41BB | BTNL3 | FcεRIβ |
| CD99 | CD137/41BB | BTNL3 | FcεRIγ |
| CD99 | CD137/41BB | BTNL3 | DAP10 |
| CD99 | CD137/41BB | BTNL3 | DAP12 |
| CD99 | CD137/41BB | BTNL3 | CD32 |
| CD99 | CD137/41BB | BTNL3 | CD79a |
| CD99 | CD137/41BB | BTNL3 | CD79b |
| CD99 | CD137/41BB | NKG2D | CD8 |
| CD99 | CD137/41BB | NKG2D | CD3ζ |
| CD99 | CD137/41BB | NKG2D | CD3δ |
| CD99 | CD137/41BB | NKG2D | CD3γ |
| CD99 | CD137/41BB | NKG2D | CD3ε |
| CD99 | CD137/41BB | NKG2D | FcγRI-γ |
| CD99 | CD137/41BB | NKG2D | FcγRIII-γ |
| CD99 | CD137/41BB | NKG2D | FcεRIβ |
| CD99 | CD137/41BB | NKG2D | FcεRIγ |
| CD99 | CD137/41BB | NKG2D | DAP10 |
| CD99 | CD137/41BB | NKG2D | DAP12 |
| CD99 | CD137/41BB | NKG2D | CD32 |
| CD99 | CD137/41BB | NKG2D | CD79a |
| CD99 | CD137/41BB | NKG2D | CD79b |
| CD99 | ICOS | CD28 | CD8 |
| CD99 | ICOS | CD28 | CD3ζ |
| CD99 | ICOS | CD28 | CD3δ |
| CD99 | ICOS | CD28 | CD3γ |
| CD99 | ICOS | CD28 | CD3ε |
| CD99 | ICOS | CD28 | FcγRI-γ |
| CD99 | ICOS | CD28 | FcγRIII-γ |
| CD99 | ICOS | CD28 | FcεRIβ |
| CD99 | ICOS | CD28 | FcεRIγ |
| CD99 | ICOS | CD28 | DAP10 |
| CD99 | ICOS | CD28 | DAP12 |
| CD99 | ICOS | CD28 | CD32 |
| CD99 | ICOS | CD28 | CD79a |

TABLE 3-continued

Third Generation CARs

| ScFv | Co-stimulatory Signal | Co-stimulatory Signal | Signal Domain |
|---|---|---|---|
| CD99 | ICOS | CD28 | CD79b |
| CD99 | ICOS | CD8 | CD8 |
| CD99 | ICOS | CD8 | CD3ζ |
| CD99 | ICOS | CD8 | CD3δ |
| CD99 | ICOS | CD8 | CD3γ |
| CD99 | ICOS | CD8 | CD3ε |
| CD99 | ICOS | CD8 | FcγRI-γ |
| CD99 | ICOS | CD8 | FcγRIII-γ |
| CD99 | ICOS | CD8 | FcεRIβ |
| CD99 | ICOS | CD8 | FcεRIγ |
| CD99 | ICOS | CD8 | DAP10 |
| CD99 | ICOS | CD8 | DAP12 |
| CD99 | ICOS | CD8 | CD32 |
| CD99 | ICOS | CD8 | CD79a |
| CD99 | ICOS | CD8 | CD79b |
| CD99 | ICOS | CD4 | CD8 |
| CD99 | ICOS | CD4 | CD3ζ |
| CD99 | ICOS | CD4 | CD3δ |
| CD99 | ICOS | CD4 | CD3γ |
| CD99 | ICOS | CD4 | CD3ε |
| CD99 | ICOS | CD4 | FcγRI-γ |
| CD99 | ICOS | CD4 | FcγRIII-γ |
| CD99 | ICOS | CD4 | FcεRIβ |
| CD99 | ICOS | CD4 | FcεRIγ |
| CD99 | ICOS | CD4 | DAP10 |
| CD99 | ICOS | CD4 | DAP12 |
| CD99 | ICOS | CD4 | CD32 |
| CD99 | ICOS | CD4 | CD79a |
| CD99 | ICOS | CD4 | CD79b |
| CD99 | ICOS | b2c | CD8 |
| CD99 | ICOS | b2c | CD3ζ |
| CD99 | ICOS | b2c | CD3δ |
| CD99 | ICOS | b2c | CD3γ |
| CD99 | ICOS | b2c | CD3ε |
| CD99 | ICOS | b2c | FcγRI-γ |
| CD99 | ICOS | b2c | FcγRIII-γ |
| CD99 | ICOS | b2c | FcεRIβ |
| CD99 | ICOS | b2c | FcεRIγ |
| CD99 | ICOS | b2c | DAP10 |
| CD99 | ICOS | b2c | DAP12 |
| CD99 | ICOS | b2c | CD32 |
| CD99 | ICOS | b2c | CD79a |
| CD99 | ICOS | b2c | CD79b |
| CD99 | ICOS | CD137/41BB | CD8 |
| CD99 | ICOS | CD137/41BB | CD3ζ |
| CD99 | ICOS | CD137/41BB | CD3δ |
| CD99 | ICOS | CD137/41BB | CD3γ |
| CD99 | ICOS | CD137/41BB | CD3ε |
| CD99 | ICOS | CD137/41BB | FcγRI-γ |
| CD99 | ICOS | CD137/41BB | FcγRIII-γ |
| CD99 | ICOS | CD137/41BB | FcεRIβ |
| CD99 | ICOS | CD137/41BB | FcεRIγ |
| CD99 | ICOS | CD137/41BB | DAP10 |
| CD99 | ICOS | CD137/41BB | DAP12 |
| CD99 | ICOS | CD137/41BB | CD32 |
| CD99 | ICOS | CD137/41BB | CD79a |
| CD99 | ICOS | CD137/41BB | CD79b |
| CD99 | ICOS | ICOS | CD8 |
| CD99 | ICOS | ICOS | CD3ζ |
| CD99 | ICOS | ICOS | CD3δ |
| CD99 | ICOS | ICOS | CD3γ |
| CD99 | ICOS | ICOS | CD3ε |
| CD99 | ICOS | ICOS | FcγRI-γ |
| CD99 | ICOS | ICOS | FcγRIII-γ |
| CD99 | ICOS | ICOS | FcεRIβ |
| CD99 | ICOS | ICOS | FcεRIγ |
| CD99 | ICOS | ICOS | DAP10 |
| CD99 | ICOS | ICOS | DAP12 |
| CD99 | ICOS | ICOS | CD32 |
| CD99 | ICOS | ICOS | CD79a |
| CD99 | ICOS | ICOS | CD79b |
| CD99 | ICOS | CD27 | CD8 |
| CD99 | ICOS | CD27 | CD3ζ |
| CD99 | ICOS | CD27 | CD3δ |
| CD99 | ICOS | CD27 | CD3γ |
| CD99 | ICOS | CD27 | CD3ε |
| CD99 | ICOS | CD27 | FcγRI-γ |
| CD99 | ICOS | CD27 | FcγRIII-γ |
| CD99 | ICOS | CD27 | FcεRIβ |
| CD99 | ICOS | CD27 | FcεRIγ |
| CD99 | ICOS | CD27 | DAP10 |
| CD99 | ICOS | CD27 | DAP12 |
| CD99 | ICOS | CD27 | CD32 |
| CD99 | ICOS | CD27 | CD79a |
| CD99 | ICOS | CD27 | CD79b |
| CD99 | ICOS | CD28δ | CD8 |
| CD99 | ICOS | CD28δ | CD3ζ |
| CD99 | ICOS | CD28δ | CD3δ |
| CD99 | ICOS | CD28δ | CD3γ |
| CD99 | ICOS | CD28δ | CD3ε |
| CD99 | ICOS | CD28δ | FcγRI-γ |
| CD99 | ICOS | CD28δ | FcγRIII-γ |
| CD99 | ICOS | CD28δ | FcεRIβ |
| CD99 | ICOS | CD28δ | FcεRIγ |
| CD99 | ICOS | CD28δ | DAP10 |
| CD99 | ICOS | CD28δ | DAP12 |
| CD99 | ICOS | CD28δ | CD32 |
| CD99 | ICOS | CD28δ | CD79a |
| CD99 | ICOS | CD28δ | CD79b |
| CD99 | ICOS | CD80 | CD8 |
| CD99 | ICOS | CD80 | CD3ζ |
| CD99 | ICOS | CD80 | CD3δ |
| CD99 | ICOS | CD80 | CD3γ |
| CD99 | ICOS | CD80 | CD3ε |
| CD99 | ICOS | CD80 | FcγRI-γ |
| CD99 | ICOS | CD80 | FcγRIII-γ |
| CD99 | ICOS | CD80 | FcεRIβ |
| CD99 | ICOS | CD80 | FcεRIγ |
| CD99 | ICOS | CD80 | DAP10 |
| CD99 | ICOS | CD80 | DAP12 |
| CD99 | ICOS | CD80 | CD32 |
| CD99 | ICOS | CD80 | CD79a |
| CD99 | ICOS | CD80 | CD79b |
| CD99 | ICOS | CD86 | CD8 |
| CD99 | ICOS | CD86 | CD3ζ |
| CD99 | ICOS | CD86 | CD3δ |
| CD99 | ICOS | CD86 | CD3γ |
| CD99 | ICOS | CD86 | CD3ε |
| CD99 | ICOS | CD86 | FcγRI-γ |
| CD99 | ICOS | CD86 | FcγRIII-γ |
| CD99 | ICOS | CD86 | FcεRIβ |
| CD99 | ICOS | CD86 | FcεRIγ |
| CD99 | ICOS | CD86 | DAP10 |
| CD99 | ICOS | CD86 | DAP12 |
| CD99 | ICOS | CD86 | CD32 |
| CD99 | ICOS | CD86 | CD79a |
| CD99 | ICOS | CD86 | CD79b |
| CD99 | ICOS | OX40 | CD8 |
| CD99 | ICOS | OX40 | CD3ζ |
| CD99 | ICOS | OX40 | CD3δ |
| CD99 | ICOS | OX40 | CD3γ |
| CD99 | ICOS | OX40 | CD3ε |
| CD99 | ICOS | OX40 | FcγRI-γ |
| CD99 | ICOS | OX40 | FcγRIII-γ |
| CD99 | ICOS | OX40 | FcεRIβ |
| CD99 | ICOS | OX40 | FcεRIγ |
| CD99 | ICOS | OX40 | DAP10 |
| CD99 | ICOS | OX40 | DAP12 |
| CD99 | ICOS | OX40 | CD32 |
| CD99 | ICOS | OX40 | CD79a |
| CD99 | ICOS | OX40 | CD79b |
| CD99 | ICOS | DAP10 | CD8 |
| CD99 | ICOS | DAP10 | CD3ζ |
| CD99 | ICOS | DAP10 | CD3δ |
| CD99 | ICOS | DAP10 | CD3γ |
| CD99 | ICOS | DAP10 | CD3ε |
| CD99 | ICOS | DAP10 | FcγRI-γ |
| CD99 | ICOS | DAP10 | FcγRIII-γ |
| CD99 | ICOS | DAP10 | FcεRIβ |
| CD99 | ICOS | DAP10 | FcεRIγ |

TABLE 3-continued

Third Generation CARs

| ScFv | Co-stimulatory Signal | Co-stimulatory Signal | Signal Domain |
|---|---|---|---|
| CD99 | ICOS | DAP10 | DAP10 |
| CD99 | ICOS | DAP10 | DAP12 |
| CD99 | ICOS | DAP10 | CD32 |
| CD99 | ICOS | DAP10 | CD79a |
| CD99 | ICOS | DAP10 | CD79b |
| CD99 | ICOS | DAP12 | CD8 |
| CD99 | ICOS | DAP12 | CD3ζ |
| CD99 | ICOS | DAP12 | CD3δ |
| CD99 | ICOS | DAP12 | CD3γ |
| CD99 | ICOS | DAP12 | CD3ε |
| CD99 | ICOS | DAP12 | FcγRI-γ |
| CD99 | ICOS | DAP12 | FcγRIII-γ |
| CD99 | ICOS | DAP12 | FcεRIβ |
| CD99 | ICOS | DAP12 | FcεRIγ |
| CD99 | ICOS | DAP12 | DAP10 |
| CD99 | ICOS | DAP12 | DAP12 |
| CD99 | ICOS | DAP12 | CD32 |
| CD99 | ICOS | DAP12 | CD79a |
| CD99 | ICOS | DAP12 | CD79b |
| CD99 | ICOS | MyD88 | CD8 |
| CD99 | ICOS | MyD88 | CD3ζ |
| CD99 | ICOS | MyD88 | CD3δ |
| CD99 | ICOS | MyD88 | CD3γ |
| CD99 | ICOS | MyD88 | CD3ε |
| CD99 | ICOS | MyD88 | FcγRI-γ |
| CD99 | ICOS | MyD88 | FcγRIII-γ |
| CD99 | ICOS | MyD88 | FcεRIβ |
| CD99 | ICOS | MyD88 | FcεRIγ |
| CD99 | ICOS | MyD88 | DAP10 |
| CD99 | ICOS | MyD88 | DAP12 |
| CD99 | ICOS | MyD88 | CD32 |
| CD99 | ICOS | MyD88 | CD79a |
| CD99 | ICOS | MyD88 | CD79b |
| CD99 | ICOS | CD7 | CD8 |
| CD99 | ICOS | CD7 | CD3ζ |
| CD99 | ICOS | CD7 | CD3δ |
| CD99 | ICOS | CD7 | CD3γ |
| CD99 | ICOS | CD7 | CD3ε |
| CD99 | ICOS | CD7 | FcγRI-γ |
| CD99 | ICOS | CD7 | FcγRIII-γ |
| CD99 | ICOS | CD7 | FcεRIβ |
| CD99 | ICOS | CD7 | FcεRIγ |
| CD99 | ICOS | CD7 | DAP10 |
| CD99 | ICOS | CD7 | DAP12 |
| CD99 | ICOS | CD7 | CD32 |
| CD99 | ICOS | CD7 | CD79a |
| CD99 | ICOS | CD7 | CD79b |
| CD99 | ICOS | BTNL3 | CD8 |
| CD99 | ICOS | BTNL3 | CD3ζ |
| CD99 | ICOS | BTNL3 | CD3δ |
| CD99 | ICOS | BTNL3 | CD3γ |
| CD99 | ICOS | BTNL3 | CD3ε |
| CD99 | ICOS | BTNL3 | FcγRI-γ |
| CD99 | ICOS | BTNL3 | FcγRIII-γ |
| CD99 | ICOS | BTNL3 | FcεRIβ |
| CD99 | ICOS | BTNL3 | FcεRIγ |
| CD99 | ICOS | BTNL3 | DAP10 |
| CD99 | ICOS | BTNL3 | DAP12 |
| CD99 | ICOS | BTNL3 | CD32 |
| CD99 | ICOS | BTNL3 | CD79a |
| CD99 | ICOS | BTNL3 | CD79b |
| CD99 | ICOS | NKG2D | CD8 |
| CD99 | ICOS | NKG2D | CD3ζ |
| CD99 | ICOS | NKG2D | CD3δ |
| CD99 | ICOS | NKG2D | CD3γ |
| CD99 | ICOS | NKG2D | CD3ε |
| CD99 | ICOS | NKG2D | FcγRI-γ |
| CD99 | ICOS | NKG2D | FcγRIII-γ |
| CD99 | ICOS | NKG2D | FcεRIβ |
| CD99 | ICOS | NKG2D | FcεRIγ |
| CD99 | ICOS | NKG2D | DAP10 |
| CD99 | ICOS | NKG2D | DAP12 |
| CD99 | ICOS | NKG2D | CD32 |
| CD99 | ICOS | NKG2D | CD79a |
| CD99 | ICOS | NKG2D | CD79b |
| CD99 | CD27 | CD28 | CD8 |
| CD99 | CD27 | CD28 | CD3ζ |
| CD99 | CD27 | CD28 | CD3δ |
| CD99 | CD27 | CD28 | CD3γ |
| CD99 | CD27 | CD28 | CD3ε |
| CD99 | CD27 | CD28 | FcγRI-γ |
| CD99 | CD27 | CD28 | FcγRIII-γ |
| CD99 | CD27 | CD28 | FcεRIβ |
| CD99 | CD27 | CD28 | FcεRIγ |
| CD99 | CD27 | CD28 | DAP10 |
| CD99 | CD27 | CD28 | DAP12 |
| CD99 | CD27 | CD28 | CD32 |
| CD99 | CD27 | CD28 | CD79a |
| CD99 | CD27 | CD28 | CD79b |
| CD99 | CD27 | CD8 | CD8 |
| CD99 | CD27 | CD8 | CD3ζ |
| CD99 | CD27 | CD8 | CD3δ |
| CD99 | CD27 | CD8 | CD3γ |
| CD99 | CD27 | CD8 | CD3ε |
| CD99 | CD27 | CD8 | FcγRI-γ |
| CD99 | CD27 | CD8 | FcγRIII-γ |
| CD99 | CD27 | CD8 | FcεRIβ |
| CD99 | CD27 | CD8 | FcεRIγ |
| CD99 | CD27 | CD8 | DAP10 |
| CD99 | CD27 | CD8 | DAP12 |
| CD99 | CD27 | CD8 | CD32 |
| CD99 | CD27 | CD8 | CD79a |
| CD99 | CD27 | CD8 | CD79b |
| CD99 | CD27 | CD4 | CD8 |
| CD99 | CD27 | CD4 | CD3ζ |
| CD99 | CD27 | CD4 | CD3δ |
| CD99 | CD27 | CD4 | CD3γ |
| CD99 | CD27 | CD4 | CD3ε |
| CD99 | CD27 | CD4 | FcγRI-γ |
| CD99 | CD27 | CD4 | FcγRIII-γ |
| CD99 | CD27 | CD4 | FcεRIβ |
| CD99 | CD27 | CD4 | FcεRIγ |
| CD99 | CD27 | CD4 | DAP10 |
| CD99 | CD27 | CD4 | DAP12 |
| CD99 | CD27 | CD4 | CD32 |
| CD99 | CD27 | CD4 | CD79a |
| CD99 | CD27 | CD4 | CD79b |
| CD99 | CD27 | b2c | CD8 |
| CD99 | CD27 | b2c | CD3ζ |
| CD99 | CD27 | b2c | CD3δ |
| CD99 | CD27 | b2c | CD3γ |
| CD99 | CD27 | b2c | CD3ε |
| CD99 | CD27 | b2c | FcγRI-γ |
| CD99 | CD27 | b2c | FcγRIII-γ |
| CD99 | CD27 | b2c | FcεRIβ |
| CD99 | CD27 | b2c | FcεRIγ |
| CD99 | CD27 | b2c | DAP10 |
| CD99 | CD27 | b2c | DAP12 |
| CD99 | CD27 | b2c | CD32 |
| CD99 | CD27 | b2c | CD79a |
| CD99 | CD27 | b2c | CD79b |
| CD99 | CD27 | CD137/41BB | CD8 |
| CD99 | CD27 | CD137/41BB | CD3ζ |
| CD99 | CD27 | CD137/41BB | CD3δ |
| CD99 | CD27 | CD137/41BB | CD3γ |
| CD99 | CD27 | CD137/41BB | CD3ε |
| CD99 | CD27 | CD137/41BB | FcγRI-γ |
| CD99 | CD27 | CD137/41BB | FcγRIII-γ |
| CD99 | CD27 | CD137/41BB | FcεRIβ |
| CD99 | CD27 | CD137/41BB | FcεRIγ |
| CD99 | CD27 | CD137/41BB | DAP10 |
| CD99 | CD27 | CD137/41BB | DAP12 |
| CD99 | CD27 | CD137/41BB | CD32 |
| CD99 | CD27 | CD137/41BB | CD79a |
| CD99 | CD27 | CD137/41BB | CD79b |
| CD99 | CD27 | ICOS | CD8 |
| CD99 | CD27 | ICOS | CD3ζ |
| CD99 | CD27 | ICOS | CD3δ |
| CD99 | CD27 | ICOS | CD3γ |
| CD99 | CD27 | ICOS | CD3ε |

TABLE 3-continued

Third Generation CARs

| ScFv | Co-stimulatory Signal | Co-stimulatory Signal | Signal Domain |
|---|---|---|---|
| CD99 | CD27 | ICOS | FcγRI-γ |
| CD99 | CD27 | ICOS | FcγRIII-γ |
| CD99 | CD27 | ICOS | FcεRIβ |
| CD99 | CD27 | ICOS | FcεRIγ |
| CD99 | CD27 | ICOS | DAP10 |
| CD99 | CD27 | ICOS | DAP12 |
| CD99 | CD27 | ICOS | CD32 |
| CD99 | CD27 | ICOS | CD79a |
| CD99 | CD27 | ICOS | CD79b |
| CD99 | CD27 | CD27 | CD8 |
| CD99 | CD27 | CD27 | CD3ζ |
| CD99 | CD27 | CD27 | CD3δ |
| CD99 | CD27 | CD27 | CD3γ |
| CD99 | CD27 | CD27 | CD3ε |
| CD99 | CD27 | CD27 | FcγRI-γ |
| CD99 | CD27 | CD27 | FcγRIII-γ |
| CD99 | CD27 | CD27 | FcεRIβ |
| CD99 | CD27 | CD27 | FcεRIγ |
| CD99 | CD27 | CD27 | DAP10 |
| CD99 | CD27 | CD27 | DAP12 |
| CD99 | CD27 | CD27 | CD32 |
| CD99 | CD27 | CD27 | CD79a |
| CD99 | CD27 | CD27 | CD79b |
| CD99 | CD27 | CD28δ | CD8 |
| CD99 | CD27 | CD28δ | CD3ζ |
| CD99 | CD27 | CD28δ | CD3δ |
| CD99 | CD27 | CD28δ | CD3γ |
| CD99 | CD27 | CD28δ | CD3ε |
| CD99 | CD27 | CD28δ | FcγRI-γ |
| CD99 | CD27 | CD28δ | FcγRIII-γ |
| CD99 | CD27 | CD28δ | FcεRIβ |
| CD99 | CD27 | CD28δ | FcεRIγ |
| CD99 | CD27 | CD28δ | DAP10 |
| CD99 | CD27 | CD28δ | DAP12 |
| CD99 | CD27 | CD28δ | CD32 |
| CD99 | CD27 | CD28δ | CD79a |
| CD99 | CD27 | CD28δ | CD79b |
| CD99 | CD27 | CD80 | CD8 |
| CD99 | CD27 | CD80 | CD3ζ |
| CD99 | CD27 | CD80 | CD3δ |
| CD99 | CD27 | CD80 | CD3γ |
| CD99 | CD27 | CD80 | CD3ε |
| CD99 | CD27 | CD80 | FcγRI-γ |
| CD99 | CD27 | CD80 | FcγRIII-γ |
| CD99 | CD27 | CD80 | FcεRIβ |
| CD99 | CD27 | CD80 | FcεRIγ |
| CD99 | CD27 | CD80 | DAP10 |
| CD99 | CD27 | CD80 | DAP12 |
| CD99 | CD27 | CD80 | CD32 |
| CD99 | CD27 | CD80 | CD79a |
| CD99 | CD27 | CD80 | CD79b |
| CD99 | CD27 | CD86 | CD8 |
| CD99 | CD27 | CD86 | CD3ζ |
| CD99 | CD27 | CD86 | CD3δ |
| CD99 | CD27 | CD86 | CD3γ |
| CD99 | CD27 | CD86 | CD3ε |
| CD99 | CD27 | CD86 | FcγRI-γ |
| CD99 | CD27 | CD86 | FcγRIII-γ |
| CD99 | CD27 | CD86 | FcεRIβ |
| CD99 | CD27 | CD86 | FcεRIγ |
| CD99 | CD27 | CD86 | DAP10 |
| CD99 | CD27 | CD86 | DAP12 |
| CD99 | CD27 | CD86 | CD32 |
| CD99 | CD27 | CD86 | CD79a |
| CD99 | CD27 | CD86 | CD79b |
| CD99 | CD27 | OX40 | CD8 |
| CD99 | CD27 | OX40 | CD3ζ |
| CD99 | CD27 | OX40 | CD3δ |
| CD99 | CD27 | OX40 | CD3γ |
| CD99 | CD27 | OX40 | CD3ε |
| CD99 | CD27 | OX40 | FcγRI-γ |
| CD99 | CD27 | OX40 | FcγRIII-γ |
| CD99 | CD27 | OX40 | FcεRIβ |
| CD99 | CD27 | OX40 | FcεRIγ |
| CD99 | CD27 | OX40 | DAP10 |
| CD99 | CD27 | OX40 | DAP12 |
| CD99 | CD27 | OX40 | CD32 |
| CD99 | CD27 | OX40 | CD79a |
| CD99 | CD27 | OX40 | CD79b |
| CD99 | CD27 | DAP10 | CD8 |
| CD99 | CD27 | DAP10 | CD3ζ |
| CD99 | CD27 | DAP10 | CD3δ |
| CD99 | CD27 | DAP10 | CD3γ |
| CD99 | CD27 | DAP10 | CD3ε |
| CD99 | CD27 | DAP10 | FcγRI-γ |
| CD99 | CD27 | DAP10 | FcγRIII-γ |
| CD99 | CD27 | DAP10 | FcεRIβ |
| CD99 | CD27 | DAP10 | FcεRIγ |
| CD99 | CD27 | DAP10 | DAP10 |
| CD99 | CD27 | DAP10 | DAP12 |
| CD99 | CD27 | DAP10 | CD32 |
| CD99 | CD27 | DAP10 | CD79a |
| CD99 | CD27 | DAP10 | CD79b |
| CD99 | CD27 | DAP12 | CD8 |
| CD99 | CD27 | DAP12 | CD3ζ |
| CD99 | CD27 | DAP12 | CD3δ |
| CD99 | CD27 | DAP12 | CD3γ |
| CD99 | CD27 | DAP12 | CD3ε |
| CD99 | CD27 | DAP12 | FcγRI-γ |
| CD99 | CD27 | DAP12 | FcγRIII-γ |
| CD99 | CD27 | DAP12 | FcεRIβ |
| CD99 | CD27 | DAP12 | FcεRIγ |
| CD99 | CD27 | DAP12 | DAP10 |
| CD99 | CD27 | DAP12 | DAP12 |
| CD99 | CD27 | DAP12 | CD32 |
| CD99 | CD27 | DAP12 | CD79a |
| CD99 | CD27 | DAP12 | CD79b |
| CD99 | CD27 | MyD88 | CD8 |
| CD99 | CD27 | MyD88 | CD3ζ |
| CD99 | CD27 | MyD88 | CD3δ |
| CD99 | CD27 | MyD88 | CD3γ |
| CD99 | CD27 | MyD88 | CD3ε |
| CD99 | CD27 | MyD88 | FcγRI-γ |
| CD99 | CD27 | MyD88 | FcγRIII-γ |
| CD99 | CD27 | MyD88 | FcεRIβ |
| CD99 | CD27 | MyD88 | FcεRIγ |
| CD99 | CD27 | MyD88 | DAP10 |
| CD99 | CD27 | MyD88 | DAP12 |
| CD99 | CD27 | MyD88 | CD32 |
| CD99 | CD27 | MyD88 | CD79a |
| CD99 | CD27 | MyD88 | CD79b |
| CD99 | CD27 | CD7 | CD8 |
| CD99 | CD27 | CD7 | CD3ζ |
| CD99 | CD27 | CD7 | CD3δ |
| CD99 | CD27 | CD7 | CD3γ |
| CD99 | CD27 | CD7 | CD3ε |
| CD99 | CD27 | CD7 | FcγRI-γ |
| CD99 | CD27 | CD7 | FcγRIII-γ |
| CD99 | CD27 | CD7 | FcεRIβ |
| CD99 | CD27 | CD7 | FcεRIγ |
| CD99 | CD27 | CD7 | DAP10 |
| CD99 | CD27 | CD7 | DAP12 |
| CD99 | CD27 | CD7 | CD32 |
| CD99 | CD27 | CD7 | CD79a |
| CD99 | CD27 | CD7 | CD79b |
| CD99 | CD27 | BTNL3 | CD8 |
| CD99 | CD27 | BTNL3 | CD3ζ |
| CD99 | CD27 | BTNL3 | CD3δ |
| CD99 | CD27 | BTNL3 | CD3γ |
| CD99 | CD27 | BTNL3 | CD3ε |
| CD99 | CD27 | BTNL3 | FcγRI-γ |
| CD99 | CD27 | BTNL3 | FcγRIII-γ |
| CD99 | CD27 | BTNL3 | FcεRIβ |
| CD99 | CD27 | BTNL3 | FcεRIγ |
| CD99 | CD27 | BTNL3 | DAP10 |
| CD99 | CD27 | BTNL3 | DAP12 |
| CD99 | CD27 | BTNL3 | CD32 |
| CD99 | CD27 | BTNL3 | CD79a |
| CD99 | CD27 | BTNL3 | CD79b |
| CD99 | CD27 | NKG2D | CD8 |

TABLE 3-continued

Third Generation CARs

| ScFv | Co-stimulatory Signal | Co-stimulatory Signal | Signal Domain |
|---|---|---|---|
| CD99 | CD27 | NKG2D | CD3ζ |
| CD99 | CD27 | NKG2D | CD3δ |
| CD99 | CD27 | NKG2D | CD3γ |
| CD99 | CD27 | NKG2D | CD3ε |
| CD99 | CD27 | NKG2D | FcγRI-γ |
| CD99 | CD27 | NKG2D | FcγRIII-γ |
| CD99 | CD27 | NKG2D | FcεRIβ |
| CD99 | CD27 | NKG2D | FcεRIγ |
| CD99 | CD27 | NKG2D | DAP10 |
| CD99 | CD27 | NKG2D | DAP12 |
| CD99 | CD27 | NKG2D | CD32 |
| CD99 | CD27 | NKG2D | CD79a |
| CD99 | CD27 | NKG2D | CD79b |
| CD99 | CD28δ | CD28 | CD8 |
| CD99 | CD28δ | CD28 | CD3ζ |
| CD99 | CD28δ | CD28 | CD3δ |
| CD99 | CD28δ | CD28 | CD3γ |
| CD99 | CD28δ | CD28 | CD3ε |
| CD99 | CD28δ | CD28 | FcγRI-γ |
| CD99 | CD28δ | CD28 | FcγRIII-γ |
| CD99 | CD28δ | CD28 | FcεRIβ |
| CD99 | CD28δ | CD28 | FcεRIγ |
| CD99 | CD28δ | CD28 | DAP10 |
| CD99 | CD28δ | CD28 | DAP12 |
| CD99 | CD28δ | CD28 | CD32 |
| CD99 | CD28δ | CD28 | CD79a |
| CD99 | CD28δ | CD28 | CD79b |
| CD99 | CD28δ | CD8 | CD8 |
| CD99 | CD28δ | CD8 | CD3ζ |
| CD99 | CD28δ | CD8 | CD3δ |
| CD99 | CD28δ | CD8 | CD3γ |
| CD99 | CD28δ | CD8 | CD3ε |
| CD99 | CD28δ | CD8 | FcγRI-γ |
| CD99 | CD28δ | CD8 | FcγRIII-γ |
| CD99 | CD28δ | CD8 | FcεRIβ |
| CD99 | CD28δ | CD8 | FcεRIγ |
| CD99 | CD28δ | CD8 | DAP10 |
| CD99 | CD28δ | CD8 | DAP12 |
| CD99 | CD28δ | CD8 | CD32 |
| CD99 | CD28δ | CD8 | CD79a |
| CD99 | CD28δ | CD8 | CD79b |
| CD99 | CD28δ | CD4 | CD8 |
| CD99 | CD28δ | CD4 | CD3ζ |
| CD99 | CD28δ | CD4 | CD3δ |
| CD99 | CD28δ | CD4 | CD3γ |
| CD99 | CD28δ | CD4 | CD3ε |
| CD99 | CD28δ | CD4 | FcγRI-γ |
| CD99 | CD28δ | CD4 | FcγRIII-γ |
| CD99 | CD28δ | CD4 | FcεRIβ |
| CD99 | CD28δ | CD4 | FcεRIγ |
| CD99 | CD28δ | CD4 | DAP10 |
| CD99 | CD28δ | CD4 | DAP12 |
| CD99 | CD28δ | CD4 | CD32 |
| CD99 | CD28δ | CD4 | CD79a |
| CD99 | CD28δ | CD4 | CD79b |
| CD99 | CD28δ | b2c | CD8 |
| CD99 | CD28δ | b2c | CD3ζ |
| CD99 | CD28δ | b2c | CD3δ |
| CD99 | CD28δ | b2c | CD3γ |
| CD99 | CD28δ | b2c | CD3ε |
| CD99 | CD28δ | b2c | FcγRI-γ |
| CD99 | CD28δ | b2c | FcγRIII-γ |
| CD99 | CD28δ | b2c | FcεRIβ |
| CD99 | CD28δ | b2c | FcεRIγ |
| CD99 | CD28δ | b2c | DAP10 |
| CD99 | CD28δ | b2c | DAP12 |
| CD99 | CD28δ | b2c | CD32 |
| CD99 | CD28δ | b2c | CD79a |
| CD99 | CD28δ | b2c | CD79b |
| CD99 | CD28δ | CD137/41BB | CD8 |
| CD99 | CD28δ | CD137/41BB | CD3ζ |
| CD99 | CD28δ | CD137/41BB | CD3δ |
| CD99 | CD28δ | CD137/41BB | CD3γ |
| CD99 | CD28δ | CD137/41BB | CD3ε |
| CD99 | CD28δ | CD137/41BB | FcγRI-γ |
| CD99 | CD28δ | CD137/41BB | FcγRIII-γ |
| CD99 | CD28δ | CD137/41BB | FcεRIβ |
| CD99 | CD28δ | CD137/41BB | FcεRIγ |
| CD99 | CD28δ | CD137/41BB | DAP10 |
| CD99 | CD28δ | CD137/41BB | DAP12 |
| CD99 | CD28δ | CD137/41BB | CD32 |
| CD99 | CD28δ | CD137/41BB | CD79a |
| CD99 | CD28δ | CD137/41BB | CD79b |
| CD99 | CD28δ | ICOS | CD8 |
| CD99 | CD28δ | ICOS | CD3ζ |
| CD99 | CD28δ | ICOS | CD3δ |
| CD99 | CD28δ | ICOS | CD3γ |
| CD99 | CD28δ | ICOS | CD3ε |
| CD99 | CD28δ | ICOS | FcγRI-γ |
| CD99 | CD28δ | ICOS | FcγRIII-γ |
| CD99 | CD28δ | ICOS | FcεRIβ |
| CD99 | CD28δ | ICOS | FcεRIγ |
| CD99 | CD28δ | ICOS | DAP10 |
| CD99 | CD28δ | ICOS | DAP12 |
| CD99 | CD28δ | ICOS | CD32 |
| CD99 | CD28δ | ICOS | CD79a |
| CD99 | CD28δ | ICOS | CD79b |
| CD99 | CD28δ | CD27 | CD8 |
| CD99 | CD28δ | CD27 | CD3ζ |
| CD99 | CD28δ | CD27 | CD3δ |
| CD99 | CD28δ | CD27 | CD3γ |
| CD99 | CD28δ | CD27 | CD3ε |
| CD99 | CD28δ | CD27 | FcγRI-γ |
| CD99 | CD28δ | CD27 | FcγRIII-γ |
| CD99 | CD28δ | CD27 | FcεRIβ |
| CD99 | CD28δ | CD27 | FcεRIγ |
| CD99 | CD28δ | CD27 | DAP10 |
| CD99 | CD28δ | CD27 | DAP12 |
| CD99 | CD28δ | CD27 | CD32 |
| CD99 | CD28δ | CD27 | CD79a |
| CD99 | CD28δ | CD27 | CD79b |
| CD99 | CD28δ | CD28δ | CD8 |
| CD99 | CD28δ | CD28δ | CD3ζ |
| CD99 | CD28δ | CD28δ | CD3δ |
| CD99 | CD28δ | CD28δ | CD3γ |
| CD99 | CD28δ | CD28δ | CD3ε |
| CD99 | CD28δ | CD28δ | FcγRI-γ |
| CD99 | CD28δ | CD28δ | FcγRIII-γ |
| CD99 | CD28δ | CD28δ | FcεRIβ |
| CD99 | CD28δ | CD28δ | FcεRIγ |
| CD99 | CD28δ | CD28δ | DAP10 |
| CD99 | CD28δ | CD28δ | DAP12 |
| CD99 | CD28δ | CD28δ | CD32 |
| CD99 | CD28δ | CD28δ | CD79a |
| CD99 | CD28δ | CD28δ | CD79b |
| CD99 | CD28δ | CD80 | CD8 |
| CD99 | CD28δ | CD80 | CD3ζ |
| CD99 | CD28δ | CD80 | CD3δ |
| CD99 | CD28δ | CD80 | CD3γ |
| CD99 | CD28δ | CD80 | CD3ε |
| CD99 | CD28δ | CD80 | FcγRI-γ |
| CD99 | CD28δ | CD80 | FcγRIII-γ |
| CD99 | CD28δ | CD80 | FcεRIβ |
| CD99 | CD28δ | CD80 | FcεRIγ |
| CD99 | CD28δ | CD80 | DAP10 |
| CD99 | CD28δ | CD80 | DAP12 |
| CD99 | CD28δ | CD80 | CD32 |
| CD99 | CD28δ | CD80 | CD79a |
| CD99 | CD28δ | CD80 | CD79b |
| CD99 | CD28δ | CD86 | CD8 |
| CD99 | CD28δ | CD86 | CD3ζ |
| CD99 | CD28δ | CD86 | CD3δ |
| CD99 | CD28δ | CD86 | CD3γ |
| CD99 | CD28δ | CD86 | CD3ε |
| CD99 | CD28δ | CD86 | FcγRI-γ |
| CD99 | CD28δ | CD86 | FcγRIII-γ |
| CD99 | CD28δ | CD86 | FcεRIβ |
| CD99 | CD28δ | CD86 | FcεRIγ |
| CD99 | CD28δ | CD86 | DAP10 |
| CD99 | CD28δ | CD86 | DAP12 |

TABLE 3-continued

Third Generation CARs

| ScFv | Co-stimulatory Signal | Co-stimulatory Signal | Signal Domain |
|---|---|---|---|
| CD99 | CD28δ | CD86 | CD32 |
| CD99 | CD28δ | CD86 | CD79a |
| CD99 | CD28δ | CD86 | CD79b |
| CD99 | CD28δ | OX40 | CD8 |
| CD99 | CD28δ | OX40 | CD3ζ |
| CD99 | CD28δ | OX40 | CD3δ |
| CD99 | CD28δ | OX40 | CD3γ |
| CD99 | CD28δ | OX40 | CD3ε |
| CD99 | CD28δ | OX40 | FcγRI-γ |
| CD99 | CD28δ | OX40 | FcγRIII-γ |
| CD99 | CD28δ | OX40 | FcεRIβ |
| CD99 | CD28δ | OX40 | FcεRIγ |
| CD99 | CD28δ | OX40 | DAP10 |
| CD99 | CD28δ | OX40 | DAP12 |
| CD99 | CD28δ | OX40 | CD32 |
| CD99 | CD28δ | OX40 | CD79a |
| CD99 | CD28δ | OX40 | CD79b |
| CD99 | CD28δ | DAP10 | CD8 |
| CD99 | CD28δ | DAP10 | CD3ζ |
| CD99 | CD28δ | DAP10 | CD3δ |
| CD99 | CD28δ | DAP10 | CD3γ |
| CD99 | CD28δ | DAP10 | CD3ε |
| CD99 | CD28δ | DAP10 | FcγRI-γ |
| CD99 | CD28δ | DAP10 | FcγRIII-γ |
| CD99 | CD28δ | DAP10 | FcεRIβ |
| CD99 | CD28δ | DAP10 | FcεRIγ |
| CD99 | CD28δ | DAP10 | DAP10 |
| CD99 | CD28δ | DAP10 | DAP12 |
| CD99 | CD28δ | DAP10 | CD32 |
| CD99 | CD28δ | DAP10 | CD79a |
| CD99 | CD28δ | DAP10 | CD79b |
| CD99 | CD28δ | DAP12 | CD8 |
| CD99 | CD28δ | DAP12 | CD3ζ |
| CD99 | CD28δ | DAP12 | CD3δ |
| CD99 | CD28δ | DAP12 | CD3γ |
| CD99 | CD28δ | DAP12 | CD3ε |
| CD99 | CD28δ | DAP12 | FcγRI-γ |
| CD99 | CD28δ | DAP12 | FcγRIII-γ |
| CD99 | CD28δ | DAP12 | FcεRIβ |
| CD99 | CD28δ | DAP12 | FcεRIγ |
| CD99 | CD28δ | DAP12 | DAP10 |
| CD99 | CD28δ | DAP12 | DAP12 |
| CD99 | CD28δ | DAP12 | CD32 |
| CD99 | CD28δ | DAP12 | CD79a |
| CD99 | CD28δ | DAP12 | CD79b |
| CD99 | CD28δ | MyD88 | CD8 |
| CD99 | CD28δ | MyD88 | CD3ζ |
| CD99 | CD28δ | MyD88 | CD3δ |
| CD99 | CD28δ | MyD88 | CD3γ |
| CD99 | CD28δ | MyD88 | CD3ε |
| CD99 | CD28δ | MyD88 | FcγRI-γ |
| CD99 | CD28δ | MyD88 | FcγRIII-γ |
| CD99 | CD28δ | MyD88 | FcεRIβ |
| CD99 | CD28δ | MyD88 | FcεRIγ |
| CD99 | CD28δ | MyD88 | DAP10 |
| CD99 | CD28δ | MyD88 | DAP12 |
| CD99 | CD28δ | MyD88 | CD32 |
| CD99 | CD28δ | MyD88 | CD79a |
| CD99 | CD28δ | MyD88 | CD79b |
| CD99 | CD28δ | CD7 | CD8 |
| CD99 | CD28δ | CD7 | CD3ζ |
| CD99 | CD28δ | CD7 | CD3δ |
| CD99 | CD28δ | CD7 | CD3γ |
| CD99 | CD28δ | CD7 | CD3ε |
| CD99 | CD28δ | CD7 | FcγRI-γ |
| CD99 | CD28δ | CD7 | FcγRIII-γ |
| CD99 | CD28δ | CD7 | FcεRIβ |
| CD99 | CD28δ | CD7 | FcεRIγ |
| CD99 | CD28δ | CD7 | DAP10 |
| CD99 | CD28δ | CD7 | DAP12 |
| CD99 | CD28δ | CD7 | CD32 |
| CD99 | CD28δ | CD7 | CD79a |
| CD99 | CD28δ | CD7 | CD79b |
| CD99 | CD28δ | BTNL3 | CD8 |
| CD99 | CD28δ | BTNL3 | CD3ζ |
| CD99 | CD28δ | BTNL3 | CD3δ |
| CD99 | CD28δ | BTNL3 | CD3γ |
| CD99 | CD28δ | BTNL3 | CD3ε |
| CD99 | CD28δ | BTNL3 | FcγRI-γ |
| CD99 | CD28δ | BTNL3 | FcγRIII-γ |
| CD99 | CD28δ | BTNL3 | FcεRIβ |
| CD99 | CD28δ | BTNL3 | FcεRIγ |
| CD99 | CD28δ | BTNL3 | DAP10 |
| CD99 | CD28δ | BTNL3 | DAP12 |
| CD99 | CD28δ | BTNL3 | CD32 |
| CD99 | CD28δ | BTNL3 | CD79a |
| CD99 | CD28δ | BTNL3 | CD79b |
| CD99 | CD28δ | NKG2D | CD8 |
| CD99 | CD28δ | NKG2D | CD3ζ |
| CD99 | CD28δ | NKG2D | CD3δ |
| CD99 | CD28δ | NKG2D | CD3γ |
| CD99 | CD28δ | NKG2D | CD3ε |
| CD99 | CD28δ | NKG2D | FcγRI-γ |
| CD99 | CD28δ | NKG2D | FcγRIII-γ |
| CD99 | CD28δ | NKG2D | FcεRIβ |
| CD99 | CD28δ | NKG2D | FcεRIγ |
| CD99 | CD28δ | NKG2D | DAP10 |
| CD99 | CD28δ | NKG2D | DAP12 |
| CD99 | CD28δ | NKG2D | CD32 |
| CD99 | CD28δ | NKG2D | CD79a |
| CD99 | CD28δ | NKG2D | CD79b |
| CD99 | CD80 | CD28 | CD8 |
| CD99 | CD80 | CD28 | CD3ζ |
| CD99 | CD80 | CD28 | CD3δ |
| CD99 | CD80 | CD28 | CD3γ |
| CD99 | CD80 | CD28 | CD3ε |
| CD99 | CD80 | CD28 | FcγRI-γ |
| CD99 | CD80 | CD28 | FcγRIII-γ |
| CD99 | CD80 | CD28 | FcεRIβ |
| CD99 | CD80 | CD28 | FcεRIγ |
| CD99 | CD80 | CD28 | DAP10 |
| CD99 | CD80 | CD28 | DAP12 |
| CD99 | CD80 | CD28 | CD32 |
| CD99 | CD80 | CD28 | CD79a |
| CD99 | CD80 | CD28 | CD79b |
| CD99 | CD80 | CD8 | CD8 |
| CD99 | CD80 | CD8 | CD3ζ |
| CD99 | CD80 | CD8 | CD3δ |
| CD99 | CD80 | CD8 | CD3γ |
| CD99 | CD80 | CD8 | CD3ε |
| CD99 | CD80 | CD8 | FcγRI-γ |
| CD99 | CD80 | CD8 | FcγRIII-γ |
| CD99 | CD80 | CD8 | FcεRIβ |
| CD99 | CD80 | CD8 | FcεRIγ |
| CD99 | CD80 | CD8 | DAP10 |
| CD99 | CD80 | CD8 | DAP12 |
| CD99 | CD80 | CD8 | CD32 |
| CD99 | CD80 | CD8 | CD79a |
| CD99 | CD80 | CD8 | CD79b |
| CD99 | CD80 | CD4 | CD8 |
| CD99 | CD80 | CD4 | CD3ζ |
| CD99 | CD80 | CD4 | CD3δ |
| CD99 | CD80 | CD4 | CD3γ |
| CD99 | CD80 | CD4 | CD3ε |
| CD99 | CD80 | CD4 | FcγRI-γ |
| CD99 | CD80 | CD4 | FcγRIII-γ |
| CD99 | CD80 | CD4 | FcεRIβ |
| CD99 | CD80 | CD4 | FcεRIγ |
| CD99 | CD80 | CD4 | DAP10 |
| CD99 | CD80 | CD4 | DAP12 |
| CD99 | CD80 | CD4 | CD32 |
| CD99 | CD80 | CD4 | CD79a |
| CD99 | CD80 | CD4 | CD79b |
| CD99 | CD80 | b2c | CD8 |
| CD99 | CD80 | b2c | CD3ζ |
| CD99 | CD80 | b2c | CD3δ |
| CD99 | CD80 | b2c | CD3γ |
| CD99 | CD80 | b2c | CD3ε |
| CD99 | CD80 | b2c | FcγRI-γ |
| CD99 | CD80 | b2c | FcγRIII-γ |

TABLE 3-continued

Third Generation CARs

| ScFv | Co-stimulatory Signal | Co-stimulatory Signal | Signal Domain |
|---|---|---|---|
| CD99 | CD80 | b2c | FcεRIβ |
| CD99 | CD80 | b2c | FcεRIγ |
| CD99 | CD80 | b2c | DAP10 |
| CD99 | CD80 | b2c | DAP12 |
| CD99 | CD80 | b2c | CD32 |
| CD99 | CD80 | b2c | CD79a |
| CD99 | CD80 | b2c | CD79b |
| CD99 | CD80 | CD137/41BB | CD8 |
| CD99 | CD80 | CD137/41BB | CD3ζ |
| CD99 | CD80 | CD137/41BB | CD3δ |
| CD99 | CD80 | CD137/41BB | CD3γ |
| CD99 | CD80 | CD137/41BB | CD3ε |
| CD99 | CD80 | CD137/41BB | FcγRI-γ |
| CD99 | CD80 | CD137/41BB | FcγRIII-γ |
| CD99 | CD80 | CD137/41BB | FcεRIβ |
| CD99 | CD80 | CD137/41BB | FcεRIγ |
| CD99 | CD80 | CD137/41BB | DAP10 |
| CD99 | CD80 | CD137/41BB | DAP12 |
| CD99 | CD80 | CD137/41BB | CD32 |
| CD99 | CD80 | CD137/41BB | CD79a |
| CD99 | CD80 | CD137/41BB | CD79b |
| CD99 | CD80 | ICOS | CD8 |
| CD99 | CD80 | ICOS | CD3ζ |
| CD99 | CD80 | ICOS | CD3δ |
| CD99 | CD80 | ICOS | CD3γ |
| CD99 | CD80 | ICOS | CD3ε |
| CD99 | CD80 | ICOS | FcγRI-γ |
| CD99 | CD80 | ICOS | FcγRIII-γ |
| CD99 | CD80 | ICOS | FcεRIβ |
| CD99 | CD80 | ICOS | FcεRIγ |
| CD99 | CD80 | ICOS | DAP10 |
| CD99 | CD80 | ICOS | DAP12 |
| CD99 | CD80 | ICOS | CD32 |
| CD99 | CD80 | ICOS | CD79a |
| CD99 | CD80 | ICOS | CD79b |
| CD99 | CD80 | CD27 | CD8 |
| CD99 | CD80 | CD27 | CD3ζ |
| CD99 | CD80 | CD27 | CD3δ |
| CD99 | CD80 | CD27 | CD3γ |
| CD99 | CD80 | CD27 | CD3ε |
| CD99 | CD80 | CD27 | FcγRI-γ |
| CD99 | CD80 | CD27 | FcγRIII-γ |
| CD99 | CD80 | CD27 | FcεRIβ |
| CD99 | CD80 | CD27 | FcεRIγ |
| CD99 | CD80 | CD27 | DAP10 |
| CD99 | CD80 | CD27 | DAP12 |
| CD99 | CD80 | CD27 | CD32 |
| CD99 | CD80 | CD27 | CD79a |
| CD99 | CD80 | CD27 | CD79b |
| CD99 | CD80 | CD28δ | CD8 |
| CD99 | CD80 | CD28δ | CD3ζ |
| CD99 | CD80 | CD28δ | CD3δ |
| CD99 | CD80 | CD28δ | CD3γ |
| CD99 | CD80 | CD28δ | CD3ε |
| CD99 | CD80 | CD28δ | FcγRI-γ |
| CD99 | CD80 | CD28δ | FcγRIII-γ |
| CD99 | CD80 | CD28δ | FcεRIβ |
| CD99 | CD80 | CD28δ | FcεRIγ |
| CD99 | CD80 | CD28δ | DAP10 |
| CD99 | CD80 | CD28δ | DAP12 |
| CD99 | CD80 | CD28δ | CD32 |
| CD99 | CD80 | CD28δ | CD79a |
| CD99 | CD80 | CD28δ | CD79b |
| CD99 | CD80 | CD80 | CD8 |
| CD99 | CD80 | CD80 | CD3ζ |
| CD99 | CD80 | CD80 | CD3δ |
| CD99 | CD80 | CD80 | CD3γ |
| CD99 | CD80 | CD80 | CD3ε |
| CD99 | CD80 | CD80 | FcγRI-γ |
| CD99 | CD80 | CD80 | FcγRIII-γ |
| CD99 | CD80 | CD80 | FcεRIβ |
| CD99 | CD80 | CD80 | FcεRIγ |
| CD99 | CD80 | CD80 | DAP10 |
| CD99 | CD80 | CD80 | DAP12 |
| CD99 | CD80 | CD80 | CD32 |
| CD99 | CD80 | CD80 | CD79a |
| CD99 | CD80 | CD80 | CD79b |
| CD99 | CD80 | CD86 | CD8 |
| CD99 | CD80 | CD86 | CD3ζ |
| CD99 | CD80 | CD86 | CD3δ |
| CD99 | CD80 | CD86 | CD3γ |
| CD99 | CD80 | CD86 | CD3ε |
| CD99 | CD80 | CD86 | FcγRI-γ |
| CD99 | CD80 | CD86 | FcγRIII-γ |
| CD99 | CD80 | CD86 | FcεRIβ |
| CD99 | CD80 | CD86 | FcεRIγ |
| CD99 | CD80 | CD86 | DAP10 |
| CD99 | CD80 | CD86 | DAP12 |
| CD99 | CD80 | CD86 | CD32 |
| CD99 | CD80 | CD86 | CD79a |
| CD99 | CD80 | CD86 | CD79b |
| CD99 | CD80 | OX40 | CD8 |
| CD99 | CD80 | OX40 | CD3ζ |
| CD99 | CD80 | OX40 | CD3δ |
| CD99 | CD80 | OX40 | CD3γ |
| CD99 | CD80 | OX40 | CD3ε |
| CD99 | CD80 | OX40 | FcγRI-γ |
| CD99 | CD80 | OX40 | FcγRIII-γ |
| CD99 | CD80 | OX40 | FcεRIβ |
| CD99 | CD80 | OX40 | FcεRIγ |
| CD99 | CD80 | OX40 | DAP10 |
| CD99 | CD80 | OX40 | DAP12 |
| CD99 | CD80 | OX40 | CD32 |
| CD99 | CD80 | OX40 | CD79a |
| CD99 | CD80 | OX40 | CD79b |
| CD99 | CD80 | DAP10 | CD8 |
| CD99 | CD80 | DAP10 | CD3ζ |
| CD99 | CD80 | DAP10 | CD3δ |
| CD99 | CD80 | DAP10 | CD3γ |
| CD99 | CD80 | DAP10 | CD3ε |
| CD99 | CD80 | DAP10 | FcγRI-γ |
| CD99 | CD80 | DAP10 | FcγRIII-γ |
| CD99 | CD80 | DAP10 | FcεRIβ |
| CD99 | CD80 | DAP10 | FcεRIγ |
| CD99 | CD80 | DAP10 | DAP10 |
| CD99 | CD80 | DAP10 | DAP12 |
| CD99 | CD80 | DAP10 | CD32 |
| CD99 | CD80 | DAP10 | CD79a |
| CD99 | CD80 | DAP10 | CD79b |
| CD99 | CD80 | DAP12 | CD8 |
| CD99 | CD80 | DAP12 | CD3ζ |
| CD99 | CD80 | DAP12 | CD3δ |
| CD99 | CD80 | DAP12 | CD3γ |
| CD99 | CD80 | DAP12 | CD3ε |
| CD99 | CD80 | DAP12 | FcγRI-γ |
| CD99 | CD80 | DAP12 | FcγRIII-γ |
| CD99 | CD80 | DAP12 | FcεRIβ |
| CD99 | CD80 | DAP12 | FcεRIγ |
| CD99 | CD80 | DAP12 | DAP10 |
| CD99 | CD80 | DAP12 | DAP12 |
| CD99 | CD80 | DAP12 | CD32 |
| CD99 | CD80 | DAP12 | CD79a |
| CD99 | CD80 | DAP12 | CD79b |
| CD99 | CD80 | MyD88 | CD8 |
| CD99 | CD80 | MyD88 | CD3ζ |
| CD99 | CD80 | MyD88 | CD3δ |
| CD99 | CD80 | MyD88 | CD3γ |
| CD99 | CD80 | MyD88 | CD3ε |
| CD99 | CD80 | MyD88 | FcγRI-γ |
| CD99 | CD80 | MyD88 | FcγRIII-γ |
| CD99 | CD80 | MyD88 | FcεRIβ |
| CD99 | CD80 | MyD88 | FcεRIγ |
| CD99 | CD80 | MyD88 | DAP10 |
| CD99 | CD80 | MyD88 | DAP12 |
| CD99 | CD80 | MyD88 | CD32 |
| CD99 | CD80 | MyD88 | CD79a |
| CD99 | CD80 | MyD88 | CD79b |
| CD99 | CD80 | CD7 | CD8 |
| CD99 | CD80 | CD7 | CD3ζ |
| CD99 | CD80 | CD7 | CD3δ |

TABLE 3-continued

Third Generation CARs

| ScFv | Co-stimulatory Signal | Co-stimulatory Signal | Signal Domain |
|---|---|---|---|
| CD99 | CD80 | CD7 | CD3γ |
| CD99 | CD80 | CD7 | CD3ε |
| CD99 | CD80 | CD7 | FcγRI-γ |
| CD99 | CD80 | CD7 | FcγRIII-γ |
| CD99 | CD80 | CD7 | FcεRIβ |
| CD99 | CD80 | CD7 | FcεRIγ |
| CD99 | CD80 | CD7 | DAP10 |
| CD99 | CD80 | CD7 | DAP12 |
| CD99 | CD80 | CD7 | CD32 |
| CD99 | CD80 | CD7 | CD79a |
| CD99 | CD80 | CD7 | CD79b |
| CD99 | CD80 | BTNL3 | CD8 |
| CD99 | CD80 | BTNL3 | CD3ζ |
| CD99 | CD80 | BTNL3 | CD3δ |
| CD99 | CD80 | BTNL3 | CD3γ |
| CD99 | CD80 | BTNL3 | CD3ε |
| CD99 | CD80 | BTNL3 | FcγRI-γ |
| CD99 | CD80 | BTNL3 | FcγRIII-γ |
| CD99 | CD80 | BTNL3 | FcεRIβ |
| CD99 | CD80 | BTNL3 | FcεRIγ |
| CD99 | CD80 | BTNL3 | DAP10 |
| CD99 | CD80 | BTNL3 | DAP12 |
| CD99 | CD80 | BTNL3 | CD32 |
| CD99 | CD80 | BTNL3 | CD79a |
| CD99 | CD80 | BTNL3 | CD79b |
| CD99 | CD80 | NKG2D | CD8 |
| CD99 | CD80 | NKG2D | CD3ζ |
| CD99 | CD80 | NKG2D | CD3δ |
| CD99 | CD80 | NKG2D | CD3γ |
| CD99 | CD80 | NKG2D | CD3ε |
| CD99 | CD80 | NKG2D | FcγRI-γ |
| CD99 | CD80 | NKG2D | FcγRIII-γ |
| CD99 | CD80 | NKG2D | FcεRIβ |
| CD99 | CD80 | NKG2D | FcεRIγ |
| CD99 | CD80 | NKG2D | DAP10 |
| CD99 | CD80 | NKG2D | DAP12 |
| CD99 | CD80 | NKG2D | CD32 |
| CD99 | CD80 | NKG2D | CD79a |
| CD99 | CD80 | NKG2D | CD79b |
| CD99 | CD86 | CD28 | CD8 |
| CD99 | CD86 | CD28 | CD3ζ |
| CD99 | CD86 | CD28 | CD3δ |
| CD99 | CD86 | CD28 | CD3γ |
| CD99 | CD86 | CD28 | CD3ε |
| CD99 | CD86 | CD28 | FcγRI-γ |
| CD99 | CD86 | CD28 | FcγRIII-γ |
| CD99 | CD86 | CD28 | FcεRIβ |
| CD99 | CD86 | CD28 | FcεRIγ |
| CD99 | CD86 | CD28 | DAP10 |
| CD99 | CD86 | CD28 | DAP12 |
| CD99 | CD86 | CD28 | CD32 |
| CD99 | CD86 | CD28 | CD79a |
| CD99 | CD86 | CD28 | CD79b |
| CD99 | CD86 | CD8 | CD8 |
| CD99 | CD86 | CD8 | CD3ζ |
| CD99 | CD86 | CD8 | CD3δ |
| CD99 | CD86 | CD8 | CD3γ |
| CD99 | CD86 | CD8 | CD3ε |
| CD99 | CD86 | CD8 | FcγRI-γ |
| CD99 | CD86 | CD8 | FcγRIII-γ |
| CD99 | CD86 | CD8 | FcεRIβ |
| CD99 | CD86 | CD8 | FcεRIγ |
| CD99 | CD86 | CD8 | DAP10 |
| CD99 | CD86 | CD8 | DAP12 |
| CD99 | CD86 | CD8 | CD32 |
| CD99 | CD86 | CD8 | CD79a |
| CD99 | CD86 | CD8 | CD79b |
| CD99 | CD86 | CD4 | CD8 |
| CD99 | CD86 | CD4 | CD3ζ |
| CD99 | CD86 | CD4 | CD3δ |
| CD99 | CD86 | CD4 | CD3γ |
| CD99 | CD86 | CD4 | CD3ε |
| CD99 | CD86 | CD4 | FcγRI-γ |
| CD99 | CD86 | CD4 | FcγRIII-γ |
| CD99 | CD86 | CD4 | FcεRIβ |
| CD99 | CD86 | CD4 | FcεRIγ |
| CD99 | CD86 | CD4 | DAP10 |
| CD99 | CD86 | CD4 | DAP12 |
| CD99 | CD86 | CD4 | CD32 |
| CD99 | CD86 | CD4 | CD79a |
| CD99 | CD86 | CD4 | CD79b |
| CD99 | CD86 | b2c | CD8 |
| CD99 | CD86 | b2c | CD3ζ |
| CD99 | CD86 | b2c | CD3δ |
| CD99 | CD86 | b2c | CD3γ |
| CD99 | CD86 | b2c | CD3ε |
| CD99 | CD86 | b2c | FcγRI-γ |
| CD99 | CD86 | b2c | FcγRIII-γ |
| CD99 | CD86 | b2c | FcεRIβ |
| CD99 | CD86 | b2c | FcεRIγ |
| CD99 | CD86 | b2c | DAP10 |
| CD99 | CD86 | b2c | DAP12 |
| CD99 | CD86 | b2c | CD32 |
| CD99 | CD86 | b2c | CD79a |
| CD99 | CD86 | b2c | CD79b |
| CD99 | CD86 | CD137/41BB | CD8 |
| CD99 | CD86 | CD137/41BB | CD3ζ |
| CD99 | CD86 | CD137/41BB | CD3δ |
| CD99 | CD86 | CD137/41BB | CD3γ |
| CD99 | CD86 | CD137/41BB | CD3ε |
| CD99 | CD86 | CD137/41BB | FcγRI-γ |
| CD99 | CD86 | CD137/41BB | FcγRIII-γ |
| CD99 | CD86 | CD137/41BB | FcεRIβ |
| CD99 | CD86 | CD137/41BB | FcεRIγ |
| CD99 | CD86 | CD137/41BB | DAP10 |
| CD99 | CD86 | CD137/41BB | DAP12 |
| CD99 | CD86 | CD137/41BB | CD32 |
| CD99 | CD86 | CD137/41BB | CD79a |
| CD99 | CD86 | CD137/41BB | CD79b |
| CD99 | CD86 | ICOS | CD8 |
| CD99 | CD86 | ICOS | CD3ζ |
| CD99 | CD86 | ICOS | CD3δ |
| CD99 | CD86 | ICOS | CD3γ |
| CD99 | CD86 | ICOS | CD3ε |
| CD99 | CD86 | ICOS | FcγRI-γ |
| CD99 | CD86 | ICOS | FcγRIII-γ |
| CD99 | CD86 | ICOS | FcεRIβ |
| CD99 | CD86 | ICOS | FcεRIγ |
| CD99 | CD86 | ICOS | DAP10 |
| CD99 | CD86 | ICOS | DAP12 |
| CD99 | CD86 | ICOS | CD32 |
| CD99 | CD86 | ICOS | CD79a |
| CD99 | CD86 | ICOS | CD79b |
| CD99 | CD86 | CD27 | CD8 |
| CD99 | CD86 | CD27 | CD3ζ |
| CD99 | CD86 | CD27 | CD3δ |
| CD99 | CD86 | CD27 | CD3γ |
| CD99 | CD86 | CD27 | CD3ε |
| CD99 | CD86 | CD27 | FcγRI-γ |
| CD99 | CD86 | CD27 | FcγRIII-γ |
| CD99 | CD86 | CD27 | FcεRIβ |
| CD99 | CD86 | CD27 | FcεRIγ |
| CD99 | CD86 | CD27 | DAP10 |
| CD99 | CD86 | CD27 | DAP12 |
| CD99 | CD86 | CD27 | CD32 |
| CD99 | CD86 | CD27 | CD79a |
| CD99 | CD86 | CD27 | CD79b |
| CD99 | CD86 | CD28δ | CD8 |
| CD99 | CD86 | CD28δ | CD3ζ |
| CD99 | CD86 | CD28δ | CD3δ |
| CD99 | CD86 | CD28δ | CD3γ |
| CD99 | CD86 | CD28δ | CD3ε |
| CD99 | CD86 | CD28δ | FcγRI-γ |
| CD99 | CD86 | CD28δ | FcγRIII-γ |
| CD99 | CD86 | CD28δ | FcεRIβ |
| CD99 | CD86 | CD28δ | FcεRIγ |
| CD99 | CD86 | CD28δ | DAP10 |
| CD99 | CD86 | CD28δ | DAP12 |
| CD99 | CD86 | CD28δ | CD32 |
| CD99 | CD86 | CD28δ | CD79a |

TABLE 3-continued

Third Generation CARs

| ScFv | Co-stimulatory Signal | Co-stimulatory Signal | Signal Domain |
|---|---|---|---|
| CD99 | CD86 | CD28 | CD79b |
| CD99 | CD86 | CD80 | CD8 |
| CD99 | CD86 | CD80 | CD3ζ |
| CD99 | CD86 | CD80 | CD3δ |
| CD99 | CD86 | CD80 | CD3γ |
| CD99 | CD86 | CD80 | CD3ε |
| CD99 | CD86 | CD80 | FcγRI-γ |
| CD99 | CD86 | CD80 | FcγRIII-γ |
| CD99 | CD86 | CD80 | FcεRIβ |
| CD99 | CD86 | CD80 | FcεRIγ |
| CD99 | CD86 | CD80 | DAP10 |
| CD99 | CD86 | CD80 | DAP12 |
| CD99 | CD86 | CD80 | CD32 |
| CD99 | CD86 | CD80 | CD79a |
| CD99 | CD86 | CD80 | CD79b |
| CD99 | CD86 | CD86 | CD8 |
| CD99 | CD86 | CD86 | CD3ζ |
| CD99 | CD86 | CD86 | CD3δ |
| CD99 | CD86 | CD86 | CD3γ |
| CD99 | CD86 | CD86 | CD3ε |
| CD99 | CD86 | CD86 | FcγRI-γ |
| CD99 | CD86 | CD86 | FcγRIII-γ |
| CD99 | CD86 | CD86 | FcεRIβ |
| CD99 | CD86 | CD86 | FcεRIγ |
| CD99 | CD86 | CD86 | DAP10 |
| CD99 | CD86 | CD86 | DAP12 |
| CD99 | CD86 | CD86 | CD32 |
| CD99 | CD86 | CD86 | CD79a |
| CD99 | CD86 | CD86 | CD79b |
| CD99 | CD86 | OX40 | CD8 |
| CD99 | CD86 | OX40 | CD3ζ |
| CD99 | CD86 | OX40 | CD3δ |
| CD99 | CD86 | OX40 | CD3γ |
| CD99 | CD86 | OX40 | CD3ε |
| CD99 | CD86 | OX40 | FcγRI-γ |
| CD99 | CD86 | OX40 | FcγRIII-γ |
| CD99 | CD86 | OX40 | FcεRIβ |
| CD99 | CD86 | OX40 | FcεRIγ |
| CD99 | CD86 | OX40 | DAP10 |
| CD99 | CD86 | OX40 | DAP12 |
| CD99 | CD86 | OX40 | CD32 |
| CD99 | CD86 | OX40 | CD79a |
| CD99 | CD86 | OX40 | CD79b |
| CD99 | CD86 | DAP10 | CD8 |
| CD99 | CD86 | DAP10 | CD3ζ |
| CD99 | CD86 | DAP10 | CD3δ |
| CD99 | CD86 | DAP10 | CD3γ |
| CD99 | CD86 | DAP10 | CD3ε |
| CD99 | CD86 | DAP10 | FcγRI-γ |
| CD99 | CD86 | DAP10 | FcγRIII-γ |
| CD99 | CD86 | DAP10 | FcεRIβ |
| CD99 | CD86 | DAP10 | FcεRIγ |
| CD99 | CD86 | DAP10 | DAP10 |
| CD99 | CD86 | DAP10 | DAP12 |
| CD99 | CD86 | DAP10 | CD32 |
| CD99 | CD86 | DAP10 | CD79a |
| CD99 | CD86 | DAP10 | CD79b |
| CD99 | CD86 | DAP12 | CD8 |
| CD99 | CD86 | DAP12 | CD3ζ |
| CD99 | CD86 | DAP12 | CD3δ |
| CD99 | CD86 | DAP12 | CD3γ |
| CD99 | CD86 | DAP12 | CD3ε |
| CD99 | CD86 | DAP12 | FcγRI-γ |
| CD99 | CD86 | DAP12 | FcγRIII-γ |
| CD99 | CD86 | DAP12 | FcεRIβ |
| CD99 | CD86 | DAP12 | FcεRIγ |
| CD99 | CD86 | DAP12 | DAP10 |
| CD99 | CD86 | DAP12 | DAP12 |
| CD99 | CD86 | DAP12 | CD32 |
| CD99 | CD86 | DAP12 | CD79a |
| CD99 | CD86 | DAP12 | CD79b |
| CD99 | CD86 | MyD88 | CD8 |
| CD99 | CD86 | MyD88 | CD3ζ |
| CD99 | CD86 | MyD88 | CD3δ |
| CD99 | CD86 | MyD88 | CD3γ |
| CD99 | CD86 | MyD88 | CD3ε |
| CD99 | CD86 | MyD88 | FcγRI-γ |
| CD99 | CD86 | MyD88 | FcγRIII-γ |
| CD99 | CD86 | MyD88 | FcεRIβ |
| CD99 | CD86 | MyD88 | FcεRIγ |
| CD99 | CD86 | MyD88 | DAP10 |
| CD99 | CD86 | MyD88 | DAP12 |
| CD99 | CD86 | MyD88 | CD32 |
| CD99 | CD86 | MyD88 | CD79a |
| CD99 | CD86 | MyD88 | CD79b |
| CD99 | CD86 | CD7 | CD8 |
| CD99 | CD86 | CD7 | CD3ζ |
| CD99 | CD86 | CD7 | CD3δ |
| CD99 | CD86 | CD7 | CD3γ |
| CD99 | CD86 | CD7 | CD3ε |
| CD99 | CD86 | CD7 | FcγRI-γ |
| CD99 | CD86 | CD7 | FcγRIII-γ |
| CD99 | CD86 | CD7 | FcεRIβ |
| CD99 | CD86 | CD7 | FcεRIγ |
| CD99 | CD86 | CD7 | DAP10 |
| CD99 | CD86 | CD7 | DAP12 |
| CD99 | CD86 | CD7 | CD32 |
| CD99 | CD86 | CD7 | CD79a |
| CD99 | CD86 | CD7 | CD79b |
| CD99 | CD86 | BTNL3 | CD8 |
| CD99 | CD86 | BTNL3 | CD3ζ |
| CD99 | CD86 | BTNL3 | CD3δ |
| CD99 | CD86 | BTNL3 | CD3γ |
| CD99 | CD86 | BTNL3 | CD3ε |
| CD99 | CD86 | BTNL3 | FcγRI-γ |
| CD99 | CD86 | BTNL3 | FcγRIII-γ |
| CD99 | CD86 | BTNL3 | FcεRIβ |
| CD99 | CD86 | BTNL3 | FcεRIγ |
| CD99 | CD86 | BTNL3 | DAP10 |
| CD99 | CD86 | BTNL3 | DAP12 |
| CD99 | CD86 | BTNL3 | CD32 |
| CD99 | CD86 | BTNL3 | CD79a |
| CD99 | CD86 | BTNL3 | CD79b |
| CD99 | CD86 | NKG2D | CD8 |
| CD99 | CD86 | NKG2D | CD3ζ |
| CD99 | CD86 | NKG2D | CD3δ |
| CD99 | CD86 | NKG2D | CD3γ |
| CD99 | CD86 | NKG2D | CD3ε |
| CD99 | CD86 | NKG2D | FcγRI-γ |
| CD99 | CD86 | NKG2D | FcγRIII-γ |
| CD99 | CD86 | NKG2D | FcεRIβ |
| CD99 | CD86 | NKG2D | FcεRIγ |
| CD99 | CD86 | NKG2D | DAP10 |
| CD99 | CD86 | NKG2D | DAP12 |
| CD99 | CD86 | NKG2D | CD32 |
| CD99 | CD86 | NKG2D | CD79a |
| CD99 | CD86 | NKG2D | CD79b |
| CD99 | OX40 | CD28 | CD8 |
| CD99 | OX40 | CD28 | CD3ζ |
| CD99 | OX40 | CD28 | CD3δ |
| CD99 | OX40 | CD28 | CD3γ |
| CD99 | OX40 | CD28 | CD3ε |
| CD99 | OX40 | CD28 | FcγRI-γ |
| CD99 | OX40 | CD28 | FcγRIII-γ |
| CD99 | OX40 | CD28 | FcεRIβ |
| CD99 | OX40 | CD28 | FcεRIγ |
| CD99 | OX40 | CD28 | DAP10 |
| CD99 | OX40 | CD28 | DAP12 |
| CD99 | OX40 | CD28 | CD32 |
| CD99 | OX40 | CD28 | CD79a |
| CD99 | OX40 | CD28 | CD79b |
| CD99 | OX40 | CD8 | CD8 |
| CD99 | OX40 | CD8 | CD3ζ |
| CD99 | OX40 | CD8 | CD3δ |
| CD99 | OX40 | CD8 | CD3γ |
| CD99 | OX40 | CD8 | CD3ε |
| CD99 | OX40 | CD8 | FcγRI-γ |
| CD99 | OX40 | CD8 | FcγRIII-γ |
| CD99 | OX40 | CD8 | FcεRIβ |
| CD99 | OX40 | CD8 | FcεRIγ |

TABLE 3-continued

Third Generation CARs

| ScFv | Co-stimulatory Signal | Co-stimulatory Signal | Signal Domain |
|---|---|---|---|
| CD99 | OX40 | CD8 | DAP10 |
| CD99 | OX40 | CD8 | DAP12 |
| CD99 | OX40 | CD8 | CD32 |
| CD99 | OX40 | CD8 | CD79a |
| CD99 | OX40 | CD8 | CD79b |
| CD99 | OX40 | CD4 | CD8 |
| CD99 | OX40 | CD4 | CD3ζ |
| CD99 | OX40 | CD4 | CD3δ |
| CD99 | OX40 | CD4 | CD3γ |
| CD99 | OX40 | CD4 | CD3ε |
| CD99 | OX40 | CD4 | FcγRI-γ |
| CD99 | OX40 | CD4 | FcγRIII-γ |
| CD99 | OX40 | CD4 | FcεRIβ |
| CD99 | OX40 | CD4 | FcεRIγ |
| CD99 | OX40 | CD4 | DAP10 |
| CD99 | OX40 | CD4 | DAP12 |
| CD99 | OX40 | CD4 | CD32 |
| CD99 | OX40 | CD4 | CD79a |
| CD99 | OX40 | CD4 | CD79b |
| CD99 | OX40 | b2c | CD8 |
| CD99 | OX40 | b2c | CD3ζ |
| CD99 | OX40 | b2c | CD3δ |
| CD99 | OX40 | b2c | CD3γ |
| CD99 | OX40 | b2c | CD3ε |
| CD99 | OX40 | b2c | FcγRI-γ |
| CD99 | OX40 | b2c | FcγRIII-γ |
| CD99 | OX40 | b2c | FcεRIβ |
| CD99 | OX40 | b2c | FcεRIγ |
| CD99 | OX40 | b2c | DAP10 |
| CD99 | OX40 | b2c | DAP12 |
| CD99 | OX40 | b2c | CD32 |
| CD99 | OX40 | b2c | CD79a |
| CD99 | OX40 | b2c | CD79b |
| CD99 | OX40 | CD137/41BB | CD8 |
| CD99 | OX40 | CD137/41BB | CD3ζ |
| CD99 | OX40 | CD137/41BB | CD3δ |
| CD99 | OX40 | CD137/41BB | CD3γ |
| CD99 | OX40 | CD137/41BB | CD3ε |
| CD99 | OX40 | CD137/41BB | FcγRI-γ |
| CD99 | OX40 | CD137/41BB | FcγRIII-γ |
| CD99 | OX40 | CD137/41BB | FcεRIβ |
| CD99 | OX40 | CD137/41BB | FcεRIγ |
| CD99 | OX40 | CD137/41BB | DAP10 |
| CD99 | OX40 | CD137/41BB | DAP12 |
| CD99 | OX40 | CD137/41BB | CD32 |
| CD99 | OX40 | CD137/41BB | CD79a |
| CD99 | OX40 | CD137/41BB | CD79b |
| CD99 | OX40 | ICOS | CD8 |
| CD99 | OX40 | ICOS | CD3ζ |
| CD99 | OX40 | ICOS | CD3δ |
| CD99 | OX40 | ICOS | CD3γ |
| CD99 | OX40 | ICOS | CD3ε |
| CD99 | OX40 | ICOS | FcγRI-γ |
| CD99 | OX40 | ICOS | FcγRIII-γ |
| CD99 | OX40 | ICOS | FcεRIβ |
| CD99 | OX40 | ICOS | FcεRIγ |
| CD99 | OX40 | ICOS | DAP10 |
| CD99 | OX40 | ICOS | DAP12 |
| CD99 | OX40 | ICOS | CD32 |
| CD99 | OX40 | ICOS | CD79a |
| CD99 | OX40 | ICOS | CD79b |
| CD99 | OX40 | CD27 | CD8 |
| CD99 | OX40 | CD27 | CD3ζ |
| CD99 | OX40 | CD27 | CD3δ |
| CD99 | OX40 | CD27 | CD3γ |
| CD99 | OX40 | CD27 | CD3ε |
| CD99 | OX40 | CD27 | FcγRI-γ |
| CD99 | OX40 | CD27 | FcγRIII-γ |
| CD99 | OX40 | CD27 | FcεRIβ |
| CD99 | OX40 | CD27 | FcεRIγ |
| CD99 | OX40 | CD27 | DAP10 |
| CD99 | OX40 | CD27 | DAP12 |
| CD99 | OX40 | CD27 | CD32 |
| CD99 | OX40 | CD27 | CD79a |
| CD99 | OX40 | CD27 | CD79b |
| CD99 | OX40 | CD28δ | CD8 |
| CD99 | OX40 | CD28δ | CD3ζ |
| CD99 | OX40 | CD28δ | CD3δ |
| CD99 | OX40 | CD28δ | CD3γ |
| CD99 | OX40 | CD28δ | CD3ε |
| CD99 | OX40 | CD28δ | FcγRI-γ |
| CD99 | OX40 | CD28δ | FcγRIII-γ |
| CD99 | OX40 | CD28δ | FcεRIβ |
| CD99 | OX40 | CD28δ | FcεRIγ |
| CD99 | OX40 | CD28δ | DAP10 |
| CD99 | OX40 | CD28δ | DAP12 |
| CD99 | OX40 | CD28δ | CD32 |
| CD99 | OX40 | CD28δ | CD79a |
| CD99 | OX40 | CD28δ | CD79b |
| CD99 | OX40 | CD80 | CD8 |
| CD99 | OX40 | CD80 | CD3ζ |
| CD99 | OX40 | CD80 | CD3δ |
| CD99 | OX40 | CD80 | CD3γ |
| CD99 | OX40 | CD80 | CD3ε |
| CD99 | OX40 | CD80 | FcγRI-γ |
| CD99 | OX40 | CD80 | FcγRIII-γ |
| CD99 | OX40 | CD80 | FcεRIβ |
| CD99 | OX40 | CD80 | FcεRIγ |
| CD99 | OX40 | CD80 | DAP10 |
| CD99 | OX40 | CD80 | DAP12 |
| CD99 | OX40 | CD80 | CD32 |
| CD99 | OX40 | CD80 | CD79a |
| CD99 | OX40 | CD80 | CD79b |
| CD99 | OX40 | CD86 | CD8 |
| CD99 | OX40 | CD86 | CD3ζ |
| CD99 | OX40 | CD86 | CD3δ |
| CD99 | OX40 | CD86 | CD3γ |
| CD99 | OX40 | CD86 | CD3ε |
| CD99 | OX40 | CD86 | FcγRI-γ |
| CD99 | OX40 | CD86 | FcγRIII-γ |
| CD99 | OX40 | CD86 | FcεRIβ |
| CD99 | OX40 | CD86 | FcεRIγ |
| CD99 | OX40 | CD86 | DAP10 |
| CD99 | OX40 | CD86 | DAP12 |
| CD99 | OX40 | CD86 | CD32 |
| CD99 | OX40 | CD86 | CD79a |
| CD99 | OX40 | CD86 | CD79b |
| CD99 | OX40 | OX40 | CD8 |
| CD99 | OX40 | OX40 | CD3ζ |
| CD99 | OX40 | OX40 | CD3δ |
| CD99 | OX40 | OX40 | CD3γ |
| CD99 | OX40 | OX40 | CD3ε |
| CD99 | OX40 | OX40 | FcγRI-γ |
| CD99 | OX40 | OX40 | FcγRIII-γ |
| CD99 | OX40 | OX40 | FcεRIβ |
| CD99 | OX40 | OX40 | FcεRIγ |
| CD99 | OX40 | OX40 | DAP10 |
| CD99 | OX40 | OX40 | DAP12 |
| CD99 | OX40 | OX40 | CD32 |
| CD99 | OX40 | OX40 | CD79a |
| CD99 | OX40 | OX40 | CD79b |
| CD99 | OX40 | DAP10 | CD8 |
| CD99 | OX40 | DAP10 | CD3ζ |
| CD99 | OX40 | DAP10 | CD3δ |
| CD99 | OX40 | DAP10 | CD3γ |
| CD99 | OX40 | DAP10 | CD3ε |
| CD99 | OX40 | DAP10 | FcγRI-γ |
| CD99 | OX40 | DAP10 | FcγRIII-γ |
| CD99 | OX40 | DAP10 | FcεRIβ |
| CD99 | OX40 | DAP10 | FcεRIγ |
| CD99 | OX40 | DAP10 | DAP10 |
| CD99 | OX40 | DAP10 | DAP12 |
| CD99 | OX40 | DAP10 | CD32 |
| CD99 | OX40 | DAP10 | CD79a |
| CD99 | OX40 | DAP10 | CD79b |
| CD99 | OX40 | DAP12 | CD8 |
| CD99 | OX40 | DAP12 | CD3ζ |
| CD99 | OX40 | DAP12 | CD3δ |
| CD99 | OX40 | DAP12 | CD3γ |
| CD99 | OX40 | DAP12 | CD3ε |

TABLE 3-continued

Third Generation CARs

| ScFv | Co-stimulatory Signal | Co-stimulatory Signal | Signal Domain |
|---|---|---|---|
| CD99 | OX40 | DAP12 | FcγRI-γ |
| CD99 | OX40 | DAP12 | FcγRIII-γ |
| CD99 | OX40 | DAP12 | FcεRIβ |
| CD99 | OX40 | DAP12 | FcεRIγ |
| CD99 | OX40 | DAP12 | DAP10 |
| CD99 | OX40 | DAP12 | DAP12 |
| CD99 | OX40 | DAP12 | CD32 |
| CD99 | OX40 | DAP12 | CD79a |
| CD99 | OX40 | DAP12 | CD79b |
| CD99 | OX40 | MyD88 | CD8 |
| CD99 | OX40 | MyD88 | CD3ζ |
| CD99 | OX40 | MyD88 | CD3δ |
| CD99 | OX40 | MyD88 | CD3γ |
| CD99 | OX40 | MyD88 | CD3ε |
| CD99 | OX40 | MyD88 | FcγRI-γ |
| CD99 | OX40 | MyD88 | FcγRIII-γ |
| CD99 | OX40 | MyD88 | FcεRIβ |
| CD99 | OX40 | MyD88 | FcεRIγ |
| CD99 | OX40 | MyD88 | DAP10 |
| CD99 | OX40 | MyD88 | DAP12 |
| CD99 | OX40 | MyD88 | CD32 |
| CD99 | OX40 | MyD88 | CD79a |
| CD99 | OX40 | MyD88 | CD79b |
| CD99 | OX40 | CD7 | CD8 |
| CD99 | OX40 | CD7 | CD3ζ |
| CD99 | OX40 | CD7 | CD3δ |
| CD99 | OX40 | CD7 | CD3γ |
| CD99 | OX40 | CD7 | CD3ε |
| CD99 | OX40 | CD7 | FcγRI-γ |
| CD99 | OX40 | CD7 | FcγRIII-γ |
| CD99 | OX40 | CD7 | FcεRIβ |
| CD99 | OX40 | CD7 | FcεRIγ |
| CD99 | OX40 | CD7 | DAP10 |
| CD99 | OX40 | CD7 | DAP12 |
| CD99 | OX40 | CD7 | CD32 |
| CD99 | OX40 | CD7 | CD79a |
| CD99 | OX40 | CD7 | CD79b |
| CD99 | OX40 | BTNL3 | CD8 |
| CD99 | OX40 | BTNL3 | CD3ζ |
| CD99 | OX40 | BTNL3 | CD3δ |
| CD99 | OX40 | BTNL3 | CD3γ |
| CD99 | OX40 | BTNL3 | CD3ε |
| CD99 | OX40 | BTNL3 | FcγRI-γ |
| CD99 | OX40 | BTNL3 | FcγRIII-γ |
| CD99 | OX40 | BTNL3 | FcεRIβ |
| CD99 | OX40 | BTNL3 | FcεRIγ |
| CD99 | OX40 | BTNL3 | DAP10 |
| CD99 | OX40 | BTNL3 | DAP12 |
| CD99 | OX40 | BTNL3 | CD32 |
| CD99 | OX40 | BTNL3 | CD79a |
| CD99 | OX40 | BTNL3 | CD79b |
| CD99 | OX40 | NKG2D | CD8 |
| CD99 | OX40 | NKG2D | CD3ζ |
| CD99 | OX40 | NKG2D | CD3δ |
| CD99 | OX40 | NKG2D | CD3γ |
| CD99 | OX40 | NKG2D | CD3ε |
| CD99 | OX40 | NKG2D | FcγRI-γ |
| CD99 | OX40 | NKG2D | FcγRIII-γ |
| CD99 | OX40 | NKG2D | FcεRIβ |
| CD99 | OX40 | NKG2D | FcεRIγ |
| CD99 | OX40 | NKG2D | DAP10 |
| CD99 | OX40 | NKG2D | DAP12 |
| CD99 | OX40 | NKG2D | CD32 |
| CD99 | OX40 | NKG2D | CD79a |
| CD99 | OX40 | NKG2D | CD79b |
| CD99 | DAP10 | CD28 | CD8 |
| CD99 | DAP10 | CD28 | CD3ζ |
| CD99 | DAP10 | CD28 | CD3δ |
| CD99 | DAP10 | CD28 | CD3γ |
| CD99 | DAP10 | CD28 | CD3ε |
| CD99 | DAP10 | CD28 | FcγRI-γ |
| CD99 | DAP10 | CD28 | FcγRIII-γ |
| CD99 | DAP10 | CD28 | FcεRIβ |
| CD99 | DAP10 | CD28 | FcεRIγ |
| CD99 | DAP10 | CD28 | DAP10 |
| CD99 | DAP10 | CD28 | DAP12 |
| CD99 | DAP10 | CD28 | CD32 |
| CD99 | DAP10 | CD28 | CD79a |
| CD99 | DAP10 | CD28 | CD79b |
| CD99 | DAP10 | CD8 | CD8 |
| CD99 | DAP10 | CD8 | CD3ζ |
| CD99 | DAP10 | CD8 | CD3δ |
| CD99 | DAP10 | CD8 | CD3γ |
| CD99 | DAP10 | CD8 | CD3ε |
| CD99 | DAP10 | CD8 | FcγRI-γ |
| CD99 | DAP10 | CD8 | FcγRIII-γ |
| CD99 | DAP10 | CD8 | FcεRIβ |
| CD99 | DAP10 | CD8 | FcεRIγ |
| CD99 | DAP10 | CD8 | DAP10 |
| CD99 | DAP10 | CD8 | DAP12 |
| CD99 | DAP10 | CD8 | CD32 |
| CD99 | DAP10 | CD8 | CD79a |
| CD99 | DAP10 | CD8 | CD79b |
| CD99 | DAP10 | CD4 | CD8 |
| CD99 | DAP10 | CD4 | CD3ζ |
| CD99 | DAP10 | CD4 | CD3δ |
| CD99 | DAP10 | CD4 | CD3γ |
| CD99 | DAP10 | CD4 | CD3ε |
| CD99 | DAP10 | CD4 | FcγRI-γ |
| CD99 | DAP10 | CD4 | FcγRIII-γ |
| CD99 | DAP10 | CD4 | FcεRIβ |
| CD99 | DAP10 | CD4 | FcεRIγ |
| CD99 | DAP10 | CD4 | DAP10 |
| CD99 | DAP10 | CD4 | DAP12 |
| CD99 | DAP10 | CD4 | CD32 |
| CD99 | DAP10 | CD4 | CD79a |
| CD99 | DAP10 | CD4 | CD79b |
| CD99 | DAP10 | b2c | CD8 |
| CD99 | DAP10 | b2c | CD3ζ |
| CD99 | DAP10 | b2c | CD3δ |
| CD99 | DAP10 | b2c | CD3γ |
| CD99 | DAP10 | b2c | CD3ε |
| CD99 | DAP10 | b2c | FcγRI-γ |
| CD99 | DAP10 | b2c | FcγRIII-γ |
| CD99 | DAP10 | b2c | FcεRIβ |
| CD99 | DAP10 | b2c | FcεRIγ |
| CD99 | DAP10 | b2c | DAP10 |
| CD99 | DAP10 | b2c | DAP12 |
| CD99 | DAP10 | b2c | CD32 |
| CD99 | DAP10 | b2c | CD79a |
| CD99 | DAP10 | b2c | CD79b |
| CD99 | DAP10 | CD137/41BB | CD8 |
| CD99 | DAP10 | CD137/41BB | CD3ζ |
| CD99 | DAP10 | CD137/41BB | CD3δ |
| CD99 | DAP10 | CD137/41BB | CD3γ |
| CD99 | DAP10 | CD137/41BB | CD3ε |
| CD99 | DAP10 | CD137/41BB | FcγRI-γ |
| CD99 | DAP10 | CD137/41BB | FcγRIII-γ |
| CD99 | DAP10 | CD137/41BB | FcεRIβ |
| CD99 | DAP10 | CD137/41BB | FcεRIγ |
| CD99 | DAP10 | CD137/41BB | DAP10 |
| CD99 | DAP10 | CD137/41BB | DAP12 |
| CD99 | DAP10 | CD137/41BB | CD32 |
| CD99 | DAP10 | CD137/41BB | CD79a |
| CD99 | DAP10 | CD137/41BB | CD79b |
| CD99 | DAP10 | ICOS | CD8 |
| CD99 | DAP10 | ICOS | CD3ζ |
| CD99 | DAP10 | ICOS | CD3δ |
| CD99 | DAP10 | ICOS | CD3γ |
| CD99 | DAP10 | ICOS | CD3ε |
| CD99 | DAP10 | ICOS | FcγRI-γ |
| CD99 | DAP10 | ICOS | FcγRIII-γ |
| CD99 | DAP10 | ICOS | FcεRIβ |
| CD99 | DAP10 | ICOS | FcεRIγ |
| CD99 | DAP10 | ICOS | DAP10 |
| CD99 | DAP10 | ICOS | DAP12 |
| CD99 | DAP10 | ICOS | CD32 |
| CD99 | DAP10 | ICOS | CD79a |
| CD99 | DAP10 | ICOS | CD79b |
| CD99 | DAP10 | CD27 | CD8 |

TABLE 3-continued

Third Generation CARs

| ScFv | Co-stimulatory Signal | Co-stimulatory Signal | Signal Domain |
|---|---|---|---|
| CD99 | DAP10 | CD27 | CD3ζ |
| CD99 | DAP10 | CD27 | CD3δ |
| CD99 | DAP10 | CD27 | CD3γ |
| CD99 | DAP10 | CD27 | CD3ε |
| CD99 | DAP10 | CD27 | FcγRI-γ |
| CD99 | DAP10 | CD27 | FcγRIII-γ |
| CD99 | DAP10 | CD27 | FcεRIβ |
| CD99 | DAP10 | CD27 | FcεRIγ |
| CD99 | DAP10 | CD27 | DAP10 |
| CD99 | DAP10 | CD27 | DAP12 |
| CD99 | DAP10 | CD27 | CD32 |
| CD99 | DAP10 | CD27 | CD79a |
| CD99 | DAP10 | CD27 | CD79b |
| CD99 | DAP10 | CD28δ | CD8 |
| CD99 | DAP10 | CD28δ | CD3ζ |
| CD99 | DAP10 | CD28δ | CD3δ |
| CD99 | DAP10 | CD28δ | CD3γ |
| CD99 | DAP10 | CD28δ | CD3ε |
| CD99 | DAP10 | CD28δ | FcγRI-γ |
| CD99 | DAP10 | CD28δ | FcγRIII-γ |
| CD99 | DAP10 | CD28δ | FcεRIβ |
| CD99 | DAP10 | CD28δ | FcεRIγ |
| CD99 | DAP10 | CD28δ | DAP10 |
| CD99 | DAP10 | CD28δ | DAP12 |
| CD99 | DAP10 | CD28δ | CD32 |
| CD99 | DAP10 | CD28δ | CD79a |
| CD99 | DAP10 | CD28δ | CD79b |
| CD99 | DAP10 | CD80 | CD8 |
| CD99 | DAP10 | CD80 | CD3ζ |
| CD99 | DAP10 | CD80 | CD3δ |
| CD99 | DAP10 | CD80 | CD3γ |
| CD99 | DAP10 | CD80 | CD3ε |
| CD99 | DAP10 | CD80 | FcγRI-γ |
| CD99 | DAP10 | CD80 | FcγRIII-γ |
| CD99 | DAP10 | CD80 | FcεRIβ |
| CD99 | DAP10 | CD80 | FcεRIγ |
| CD99 | DAP10 | CD80 | DAP10 |
| CD99 | DAP10 | CD80 | DAP12 |
| CD99 | DAP10 | CD80 | CD32 |
| CD99 | DAP10 | CD80 | CD79a |
| CD99 | DAP10 | CD80 | CD79b |
| CD99 | DAP10 | CD86 | CD8 |
| CD99 | DAP10 | CD86 | CD3ζ |
| CD99 | DAP10 | CD86 | CD3δ |
| CD99 | DAP10 | CD86 | CD3γ |
| CD99 | DAP10 | CD86 | CD3ε |
| CD99 | DAP10 | CD86 | FcγRI-γ |
| CD99 | DAP10 | CD86 | FcγRIII-γ |
| CD99 | DAP10 | CD86 | FcεRIβ |
| CD99 | DAP10 | CD86 | FcεRIγ |
| CD99 | DAP10 | CD86 | DAP10 |
| CD99 | DAP10 | CD86 | DAP12 |
| CD99 | DAP10 | CD86 | CD32 |
| CD99 | DAP10 | CD86 | CD79a |
| CD99 | DAP10 | CD86 | CD79b |
| CD99 | DAP10 | OX40 | CD8 |
| CD99 | DAP10 | OX40 | CD3ζ |
| CD99 | DAP10 | OX40 | CD3δ |
| CD99 | DAP10 | OX40 | CD3γ |
| CD99 | DAP10 | OX40 | CD3ε |
| CD99 | DAP10 | OX40 | FcγRI-γ |
| CD99 | DAP10 | OX40 | FcγRIII-γ |
| CD99 | DAP10 | OX40 | FcεRIβ |
| CD99 | DAP10 | OX40 | FcεRIγ |
| CD99 | DAP10 | OX40 | DAP10 |
| CD99 | DAP10 | OX40 | DAP12 |
| CD99 | DAP10 | OX40 | CD32 |
| CD99 | DAP10 | OX40 | CD79a |
| CD99 | DAP10 | OX40 | CD79b |
| CD99 | DAP10 | DAP10 | CD8 |
| CD99 | DAP10 | DAP10 | CD3ζ |
| CD99 | DAP10 | DAP10 | CD3δ |
| CD99 | DAP10 | DAP10 | CD3γ |
| CD99 | DAP10 | DAP10 | CD3ε |
| CD99 | DAP10 | DAP10 | FcγRI-γ |
| CD99 | DAP10 | DAP10 | FcγRIII-γ |
| CD99 | DAP10 | DAP10 | FcεRIβ |
| CD99 | DAP10 | DAP10 | FcεRIγ |
| CD99 | DAP10 | DAP10 | DAP10 |
| CD99 | DAP10 | DAP10 | DAP12 |
| CD99 | DAP10 | DAP10 | CD32 |
| CD99 | DAP10 | DAP10 | CD79a |
| CD99 | DAP10 | DAP10 | CD79b |
| CD99 | DAP10 | DAP12 | CD8 |
| CD99 | DAP10 | DAP12 | CD3ζ |
| CD99 | DAP10 | DAP12 | CD3δ |
| CD99 | DAP10 | DAP12 | CD3γ |
| CD99 | DAP10 | DAP12 | CD3ε |
| CD99 | DAP10 | DAP12 | FcγRI-γ |
| CD99 | DAP10 | DAP12 | FcγRIII-γ |
| CD99 | DAP10 | DAP12 | FcεRIβ |
| CD99 | DAP10 | DAP12 | FcεRIγ |
| CD99 | DAP10 | DAP12 | DAP10 |
| CD99 | DAP10 | DAP12 | DAP12 |
| CD99 | DAP10 | DAP12 | CD32 |
| CD99 | DAP10 | DAP12 | CD79a |
| CD99 | DAP10 | DAP12 | CD79b |
| CD99 | DAP10 | MyD88 | CD8 |
| CD99 | DAP10 | MyD88 | CD3ζ |
| CD99 | DAP10 | MyD88 | CD3δ |
| CD99 | DAP10 | MyD88 | CD3γ |
| CD99 | DAP10 | MyD88 | CD3ε |
| CD99 | DAP10 | MyD88 | FcγRI-γ |
| CD99 | DAP10 | MyD88 | FcγRIII-γ |
| CD99 | DAP10 | MyD88 | FcεRIβ |
| CD99 | DAP10 | MyD88 | FcεRIγ |
| CD99 | DAP10 | MyD88 | DAP10 |
| CD99 | DAP10 | MyD88 | DAP12 |
| CD99 | DAP10 | MyD88 | CD32 |
| CD99 | DAP10 | MyD88 | CD79a |
| CD99 | DAP10 | MyD88 | CD79b |
| CD99 | DAP10 | CD7 | CD8 |
| CD99 | DAP10 | CD7 | CD3ζ |
| CD99 | DAP10 | CD7 | CD3δ |
| CD99 | DAP10 | CD7 | CD3γ |
| CD99 | DAP10 | CD7 | CD3ε |
| CD99 | DAP10 | CD7 | FcγRI-γ |
| CD99 | DAP10 | CD7 | FcγRIII-γ |
| CD99 | DAP10 | CD7 | FcεRIβ |
| CD99 | DAP10 | CD7 | FcεRIγ |
| CD99 | DAP10 | CD7 | DAP10 |
| CD99 | DAP10 | CD7 | DAP12 |
| CD99 | DAP10 | CD7 | CD32 |
| CD99 | DAP10 | CD7 | CD79a |
| CD99 | DAP10 | CD7 | CD79b |
| CD99 | DAP10 | BTNL3 | CD8 |
| CD99 | DAP10 | BTNL3 | CD3ζ |
| CD99 | DAP10 | BTNL3 | CD3δ |
| CD99 | DAP10 | BTNL3 | CD3γ |
| CD99 | DAP10 | BTNL3 | CD3ε |
| CD99 | DAP10 | BTNL3 | FcγRI-γ |
| CD99 | DAP10 | BTNL3 | FcγRIII-γ |
| CD99 | DAP10 | BTNL3 | FcεRIβ |
| CD99 | DAP10 | BTNL3 | FcεRIγ |
| CD99 | DAP10 | BTNL3 | DAP10 |
| CD99 | DAP10 | BTNL3 | DAP12 |
| CD99 | DAP10 | BTNL3 | CD32 |
| CD99 | DAP10 | BTNL3 | CD79a |
| CD99 | DAP10 | BTNL3 | CD79b |
| CD99 | DAP10 | NKG2D | CD8 |
| CD99 | DAP10 | NKG2D | CD3ζ |
| CD99 | DAP10 | NKG2D | CD3δ |
| CD99 | DAP10 | NKG2D | CD3γ |
| CD99 | DAP10 | NKG2D | CD3ε |
| CD99 | DAP10 | NKG2D | FcγRI-γ |
| CD99 | DAP10 | NKG2D | FcγRIII-γ |
| CD99 | DAP10 | NKG2D | FcεRIβ |
| CD99 | DAP10 | NKG2D | FcεRIγ |
| CD99 | DAP10 | NKG2D | DAP10 |
| CD99 | DAP10 | NKG2D | DAP12 |

TABLE 3-continued

Third Generation CARs

| ScFv | Co-stimulatory Signal | Co-stimulatory Signal | Signal Domain |
|---|---|---|---|
| CD99 | DAP10 | NKG2D | CD32 |
| CD99 | DAP10 | NKG2D | CD79a |
| CD99 | DAP10 | NKG2D | CD79b |
| CD99 | DAP12 | CD28 | CD8 |
| CD99 | DAP12 | CD28 | CD3ζ |
| CD99 | DAP12 | CD28 | CD3δ |
| CD99 | DAP12 | CD28 | CD3γ |
| CD99 | DAP12 | CD28 | CD3ε |
| CD99 | DAP12 | CD28 | FcγRI-γ |
| CD99 | DAP12 | CD28 | FcγRIII-γ |
| CD99 | DAP12 | CD28 | FcεRIβ |
| CD99 | DAP12 | CD28 | FcεRIγ |
| CD99 | DAP12 | CD28 | DAP10 |
| CD99 | DAP12 | CD28 | DAP12 |
| CD99 | DAP12 | CD28 | CD32 |
| CD99 | DAP12 | CD28 | CD79a |
| CD99 | DAP12 | CD28 | CD79b |
| CD99 | DAP12 | CD8 | CD8 |
| CD99 | DAP12 | CD8 | CD3ζ |
| CD99 | DAP12 | CD8 | CD3δ |
| CD99 | DAP12 | CD8 | CD3γ |
| CD99 | DAP12 | CD8 | CD3ε |
| CD99 | DAP12 | CD8 | FcγRI-γ |
| CD99 | DAP12 | CD8 | FcγRIII-γ |
| CD99 | DAP12 | CD8 | FcεRIβ |
| CD99 | DAP12 | CD8 | FcεRIγ |
| CD99 | DAP12 | CD8 | DAP10 |
| CD99 | DAP12 | CD8 | DAP12 |
| CD99 | DAP12 | CD8 | CD32 |
| CD99 | DAP12 | CD8 | CD79a |
| CD99 | DAP12 | CD8 | CD79b |
| CD99 | DAP12 | CD4 | CD8 |
| CD99 | DAP12 | CD4 | CD3ζ |
| CD99 | DAP12 | CD4 | CD3δ |
| CD99 | DAP12 | CD4 | CD3γ |
| CD99 | DAP12 | CD4 | CD3ε |
| CD99 | DAP12 | CD4 | FcγRI-γ |
| CD99 | DAP12 | CD4 | FcγRIII-γ |
| CD99 | DAP12 | CD4 | FcεRIβ |
| CD99 | DAP12 | CD4 | FcεRIγ |
| CD99 | DAP12 | CD4 | DAP10 |
| CD99 | DAP12 | CD4 | DAP12 |
| CD99 | DAP12 | CD4 | CD32 |
| CD99 | DAP12 | CD4 | CD79a |
| CD99 | DAP12 | CD4 | CD79b |
| CD99 | DAP12 | b2c | CD8 |
| CD99 | DAP12 | b2c | CD3ζ |
| CD99 | DAP12 | b2c | CD3δ |
| CD99 | DAP12 | b2c | CD3γ |
| CD99 | DAP12 | b2c | CD3ε |
| CD99 | DAP12 | b2c | FcγRI-γ |
| CD99 | DAP12 | b2c | FcγRIII-γ |
| CD99 | DAP12 | b2c | FcεRIβ |
| CD99 | DAP12 | b2c | FcεRIγ |
| CD99 | DAP12 | b2c | DAP10 |
| CD99 | DAP12 | b2c | DAP12 |
| CD99 | DAP12 | b2c | CD32 |
| CD99 | DAP12 | b2c | CD79a |
| CD99 | DAP12 | b2c | CD79b |
| CD99 | DAP12 | CD137/41BB | CD8 |
| CD99 | DAP12 | CD137/41BB | CD3ζ |
| CD99 | DAP12 | CD137/41BB | CD3δ |
| CD99 | DAP12 | CD137/41BB | CD3γ |
| CD99 | DAP12 | CD137/41BB | CD3ε |
| CD99 | DAP12 | CD137/41BB | FcγRI-γ |
| CD99 | DAP12 | CD137/41BB | FcγRIII-γ |
| CD99 | DAP12 | CD137/41BB | FcεRIβ |
| CD99 | DAP12 | CD137/41BB | FcεRIγ |
| CD99 | DAP12 | CD137/41BB | DAP10 |
| CD99 | DAP12 | CD137/41BB | DAP12 |
| CD99 | DAP12 | CD137/41BB | CD32 |
| CD99 | DAP12 | CD137/41BB | CD79a |
| CD99 | DAP12 | CD137/41BB | CD79b |
| CD99 | DAP12 | ICOS | CD8 |
| CD99 | DAP12 | ICOS | CD3ζ |
| CD99 | DAP12 | ICOS | CD3δ |
| CD99 | DAP12 | ICOS | CD3γ |
| CD99 | DAP12 | ICOS | CD3ε |
| CD99 | DAP12 | ICOS | FcγRI-γ |
| CD99 | DAP12 | ICOS | FcγRIII-γ |
| CD99 | DAP12 | ICOS | FcεRIβ |
| CD99 | DAP12 | ICOS | FcεRIγ |
| CD99 | DAP12 | ICOS | DAP10 |
| CD99 | DAP12 | ICOS | DAP12 |
| CD99 | DAP12 | ICOS | CD32 |
| CD99 | DAP12 | ICOS | CD79a |
| CD99 | DAP12 | ICOS | CD79b |
| CD99 | DAP12 | CD27 | CD8 |
| CD99 | DAP12 | CD27 | CD3ζ |
| CD99 | DAP12 | CD27 | CD3δ |
| CD99 | DAP12 | CD27 | CD3γ |
| CD99 | DAP12 | CD27 | CD3ε |
| CD99 | DAP12 | CD27 | FcγRI-γ |
| CD99 | DAP12 | CD27 | FcγRIII-γ |
| CD99 | DAP12 | CD27 | FcεRIβ |
| CD99 | DAP12 | CD27 | FcεRIγ |
| CD99 | DAP12 | CD27 | DAP10 |
| CD99 | DAP12 | CD27 | DAP12 |
| CD99 | DAP12 | CD27 | CD32 |
| CD99 | DAP12 | CD27 | CD79a |
| CD99 | DAP12 | CD27 | CD79b |
| CD99 | DAP12 | CD28δ | CD8 |
| CD99 | DAP12 | CD28δ | CD3ζ |
| CD99 | DAP12 | CD28δ | CD3δ |
| CD99 | DAP12 | CD28δ | CD3γ |
| CD99 | DAP12 | CD28δ | CD3ε |
| CD99 | DAP12 | CD28δ | FcγRI-γ |
| CD99 | DAP12 | CD28δ | FcγRIII-γ |
| CD99 | DAP12 | CD28δ | FcεRIβ |
| CD99 | DAP12 | CD28δ | FcεRIγ |
| CD99 | DAP12 | CD28δ | DAP10 |
| CD99 | DAP12 | CD28δ | DAP12 |
| CD99 | DAP12 | CD28δ | CD32 |
| CD99 | DAP12 | CD28δ | CD79a |
| CD99 | DAP12 | CD28δ | CD79b |
| CD99 | DAP12 | CD80 | CD8 |
| CD99 | DAP12 | CD80 | CD3ζ |
| CD99 | DAP12 | CD80 | CD3δ |
| CD99 | DAP12 | CD80 | CD3γ |
| CD99 | DAP12 | CD80 | CD3ε |
| CD99 | DAP12 | CD80 | FcγRI-γ |
| CD99 | DAP12 | CD80 | FcγRIII-γ |
| CD99 | DAP12 | CD80 | FcεRIβ |
| CD99 | DAP12 | CD80 | FcεRIγ |
| CD99 | DAP12 | CD80 | DAP10 |
| CD99 | DAP12 | CD80 | DAP12 |
| CD99 | DAP12 | CD80 | CD32 |
| CD99 | DAP12 | CD80 | CD79a |
| CD99 | DAP12 | CD80 | CD79b |
| CD99 | DAP12 | CD86 | CD8 |
| CD99 | DAP12 | CD86 | CD3ζ |
| CD99 | DAP12 | CD86 | CD3δ |
| CD99 | DAP12 | CD86 | CD3γ |
| CD99 | DAP12 | CD86 | CD3ε |
| CD99 | DAP12 | CD86 | FcγRI-γ |
| CD99 | DAP12 | CD86 | FcγRIII-γ |
| CD99 | DAP12 | CD86 | FcεRIβ |
| CD99 | DAP12 | CD86 | FcεRIγ |
| CD99 | DAP12 | CD86 | DAP10 |
| CD99 | DAP12 | CD86 | DAP12 |
| CD99 | DAP12 | CD86 | CD32 |
| CD99 | DAP12 | CD86 | CD79a |
| CD99 | DAP12 | CD86 | CD79b |
| CD99 | DAP12 | OX40 | CD8 |
| CD99 | DAP12 | OX40 | CD3ζ |
| CD99 | DAP12 | OX40 | CD3δ |
| CD99 | DAP12 | OX40 | CD3γ |
| CD99 | DAP12 | OX40 | CD3ε |
| CD99 | DAP12 | OX40 | FcγRI-γ |
| CD99 | DAP12 | OX40 | FcγRIII-γ |

TABLE 3-continued

Third Generation CARs

| ScFv | Co-stimulatory Signal | Co-stimulatory Signal | Signal Domain |
|---|---|---|---|
| CD99 | DAP12 | OX40 | FcεRIβ |
| CD99 | DAP12 | OX40 | FcεRIγ |
| CD99 | DAP12 | OX40 | DAP10 |
| CD99 | DAP12 | OX40 | DAP12 |
| CD99 | DAP12 | OX40 | CD32 |
| CD99 | DAP12 | OX40 | CD79a |
| CD99 | DAP12 | OX40 | CD79b |
| CD99 | DAP12 | DAP10 | CD8 |
| CD99 | DAP12 | DAP10 | CD3ζ |
| CD99 | DAP12 | DAP10 | CD3δ |
| CD99 | DAP12 | DAP10 | CD3γ |
| CD99 | DAP12 | DAP10 | CD3ε |
| CD99 | DAP12 | DAP10 | FcγRI-γ |
| CD99 | DAP12 | DAP10 | FcγRIII-γ |
| CD99 | DAP12 | DAP10 | FcεRIβ |
| CD99 | DAP12 | DAP10 | FcεRIγ |
| CD99 | DAP12 | DAP10 | DAP10 |
| CD99 | DAP12 | DAP10 | DAP12 |
| CD99 | DAP12 | DAP10 | CD32 |
| CD99 | DAP12 | DAP10 | CD79a |
| CD99 | DAP12 | DAP10 | CD79b |
| CD99 | DAP12 | DAP12 | CD8 |
| CD99 | DAP12 | DAP12 | CD3ζ |
| CD99 | DAP12 | DAP12 | CD3δ |
| CD99 | DAP12 | DAP12 | CD3γ |
| CD99 | DAP12 | DAP12 | CD3ε |
| CD99 | DAP12 | DAP12 | FcγRI-γ |
| CD99 | DAP12 | DAP12 | FcγRIII-γ |
| CD99 | DAP12 | DAP12 | FcεRIβ |
| CD99 | DAP12 | DAP12 | FcεRIγ |
| CD99 | DAP12 | DAP12 | DAP10 |
| CD99 | DAP12 | DAP12 | DAP12 |
| CD99 | DAP12 | DAP12 | CD32 |
| CD99 | DAP12 | DAP12 | CD79a |
| CD99 | DAP12 | DAP12 | CD79b |
| CD99 | DAP12 | MyD88 | CD8 |
| CD99 | DAP12 | MyD88 | CD3ζ |
| CD99 | DAP12 | MyD88 | CD3δ |
| CD99 | DAP12 | MyD88 | CD3γ |
| CD99 | DAP12 | MyD88 | CD3ε |
| CD99 | DAP12 | MyD88 | FcγRI-γ |
| CD99 | DAP12 | MyD88 | FcγRIII-γ |
| CD99 | DAP12 | MyD88 | FcεRIβ |
| CD99 | DAP12 | MyD88 | FcεRIγ |
| CD99 | DAP12 | MyD88 | DAP10 |
| CD99 | DAP12 | MyD88 | DAP12 |
| CD99 | DAP12 | MyD88 | CD32 |
| CD99 | DAP12 | MyD88 | CD79a |
| CD99 | DAP12 | MyD88 | CD79b |
| CD99 | DAP12 | CD7 | CD8 |
| CD99 | DAP12 | CD7 | CD3ζ |
| CD99 | DAP12 | CD7 | CD3δ |
| CD99 | DAP12 | CD7 | CD3γ |
| CD99 | DAP12 | CD7 | CD3ε |
| CD99 | DAP12 | CD7 | FcγRI-γ |
| CD99 | DAP12 | CD7 | FcγRIII-γ |
| CD99 | DAP12 | CD7 | FcεRIβ |
| CD99 | DAP12 | CD7 | FcεRIγ |
| CD99 | DAP12 | CD7 | DAP10 |
| CD99 | DAP12 | CD7 | DAP12 |
| CD99 | DAP12 | CD7 | CD32 |
| CD99 | DAP12 | CD7 | CD79a |
| CD99 | DAP12 | CD7 | CD79b |
| CD99 | DAP12 | BTNL3 | CD8 |
| CD99 | DAP12 | BTNL3 | CD3ζ |
| CD99 | DAP12 | BTNL3 | CD3δ |
| CD99 | DAP12 | BTNL3 | CD3γ |
| CD99 | DAP12 | BTNL3 | CD3ε |
| CD99 | DAP12 | BTNL3 | FcγRI-γ |
| CD99 | DAP12 | BTNL3 | FcγRIII-γ |
| CD99 | DAP12 | BTNL3 | FcεRIβ |
| CD99 | DAP12 | BTNL3 | FcεRIγ |
| CD99 | DAP12 | BTNL3 | DAP10 |
| CD99 | DAP12 | BTNL3 | DAP12 |
| CD99 | DAP12 | BTNL3 | CD32 |
| CD99 | DAP12 | BTNL3 | CD79a |
| CD99 | DAP12 | BTNL3 | CD79b |
| CD99 | DAP12 | NKG2D | CD8 |
| CD99 | DAP12 | NKG2D | CD3ζ |
| CD99 | DAP12 | NKG2D | CD3δ |
| CD99 | DAP12 | NKG2D | CD3γ |
| CD99 | DAP12 | NKG2D | CD3ε |
| CD99 | DAP12 | NKG2D | FcγRI-γ |
| CD99 | DAP12 | NKG2D | FcγRIII-γ |
| CD99 | DAP12 | NKG2D | FcεRIβ |
| CD99 | DAP12 | NKG2D | FcεRIγ |
| CD99 | DAP12 | NKG2D | DAP10 |
| CD99 | DAP12 | NKG2D | DAP12 |
| CD99 | DAP12 | NKG2D | CD32 |
| CD99 | DAP12 | NKG2D | CD79a |
| CD99 | DAP12 | NKG2D | CD79b |
| CD99 | MyD88 | CD28 | CD8 |
| CD99 | MyD88 | CD28 | CD3ζ |
| CD99 | MyD88 | CD28 | CD3δ |
| CD99 | MyD88 | CD28 | CD3γ |
| CD99 | MyD88 | CD28 | CD3ε |
| CD99 | MyD88 | CD28 | FcγRI-γ |
| CD99 | MyD88 | CD28 | FcγRIII-γ |
| CD99 | MyD88 | CD28 | FcεRIβ |
| CD99 | MyD88 | CD28 | FcεRIγ |
| CD99 | MyD88 | CD28 | DAP10 |
| CD99 | MyD88 | CD28 | DAP12 |
| CD99 | MyD88 | CD28 | CD32 |
| CD99 | MyD88 | CD28 | CD79a |
| CD99 | MyD88 | CD28 | CD79b |
| CD99 | MyD88 | CD8 | CD8 |
| CD99 | MyD88 | CD8 | CD3ζ |
| CD99 | MyD88 | CD8 | CD3δ |
| CD99 | MyD88 | CD8 | CD3γ |
| CD99 | MyD88 | CD8 | CD3ε |
| CD99 | MyD88 | CD8 | FcγRI-γ |
| CD99 | MyD88 | CD8 | FcγRIII-γ |
| CD99 | MyD88 | CD8 | FcεRIβ |
| CD99 | MyD88 | CD8 | FcεRIγ |
| CD99 | MyD88 | CD8 | DAP10 |
| CD99 | MyD88 | CD8 | DAP12 |
| CD99 | MyD88 | CD8 | CD32 |
| CD99 | MyD88 | CD8 | CD79a |
| CD99 | MyD88 | CD8 | CD79b |
| CD99 | MyD88 | CD4 | CD8 |
| CD99 | MyD88 | CD4 | CD3ζ |
| CD99 | MyD88 | CD4 | CD3δ |
| CD99 | MyD88 | CD4 | CD3γ |
| CD99 | MyD88 | CD4 | CD3ε |
| CD99 | MyD88 | CD4 | FcγRI-γ |
| CD99 | MyD88 | CD4 | FcγRIII-γ |
| CD99 | MyD88 | CD4 | FcεRIβ |
| CD99 | MyD88 | CD4 | FcεRIγ |
| CD99 | MyD88 | CD4 | DAP10 |
| CD99 | MyD88 | CD4 | DAP12 |
| CD99 | MyD88 | CD4 | CD32 |
| CD99 | MyD88 | CD4 | CD79a |
| CD99 | MyD88 | CD4 | CD79b |
| CD99 | MyD88 | b2c | CD8 |
| CD99 | MyD88 | b2c | CD3ζ |
| CD99 | MyD88 | b2c | CD3δ |
| CD99 | MyD88 | b2c | CD3γ |
| CD99 | MyD88 | b2c | CD3ε |
| CD99 | MyD88 | b2c | FcγRI-γ |
| CD99 | MyD88 | b2c | FcγRIII-γ |
| CD99 | MyD88 | b2c | FcεRIβ |
| CD99 | MyD88 | b2c | FcεRIγ |
| CD99 | MyD88 | b2c | DAP10 |
| CD99 | MyD88 | b2c | DAP12 |
| CD99 | MyD88 | b2c | CD32 |
| CD99 | MyD88 | b2c | CD79a |
| CD99 | MyD88 | b2c | CD79b |
| CD99 | MyD88 | CD137/41BB | CD8 |
| CD99 | MyD88 | CD137/41BB | CD3ζ |
| CD99 | MyD88 | CD137/41BB | CD3δ |

TABLE 3-continued

Third Generation CARs

| ScFv | Co-stimulatory Signal | Co-stimulatory Signal | Signal Domain |
|---|---|---|---|
| CD99 | MyD88 | CD137/41BB | CD3γ |
| CD99 | MyD88 | CD137/41BB | CD3ε |
| CD99 | MyD88 | CD137/41BB | FcγRI-γ |
| CD99 | MyD88 | CD137/41BB | FcγRIII-γ |
| CD99 | MyD88 | CD137/41BB | FcεRIβ |
| CD99 | MyD88 | CD137/41BB | FcεRIγ |
| CD99 | MyD88 | CD137/41BB | DAP10 |
| CD99 | MyD88 | CD137/41BB | DAP12 |
| CD99 | MyD88 | CD137/41BB | CD32 |
| CD99 | MyD88 | CD137/41BB | CD79a |
| CD99 | MyD88 | CD137/41BB | CD79b |
| CD99 | MyD88 | ICOS | CD8 |
| CD99 | MyD88 | ICOS | CD3ζ |
| CD99 | MyD88 | ICOS | CD3δ |
| CD99 | MyD88 | ICOS | CD3γ |
| CD99 | MyD88 | ICOS | CD3ε |
| CD99 | MyD88 | ICOS | FcγRI-γ |
| CD99 | MyD88 | ICOS | FcγRIII-γ |
| CD99 | MyD88 | ICOS | FcεRIβ |
| CD99 | MyD88 | ICOS | FcεRIγ |
| CD99 | MyD88 | ICOS | DAP10 |
| CD99 | MyD88 | ICOS | DAP12 |
| CD99 | MyD88 | ICOS | CD32 |
| CD99 | MyD88 | ICOS | CD79a |
| CD99 | MyD88 | ICOS | CD79b |
| CD99 | MyD88 | CD27 | CD8 |
| CD99 | MyD88 | CD27 | CD3ζ |
| CD99 | MyD88 | CD27 | CD3δ |
| CD99 | MyD88 | CD27 | CD3γ |
| CD99 | MyD88 | CD27 | CD3ε |
| CD99 | MyD88 | CD27 | FcγRI-γ |
| CD99 | MyD88 | CD27 | FcγRIII-γ |
| CD99 | MyD88 | CD27 | FcεRIβ |
| CD99 | MyD88 | CD27 | FcεRIγ |
| CD99 | MyD88 | CD27 | DAP10 |
| CD99 | MyD88 | CD27 | DAP12 |
| CD99 | MyD88 | CD27 | CD32 |
| CD99 | MyD88 | CD27 | CD79a |
| CD99 | MyD88 | CD27 | CD79b |
| CD99 | MyD88 | CD28δ | CD8 |
| CD99 | MyD88 | CD28δ | CD3ζ |
| CD99 | MyD88 | CD28δ | CD3δ |
| CD99 | MyD88 | CD28δ | CD3γ |
| CD99 | MyD88 | CD28δ | CD3ε |
| CD99 | MyD88 | CD28δ | FcγRI-γ |
| CD99 | MyD88 | CD28δ | FcγRIII-γ |
| CD99 | MyD88 | CD28δ | FcεRIβ |
| CD99 | MyD88 | CD28δ | FcεRIγ |
| CD99 | MyD88 | CD28δ | DAP10 |
| CD99 | MyD88 | CD28δ | DAP12 |
| CD99 | MyD88 | CD28δ | CD32 |
| CD99 | MyD88 | CD28δ | CD79a |
| CD99 | MyD88 | CD28δ | CD79b |
| CD99 | MyD88 | CD80 | CD8 |
| CD99 | MyD88 | CD80 | CD3ζ |
| CD99 | MyD88 | CD80 | CD3δ |
| CD99 | MyD88 | CD80 | CD3γ |
| CD99 | MyD88 | CD80 | CD3ε |
| CD99 | MyD88 | CD80 | FcγRI-γ |
| CD99 | MyD88 | CD80 | FcγRIII-γ |
| CD99 | MyD88 | CD80 | FcεRIβ |
| CD99 | MyD88 | CD80 | FcεRIγ |
| CD99 | MyD88 | CD80 | DAP10 |
| CD99 | MyD88 | CD80 | DAP12 |
| CD99 | MyD88 | CD80 | CD32 |
| CD99 | MyD88 | CD80 | CD79a |
| CD99 | MyD88 | CD80 | CD79b |
| CD99 | MyD88 | CD86 | CD8 |
| CD99 | MyD88 | CD86 | CD3ζ |
| CD99 | MyD88 | CD86 | CD3δ |
| CD99 | MyD88 | CD86 | CD3γ |
| CD99 | MyD88 | CD86 | CD3ε |
| CD99 | MyD88 | CD86 | FcγRI-γ |
| CD99 | MyD88 | CD86 | FcγRIII-γ |
| CD99 | MyD88 | CD86 | FcεRIβ |
| CD99 | MyD88 | CD86 | FcεRIγ |
| CD99 | MyD88 | CD86 | DAP10 |
| CD99 | MyD88 | CD86 | DAP12 |
| CD99 | MyD88 | CD86 | CD32 |
| CD99 | MyD88 | CD86 | CD79a |
| CD99 | MyD88 | CD86 | CD79b |
| CD99 | MyD88 | OX40 | CD8 |
| CD99 | MyD88 | OX40 | CD3ζ |
| CD99 | MyD88 | OX40 | CD3δ |
| CD99 | MyD88 | OX40 | CD3γ |
| CD99 | MyD88 | OX40 | CD3ε |
| CD99 | MyD88 | OX40 | FcγRI-γ |
| CD99 | MyD88 | OX40 | FcγRIII-γ |
| CD99 | MyD88 | OX40 | FcεRIβ |
| CD99 | MyD88 | OX40 | FcεRIγ |
| CD99 | MyD88 | OX40 | DAP10 |
| CD99 | MyD88 | OX40 | DAP12 |
| CD99 | MyD88 | OX40 | CD32 |
| CD99 | MyD88 | OX40 | CD79a |
| CD99 | MyD88 | OX40 | CD79b |
| CD99 | MyD88 | DAP10 | CD8 |
| CD99 | MyD88 | DAP10 | CD3ζ |
| CD99 | MyD88 | DAP10 | CD3δ |
| CD99 | MyD88 | DAP10 | CD3γ |
| CD99 | MyD88 | DAP10 | CD3ε |
| CD99 | MyD88 | DAP10 | FcγRI-γ |
| CD99 | MyD88 | DAP10 | FcγRIII-γ |
| CD99 | MyD88 | DAP10 | FcεRIβ |
| CD99 | MyD88 | DAP10 | FcεRIγ |
| CD99 | MyD88 | DAP10 | DAP10 |
| CD99 | MyD88 | DAP10 | DAP12 |
| CD99 | MyD88 | DAP10 | CD32 |
| CD99 | MyD88 | DAP10 | CD79a |
| CD99 | MyD88 | DAP10 | CD79b |
| CD99 | MyD88 | DAP12 | CD8 |
| CD99 | MyD88 | DAP12 | CD3ζ |
| CD99 | MyD88 | DAP12 | CD3δ |
| CD99 | MyD88 | DAP12 | CD3γ |
| CD99 | MyD88 | DAP12 | CD3ε |
| CD99 | MyD88 | DAP12 | FcγRI-γ |
| CD99 | MyD88 | DAP12 | FcγRIII-γ |
| CD99 | MyD88 | DAP12 | FcεRIβ |
| CD99 | MyD88 | DAP12 | FcεRIγ |
| CD99 | MyD88 | DAP12 | DAP10 |
| CD99 | MyD88 | DAP12 | DAP12 |
| CD99 | MyD88 | DAP12 | CD32 |
| CD99 | MyD88 | DAP12 | CD79a |
| CD99 | MyD88 | DAP12 | CD79b |
| CD99 | MyD88 | MyD88 | CD8 |
| CD99 | MyD88 | MyD88 | CD3ζ |
| CD99 | MyD88 | MyD88 | CD3δ |
| CD99 | MyD88 | MyD88 | CD3γ |
| CD99 | MyD88 | MyD88 | CD3ε |
| CD99 | MyD88 | MyD88 | FcγRI-γ |
| CD99 | MyD88 | MyD88 | FcγRIII-γ |
| CD99 | MyD88 | MyD88 | FcεRIβ |
| CD99 | MyD88 | MyD88 | FcεRIγ |
| CD99 | MyD88 | MyD88 | DAP10 |
| CD99 | MyD88 | MyD88 | DAP12 |
| CD99 | MyD88 | MyD88 | CD32 |
| CD99 | MyD88 | MyD88 | CD79a |
| CD99 | MyD88 | MyD88 | CD79b |
| CD99 | MyD88 | CD7 | CD8 |
| CD99 | MyD88 | CD7 | CD3ζ |
| CD99 | MyD88 | CD7 | CD3δ |
| CD99 | MyD88 | CD7 | CD3γ |
| CD99 | MyD88 | CD7 | CD3ε |
| CD99 | MyD88 | CD7 | FcγRI-γ |
| CD99 | MyD88 | CD7 | FcγRIII-γ |
| CD99 | MyD88 | CD7 | FcεRIβ |
| CD99 | MyD88 | CD7 | FcεRIγ |
| CD99 | MyD88 | CD7 | DAP10 |
| CD99 | MyD88 | CD7 | DAP12 |
| CD99 | MyD88 | CD7 | CD32 |
| CD99 | MyD88 | CD7 | CD79a |

TABLE 3-continued

Third Generation CARs

| ScFv | Co-stimulatory Signal | Co-stimulatory Signal | Signal Domain |
|---|---|---|---|
| CD99 | MyD88 | CD7 | CD79b |
| CD99 | MyD88 | BTNL3 | CD8 |
| CD99 | MyD88 | BTNL3 | CD3ζ |
| CD99 | MyD88 | BTNL3 | CD3δ |
| CD99 | MyD88 | BTNL3 | CD3γ |
| CD99 | MyD88 | BTNL3 | CD3ε |
| CD99 | MyD88 | BTNL3 | FcγRI-γ |
| CD99 | MyD88 | BTNL3 | FcγRIII-γ |
| CD99 | MyD88 | BTNL3 | FcεRIβ |
| CD99 | MyD88 | BTNL3 | FcεRIγ |
| CD99 | MyD88 | BTNL3 | DAP10 |
| CD99 | MyD88 | BTNL3 | DAP12 |
| CD99 | MyD88 | BTNL3 | CD32 |
| CD99 | MyD88 | BTNL3 | CD79a |
| CD99 | MyD88 | BTNL3 | CD79b |
| CD99 | MyD88 | NKG2D | CD8 |
| CD99 | MyD88 | NKG2D | CD3ζ |
| CD99 | MyD88 | NKG2D | CD3δ |
| CD99 | MyD88 | NKG2D | CD3γ |
| CD99 | MyD88 | NKG2D | CD3ε |
| CD99 | MyD88 | NKG2D | FcγRI-γ |
| CD99 | MyD88 | NKG2D | FcγRIII-γ |
| CD99 | MyD88 | NKG2D | FcεRIβ |
| CD99 | MyD88 | NKG2D | FcεRIγ |
| CD99 | MyD88 | NKG2D | DAP10 |
| CD99 | MyD88 | NKG2D | DAP12 |
| CD99 | MyD88 | NKG2D | CD32 |
| CD99 | MyD88 | NKG2D | CD79a |
| CD99 | MyD88 | NKG2D | CD79b |
| CD99 | CD7 | CD28 | CD8 |
| CD99 | CD7 | CD28 | CD3ζ |
| CD99 | CD7 | CD28 | CD3δ |
| CD99 | CD7 | CD28 | CD3γ |
| CD99 | CD7 | CD28 | CD3ε |
| CD99 | CD7 | CD28 | FcγRI-γ |
| CD99 | CD7 | CD28 | FcγRIII-γ |
| CD99 | CD7 | CD28 | FcεRIβ |
| CD99 | CD7 | CD28 | FcεRIγ |
| CD99 | CD7 | CD28 | DAP10 |
| CD99 | CD7 | CD28 | DAP12 |
| CD99 | CD7 | CD28 | CD32 |
| CD99 | CD7 | CD28 | CD79a |
| CD99 | CD7 | CD28 | CD79b |
| CD99 | CD7 | CD8 | CD8 |
| CD99 | CD7 | CD8 | CD3ζ |
| CD99 | CD7 | CD8 | CD3δ |
| CD99 | CD7 | CD8 | CD3γ |
| CD99 | CD7 | CD8 | CD3ε |
| CD99 | CD7 | CD8 | FcγRI-γ |
| CD99 | CD7 | CD8 | FcγRIII-γ |
| CD99 | CD7 | CD8 | FcεRIβ |
| CD99 | CD7 | CD8 | FcεRIγ |
| CD99 | CD7 | CD8 | DAP10 |
| CD99 | CD7 | CD8 | DAP12 |
| CD99 | CD7 | CD8 | CD32 |
| CD99 | CD7 | CD8 | CD79a |
| CD99 | CD7 | CD8 | CD79b |
| CD99 | CD7 | CD4 | CD8 |
| CD99 | CD7 | CD4 | CD3ζ |
| CD99 | CD7 | CD4 | CD3δ |
| CD99 | CD7 | CD4 | CD3γ |
| CD99 | CD7 | CD4 | CD3ε |
| CD99 | CD7 | CD4 | FcγRI-γ |
| CD99 | CD7 | CD4 | FcγRIII-γ |
| CD99 | CD7 | CD4 | FcεRIβ |
| CD99 | CD7 | CD4 | FcεRIγ |
| CD99 | CD7 | CD4 | DAP10 |
| CD99 | CD7 | CD4 | DAP12 |
| CD99 | CD7 | CD4 | CD32 |
| CD99 | CD7 | CD4 | CD79a |
| CD99 | CD7 | CD4 | CD79b |
| CD99 | CD7 | b2c | CD8 |
| CD99 | CD7 | b2c | CD3ζ |
| CD99 | CD7 | b2c | CD3δ |
| CD99 | CD7 | b2c | CD3γ |
| CD99 | CD7 | b2c | CD3ε |
| CD99 | CD7 | b2c | FcγRI-γ |
| CD99 | CD7 | b2c | FcγRIII-γ |
| CD99 | CD7 | b2c | FcεRIβ |
| CD99 | CD7 | b2c | DAP10 |
| CD99 | CD7 | b2c | DAP12 |
| CD99 | CD7 | b2c | CD32 |
| CD99 | CD7 | b2c | CD79a |
| CD99 | CD7 | b2c | CD79b |
| CD99 | CD7 | CD137/41BB | CD8 |
| CD99 | CD7 | CD137/41BB | CD3ζ |
| CD99 | CD7 | CD137/41BB | CD3δ |
| CD99 | CD7 | CD137/41BB | CD3γ |
| CD99 | CD7 | CD137/41BB | CD3ε |
| CD99 | CD7 | CD137/41BB | FcγRI-γ |
| CD99 | CD7 | CD137/41BB | FcγRIII-γ |
| CD99 | CD7 | CD137/41BB | FcεRIβ |
| CD99 | CD7 | CD137/41BB | FcεRIγ |
| CD99 | CD7 | CD137/41BB | DAP10 |
| CD99 | CD7 | CD137/41BB | DAP12 |
| CD99 | CD7 | CD137/41BB | CD32 |
| CD99 | CD7 | CD137/41BB | CD79a |
| CD99 | CD7 | CD137/41BB | CD79b |
| CD99 | CD7 | ICOS | CD8 |
| CD99 | CD7 | ICOS | CD3ζ |
| CD99 | CD7 | ICOS | CD3δ |
| CD99 | CD7 | ICOS | CD3γ |
| CD99 | CD7 | ICOS | CD3ε |
| CD99 | CD7 | ICOS | FcγRI-γ |
| CD99 | CD7 | ICOS | FcγRIII-γ |
| CD99 | CD7 | ICOS | FcεRIβ |
| CD99 | CD7 | ICOS | FcεRIγ |
| CD99 | CD7 | ICOS | DAP10 |
| CD99 | CD7 | ICOS | DAP12 |
| CD99 | CD7 | ICOS | CD32 |
| CD99 | CD7 | ICOS | CD79a |
| CD99 | CD7 | ICOS | CD79b |
| CD99 | CD7 | CD27 | CD8 |
| CD99 | CD7 | CD27 | CD3ζ |
| CD99 | CD7 | CD27 | CD3δ |
| CD99 | CD7 | CD27 | CD3γ |
| CD99 | CD7 | CD27 | CD3ε |
| CD99 | CD7 | CD27 | FcγRI-γ |
| CD99 | CD7 | CD27 | FcγRIII-γ |
| CD99 | CD7 | CD27 | FcεRIβ |
| CD99 | CD7 | CD27 | FcεRIγ |
| CD99 | CD7 | CD27 | DAP10 |
| CD99 | CD7 | CD27 | DAP12 |
| CD99 | CD7 | CD27 | CD32 |
| CD99 | CD7 | CD27 | CD79a |
| CD99 | CD7 | CD27 | CD79b |
| CD99 | CD7 | CD28δ | CD8 |
| CD99 | CD7 | CD28δ | CD3ζ |
| CD99 | CD7 | CD28δ | CD3δ |
| CD99 | CD7 | CD28δ | CD3γ |
| CD99 | CD7 | CD28δ | CD3ε |
| CD99 | CD7 | CD28δ | FcγRI-γ |
| CD99 | CD7 | CD28δ | FcγRIII-γ |
| CD99 | CD7 | CD28δ | FcεRIβ |
| CD99 | CD7 | CD28δ | FcεRIγ |
| CD99 | CD7 | CD28δ | DAP10 |
| CD99 | CD7 | CD28δ | DAP12 |
| CD99 | CD7 | CD28δ | CD32 |
| CD99 | CD7 | CD28δ | CD79a |
| CD99 | CD7 | CD28δ | CD79b |
| CD99 | CD7 | CD80 | CD8 |
| CD99 | CD7 | CD80 | CD3ζ |
| CD99 | CD7 | CD80 | CD3δ |
| CD99 | CD7 | CD80 | CD3γ |
| CD99 | CD7 | CD80 | CD3ε |
| CD99 | CD7 | CD80 | FcγRI-γ |
| CD99 | CD7 | CD80 | FcγRIII-γ |
| CD99 | CD7 | CD80 | FcεRIβ |
| CD99 | CD7 | CD80 | FcεRIγ |

TABLE 3-continued

Third Generation CARs

| ScFv | Co-stimulatory Signal | Co-stimulatory Signal | Signal Domain |
|---|---|---|---|
| CD99 | CD7 | CD80 | DAP10 |
| CD99 | CD7 | CD80 | DAP12 |
| CD99 | CD7 | CD80 | CD32 |
| CD99 | CD7 | CD80 | CD79a |
| CD99 | CD7 | CD80 | CD79b |
| CD99 | CD7 | CD86 | CD8 |
| CD99 | CD7 | CD86 | CD3ζ |
| CD99 | CD7 | CD86 | CD3δ |
| CD99 | CD7 | CD86 | CD3γ |
| CD99 | CD7 | CD86 | CD3ε |
| CD99 | CD7 | CD86 | FcγRI-γ |
| CD99 | CD7 | CD86 | FcγRIII-γ |
| CD99 | CD7 | CD86 | FcεRIβ |
| CD99 | CD7 | CD86 | FcεRIγ |
| CD99 | CD7 | CD86 | DAP10 |
| CD99 | CD7 | CD86 | DAP12 |
| CD99 | CD7 | CD86 | CD32 |
| CD99 | CD7 | CD86 | CD79a |
| CD99 | CD7 | CD86 | CD79b |
| CD99 | CD7 | OX40 | CD8 |
| CD99 | CD7 | OX40 | CD3ζ |
| CD99 | CD7 | OX40 | CD3δ |
| CD99 | CD7 | OX40 | CD3γ |
| CD99 | CD7 | OX40 | CD3ε |
| CD99 | CD7 | OX40 | FcγRI-γ |
| CD99 | CD7 | OX40 | FcγRIII-γ |
| CD99 | CD7 | OX40 | FcεRIβ |
| CD99 | CD7 | OX40 | FcεRIγ |
| CD99 | CD7 | OX40 | DAP10 |
| CD99 | CD7 | OX40 | DAP12 |
| CD99 | CD7 | OX40 | CD32 |
| CD99 | CD7 | OX40 | CD79a |
| CD99 | CD7 | OX40 | CD79b |
| CD99 | CD7 | DAP10 | CD8 |
| CD99 | CD7 | DAP10 | CD3ζ |
| CD99 | CD7 | DAP10 | CD3δ |
| CD99 | CD7 | DAP10 | CD3γ |
| CD99 | CD7 | DAP10 | CD3ε |
| CD99 | CD7 | DAP10 | FcγRI-γ |
| CD99 | CD7 | DAP10 | FcγRIII-γ |
| CD99 | CD7 | DAP10 | FcεRIβ |
| CD99 | CD7 | DAP10 | FcεRIγ |
| CD99 | CD7 | DAP10 | DAP10 |
| CD99 | CD7 | DAP10 | DAP12 |
| CD99 | CD7 | DAP10 | CD32 |
| CD99 | CD7 | DAP10 | CD79a |
| CD99 | CD7 | DAP10 | CD79b |
| CD99 | CD7 | DAP12 | CD8 |
| CD99 | CD7 | DAP12 | CD3ζ |
| CD99 | CD7 | DAP12 | CD3δ |
| CD99 | CD7 | DAP12 | CD3γ |
| CD99 | CD7 | DAP12 | CD3ε |
| CD99 | CD7 | DAP12 | FcγRI-γ |
| CD99 | CD7 | DAP12 | FcγRIII-γ |
| CD99 | CD7 | DAP12 | FcεRIβ |
| CD99 | CD7 | DAP12 | FcεRIγ |
| CD99 | CD7 | DAP12 | DAP10 |
| CD99 | CD7 | DAP12 | DAP12 |
| CD99 | CD7 | DAP12 | CD32 |
| CD99 | CD7 | DAP12 | CD79a |
| CD99 | CD7 | DAP12 | CD79b |
| CD99 | CD7 | MyD88 | CD8 |
| CD99 | CD7 | MyD88 | CD3ζ |
| CD99 | CD7 | MyD88 | CD3δ |
| CD99 | CD7 | MyD88 | CD3γ |
| CD99 | CD7 | MyD88 | CD3ε |
| CD99 | CD7 | MyD88 | FcγRI-γ |
| CD99 | CD7 | MyD88 | FcγRIII-γ |
| CD99 | CD7 | MyD88 | FcεRIβ |
| CD99 | CD7 | MyD88 | FcεRIγ |
| CD99 | CD7 | MyD88 | DAP10 |
| CD99 | CD7 | MyD88 | DAP12 |
| CD99 | CD7 | MyD88 | CD32 |
| CD99 | CD7 | MyD88 | CD79a |
| CD99 | CD7 | MyD88 | CD79b |
| CD99 | CD7 | CD7 | CD8 |
| CD99 | CD7 | CD7 | CD3ζ |
| CD99 | CD7 | CD7 | CD3δ |
| CD99 | CD7 | CD7 | CD3γ |
| CD99 | CD7 | CD7 | CD3ε |
| CD99 | CD7 | CD7 | FcγRI-γ |
| CD99 | CD7 | CD7 | FcγRIII-γ |
| CD99 | CD7 | CD7 | FcεRIβ |
| CD99 | CD7 | CD7 | FcεRIγ |
| CD99 | CD7 | CD7 | DAP10 |
| CD99 | CD7 | CD7 | DAP12 |
| CD99 | CD7 | CD7 | CD32 |
| CD99 | CD7 | CD7 | CD79a |
| CD99 | CD7 | CD7 | CD79b |
| CD99 | CD7 | BTNL3 | CD8 |
| CD99 | CD7 | BTNL3 | CD3ζ |
| CD99 | CD7 | BTNL3 | CD3δ |
| CD99 | CD7 | BTNL3 | CD3γ |
| CD99 | CD7 | BTNL3 | CD3ε |
| CD99 | CD7 | BTNL3 | FcγRI-γ |
| CD99 | CD7 | BTNL3 | FcγRIII-γ |
| CD99 | CD7 | BTNL3 | FcεRIβ |
| CD99 | CD7 | BTNL3 | FcεRIγ |
| CD99 | CD7 | BTNL3 | DAP10 |
| CD99 | CD7 | BTNL3 | DAP12 |
| CD99 | CD7 | BTNL3 | CD32 |
| CD99 | CD7 | BTNL3 | CD79a |
| CD99 | CD7 | BTNL3 | CD79b |
| CD99 | CD7 | NKG2D | CD8 |
| CD99 | CD7 | NKG2D | CD3ζ |
| CD99 | CD7 | NKG2D | CD3δ |
| CD99 | CD7 | NKG2D | CD3γ |
| CD99 | CD7 | NKG2D | CD3ε |
| CD99 | CD7 | NKG2D | FcγRI-γ |
| CD99 | CD7 | NKG2D | FcγRIII-γ |
| CD99 | CD7 | NKG2D | FcεRIβ |
| CD99 | CD7 | NKG2D | FcεRIγ |
| CD99 | CD7 | NKG2D | DAP10 |
| CD99 | CD7 | NKG2D | DAP12 |
| CD99 | CD7 | NKG2D | CD32 |
| CD99 | CD7 | NKG2D | CD79a |
| CD99 | CD7 | NKG2D | CD79b |
| CD99 | BTNL3 | CD28 | CD8 |
| CD99 | BTNL3 | CD28 | CD3ζ |
| CD99 | BTNL3 | CD28 | CD3δ |
| CD99 | BTNL3 | CD28 | CD3γ |
| CD99 | BTNL3 | CD28 | CD3ε |
| CD99 | BTNL3 | CD28 | FcγRI-γ |
| CD99 | BTNL3 | CD28 | FcγRIII-γ |
| CD99 | BTNL3 | CD28 | FcεRIβ |
| CD99 | BTNL3 | CD28 | FcεRIγ |
| CD99 | BTNL3 | CD28 | DAP10 |
| CD99 | BTNL3 | CD28 | DAP12 |
| CD99 | BTNL3 | CD28 | CD32 |
| CD99 | BTNL3 | CD28 | CD79a |
| CD99 | BTNL3 | CD28 | CD79b |
| CD99 | BTNL3 | CD8 | CD8 |
| CD99 | BTNL3 | CD8 | CD3ζ |
| CD99 | BTNL3 | CD8 | CD3δ |
| CD99 | BTNL3 | CD8 | CD3γ |
| CD99 | BTNL3 | CD8 | CD3ε |
| CD99 | BTNL3 | CD8 | FcγRI-γ |
| CD99 | BTNL3 | CD8 | FcγRIII-γ |
| CD99 | BTNL3 | CD8 | FcεRIβ |
| CD99 | BTNL3 | CD8 | FcεRIγ |
| CD99 | BTNL3 | CD8 | DAP10 |
| CD99 | BTNL3 | CD8 | DAP12 |
| CD99 | BTNL3 | CD8 | CD32 |
| CD99 | BTNL3 | CD8 | CD79a |
| CD99 | BTNL3 | CD8 | CD79b |
| CD99 | BTNL3 | CD4 | CD8 |
| CD99 | BTNL3 | CD4 | CD3ζ |
| CD99 | BTNL3 | CD4 | CD3δ |
| CD99 | BTNL3 | CD4 | CD3γ |
| CD99 | BTNL3 | CD4 | CD3ε |

TABLE 3-continued

Third Generation CARs

| ScFv | Co-stimulatory Signal | Co-stimulatory Signal | Signal Domain |
|---|---|---|---|
| CD99 | BTNL3 | CD4 | FcγRI-γ |
| CD99 | BTNL3 | CD4 | FcγRIII-γ |
| CD99 | BTNL3 | CD4 | FcεRIβ |
| CD99 | BTNL3 | CD4 | FcεRIγ |
| CD99 | BTNL3 | CD4 | DAP10 |
| CD99 | BTNL3 | CD4 | DAP12 |
| CD99 | BTNL3 | CD4 | CD32 |
| CD99 | BTNL3 | CD4 | CD79a |
| CD99 | BTNL3 | CD4 | CD79b |
| CD99 | BTNL3 | b2c | CD8 |
| CD99 | BTNL3 | b2c | CD3ζ |
| CD99 | BTNL3 | b2c | CD3δ |
| CD99 | BTNL3 | b2c | CD3γ |
| CD99 | BTNL3 | b2c | CD3ε |
| CD99 | BTNL3 | b2c | FcγRI-γ |
| CD99 | BTNL3 | b2c | FcγRIII-γ |
| CD99 | BTNL3 | b2c | FcεRIβ |
| CD99 | BTNL3 | b2c | FcεRIγ |
| CD99 | BTNL3 | b2c | DAP10 |
| CD99 | BTNL3 | b2c | DAP12 |
| CD99 | BTNL3 | b2c | CD32 |
| CD99 | BTNL3 | b2c | CD79a |
| CD99 | BTNL3 | b2c | CD79b |
| CD99 | BTNL3 | CD137/41BB | CD8 |
| CD99 | BTNL3 | CD137/41BB | CD3ζ |
| CD99 | BTNL3 | CD137/41BB | CD3δ |
| CD99 | BTNL3 | CD137/41BB | CD3γ |
| CD99 | BTNL3 | CD137/41BB | CD3ε |
| CD99 | BTNL3 | CD137/41BB | FcγRI-γ |
| CD99 | BTNL3 | CD137/41BB | FcγRIII-γ |
| CD99 | BTNL3 | CD137/41BB | FcεRIβ |
| CD99 | BTNL3 | CD137/41BB | FcεRIγ |
| CD99 | BTNL3 | CD137/41BB | DAP10 |
| CD99 | BTNL3 | CD137/41BB | DAP12 |
| CD99 | BTNL3 | CD137/41BB | CD32 |
| CD99 | BTNL3 | CD137/41BB | CD79a |
| CD99 | BTNL3 | CD137/41BB | CD79b |
| CD99 | BTNL3 | ICOS | CD8 |
| CD99 | BTNL3 | ICOS | CD3ζ |
| CD99 | BTNL3 | ICOS | CD3δ |
| CD99 | BTNL3 | ICOS | CD3γ |
| CD99 | BTNL3 | ICOS | CD3ε |
| CD99 | BTNL3 | ICOS | FcγRI-γ |
| CD99 | BTNL3 | ICOS | FcγRIII-γ |
| CD99 | BTNL3 | ICOS | FcεRIβ |
| CD99 | BTNL3 | ICOS | FcεRIγ |
| CD99 | BTNL3 | ICOS | DAP10 |
| CD99 | BTNL3 | ICOS | DAP12 |
| CD99 | BTNL3 | ICOS | CD32 |
| CD99 | BTNL3 | ICOS | CD79a |
| CD99 | BTNL3 | ICOS | CD79b |
| CD99 | BTNL3 | CD27 | CD8 |
| CD99 | BTNL3 | CD27 | CD3ζ |
| CD99 | BTNL3 | CD27 | CD3δ |
| CD99 | BTNL3 | CD27 | CD3γ |
| CD99 | BTNL3 | CD27 | CD3ε |
| CD99 | BTNL3 | CD27 | FcγRI-γ |
| CD99 | BTNL3 | CD27 | FcγRIII-γ |
| CD99 | BTNL3 | CD27 | FcεRIβ |
| CD99 | BTNL3 | CD27 | FcεRIγ |
| CD99 | BTNL3 | CD27 | DAP10 |
| CD99 | BTNL3 | CD27 | DAP12 |
| CD99 | BTNL3 | CD27 | CD32 |
| CD99 | BTNL3 | CD27 | CD79a |
| CD99 | BTNL3 | CD27 | CD79b |
| CD99 | BTNL3 | CD28δ | CD8 |
| CD99 | BTNL3 | CD28δ | CD3ζ |
| CD99 | BTNL3 | CD28δ | CD3δ |
| CD99 | BTNL3 | CD28δ | CD3γ |
| CD99 | BTNL3 | CD28δ | CD3ε |
| CD99 | BTNL3 | CD28δ | FcγRI-γ |
| CD99 | BTNL3 | CD28δ | FcγRIII-γ |
| CD99 | BTNL3 | CD28δ | FcεRIβ |
| CD99 | BTNL3 | CD28δ | FcεRIγ |
| CD99 | BTNL3 | CD28δ | DAP10 |
| CD99 | BTNL3 | CD28δ | DAP12 |
| CD99 | BTNL3 | CD28δ | CD32 |
| CD99 | BTNL3 | CD28δ | CD79a |
| CD99 | BTNL3 | CD28δ | CD79b |
| CD99 | BTNL3 | CD80 | CD8 |
| CD99 | BTNL3 | CD80 | CD3ζ |
| CD99 | BTNL3 | CD80 | CD3δ |
| CD99 | BTNL3 | CD80 | CD3γ |
| CD99 | BTNL3 | CD80 | CD3ε |
| CD99 | BTNL3 | CD80 | FcγRI-γ |
| CD99 | BTNL3 | CD80 | FcγRIII-γ |
| CD99 | BTNL3 | CD80 | FcεRIβ |
| CD99 | BTNL3 | CD80 | FcεRIγ |
| CD99 | BTNL3 | CD80 | DAP10 |
| CD99 | BTNL3 | CD80 | DAP12 |
| CD99 | BTNL3 | CD80 | CD32 |
| CD99 | BTNL3 | CD80 | CD79a |
| CD99 | BTNL3 | CD80 | CD79b |
| CD99 | BTNL3 | CD86 | CD8 |
| CD99 | BTNL3 | CD86 | CD3ζ |
| CD99 | BTNL3 | CD86 | CD3δ |
| CD99 | BTNL3 | CD86 | CD3γ |
| CD99 | BTNL3 | CD86 | CD3ε |
| CD99 | BTNL3 | CD86 | FcγRI-γ |
| CD99 | BTNL3 | CD86 | FcγRIII-γ |
| CD99 | BTNL3 | CD86 | FcεRIβ |
| CD99 | BTNL3 | CD86 | FcεRIγ |
| CD99 | BTNL3 | CD86 | DAP10 |
| CD99 | BTNL3 | CD86 | DAP12 |
| CD99 | BTNL3 | CD86 | CD32 |
| CD99 | BTNL3 | CD86 | CD79a |
| CD99 | BTNL3 | CD86 | CD79b |
| CD99 | BTNL3 | OX40 | CD8 |
| CD99 | BTNL3 | OX40 | CD3ζ |
| CD99 | BTNL3 | OX40 | CD3δ |
| CD99 | BTNL3 | OX40 | CD3γ |
| CD99 | BTNL3 | OX40 | CD3ε |
| CD99 | BTNL3 | OX40 | FcγRI-γ |
| CD99 | BTNL3 | OX40 | FcγRIII-γ |
| CD99 | BTNL3 | OX40 | FcεRIβ |
| CD99 | BTNL3 | OX40 | FcεRIγ |
| CD99 | BTNL3 | OX40 | DAP10 |
| CD99 | BTNL3 | OX40 | DAP12 |
| CD99 | BTNL3 | OX40 | CD32 |
| CD99 | BTNL3 | OX40 | CD79a |
| CD99 | BTNL3 | OX40 | CD79b |
| CD99 | BTNL3 | DAP10 | CD8 |
| CD99 | BTNL3 | DAP10 | CD3ζ |
| CD99 | BTNL3 | DAP10 | CD3δ |
| CD99 | BTNL3 | DAP10 | CD3γ |
| CD99 | BTNL3 | DAP10 | CD3ε |
| CD99 | BTNL3 | DAP10 | FcγRI-γ |
| CD99 | BTNL3 | DAP10 | FcγRIII-γ |
| CD99 | BTNL3 | DAP10 | FcεRIβ |
| CD99 | BTNL3 | DAP10 | FcεRIγ |
| CD99 | BTNL3 | DAP10 | DAP10 |
| CD99 | BTNL3 | DAP10 | DAP12 |
| CD99 | BTNL3 | DAP10 | CD32 |
| CD99 | BTNL3 | DAP10 | CD79a |
| CD99 | BTNL3 | DAP10 | CD79b |
| CD99 | BTNL3 | DAP12 | CD8 |
| CD99 | BTNL3 | DAP12 | CD3ζ |
| CD99 | BTNL3 | DAP12 | CD3δ |
| CD99 | BTNL3 | DAP12 | CD3γ |
| CD99 | BTNL3 | DAP12 | CD3ε |
| CD99 | BTNL3 | DAP12 | FcγRI-γ |
| CD99 | BTNL3 | DAP12 | FcγRIII-γ |
| CD99 | BTNL3 | DAP12 | FcεRIβ |
| CD99 | BTNL3 | DAP12 | FcεRIγ |
| CD99 | BTNL3 | DAP12 | DAP10 |
| CD99 | BTNL3 | DAP12 | DAP12 |
| CD99 | BTNL3 | DAP12 | CD32 |
| CD99 | BTNL3 | DAP12 | CD79a |
| CD99 | BTNL3 | DAP12 | CD79b |
| CD99 | BTNL3 | MyD88 | CD8 |

TABLE 3-continued

Third Generation CARs

| ScFv | Co-stimulatory Signal | Co-stimulatory Signal | Signal Domain |
|---|---|---|---|
| CD99 | BTNL3 | MyD88 | CD3ζ |
| CD99 | BTNL3 | MyD88 | CD3δ |
| CD99 | BTNL3 | MyD88 | CD3γ |
| CD99 | BTNL3 | MyD88 | CD3ε |
| CD99 | BTNL3 | MyD88 | FcγRI-γ |
| CD99 | BTNL3 | MyD88 | FcγRIII-γ |
| CD99 | BTNL3 | MyD88 | FcεRIβ |
| CD99 | BTNL3 | MyD88 | FcεRIγ |
| CD99 | BTNL3 | MyD88 | DAP10 |
| CD99 | BTNL3 | MyD88 | DAP12 |
| CD99 | BTNL3 | MyD88 | CD32 |
| CD99 | BTNL3 | MyD88 | CD79a |
| CD99 | BTNL3 | MyD88 | CD79b |
| CD99 | BTNL3 | CD7 | CD8 |
| CD99 | BTNL3 | CD7 | CD3ζ |
| CD99 | BTNL3 | CD7 | CD3δ |
| CD99 | BTNL3 | CD7 | CD3γ |
| CD99 | BTNL3 | CD7 | CD3ε |
| CD99 | BTNL3 | CD7 | FcγRI-γ |
| CD99 | BTNL3 | CD7 | FcγRIII-γ |
| CD99 | BTNL3 | CD7 | FcεRIβ |
| CD99 | BTNL3 | CD7 | FcεRIγ |
| CD99 | BTNL3 | CD7 | DAP10 |
| CD99 | BTNL3 | CD7 | DAP12 |
| CD99 | BTNL3 | CD7 | CD32 |
| CD99 | BTNL3 | CD7 | CD79a |
| CD99 | BTNL3 | CD7 | CD79b |
| CD99 | BTNL3 | BTNL3 | CD8 |
| CD99 | BTNL3 | BTNL3 | CD3ζ |
| CD99 | BTNL3 | BTNL3 | CD3δ |
| CD99 | BTNL3 | BTNL3 | CD3γ |
| CD99 | BTNL3 | BTNL3 | CD3ε |
| CD99 | BTNL3 | BTNL3 | FcγRI-γ |
| CD99 | BTNL3 | BTNL3 | FcγRIII-γ |
| CD99 | BTNL3 | BTNL3 | FcεRIβ |
| CD99 | BTNL3 | BTNL3 | FcεRIγ |
| CD99 | BTNL3 | BTNL3 | DAP10 |
| CD99 | BTNL3 | BTNL3 | DAP12 |
| CD99 | BTNL3 | BTNL3 | CD32 |
| CD99 | BTNL3 | BTNL3 | CD79a |
| CD99 | BTNL3 | BTNL3 | CD79b |
| CD99 | BTNL3 | NKG2D | CD8 |
| CD99 | BTNL3 | NKG2D | CD3ζ |
| CD99 | BTNL3 | NKG2D | CD3δ |
| CD99 | BTNL3 | NKG2D | CD3γ |
| CD99 | BTNL3 | NKG2D | CD3ε |
| CD99 | BTNL3 | NKG2D | FcγRI-γ |
| CD99 | BTNL3 | NKG2D | FcγRIII-γ |
| CD99 | BTNL3 | NKG2D | FcεRIβ |
| CD99 | BTNL3 | NKG2D | FcεRIγ |
| CD99 | BTNL3 | NKG2D | DAP10 |
| CD99 | BTNL3 | NKG2D | DAP12 |
| CD99 | BTNL3 | NKG2D | CD32 |
| CD99 | BTNL3 | NKG2D | CD79a |
| CD99 | BTNL3 | NKG2D | CD79b |
| CD99 | NKG2D | CD28 | CD8 |
| CD99 | NKG2D | CD28 | CD3ζ |
| CD99 | NKG2D | CD28 | CD3δ |
| CD99 | NKG2D | CD28 | CD3γ |
| CD99 | NKG2D | CD28 | CD3ε |
| CD99 | NKG2D | CD28 | FcγRI-γ |
| CD99 | NKG2D | CD28 | FcγRIII-γ |
| CD99 | NKG2D | CD28 | FcεRIβ |
| CD99 | NKG2D | CD28 | FcεRIγ |
| CD99 | NKG2D | CD28 | DAP10 |
| CD99 | NKG2D | CD28 | DAP12 |
| CD99 | NKG2D | CD28 | CD32 |
| CD99 | NKG2D | CD28 | CD79a |
| CD99 | NKG2D | CD28 | CD79b |
| CD99 | NKG2D | CD8 | CD8 |
| CD99 | NKG2D | CD8 | CD3ζ |
| CD99 | NKG2D | CD8 | CD3δ |
| CD99 | NKG2D | CD8 | CD3γ |
| CD99 | NKG2D | CD8 | CD3ε |
| CD99 | NKG2D | CD8 | FcγRI-γ |
| CD99 | NKG2D | CD8 | FcγRIII-γ |
| CD99 | NKG2D | CD8 | FcεRIβ |
| CD99 | NKG2D | CD8 | FcεRIγ |
| CD99 | NKG2D | CD8 | DAP10 |
| CD99 | NKG2D | CD8 | DAP12 |
| CD99 | NKG2D | CD8 | CD32 |
| CD99 | NKG2D | CD8 | CD79a |
| CD99 | NKG2D | CD8 | CD79b |
| CD99 | NKG2D | CD4 | CD8 |
| CD99 | NKG2D | CD4 | CD3ζ |
| CD99 | NKG2D | CD4 | CD3δ |
| CD99 | NKG2D | CD4 | CD3γ |
| CD99 | NKG2D | CD4 | CD3ε |
| CD99 | NKG2D | CD4 | FcγRI-γ |
| CD99 | NKG2D | CD4 | FcγRIII-γ |
| CD99 | NKG2D | CD4 | FcεRIβ |
| CD99 | NKG2D | CD4 | FcεRIγ |
| CD99 | NKG2D | CD4 | DAP10 |
| CD99 | NKG2D | CD4 | DAP12 |
| CD99 | NKG2D | CD4 | CD32 |
| CD99 | NKG2D | CD4 | CD79a |
| CD99 | NKG2D | CD4 | CD79b |
| CD99 | NKG2D | b2c | CD8 |
| CD99 | NKG2D | b2c | CD3ζ |
| CD99 | NKG2D | b2c | CD3δ |
| CD99 | NKG2D | b2c | CD3γ |
| CD99 | NKG2D | b2c | CD3ε |
| CD99 | NKG2D | b2c | FcγRI-γ |
| CD99 | NKG2D | b2c | FcγRIII-γ |
| CD99 | NKG2D | b2c | FcεRIβ |
| CD99 | NKG2D | b2c | FcεRIγ |
| CD99 | NKG2D | b2c | DAP10 |
| CD99 | NKG2D | b2c | DAP12 |
| CD99 | NKG2D | b2c | CD32 |
| CD99 | NKG2D | b2c | CD79a |
| CD99 | NKG2D | b2c | CD79b |
| CD99 | NKG2D | CD137/41BB | CD8 |
| CD99 | NKG2D | CD137/41BB | CD3ζ |
| CD99 | NKG2D | CD137/41BB | CD3δ |
| CD99 | NKG2D | CD137/41BB | CD3γ |
| CD99 | NKG2D | CD137/41BB | CD3ε |
| CD99 | NKG2D | CD137/41BB | FcγRI-γ |
| CD99 | NKG2D | CD137/41BB | FcγRIII-γ |
| CD99 | NKG2D | CD137/41BB | FcεRIβ |
| CD99 | NKG2D | CD137/41BB | FcεRIγ |
| CD99 | NKG2D | CD137/41BB | DAP10 |
| CD99 | NKG2D | CD137/41BB | DAP12 |
| CD99 | NKG2D | CD137/41BB | CD32 |
| CD99 | NKG2D | CD137/41BB | CD79a |
| CD99 | NKG2D | CD137/41BB | CD79b |
| CD99 | NKG2D | ICOS | CD8 |
| CD99 | NKG2D | ICOS | CD3ζ |
| CD99 | NKG2D | ICOS | CD3δ |
| CD99 | NKG2D | ICOS | CD3γ |
| CD99 | NKG2D | ICOS | CD3ε |
| CD99 | NKG2D | ICOS | FcγRI-γ |
| CD99 | NKG2D | ICOS | FcγRIII-γ |
| CD99 | NKG2D | ICOS | FcεRIβ |
| CD99 | NKG2D | ICOS | FcεRIγ |
| CD99 | NKG2D | ICOS | DAP10 |
| CD99 | NKG2D | ICOS | DAP12 |
| CD99 | NKG2D | ICOS | CD32 |
| CD99 | NKG2D | ICOS | CD79a |
| CD99 | NKG2D | ICOS | CD79b |
| CD99 | NKG2D | CD27 | CD8 |
| CD99 | NKG2D | CD27 | CD3ζ |
| CD99 | NKG2D | CD27 | CD3δ |
| CD99 | NKG2D | CD27 | CD3γ |
| CD99 | NKG2D | CD27 | CD3ε |
| CD99 | NKG2D | CD27 | FcγRI-γ |
| CD99 | NKG2D | CD27 | FcγRIII-γ |
| CD99 | NKG2D | CD27 | FcεRIβ |
| CD99 | NKG2D | CD27 | FcεRIγ |
| CD99 | NKG2D | CD27 | DAP10 |
| CD99 | NKG2D | CD27 | DAP12 |

TABLE 3-continued

Third Generation CARs

| ScFv | Co-stimulatory Signal | Co-stimulatory Signal | Signal Domain |
|---|---|---|---|
| CD99 | NKG2D | CD27 | CD32 |
| CD99 | NKG2D | CD27 | CD79a |
| CD99 | NKG2D | CD27 | CD79b |
| CD99 | NKG2D | CD28δ | CD8 |
| CD99 | NKG2D | CD28δ | CD3ζ |
| CD99 | NKG2D | CD28δ | CD3δ |
| CD99 | NKG2D | CD28δ | CD3γ |
| CD99 | NKG2D | CD28δ | CD3ε |
| CD99 | NKG2D | CD28δ | FcγRI-γ |
| CD99 | NKG2D | CD28δ | FcγRIII-γ |
| CD99 | NKG2D | CD28δ | FcεRIβ |
| CD99 | NKG2D | CD28δ | FcεRIγ |
| CD99 | NKG2D | CD28δ | DAP10 |
| CD99 | NKG2D | CD28δ | DAP12 |
| CD99 | NKG2D | CD28δ | CD32 |
| CD99 | NKG2D | CD28δ | CD79a |
| CD99 | NKG2D | CD28δ | CD79b |
| CD99 | NKG2D | CD80 | CD8 |
| CD99 | NKG2D | CD80 | CD3ζ |
| CD99 | NKG2D | CD80 | CD3δ |
| CD99 | NKG2D | CD80 | CD3γ |
| CD99 | NKG2D | CD80 | CD3ε |
| CD99 | NKG2D | CD80 | FcγRI-γ |
| CD99 | NKG2D | CD80 | FcγRIII-γ |
| CD99 | NKG2D | CD80 | FcεRIβ |
| CD99 | NKG2D | CD80 | FcεRIγ |
| CD99 | NKG2D | CD80 | DAP10 |
| CD99 | NKG2D | CD80 | DAP12 |
| CD99 | NKG2D | CD80 | CD32 |
| CD99 | NKG2D | CD80 | CD79a |
| CD99 | NKG2D | CD80 | CD79b |
| CD99 | NKG2D | CD86 | CD8 |
| CD99 | NKG2D | CD86 | CD3ζ |
| CD99 | NKG2D | CD86 | CD3δ |
| CD99 | NKG2D | CD86 | CD3γ |
| CD99 | NKG2D | CD86 | CD3ε |
| CD99 | NKG2D | CD86 | FcγRI-γ |
| CD99 | NKG2D | CD86 | FcγRIII-γ |
| CD99 | NKG2D | CD86 | FcεRIβ |
| CD99 | NKG2D | CD86 | FcεRIγ |
| CD99 | NKG2D | CD86 | DAP10 |
| CD99 | NKG2D | CD86 | DAP12 |
| CD99 | NKG2D | CD86 | CD32 |
| CD99 | NKG2D | CD86 | CD79a |
| CD99 | NKG2D | CD86 | CD79b |
| CD99 | NKG2D | OX40 | CD8 |
| CD99 | NKG2D | OX40 | CD3ζ |
| CD99 | NKG2D | OX40 | CD3δ |
| CD99 | NKG2D | OX40 | CD3γ |
| CD99 | NKG2D | OX40 | CD3ε |
| CD99 | NKG2D | OX40 | FcγRI-γ |
| CD99 | NKG2D | OX40 | FcγRIII-γ |
| CD99 | NKG2D | OX40 | FcεRIβ |
| CD99 | NKG2D | OX40 | FcεRIγ |
| CD99 | NKG2D | OX40 | DAP10 |
| CD99 | NKG2D | OX40 | DAP12 |
| CD99 | NKG2D | OX40 | CD32 |
| CD99 | NKG2D | OX40 | CD79a |
| CD99 | NKG2D | OX40 | CD79b |
| CD99 | NKG2D | DAP10 | CD8 |
| CD99 | NKG2D | DAP10 | CD3ζ |
| CD99 | NKG2D | DAP10 | CD3δ |
| CD99 | NKG2D | DAP10 | CD3γ |
| CD99 | NKG2D | DAP10 | CD3ε |
| CD99 | NKG2D | DAP10 | FcγRI-γ |
| CD99 | NKG2D | DAP10 | FcγRIII-γ |
| CD99 | NKG2D | DAP10 | FcεRIβ |
| CD99 | NKG2D | DAP10 | FcεRIγ |
| CD99 | NKG2D | DAP10 | DAP10 |
| CD99 | NKG2D | DAP10 | DAP12 |
| CD99 | NKG2D | DAP10 | CD32 |
| CD99 | NKG2D | DAP10 | CD79a |
| CD99 | NKG2D | DAP10 | CD79b |
| CD99 | NKG2D | DAP12 | CD8 |
| CD99 | NKG2D | DAP12 | CD3ζ |
| CD99 | NKG2D | DAP12 | CD3δ |
| CD99 | NKG2D | DAP12 | CD3γ |
| CD99 | NKG2D | DAP12 | CD3ε |
| CD99 | NKG2D | DAP12 | FcγRI-γ |
| CD99 | NKG2D | DAP12 | FcγRIII-γ |
| CD99 | NKG2D | DAP12 | FcεRIβ |
| CD99 | NKG2D | DAP12 | FcεRIγ |
| CD99 | NKG2D | DAP12 | DAP10 |
| CD99 | NKG2D | DAP12 | DAP12 |
| CD99 | NKG2D | DAP12 | CD32 |
| CD99 | NKG2D | DAP12 | CD79a |
| CD99 | NKG2D | DAP12 | CD79b |
| CD99 | NKG2D | MyD88 | CD8 |
| CD99 | NKG2D | MyD88 | CD3ζ |
| CD99 | NKG2D | MyD88 | CD3δ |
| CD99 | NKG2D | MyD88 | CD3γ |
| CD99 | NKG2D | MyD88 | CD3ε |
| CD99 | NKG2D | MyD88 | FcγRI-γ |
| CD99 | NKG2D | MyD88 | FcγRIII-γ |
| CD99 | NKG2D | MyD88 | FcεRIβ |
| CD99 | NKG2D | MyD88 | FcεRIγ |
| CD99 | NKG2D | MyD88 | DAP10 |
| CD99 | NKG2D | MyD88 | DAP12 |
| CD99 | NKG2D | MyD88 | CD32 |
| CD99 | NKG2D | MyD88 | CD79a |
| CD99 | NKG2D | MyD88 | CD79b |
| CD99 | NKG2D | CD7 | CD8 |
| CD99 | NKG2D | CD7 | CD3ζ |
| CD99 | NKG2D | CD7 | CD3δ |
| CD99 | NKG2D | CD7 | CD3γ |
| CD99 | NKG2D | CD7 | CD3ε |
| CD99 | NKG2D | CD7 | FcγRI-γ |
| CD99 | NKG2D | CD7 | FcγRIII-γ |
| CD99 | NKG2D | CD7 | FcεRIβ |
| CD99 | NKG2D | CD7 | FcεRIγ |
| CD99 | NKG2D | CD7 | DAP10 |
| CD99 | NKG2D | CD7 | DAP12 |
| CD99 | NKG2D | CD7 | CD32 |
| CD99 | NKG2D | CD7 | CD79a |
| CD99 | NKG2D | CD7 | CD79b |
| CD99 | NKG2D | BTNL3 | CD8 |
| CD99 | NKG2D | BTNL3 | CD3ζ |
| CD99 | NKG2D | BTNL3 | CD3δ |
| CD99 | NKG2D | BTNL3 | CD3γ |
| CD99 | NKG2D | BTNL3 | CD3ε |
| CD99 | NKG2D | BTNL3 | FcγRI-γ |
| CD99 | NKG2D | BTNL3 | FcγRIII-γ |
| CD99 | NKG2D | BTNL3 | FcεRIβ |
| CD99 | NKG2D | BTNL3 | FcεRIγ |
| CD99 | NKG2D | BTNL3 | DAP10 |
| CD99 | NKG2D | BTNL3 | DAP12 |
| CD99 | NKG2D | BTNL3 | CD32 |
| CD99 | NKG2D | BTNL3 | CD79a |
| CD99 | NKG2D | BTNL3 | CD79b |
| CD99 | NKG2D | NKG2D | CD8 |
| CD99 | NKG2D | NKG2D | CD3ζ |
| CD99 | NKG2D | NKG2D | CD3δ |
| CD99 | NKG2D | NKG2D | CD3γ |
| CD99 | NKG2D | NKG2D | CD3ε |
| CD99 | NKG2D | NKG2D | FcγRI-γ |
| CD99 | NKG2D | NKG2D | FcγRIII-γ |
| CD99 | NKG2D | NKG2D | FcεRIβ |
| CD99 | NKG2D | NKG2D | FcεRIγ |
| CD99 | NKG2D | NKG2D | DAP10 |
| CD99 | NKG2D | NKG2D | DAP12 |
| CD99 | NKG2D | NKG2D | CD32 |
| CD99 | NKG2D | NKG2D | CD79a |
| CD99 | NKG2D | NKG2D | CD79b |

TABLE 4

CARs lacking Co-Simulatory Signal (for dual CAR approach)

| ScFv | Co-stimulatory Signal | Signal Domain |
|---|---|---|
| CD99 | none | CD8 |
| CD99 | none | CD3ζ |
| CD99 | none | CD3δ |
| CD99 | none | CD3γ |
| CD99 | none | CD3ε |
| CD99 | none | FcγRI-γ |
| CD99 | none | FcγRIII-γ |
| CD99 | none | FcεRIβ |
| CD99 | none | FcεRIγ |
| CD99 | none | DAP10 |
| CD99 | none | DAP12 |
| CD99 | none | CD32 |
| CD99 | none | CD79a |
| CD99 | none | CD8 |
| CD99 | none | CD3ζ |
| CD99 | none | CD3δ |
| CD99 | none | CD3γ |
| CD99 | none | CD3ε |
| CD99 | none | FcγRI-γ |

TABLE 5

CARs lacking Signal Domain (for dual CAR approach)

| ScFv | Co-stimulatory Signal | Signal Domain |
|---|---|---|
| CD99 | CD28 | none |
| CD99 | CD8 | none |
| CD99 | CD4 | none |
| CD99 | b2c | none |
| CD99 | CD137/41BB | none |
| CD99 | ICOS | none |
| CD99 | CD27 | none |
| CD99 | CD28δ | none |
| CD99 | CD80 | none |
| CD99 | CD86 | none |
| CD99 | OX40 | none |
| CD99 | DAP10 | none |
| CD99 | MyD88 | none |
| CD99 | CD7 | none |
| CD99 | DAP12 | none |
| CD99 | MyD88 | none |
| CD99 | CD7 | none |
| CD99 | BTNL3 | none |
| CD99 | NKG2D | none |

TABLE 6

Third Generation CARs lacking Signal Domain (for dual CAR approach)

| ScFv | Co-stimulatory Signal | Co-stimulatory Signal | Signal Domain |
|---|---|---|---|
| CD99 | CD28 | CD28 | none |
| CD99 | CD28 | CD8 | none |
| CD99 | CD28 | CD4 | none |
| CD99 | CD28 | b2c | none |
| CD99 | CD28 | CD137/41BB | none |
| CD99 | CD28 | ICOS | none |
| CD99 | CD28 | CD27 | none |
| CD99 | CD28 | CD28δ | none |
| CD99 | CD28 | CD80 | none |
| CD99 | CD28 | CD86 | none |
| CD99 | CD28 | OX40 | none |
| CD99 | CD28 | DAP10 | none |
| CD99 | CD28 | MyD88 | none |
| CD99 | CD28 | CD7 | none |
| CD99 | CD28 | DAP12 | none |
| CD99 | CD28 | MyD88 | none |
| CD99 | CD28 | CD7 | none |
| CD99 | CD8 | CD28 | none |
| CD99 | CD8 | CD8 | none |
| CD99 | CD8 | CD4 | none |
| CD99 | CD8 | b2c | none |
| CD99 | CD8 | CD137/41BB | none |
| CD99 | CD8 | ICOS | none |
| CD99 | CD8 | CD27 | none |
| CD99 | CD8 | CD28δ | none |
| CD99 | CD8 | CD80 | none |
| CD99 | CD8 | CD86 | none |
| CD99 | CD8 | OX40 | none |
| CD99 | CD8 | DAP10 | none |
| CD99 | CD8 | MyD88 | none |
| CD99 | CD8 | CD7 | none |
| CD99 | CD8 | DAP12 | none |
| CD99 | CD8 | MyD88 | none |
| CD99 | CD8 | CD7 | none |
| CD99 | CD4 | CD28 | none |
| CD99 | CD4 | CD8 | none |
| CD99 | CD4 | CD4 | none |
| CD99 | CD4 | b2c | none |
| CD99 | CD4 | CD137/41BB | none |
| CD99 | CD4 | ICOS | none |
| CD99 | CD4 | CD27 | none |
| CD99 | CD4 | CD28δ | none |
| CD99 | CD4 | CD80 | none |
| CD99 | CD4 | CD86 | none |
| CD99 | CD4 | OX40 | none |
| CD99 | CD4 | DAP10 | none |
| CD99 | CD4 | MyD88 | none |
| CD99 | CD4 | CD7 | none |
| CD99 | CD4 | DAP12 | none |
| CD99 | CD4 | MyD88 | none |
| CD99 | CD4 | CD7 | none |
| CD99 | b2c | CD28 | none |
| CD99 | b2c | CD8 | none |
| CD99 | b2c | CD4 | none |
| CD99 | b2c | b2c | none |
| CD99 | b2c | CD137/41BB | none |
| CD99 | b2c | ICOS | none |
| CD99 | b2c | CD27 | none |
| CD99 | b2c | CD28δ | none |
| CD99 | b2c | CD80 | none |
| CD99 | b2c | CD86 | none |
| CD99 | b2c | OX40 | none |
| CD99 | b2c | DAP10 | none |
| CD99 | b2c | MyD88 | none |
| CD99 | b2c | CD7 | none |
| CD99 | b2c | DAP12 | none |
| CD99 | b2c | MyD88 | none |
| CD99 | b2c | CD7 | none |
| CD99 | CD137/41BB | CD28 | none |
| CD99 | CD137/41BB | CD8 | none |
| CD99 | CD137/41BB | CD4 | none |
| CD99 | CD137/41BB | b2c | none |
| CD99 | CD137/41BB | CD137/41BB | none |
| CD99 | CD137/41BB | ICOS | none |
| CD99 | CD137/41BB | CD27 | none |
| CD99 | CD137/41BB | CD28δ | none |
| CD99 | CD137/41BB | CD80 | none |
| CD99 | CD137/41BB | CD86 | none |
| CD99 | CD137/41BB | OX40 | none |
| CD99 | CD137/41BB | DAP10 | none |
| CD99 | CD137/41BB | MyD88 | none |
| CD99 | CD137/41BB | CD7 | none |
| CD99 | CD137/41BB | DAP12 | none |
| CD99 | CD137/41BB | MyD88 | none |
| CD99 | CD137/41BB | CD7 | none |
| CD99 | ICOS | CD28 | none |
| CD99 | ICOS | CD8 | none |
| CD99 | ICOS | CD4 | none |
| CD99 | ICOS | b2c | none |

TABLE 6-continued

Third Generation CARs lacking Signal Domain (for dual CAR approach)

| ScFv | Co-stimulatory Signal | Co-stimulatory Signal | Signal Domain |
|---|---|---|---|
| CD99 | ICOS | CD137/41BB | none |
| CD99 | ICOS | ICOS | none |
| CD99 | ICOS | CD27 | none |
| CD99 | ICOS | CD28δ | none |
| CD99 | ICOS | CD80 | none |
| CD99 | ICOS | CD86 | none |
| CD99 | ICOS | OX40 | none |
| CD99 | ICOS | DAP10 | none |
| CD99 | ICOS | MyD88 | none |
| CD99 | ICOS | CD7 | none |
| CD99 | ICOS | DAP12 | none |
| CD99 | ICOS | MyD88 | none |
| CD99 | ICOS | CD7 | none |
| CD99 | ICOS | CD28 | none |
| CD99 | ICOS | CD8 | none |
| CD99 | ICOS | CD4 | none |
| CD99 | ICOS | b2c | none |
| CD99 | ICOS | CD137/41BB | none |
| CD99 | ICOS | ICOS | none |
| CD99 | ICOS | CD27 | none |
| CD99 | ICOS | CD28δ | none |
| CD99 | ICOS | CD80 | none |
| CD99 | ICOS | CD86 | none |
| CD99 | ICOS | OX40 | none |
| CD99 | ICOS | DAP10 | none |
| CD99 | ICOS | MyD88 | none |
| CD99 | ICOS | CD7 | none |
| CD99 | ICOS | DAP12 | none |
| CD99 | ICOS | MyD88 | none |
| CD99 | ICOS | CD7 | none |
| CD99 | CD27 | CD28 | none |
| CD99 | CD27 | CD8 | none |
| CD99 | CD27 | CD4 | none |
| CD99 | CD27 | b2c | none |
| CD99 | CD27 | CD137/41BB | none |
| CD99 | CD27 | ICOS | none |
| CD99 | CD27 | CD27 | none |
| CD99 | CD27 | CD28δ | none |
| CD99 | CD27 | CD80 | none |
| CD99 | CD27 | CD86 | none |
| CD99 | CD27 | OX40 | none |
| CD99 | CD27 | DAP10 | none |
| CD99 | CD27 | MyD88 | none |
| CD99 | CD27 | CD7 | none |
| CD99 | CD27 | DAP12 | none |
| CD99 | CD27 | MyD88 | none |
| CD99 | CD27 | CD7 | none |
| CD99 | CD28δ | CD28 | none |
| CD99 | CD28δ | CD8 | none |
| CD99 | CD28δ | CD4 | none |
| CD99 | CD28δ | b2c | none |
| CD99 | CD28δ | CD137/41BB | none |
| CD99 | CD28δ | ICOS | none |
| CD99 | CD28δ | CD27 | none |
| CD99 | CD28δ | CD28δ | none |
| CD99 | CD28δ | CD80 | none |
| CD99 | CD28δ | CD86 | none |
| CD99 | CD28δ | OX40 | none |
| CD99 | CD28δ | DAP10 | none |
| CD99 | CD28δ | MyD88 | none |
| CD99 | CD28δ | CD7 | none |
| CD99 | CD28δ | DAP12 | none |
| CD99 | CD28δ | MyD88 | none |
| CD99 | CD28δ | CD7 | none |
| CD99 | CD80 | CD28 | none |
| CD99 | CD80 | CD8 | none |
| CD99 | CD80 | CD4 | none |
| CD99 | CD80 | b2c | none |
| CD99 | CD80 | CD137/41BB | none |
| CD99 | CD80 | ICOS | none |
| CD99 | CD80 | CD27 | none |
| CD99 | CD80 | CD28δ | none |
| CD99 | CD80 | CD80 | none |
| CD99 | CD80 | CD86 | none |
| CD99 | CD80 | OX40 | none |
| CD99 | CD80 | DAP10 | none |
| CD99 | CD80 | MyD88 | none |
| CD99 | CD80 | CD7 | none |
| CD99 | CD80 | DAP12 | none |
| CD99 | CD80 | MyD88 | none |
| CD99 | CD80 | CD7 | none |
| CD99 | CD86 | CD28 | none |
| CD99 | CD86 | CD8 | none |
| CD99 | CD86 | CD4 | none |
| CD99 | CD86 | b2c | none |
| CD99 | CD86 | CD137/41BB | none |
| CD99 | CD86 | ICOS | none |
| CD99 | CD86 | CD27 | none |
| CD99 | CD86 | CD28δ | none |
| CD99 | CD86 | CD80 | none |
| CD99 | CD86 | CD86 | none |
| CD99 | CD86 | OX40 | none |
| CD99 | CD86 | DAP10 | none |
| CD99 | CD86 | MyD88 | none |
| CD99 | CD86 | CD7 | none |
| CD99 | CD86 | DAP12 | none |
| CD99 | CD86 | MyD88 | none |
| CD99 | CD86 | CD7 | none |
| CD99 | OX40 | CD28 | none |
| CD99 | OX40 | CD8 | none |
| CD99 | OX40 | CD4 | none |
| CD99 | OX40 | b2c | none |
| CD99 | OX40 | CD137/41BB | none |
| CD99 | OX40 | ICOS | none |
| CD99 | OX40 | CD27 | none |
| CD99 | OX40 | CD28δ | none |
| CD99 | OX40 | CD80 | none |
| CD99 | OX40 | CD86 | none |
| CD99 | OX40 | OX40 | none |
| CD99 | OX40 | DAP10 | none |
| CD99 | OX40 | MyD88 | none |
| CD99 | OX40 | CD7 | none |
| CD99 | OX40 | DAP12 | none |
| CD99 | OX40 | MyD88 | none |
| CD99 | OX40 | CD7 | none |
| CD99 | DAP10 | CD28 | none |
| CD99 | DAP10 | CD8 | none |
| CD99 | DAP10 | CD4 | none |
| CD99 | DAP10 | b2c | none |
| CD99 | DAP10 | CD137/41BB | none |
| CD99 | DAP10 | ICOS | none |
| CD99 | DAP10 | CD27 | none |
| CD99 | DAP10 | CD28δ | none |
| CD99 | DAP10 | CD80 | none |
| CD99 | DAP10 | CD86 | none |
| CD99 | DAP10 | OX40 | none |
| CD99 | DAP10 | DAP10 | none |
| CD99 | DAP10 | MyD88 | none |
| CD99 | DAP10 | CD7 | none |
| CD99 | DAP10 | DAP12 | none |
| CD99 | DAP10 | MyD88 | none |
| CD99 | DAP10 | CD7 | none |
| CD99 | DAP12 | CD28 | none |
| CD99 | DAP12 | CD8 | none |
| CD99 | DAP12 | CD4 | none |
| CD99 | DAP12 | b2c | none |
| CD99 | DAP12 | CD137/41BB | none |
| CD99 | DAP12 | ICOS | none |
| CD99 | DAP12 | CD27 | none |
| CD99 | DAP12 | CD28δ | none |
| CD99 | DAP12 | CD80 | none |
| CD99 | DAP12 | CD86 | none |
| CD99 | DAP12 | OX40 | none |
| CD99 | DAP12 | DAP10 | none |
| CD99 | DAP12 | MyD88 | none |
| CD99 | DAP12 | CD7 | none |
| CD99 | DAP12 | DAP12 | none |
| CD99 | DAP12 | MyD88 | none |

TABLE 6-continued

Third Generation CARs lacking Signal Domain (for dual CAR approach)

| ScFv | Co-stimulatory Signal | Co-stimulatory Signal | Signal Domain |
|---|---|---|---|
| CD99 | DAP12 | CD7 | none |
| CD99 | MyD88 | CD28 | none |
| CD99 | MyD88 | CD8 | none |
| CD99 | MyD88 | CD4 | none |
| CD99 | MyD88 | b2c | none |
| CD99 | MyD88 | CD137/41BB | none |
| CD99 | MyD88 | ICOS | none |
| CD99 | MyD88 | CD27 | none |
| CD99 | MyD88 | CD28δ | none |
| CD99 | MyD88 | CD80 | none |
| CD99 | MyD88 | CD86 | none |
| CD99 | MyD88 | OX40 | none |
| CD99 | MyD88 | DAP10 | none |
| CD99 | MyD88 | MyD88 | none |
| CD99 | MyD88 | CD7 | none |
| CD99 | MyD88 | DAP12 | none |
| CD99 | MyD88 | MyD88 | none |
| CD99 | MyD88 | CD7 | none |
| CD99 | CD7 | CD28 | none |
| CD99 | CD7 | CD8 | none |
| CD99 | CD7 | CD4 | none |
| CD99 | CD7 | b2c | none |
| CD99 | CD7 | CD137/41BB | none |
| CD99 | CD7 | ICOS | none |
| CD99 | CD7 | CD27 | none |
| CD99 | CD7 | CD28δ | none |
| CD99 | CD7 | CD80 | none |
| CD99 | CD7 | CD86 | none |
| CD99 | CD7 | OX40 | none |
| CD99 | CD7 | DAP10 | none |
| CD99 | CD7 | MyD88 | none |
| CD99 | CD7 | CD7 | none |
| CD99 | CD7 | DAP12 | none |
| CD99 | CD7 | MyD88 | none |
| CD99 | CD7 | CD7 | none |
| CD99 | BTNL3 | CD28 | none |
| CD99 | BTNL3 | CD8 | none |
| CD99 | BTNL3 | CD4 | none |
| CD99 | BTNL3 | b2c | none |
| CD99 | BTNL3 | CD137/41BB | none |
| CD99 | BTNL3 | ICOS | none |
| CD99 | BTNL3 | CD27 | none |
| CD99 | BTNL3 | CD28δ | none |
| CD99 | BTNL3 | CD80 | none |
| CD99 | BTNL3 | CD86 | none |
| CD99 | BTNL3 | OX40 | none |
| CD99 | BTNL3 | DAP10 | none |
| CD99 | BTNL3 | MyD88 | none |
| CD99 | BTNL3 | CD7 | none |
| CD99 | BTNL3 | DAP12 | none |
| CD99 | BTNL3 | MyD88 | none |
| CD99 | BTNL3 | CD7 | none |
| CD99 | NKG2D | CD28 | none |
| CD99 | NKG2D | CD8 | none |
| CD99 | NKG2D | CD4 | none |
| CD99 | NKG2D | b2c | none |
| CD99 | NKG2D | CD137/41BB | none |
| CD99 | NKG2D | ICOS | none |
| CD99 | NKG2D | CD27 | none |
| CD99 | NKG2D | CD28δ | none |
| CD99 | NKG2D | CD80 | none |
| CD99 | NKG2D | CD86 | none |
| CD99 | NKG2D | OX40 | none |
| CD99 | NKG2D | DAP10 | none |
| CD99 | NKG2D | MyD88 | none |
| CD99 | NKG2D | CD7 | none |
| CD99 | NKG2D | DAP12 | none |
| CD99 | NKG2D | MyD88 | none |
| CD99 | NKG2D | CD7 | none |

In some embodiments, the anti-CD99 binding agent is single chain variable fragment (scFv) antibody. The affinity/specificity of an anti-CD99 scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3).

In some embodiments, the anti-CD99 binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Also disclosed are bi-specific CARs that target CD99 and at least one additional tumor antigen. Also disclosed are CARs designed to work only in conjunction with another CAR that binds a different antigen, such as a tumor antigen. For example, in these embodiments, the endodomain of the disclosed CAR can contain only an signaling domain (SD) or a co-stimulatory signaling region (CSR), but not both. The second CAR (or endogenous T-cell) provides the missing signal if it is activated. For example, if the disclosed CAR contains an SD but not a CSR, then the immune effector cell containing this CAR is only activated if another CAR (or T-cell) containing a CSR binds its respective antigen. Likewise, if the disclosed CAR contains a CSR but not a SD, then the immune effector cell containing this CAR is only activated if another CAR (or T-cell) containing an SD binds its respective antigen.

Tumor antigens are proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated. Tumor antigens are well known in the art and include, for example, a glioma-associated antigen, carcinoembryonic antigen (CEA), EGFRvIII, IL-IIRa, IL-13Ra, EGFR, FAP, B7H3, Kit, CA LX, CS-1, MUC1, BCMA, bcr-abl, HER2, β-human chorionic gonadotropin, alphafetoprotein (AFP), ALK, CD19, CD123, cyclin BI, lectin-reactive AFP, Fos-related antigen 1, ADRB3, thyroglobulin, EphA2, RAGE-1, RUI, RU2, SSX2, AKAP-4, LCK, OY-TESI, PAX5, SART3, CLL-1, fucosyl GM1, GloboH, MN-CA IX, EPCAM, EVT6-AML, TGS5, human telomerase reverse transcriptase, plysialic acid, PLAC1, RUI, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LAGE-la, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFR-beta, survivin and telomerase, legumain, HPV E6,E7, sperm protein 17, SSEA-4, tyrosinase, TARP, WT1, prostate-carcinoma tumor antigen- 1 (PCTA-1), ML-IAP, MAGE, MAGE-A1,MAD-CT-1, MAD-CT-2, MelanA/MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, TIM3, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRC5D, GPR20, CXORF61, folate receptor (FRa), folate receptor beta, ROR1, FIt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, CD123, CD19, TIM3, BCMA, GD2, CLL-1, CA-IX, MUCI, HER2, and any combination thereof.

Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, pl85 erbB2, pl80 erbB-3, c-met, nm- 23H1, PSA, CA 19-9, CA 72-4, CAM 17.1, NuMa, K-ras, beta-Catenin, CDK4, Mum-1, p 15, p 16, 43-9F, 5T4, 791 Tgp72, alpha-fetoprotein, beta-HCG, BCA225, BTAA, CA 125, CA 15-3CA 27.29 BCAA, CA 195, CA 242, CA-50, CAM43, CD68P1, CO-029, FGF-5, G250, Ga733/EpCAM, HTgp-175, M344, MA-50, MG7-Ag, MOV18, NB/70K, NY-CO-1, RCASI, SDCCAG1 6, TA-90/Mac-2 binding proteincyclophilm C-associated protein, TAAL6, TAG72, TLP, TPS, GPC3, MUC16, LMP1, EBMA-1, BARF-1, CS1, CD319, HER1, B7H6, L1CAM, IL6, and MET.

Nucleic Acids and Vectors

Also disclosed are polynucleotides and polynucleotide vectors encoding the disclosed CD99-specific CARs that allow expression of the CD99-specific CARs in the disclosed immune effector cells.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1a (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

Also disclosed are immune effector cells that are engineered to express the disclosed CARs (also referred to herein as "CAR-T cells." These cells are preferably obtained from the subject to be treated (i.e. are autologous). However, in some embodiments, immune effector cell lines or donor effector cells (allogeneic) are used.

Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dentritic cells, mast cells, neutrophils, basophils, eosinophils, or any combinations thereof. For example, the immune effector cells can comprise T lymphocytes.

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate a different type of immune response.

Cytotoxic T cells (Tc cells, or CTLs) destroy virally infected cells and tumor cells, and are also implicated in transplant rejection. These cells are also known as CD8+ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections.

Memory cells may be either CD4+ or CD8+. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of CD4+$T_{reg}$ cells have been described— naturally occurring $T_{reg}$ cells and adaptive $T_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4+ cells. In other embodiments, the T cells are enriched for one or more subsets based on cell surface expression. For example, in some cases, the T comprise are cytotoxic CD8+T lymphocytes. In some embodiments, the T cells comprise γō T cells, which possess a distinct T-cell receptor (TCR) having one γ chain and one ō chain instead of α and p chains.

Natural-killer (NK) cells are CD56+CD3- large granular lymphocytes that can kill virally infected and transformed cells, and constitute a critical cellular subset of the innate immune system (Godfrey J, et al. Leuk Lymphoma 2012 53:1666-1676). Unlike cytotoxic CD8+ T lymphocytes, NK cells launch cytotoxicity against tumor cells without the requirement for prior sensitization, and can also eradicate MHC-1-negative cells (Narni-Mancinelli E, et al. Int Immunol 2011 23:427-431). NK cells are safer effector cells, as they may avoid the potentially lethal complications of cytokine storms (Morgan RA, et al. Mol Ther 2010 18:843-851), tumor lysis syndrome (Porter DL, et al. N Engl J Med 2011 365:725-733), and on-target, off-tumor effects. Although NK cells have a well-known role as killers of cancer cells, and NK cell impairment has been extensively documented as crucial for progression of MM (Godfrey J, et al. Leuk Lymphoma 2012 53:1666-1676; Fauriat C, et al. Leukemia 2006 20:732-733), the means by which one might enhance NK cell-mediated anti-MM activity has been largely unexplored prior to the disclosed CARs.

Epstein-Barr virus (EBV)-induced lymphoproliferative diseases (EBV-LPDs) are a significant cause of morbidity and mortality for recipients of allogeneic hematopoietic cell transplantation (HCT), particularly in those who have received certain T-cell reactive Abs to prevent or treat GVHD. Prophylaxis and treatment by the adoptive transfer of EBV-specific T cells and the subsequent long-term restoration of immunity against EBV-associated lymphoproliferation have provided positive outcomes in the management of this uniformly fatal complication of bone marrow transfer. Therefore, in some embodiments, the disclosed immune effector cells are allogeneic or autologous EBV-specific cytotoxic T lymphocytes (CTLs). For example, this can involve isolating PBMCs from of an autologous or allogenic donor and enriching them for T cells by depletion of monocytes and NK cells. For example, the donor can be an EBV-seropositive donor. These T cells can then be stimulated with autologous EBV-seropostive or transformed lymphocytes. EBV antigens include latent membrane protein (LMP) and EBV nuclear antigen (EBNA) proteins, such as LMP-1, LMP-2A, and LMP-2B and EBNA-1, EBNA-2, EBNA-3A, EBNA-3B, EBNA-3C and EBNA-LP. These methods are described, for example, in Barker et al., Blood 2010 116(23):5045-49; Doubrovina, et al., Blood 2012 119(11):2644-56; Koehne, et al. Blood 2002 99(5):1730-40; and Smith et al. Cancer Res 2012 72(5):1116-25, which are incorporated by reference for these teachings.

Therapeutic Methods

Immune effector cells expressing the disclosed CARs can elicit an anti-tumor immune response against CD99-expressing cancer cells. The anti-tumor immune response elicited by the disclosed CAR-modified immune effector cells may be an active or a passive immune response. In addition, the CAR-mediated immune response may be part of an adoptive immunotherapy approach in which CAR-modified immune effector cells induce an immune response specific to CD99.

Adoptive transfer of immune effector cells expressing chimeric antigen receptors is a promising anti-cancer therapeutic. Following the collection of a patient's immune effector cells, the cells may be genetically engineered to express the disclosed CD99-specific CARs, then infused back into the patient.

The disclosed CAR-modified immune effector cells may be administered either alone, or as a pharmaceutical composition in combination with diluents and/or with other components such as IL-2, IL-15, or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodiments formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The cancer of the disclosed methods can be any CD99-expressing cell in a subject undergoing unregulated growth, invasion, or metastasis. Cancers that express CD99 include prostate cancer, ovarian cancer, adenocarcinoma of the lung, breast cancer, endometrial cancer, gastric cancer, colon cancer, and pancreatic cancer. CD99 has also been found on Jurkat cells. In some aspects, the cancer is a gallbladder cancer, exocrine adenocarcinoma, or apocrine adenocarcinomas. In some cases, the cancer comprises myelodysplastic syndrome, acute myeloid leukemia, or bi-phenotypic leukemia.

In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed CARs can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed CARs can be used in combination with a checkpoint inhibitor.

The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHlgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed CARs can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbBI (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec STI571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with a CARs for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-la from the human CXC and C-C chemokine families. Suitable cytokines include cytokine derivatives, cytokine variants, cytokine fragments, and cytokine fusion proteins.

In some embodiments, a therapeutic agent for use in combination with a CARs for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. 6,440,735 and U.S. 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a CARs for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy- progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with an CARs for treating the disorders as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed CARs is administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111. In some embodiments, the disclosed CARs is administered in combination with surgery.

CAR-T cells may be designed in several ways that enhance tumor cytotoxicity and specificity, evade tumor immunosuppression, avoid host rejection, and prolong their therapeutic half-life. TRUCK (T-cells Redirected for Universal Cytokine Killing) T cells for example, possess a CAR but are also engineered to release cytokines such as IL-12 that promote tumor killing. Because these cells are designed to release a molecular payload upon activation of the CAR once localized to the tumor environment, these CAR-T cells are sometimes also referred to as 'armored CARs'. Several cytokines as cancer therapies are being investigated both pre-clinically and clinically, and may also prove useful when similarly incorporated into a TRUCK form of CAR-T therapy. Among these include IL-2, IL-3. IL-4, IL-5, IL-6, IL-7, IL-10, IL-12, IL-13, IL-15, IL-18, M-CSF, GM-CSF, IFN-α, IFN-γ, TNF-α, TRAIL, FLT3 ligand, Lymphotactin, and TGF-p (Dranoff 2004). "Self-driving" or "homing" CAR-T cells are engineered to express a chemokine receptor in addition to their CAR. As certain chemokines can be upregulated in tumors, incorporation of a chemokine receptor aids in tumor trafficking to and infiltration by the adoptive T-cell, thereby enhancing both specificity and functionality of the CAR-T (Moon 2011). Universal CAR-T cells also possess a CAR, but are engineered such that they do not express endogenous TCR (T-cell receptor) or MHC (major histocompatibility complex) proteins. Removal of these two proteins from the signaling repertoire of the adoptive T-cell therapy prevents graft-versus-host-disease and rejection, respectively. Armored CAR-T cells are additionally so named for their ability to evade tumor immunosuppression and tumor-induced CAR-T hypofunction. These particular CAR-Ts possess a CAR, and may be engineered to not express checkpoint inhibitors. Alternatively, these CAR-Ts can be co-administered with a monoclonal antibody (mAb) that blocks checkpoint signaling. Administration of an anti-PDL1 antibody significantly restored the killing ability of CAR TILs (tumor infiltrating lymphocytes). While PD1-PDL1 and CTLA-4-CD80/CD86 signaling pathways have been investigated, it is possible to target other immune checkpoint signaling molecules in the design of an armored CAR-T including LAG-3, Tim-3, IDO-1, 2B4, and KIR. Other intracellular inhibitors of TILs include phosphatases (SHP1), ubiquitin-ligases (i.e., cbl-b), and kinases (i.e., diacylglycerol kinase). Armored CAR-Ts may also be engineered to express proteins or receptors that protect them against or make them resistant to the effects of tumor-secreted cytokines. For example, CTLs (cytotoxic T lymphocytes) transduced with the double negative form of the TGF-p receptor are resistant to the immunosuppression by lymphoma secreted TGF-p. These transduced cells showed notably increased antitumor activity in vivo when compared to their control counterparts.

Tandem and dual CAR-T cells are unique in that they possess two distinct antigen binding domains. A tandem CAR contains two sequential antigen binding domains facing the extracellular environment connected to the intracellular costimulatory and stimulatory domains. A dual CAR is engineered such that one extracellular antigen binding domain is connected to the intracellular costimulatory domain and a second, distinct extracellular antigen binding domain is connected to the intracellular stimulatory domain. Because the stimulatory and costimulatory domains are split between two separate antigen binding domains, dual CARs are also referred to as "split CARs". In both tandem and dual CAR designs, binding of both antigen binding domains is necessary to allow signaling of the CAR circuit in the T-cell. Because these two CAR designs have binding affinities for different, distinct antigens, they are also referred to as "bi-specific" CARs.

One primary concern with CAR-T cells as a form of "living therapeutic" is their manipulability in vivo and their potential immune-stimulating side effects. To better control CAR-T therapy and prevent against unwanted side effects, a variety of features have been engineered including off-switches, safety mechanisms, and conditional control mechanisms. Both self-destruct and marked/tagged CAR-T cells for example, are engineered to have an "off-switch" that promotes clearance of the CAR-expressing T-cell. A self-destruct CAR-T contains a CAR, but is also engineered to express a pro-apoptotic suicide gene or "elimination gene" inducible upon administration of an exogenous molecule. A variety of suicide genes may be employed for this purpose, including HSV-TK (herpes simplex virus thymidine kinase), Fas, iCasp9 (inducible caspase 9), CD20, MYC TAG, and truncated EGFR (endothelial growth factor receptor). HSK for example, will convert the prodrug ganciclovir (GCV) into GCV-triphosphate that incorporates itself into replicating DNA, ultimately leading to cell death. iCasp9 is a chimeric protein containing components of FK506-binding protein that binds the small molecule AP1903, leading to caspase 9 dimerization and apoptosis. A marked/tagged CAR-T cell however, is one that possesses a CAR but also is engineered to express a selection marker.

Administration of a mAb against this selection marker will promote clearance of the CAR-T cell. Truncated EGFR is one such targetable antigen by the anti-EGFR mAb, and administration of cetuximab works to promotes elimination of the CAR-T cell. CARs created to have these features are also referred to as sCARs for 'switchable CARs', and RCARs for 'regulatable CARs'. A "safety CAR", also known as an "inhibitory CAR" (iCAR), is engineered to express two antigen binding domains. One of these extracellular domains is directed against a tumor related antigen and bound to an intracellular costimulatory and stimulatory domain. The second extracellular antigen binding domain however is specific for normal tissue and bound to an intracellular checkpoint domain such as CTLA4, PD1, or CD45. Incorporation of multiple intracellular inhibitory domains to the iCAR is also possible. Some inhibitory molecules that may provide these inhibitory domains include B7-H1, B7-1, CD160, PIH, 2B4, CEACAM (CEACAM-1. CEACAM-3, and/or CEACAM-5), LAG-3, TIGIT, BTLA, LAIR1, and TGFp-R. In the presence of normal tissue, stimulation of this second antigen binding domain will work to inhibit the CAR. It should be noted that due to this dual antigen specificity, iCARs are also a form of bi-specific CAR-T cells.

The safety CAR-T engineering enhances specificity of the CAR-T cell for tumor tissue, and is advantageous in situations where certain normal tissues may express very low levels of a tumor associated antigen that would lead to off target effects with a standard CAR (Morgan 2010). A conditional CAR-T cell expresses an extracellular antigen binding domain connected to an intracellular costimulatory domain and a separate, intracellular costimulator. The costimulatory and stimulatory domain sequences are engineered in such a way that upon administration of an exogenous molecule the resultant proteins will come together intracellularly to complete the CAR circuit. In this way, CAR-T activation can be modulated, and possibly even 'fine-tuned' or personalized to a specific patient. Similar to a dual CAR design, the stimulatory and costimulatory domains are physically separated when inactive in the conditional CAR; for this reason these too are also referred to as a "split CAR".

In some embodiments, two or more of these engineered features may be combined to create an enhanced, multifunctional CAR-T. For example, it is possible to create a CAR-T cell with either dual- or conditional- CAR design that also releases cytokines like a TRUCK. In some embodiments, a dual-conditional CAR-T cell could be made such that it expresses two CARs with two separate antigen binding domains against two distinct cancer antigens, each bound to their respective costimulatory domains. The costimulatory domain would only become functional with the stimulatory domain after the activating molecule is administered. For this CAR-T cell to be effective the cancer must express both cancer antigens and the activating molecule must be administered to the patient; this design thereby incorporating features of both dual and conditional CAR-T cells.

Typically, CAR-T cells are created using a-p T cells, however y-b T cells may also be used. In some embodiments, the described CAR constructs, domains, and engineered features used to generate CAR-T cells could similarly be employed in the generation of other types of CAR-expressing immune cells including NK (natural killer) cells, B cells, mast cells, myeloid-derived phagocytes, and NKT cells. Alternatively, a CAR-expressing cell may be created to have properties of both T-cell and NK cells. In an additional embodiment, the transduced with CARs may be autologous or allogeneic.

Several different methods for CAR expression may be used including retroviral transduction (including y-retroviral), lentiviral transduction, transposon/transposases (Sleeping Beauty and PiggyBac systems), and messenger RNA transfer-mediated gene expression. Gene editing (gene insertion or gene deletion/disruption) has become of increasing importance with respect to the possibility for engineering CAR-T cells as well. CRISPR-Cas9, ZFN (zinc finger nuclease), and TALEN (transcription activator like effector nuclease) systems are three potential methods through which CAR-T cells may be generated.

Definitions

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "protein domain" refers to a portion of a protein, portions of a protein, or an entire protein showing structural integrity; this determination may be based on amino acid composition of a portion of a protein, portions of a protein, or the entire protein.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule.

Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

A number of embodiments of the invention have been described. Nevertheless, it will be understood that various modifications may be made without departing from the spirit and scope of the invention. Accordingly, other embodiments are within the scope of the following claims.

Examples

Example 1: CD99 Hybridoma Screening

Figure 2:
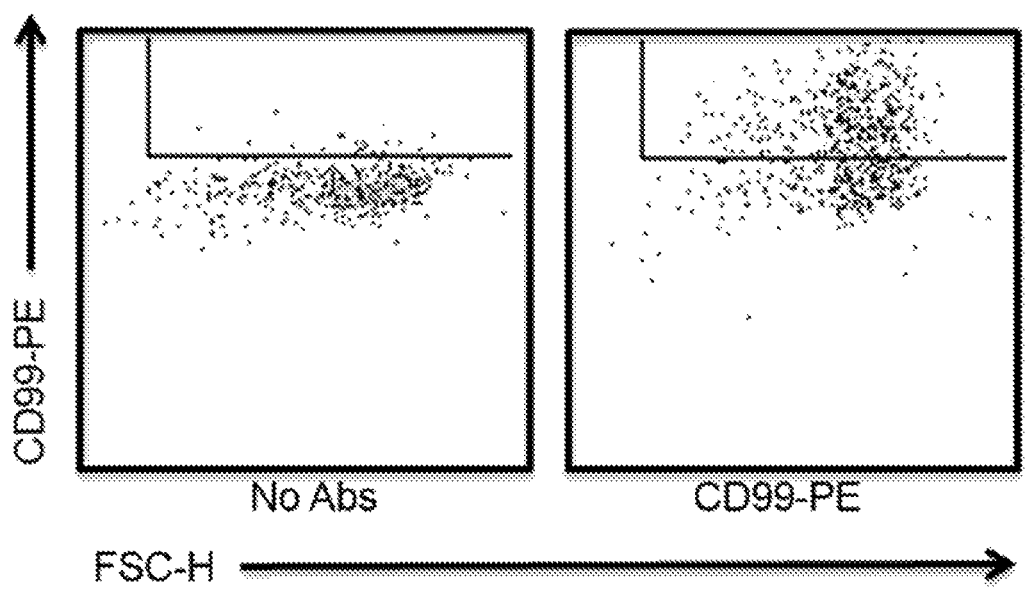
FIG. 2 contains flow cytometry plots showing positive (right) and negative (left) controls used for CD99-PE analysis FIG. 3 contains flow cytometry plots showing hybridomas positive for CD99.
Figure 3:
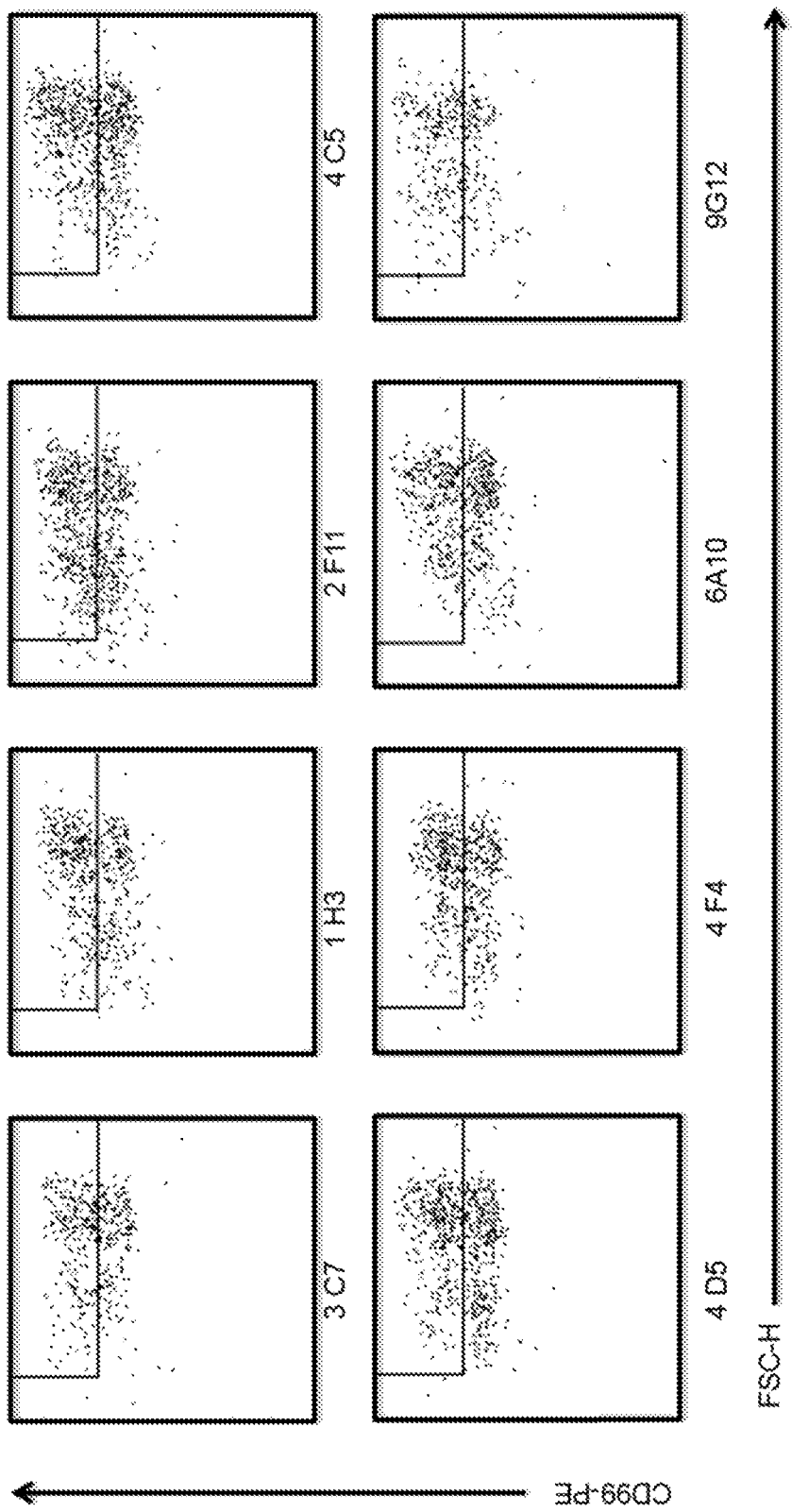

EL4-hCD99 Cells were incubated with antibodies/supernatant from hybridomas. Cells were then stained with Live dead Zombie Green dye and stained with F(ab2) anti-mIgG-PE. INTELLICYT high throughput screener (iQue) was used to asses the cells positive for CD99 PE. FIG. 1 contains a flow cytometry plot showing gate used for live cells in CD99-PE analysis. FIG. 2 contains flow cytometry plots showing positive (right) and negative (left) controls used for CD99-PE analysis. The left histogram is of a control sample in which no supernatant i.e antibodies(abs) was used. The right histogram is of a positive control in which PE labeled CD99 antibody was used. The gate represents CD99-PE positive population. FIG. 3 contains flow cytometry plots showing hybridomas positive for CD99. Numbers on the bottom of the histogram represent wells/hybridomas.

Hybridomas selected from primary screening were sub cloned. ELISA Plates were coated with CD99 antigen (Origene, Sku #TP304058, lot ##105470), 0.5 ug/ml in DPBS (Lonza cat #17-512F, lot #0000615334), 50 ul/well, at room temperature for 1 hour, and then blocked with 1% BSA/DPBS 100 ul/well, room temperature for 1 hour. Supernatant from monoclonal hybridomas were then added to the coated plates (50 ul/well). Antibody was detected using goat anti Mouse Ig-HRP (1010-05), 1:4000 in TBST, 50 ul/well, room temperature for 40 mins, followed by ABTs/H$_2$O$_2$ for 10 mins. Tables 7 to 12 show the results of this screen.

TABLE 7

1H3-A subclone screening

|   | 1 | 2 | 3 | 4 | 5 | 6 | 7 | 8 | 9 | 10 | 11 | 12 |
|---|---|---|---|---|---|---|---|---|---|----|----|----|
| A | 0.231 | 0.883 | 0.853 | 0.835 | 0.779 | 0.709 | 0.125 | 0.751 | 0.493 | 0.324 | 0.143 | 0.088 |
| B | 0.152 | 0.877 | 0.827 | 0.891 | 0.077 | 0.717 | 0.693 | 0.713 | 0.363 | 0.597 | 0.481 | 0.085 |
| C | 0.17 | 0.091 | 0.894 | 0.776 | 0.096 | 0.141 | 0.727 | 0.715 | 0.703 | 0.632 | 0.51 | 0.498 |
| D | 0.096 | 0.83 | 0.715 | 0.832 | 0.84 | 0.837 | 0.419 | 0.804 | 0.266 | 0.689 | 0.569 | 0.071 |
| E | 0.914 | 0.842 | 0.816 | 0.14 | 0.809 | 0.782 | 0.233 | 0.122 | 0.832 | 0.084 | 0.554 | 0.546 |
| F | 0.777 | 0.149 | 0.112 | 0.828 | 0.797 | 0.898 | 0.8 | 0.736 | 0.343 | 0.434 | 0.09 | 0.573 |
| G | 0.342 | 0.134 | 0.744 | 0.781 | 0.074 | 0.529 | 0.206 | 0.748 | 0.162 | 0.046 | 0.045 | 0.041 |
| H | 0.404 | 0.816 | 0.083 | 0.258 | 0.742 | 0.811 | 0.72 | 0.088 | 0.658 | 0.652 | 0.711 | 0 |

TABLE 8

4D5-A subclone screening

|   | 1 | 2 | 3 | 4 | 5 | 6 | 7 | 8 | 9 | 10 | 11 | 12 |
|---|---|---|---|---|---|---|---|---|---|----|----|----|
| A | 0.006 | 0.016 | 0.008 | 0.016 | 0.02 | 0.009 | 0.002 | −0.005 | −0.007 | −0.008 | −0.006 | −0.001 |
| B | 0.006 | 0.008 | 0.01 | 0.009 | 0.019 | 0.004 | −0.001 | 0.003 | −0.004 | 0.001 | −0.012 | −0.009 |
| C | 0.025 | 0.01 | 0.002 | 0.01 | −0.006 | 0.004 | 0.004 | −0.005 | 0.005 | −0.012 | −0.006 | 0.006 |
| D | 0.018 | 0.005 | 0.006 | 0.025 | 0.004 | 0.003 | 0 | −0.005 | 0.002 | −0.016 | −0.015 | −0.022 |
| E | 0.009 | 0.002 | 0 | 0.002 | 0.001 | 0.005 | −0.003 | −0.003 | −0.01 | −0.016 | −0.014 | −0.017 |
| F | 0.008 | −0.003 | 0.005 | −0.012 | 0.007 | 0 | −0.003 | −0.008 | −0.007 | −0.011 | −0.01 | −0.016 |
| G | 0.009 | 0 | 0.005 | 0.003 | 0.015 | −0.001 | −0.004 | −0.004 | −0.009 | 0.009 | −0.018 | −0.018 |
| H | 0 | 0.005 | 0.003 | 0.013 | 0.008 | −0.004 | −0.004 | −0.012 | −0.005 | −0.011 | −0.021 | −0.02 |

TABLE 9

4C5-A subclone screening

|   | 1 | 2 | 3 | 4 | 5 | 6 | 7 | 8 | 9 | 10 | 11 | 12 |
|---|---|---|---|---|---|---|---|---|---|----|----|----|
| A | 0.802 | 0.85 | 0.655 | 0.758 | 0.699 | 0.638 | 0.707 | 0.741 | 0.578 | 0.535 | 0.584 | 0.521 |
| B | 0.61 | 0.647 | 0.662 | 0.572 | 0.719 | 0.639 | 0.583 | 0.585 | 0.587 | 0.599 | 0.571 | 0.476 |
| C | 0.806 | 0.79 | 0.776 | 0.742 | 0.648 | 0.671 | 0.659 | 0.618 | 0.597 | 0.44 | 0.525 | 0.483 |
| D | 0.727 | 0.754 | 0.761 | 0.739 | 0.669 | 0.635 | 0.745 | 0.583 | 0.487 | 0.378 | 0.541 | 0.459 |
| E | 0.806 | 0.735 | 0.622 | 0.646 | 0.682 | 0.773 | 0.626 | 0.627 | 0.399 | 0.514 | 0.412 | 0.468 |
| F | 0.788 | 0.678 | 0.694 | 0.752 | 0.638 | 0.625 | 0.641 | 0.661 | 0.394 | 0.443 | 0.424 | 0.471 |
| G | 0.573 | 0.712 | 0.736 | 0.72 | 0.742 | 0.683 | 0.658 | 0.626 | 0.488 | 0.551 | 0.495 | 0.462 |
| H | 0.561 | 0.738 | 0.769 | 0.758 | 0.808 | 0.842 | 0.748 | 0.741 | 0.619 | 0.533 | 0.502 | 0 |

TABLE 10

4C5-B subclone screening

|   | 1 | 2 | 3 | 4 | 5 | 6 | 7 | 8 | 9 | 10 | 11 | 12 |
|---|---|---|---|---|---|---|---|---|---|----|----|----|
| A | 0.087 | 0.855 | 0.662 | 0.891 | 0.077 | 0.058 | 0.034 | 0.141 | 0.026 | 0.065 | 0.041 | 0.215 |
| B | 0.897 | 0.129 | 0.056 | 0.911 | 0.876 | 0.08 | 0.269 | 0.688 | 0.024 | 0.067 | 0.63 | 0.043 |
| C | 0.263 | 0.914 | 0.055 | 0.06 | 0.082 | 0.044 | 0.046 | 0.744 | 0.437 | 0.027 | 0.672 | 0.388 |
| D | 0.123 | 0.803 | 0.302 | 0.599 | 0.105 | 0.047 | 0.069 | 0.219 | 0.115 | 0.03 | 0.089 | 0.683 |
| E | 0.907 | 0.892 | 0.276 | 0.892 | 0.043 | 0.937 | 0.552 | 0.367 | 0.032 | 0.189 | 0.028 | 0.512 |

TABLE 10-continued

4C5-B subclone screening

|   | 1 | 2 | 3 | 4 | 5 | 6 | 7 | 8 | 9 | 10 | 11 | 12 |
|---|---|---|---|---|---|---|---|---|---|----|----|----|
| F | 0.662 | 0.757 | 0.161 | 0.043 | 0.868 | 0.054 | 0.038 | 0.787 | 0.052 | 0.078 | 0.107 | 0.026 |
| G | 0.891 | 0.048 | 0.15 | 0.964 | 0.88 | 0.048 | 0.378 | 0.048 | 0.062 | 0.089 | 0.08 | 0.035 |
| H | 0.065 | 0.155 | 0.974 | 0.095 | 0.232 | 0.788 | 0.197 | 0.112 | 0.164 | 0.756 | 0.146 | 0 |

TABLE 11

9G12-A subclone screening

|   | 1 | 2 | 3 | 4 | 5 | 6 | 7 | 8 | 9 | 10 | 11 | 12 |
|---|---|---|---|---|---|---|---|---|---|----|----|----|
| A | 0.663 | 0.722 | 0.904 | 0.847 | 1.016 | 0.999 | 0.924 | 0.788 | 0.829 | 0.94 | 0.851 | 0.771 |
| B | 0.479 | 0.67 | 0.705 | 0.806 | 0.969 | 0.746 | 0.839 | 0.933 | 0.858 | 0.885 | 0.754 | 0.92 |
| C | 0.553 | 0.567 | 0.726 | 0.683 | 0.71 | 0.739 | 0.872 | 0.95 | 0.926 | 0.915 | 0.801 | 0.758 |
| D | 0.609 | 0.722 | 0.649 | 0.671 | 0.78 | 0.685 | 0.83 | 0.822 | 1.003 | 0.79 | 0.93 | 0.856 |
| E | 0.78 | 0.545 | 0.663 | 0.787 | 0.618 | 0.767 | 0.813 | 0.794 | 0.922 | 0.853 | 0.814 | 0.825 |
| F | 0.708 | 0.553 | 0.695 | 0.702 | 0.598 | 0.707 | 0.734 | 1.041 | 0.944 | 0.785 | 0.724 | 0.893 |
| G | 0.586 | 0.586 | 0.555 | 0.755 | 0.764 | 0.739 | 0.802 | 0.949 | 0.827 | 0.718 | 0.86 | 0.796 |
| H | 0.728 | 0.709 | 0.742 | 0.597 | 0.765 | 0.723 | 0.702 | 0.909 | 0.834 | 0.903 | 0.995 | 0 |

TABLE 12

9G12-B subclone screening

|   | 1 | 2 | 3 | 4 | 5 | 6 | 7 | 8 | 9 | 10 | 11 | 12 |
|---|---|---|---|---|---|---|---|---|---|----|----|----|
| A | 1.229 | 1.273 | 1.262 | 0.084 | 1.236 | 0.092 | 0.26 | 1.108 | 0.102 | 0.845 | 0.268 | 0.245 |
| B | 1.03 | 0.993 | 0.58 | 0.088 | 1.239 | 1.193 | 1.17 | 0.184 | 0.746 | 0.108 | 0.149 | 0.989 |
| C | 1.284 | 1.091 | 1.164 | 0.552 | 1.196 | 1.237 | 0.889 | 0.08 | 1.124 | 0.337 | 0.057 | 0.958 |
| D | 1.289 | 1.039 | 0.097 | 0.095 | 0.157 | 0.09 | 1.14 | 1.053 | 0.639 | 0.081 | 0.304 | 0.933 |
| E | 1.179 | 0.721 | 0.14 | 0.122 | 0.136 | 1.211 | 0.152 | 0.129 | 0.09 | 0.647 | 0.962 | 0.737 |
| F | 0.119 | 0.116 | 1.189 | 0.239 | 1.206 | 1.199 | 1.22 | 1.092 | 1.055 | 0.309 | 0.983 | 0.09 |
| G | 1.175 | 0.104 | 1.129 | 0.093 | 1.14 | 1.126 | 1.184 | 0.087 | 0.282 | 1.016 | 0.047 | 0.272 |
| H | 1.193 | 1.261 | 0.159 | 0.188 | 0.244 | 0.608 | 1.109 | 1.169 | 0.677 | 0.174 | 1.004 | 0 |

Figure 4:
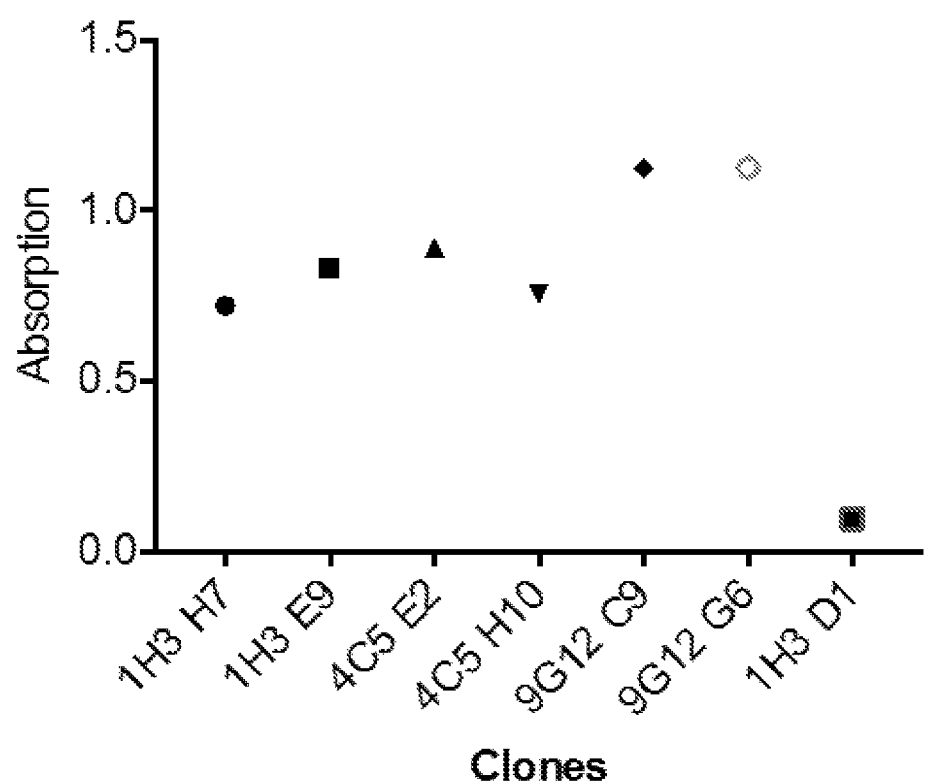
FIG. 4 contains a plot depicting CD99 binding by ELISA absorption for each hybridoma.
Figure 5:
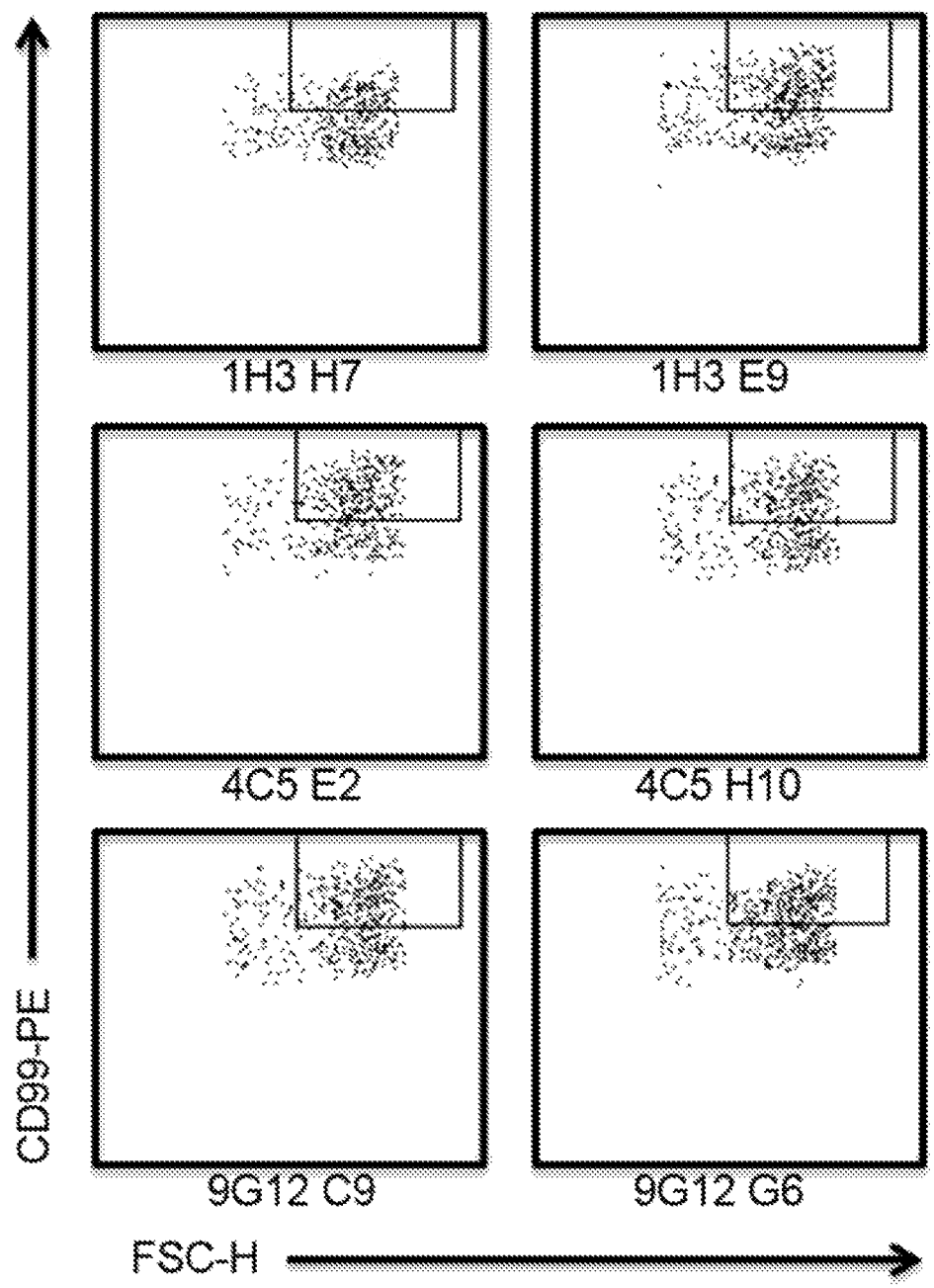
FIG. 5 contains flow cytometry plots showing secondary screening of 1H3H7, IH3E9, 4C5E2, 4C5H10, 9G12C9, and 9G12G6.
Figures 6A, 6B:
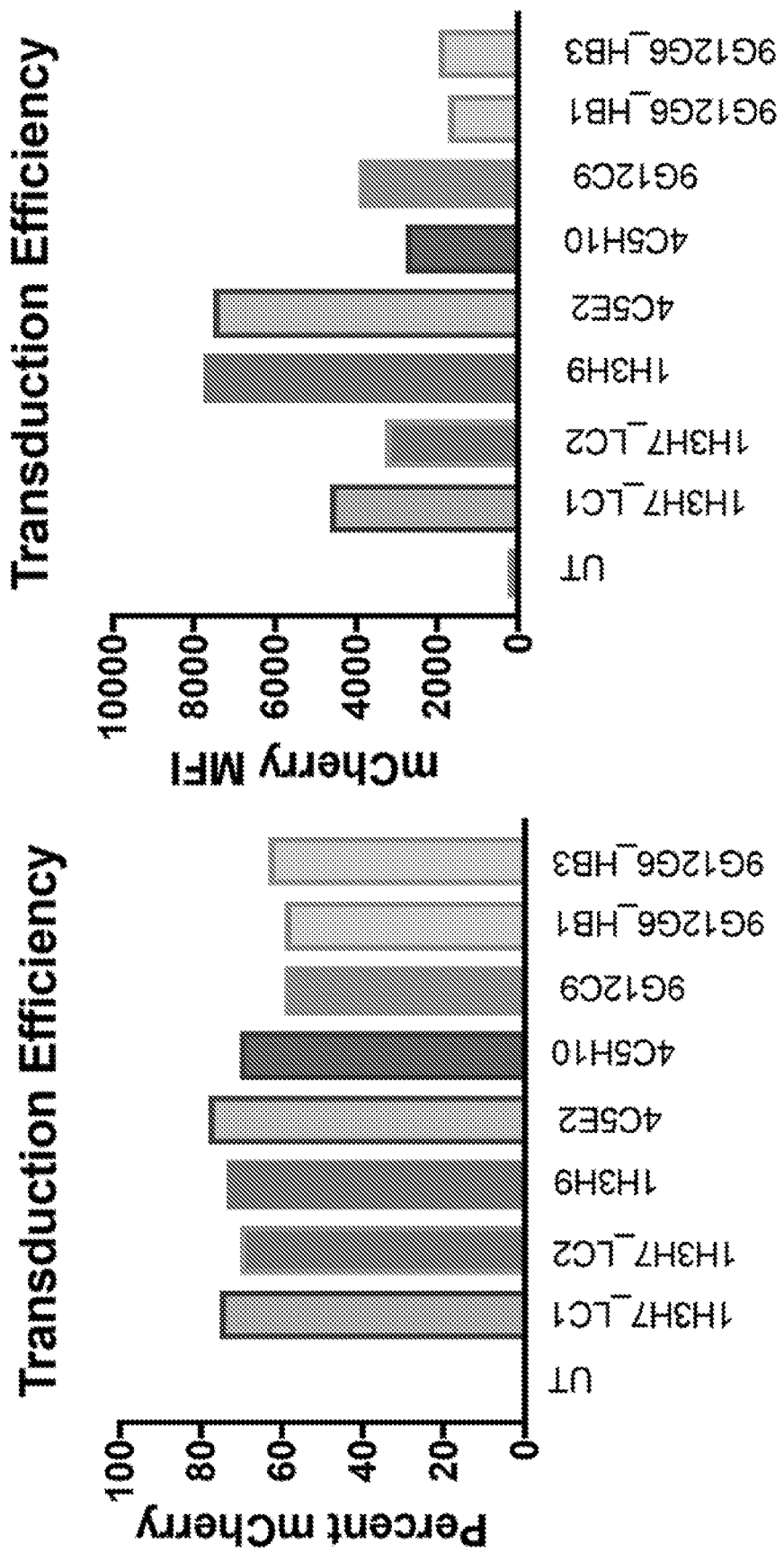
FIGS. 6A to 6D show cytotoxic activities of anti-CD99 CARs. CHO cells overexpressing CD99 (CHO-CD99) were used as target cells. Gammaretroviruses expressing anti-CD99 CARs were transduced into primary T cells isolated from healthy PBMCs. Transduction efficiency of each CAR was determined by flow cytometric analysis of mCherry expression (FIGS. 6A and 6B). CAR positive cells were added to target cells at effector to target ratios of either 1:1 (FIG. 6C) or 1:5 (FIG. 6D). UT=Untransduced, MFI=median fluorescent intensity.
Figure 6C:
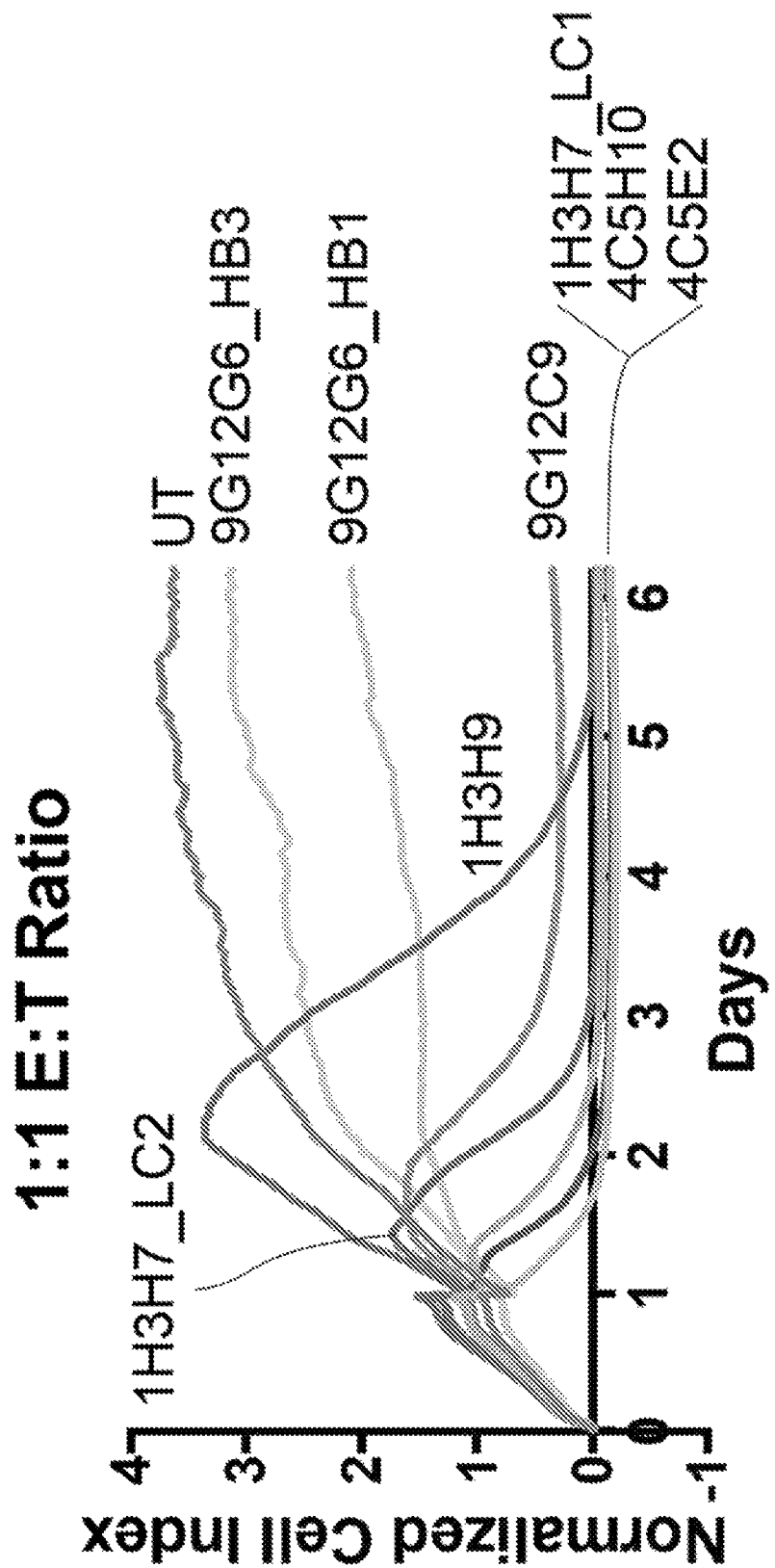
Figure 6D:
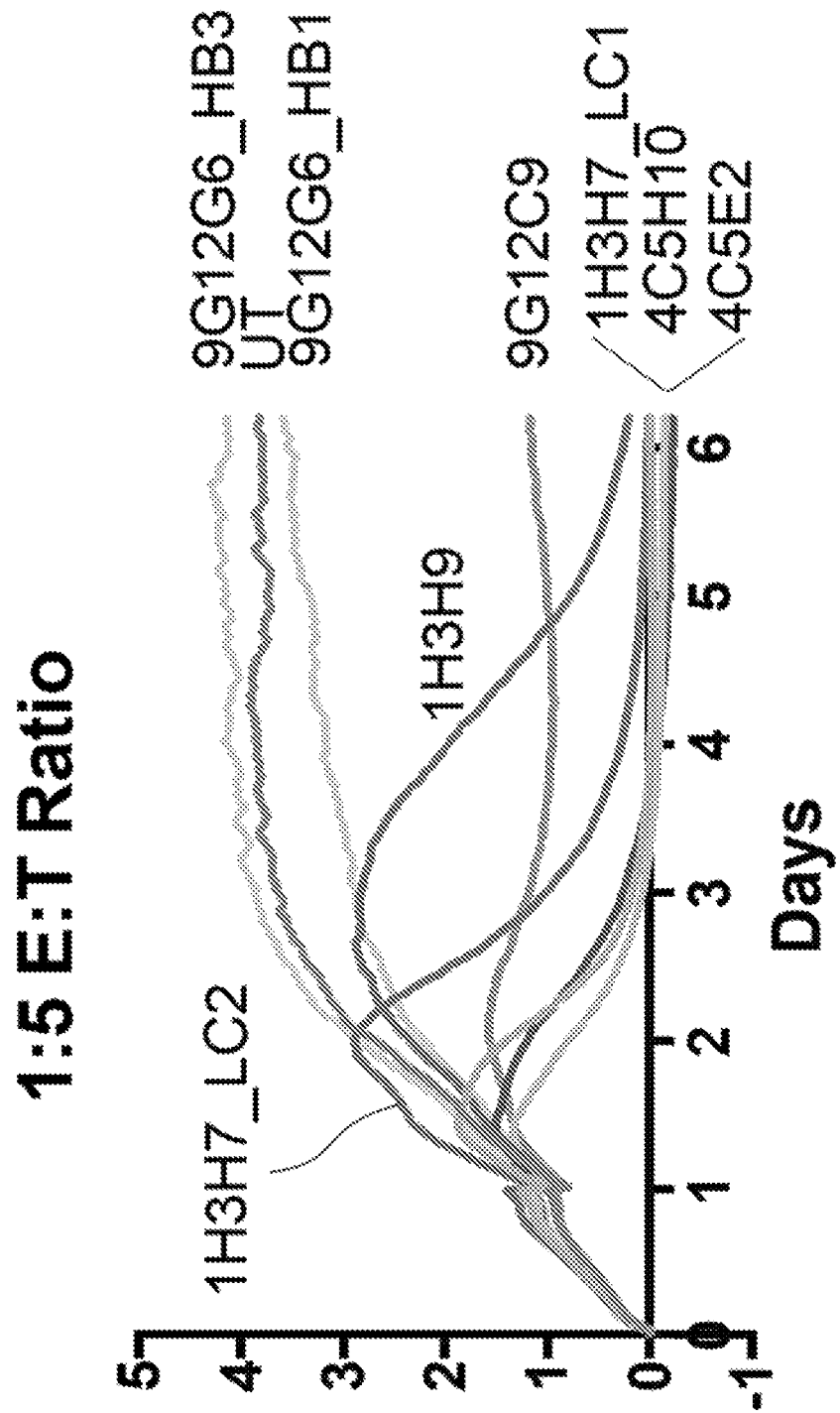
Figures 7A, 7B:
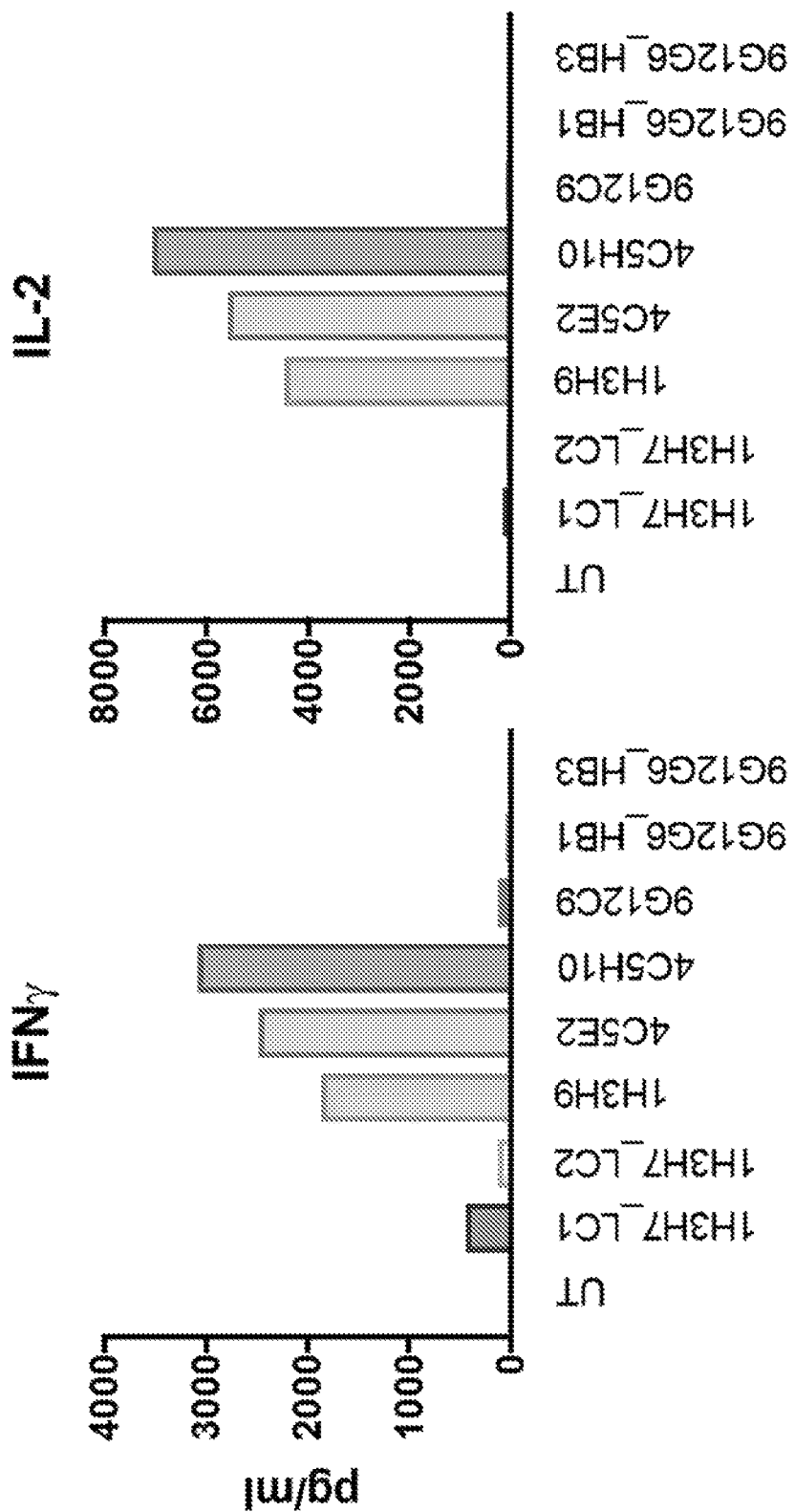
FIGS. 7A to 7C show cytokine secretion by anti-CD99 CARs. CAR positive cells were co-incubated with CHO-CD99 target cells at an effector to target ratios of 1:1 overnight. Following co-incubation, supernatants were collected and production of the cytokines IFNy (FIG. 7A), IL-2 (FIG. 7B), and IL-6 (FIG. 7C) was analyzed. UT=Untransduced.
Figure 7C:
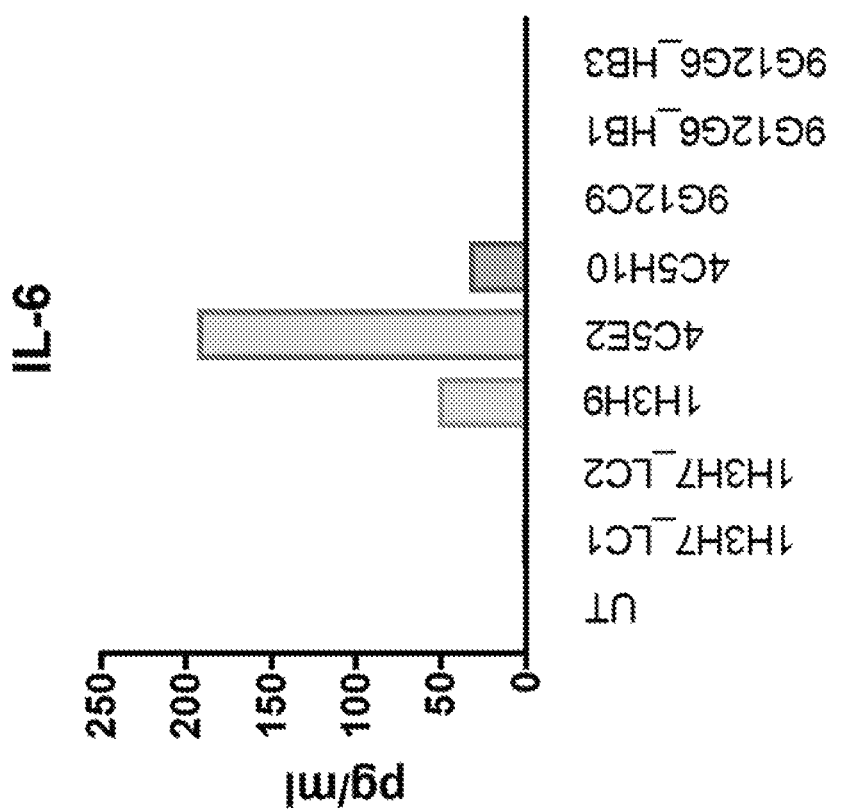
Figures 8C, 8D:
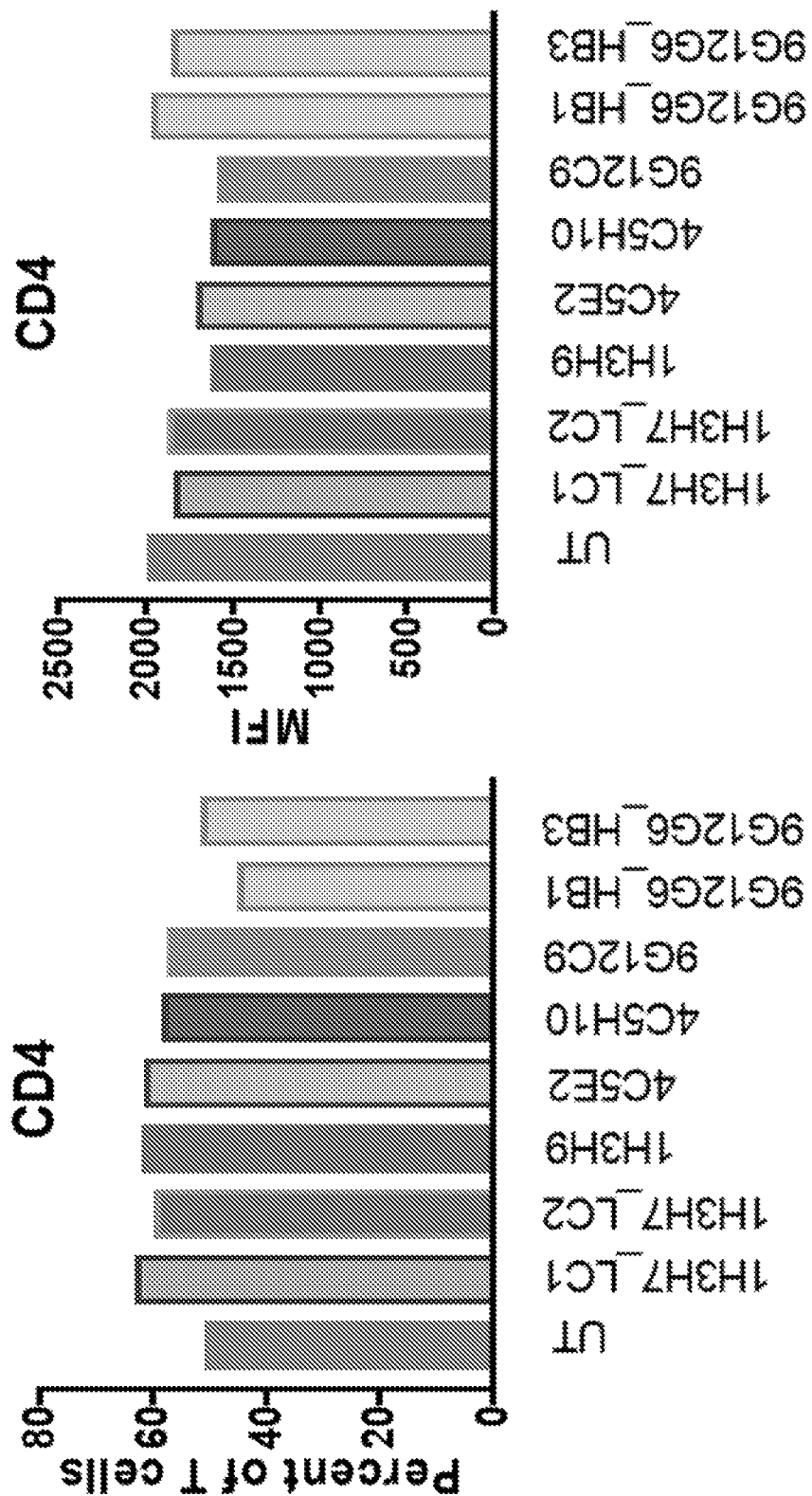
Figures 8G, 8H:
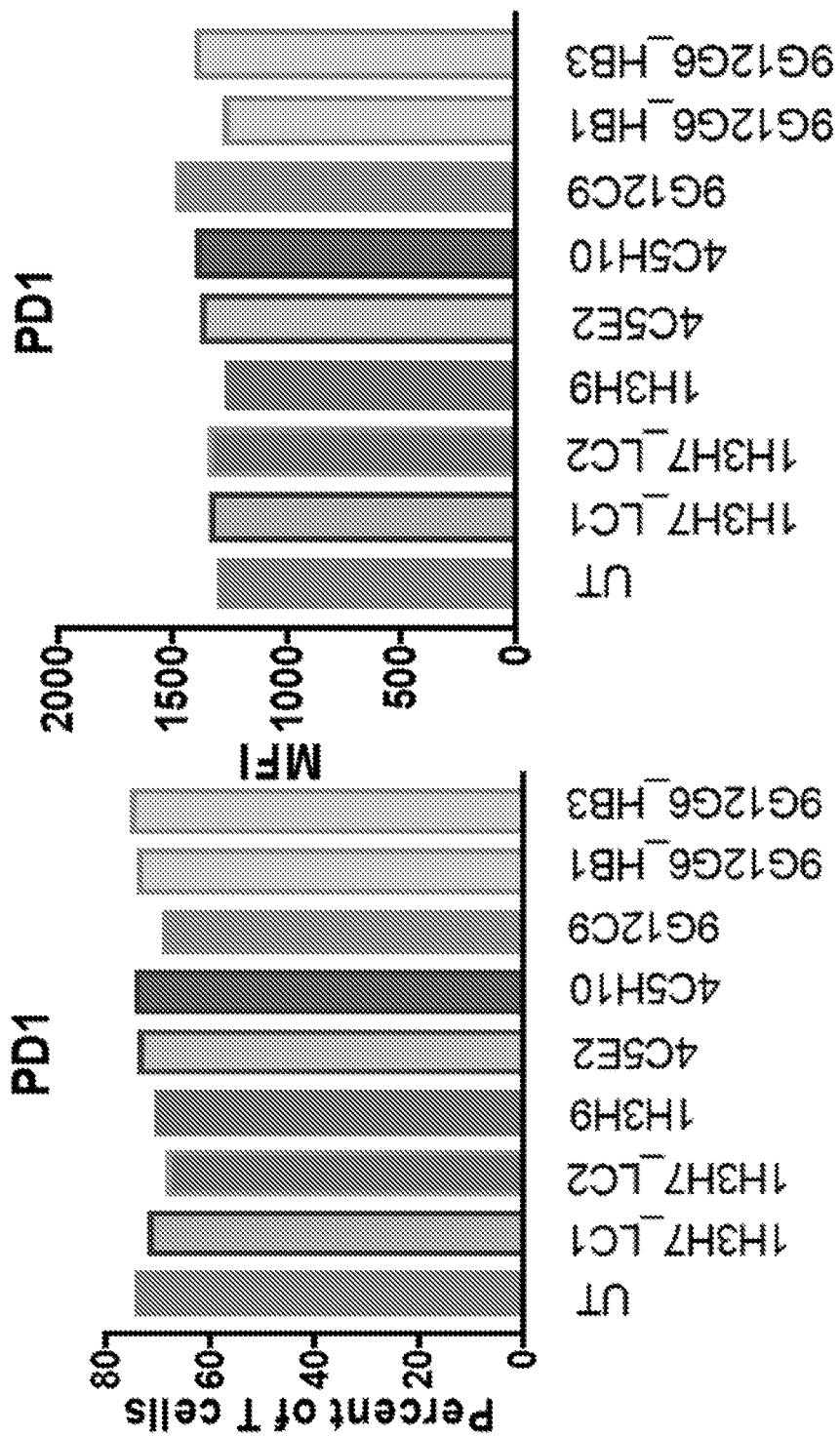
Figure 8I:
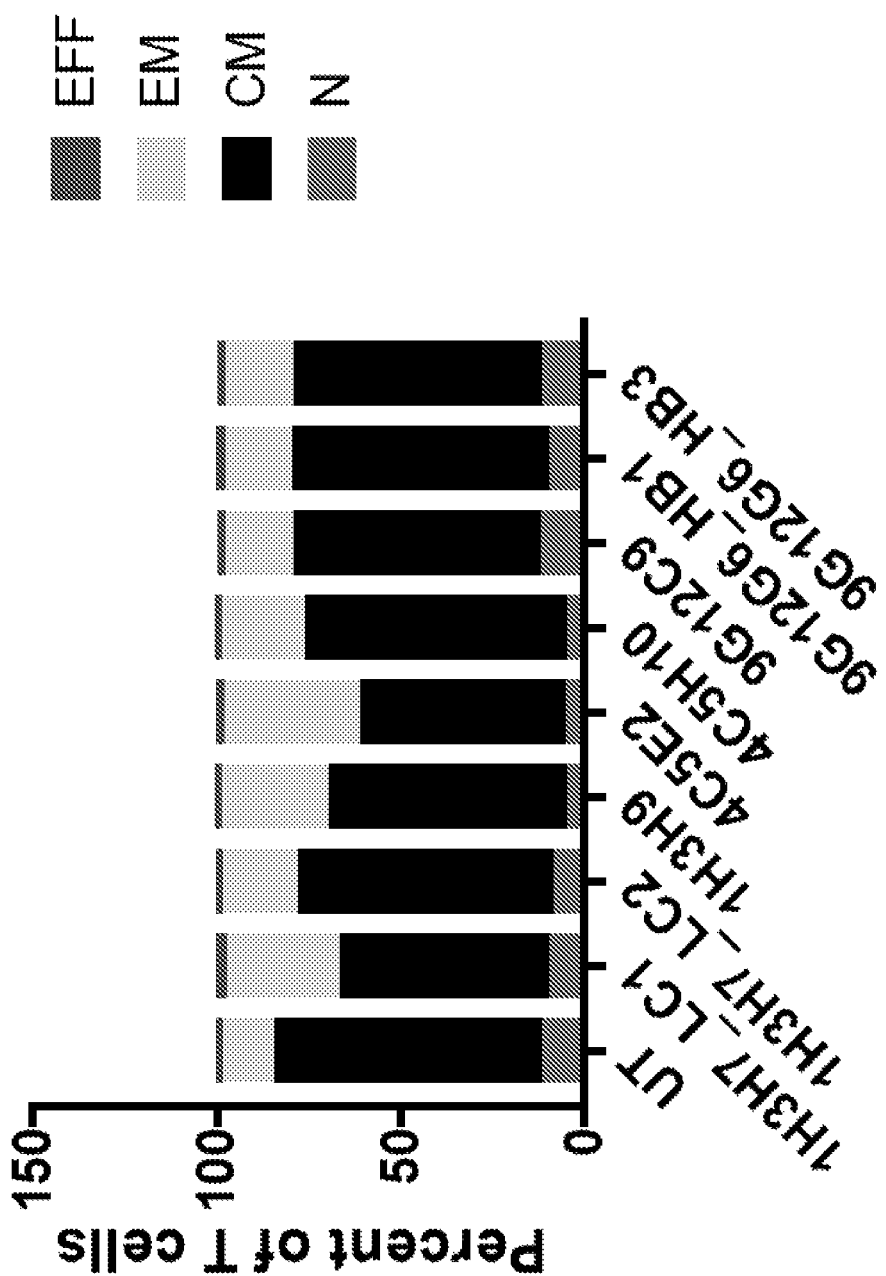
Figures 9A, 9B:
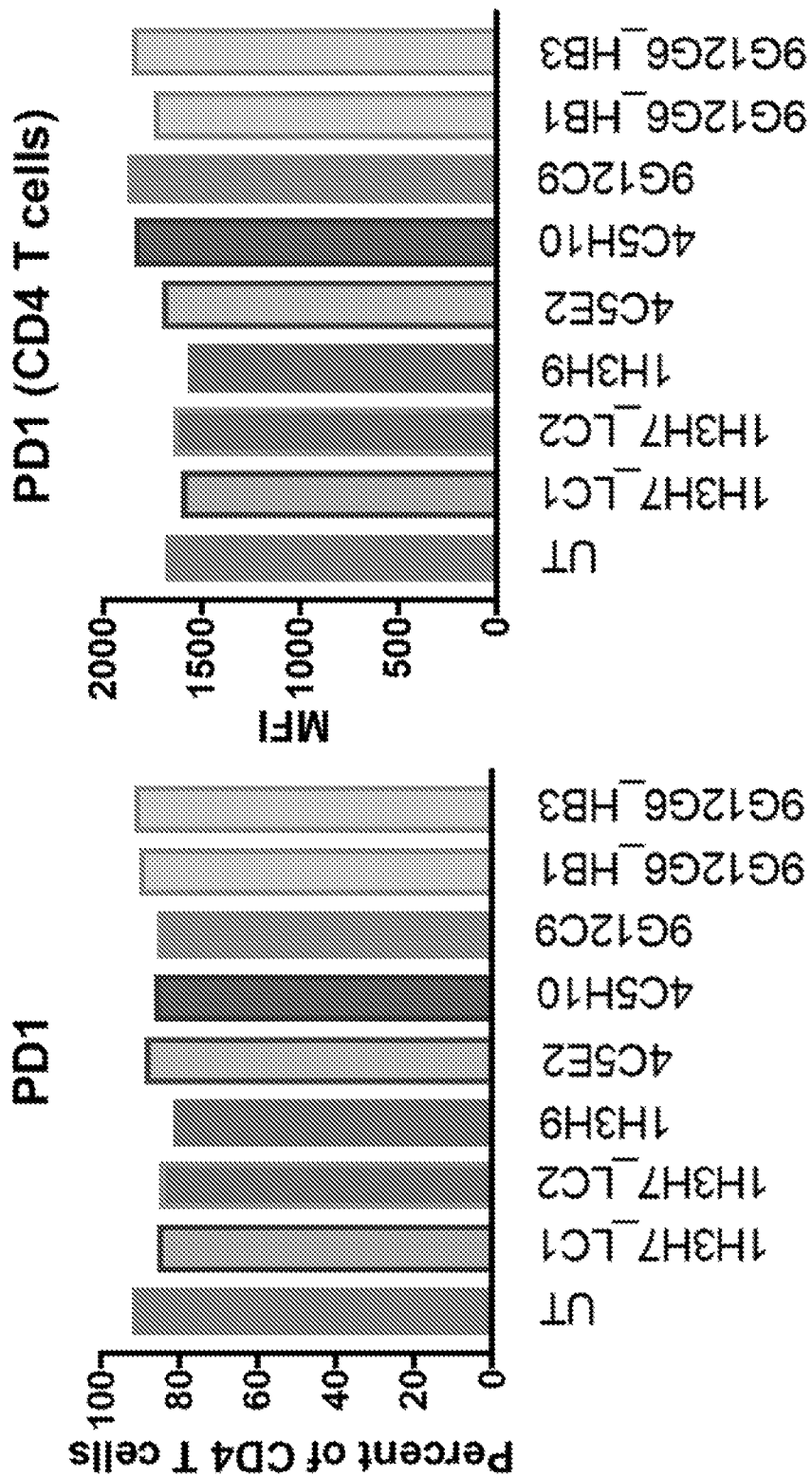
FIGS. 9A to 9E show CD4 and CD8 immunephenotype of anti-CD99 CARs. CD4 and CD8 T cells were analyzed for expression of PD1 (FIGS., 9A & 9B, 9D & 9E) and for T cells subsets (FIG. 9C). EFF=effector, EM=effector memory, CM=central memory, N=Naïve.
Figure 9C:
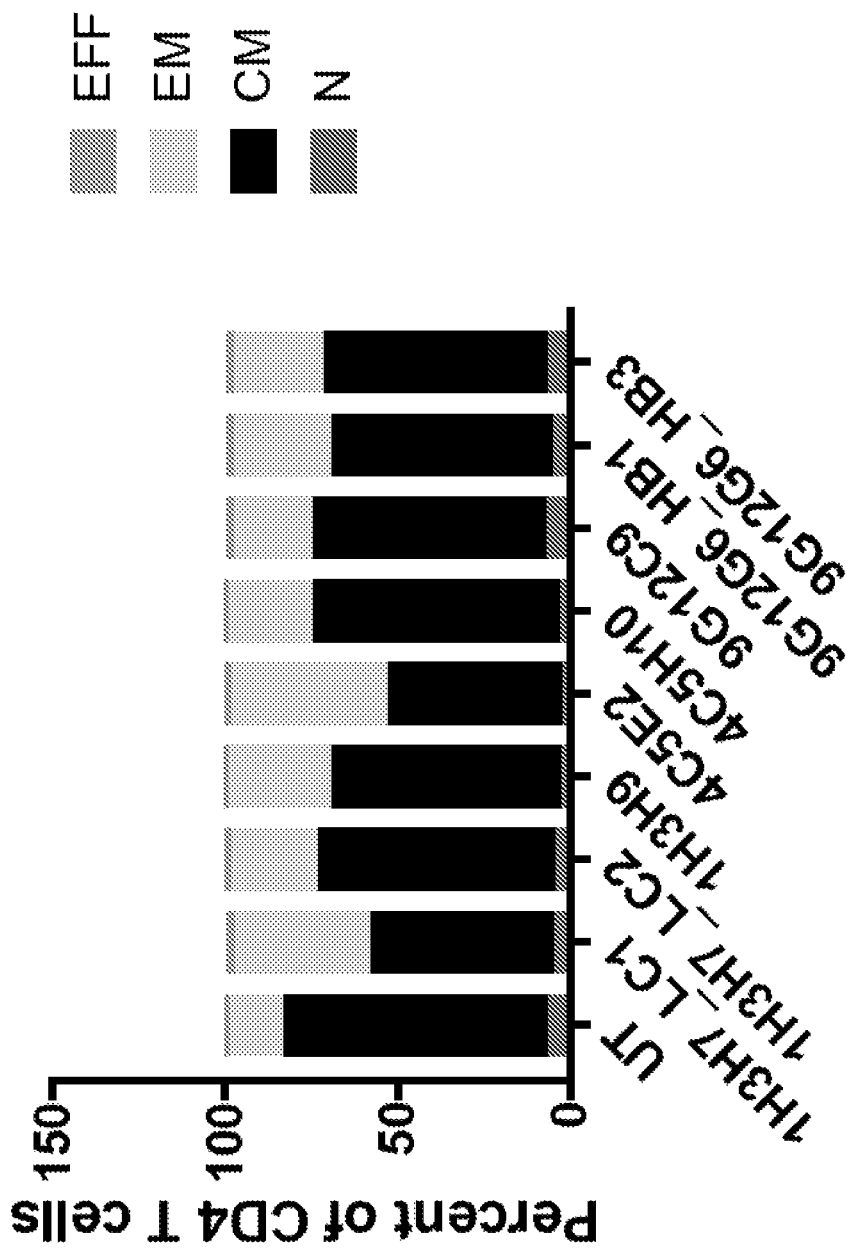
Figures 9D, 9E:
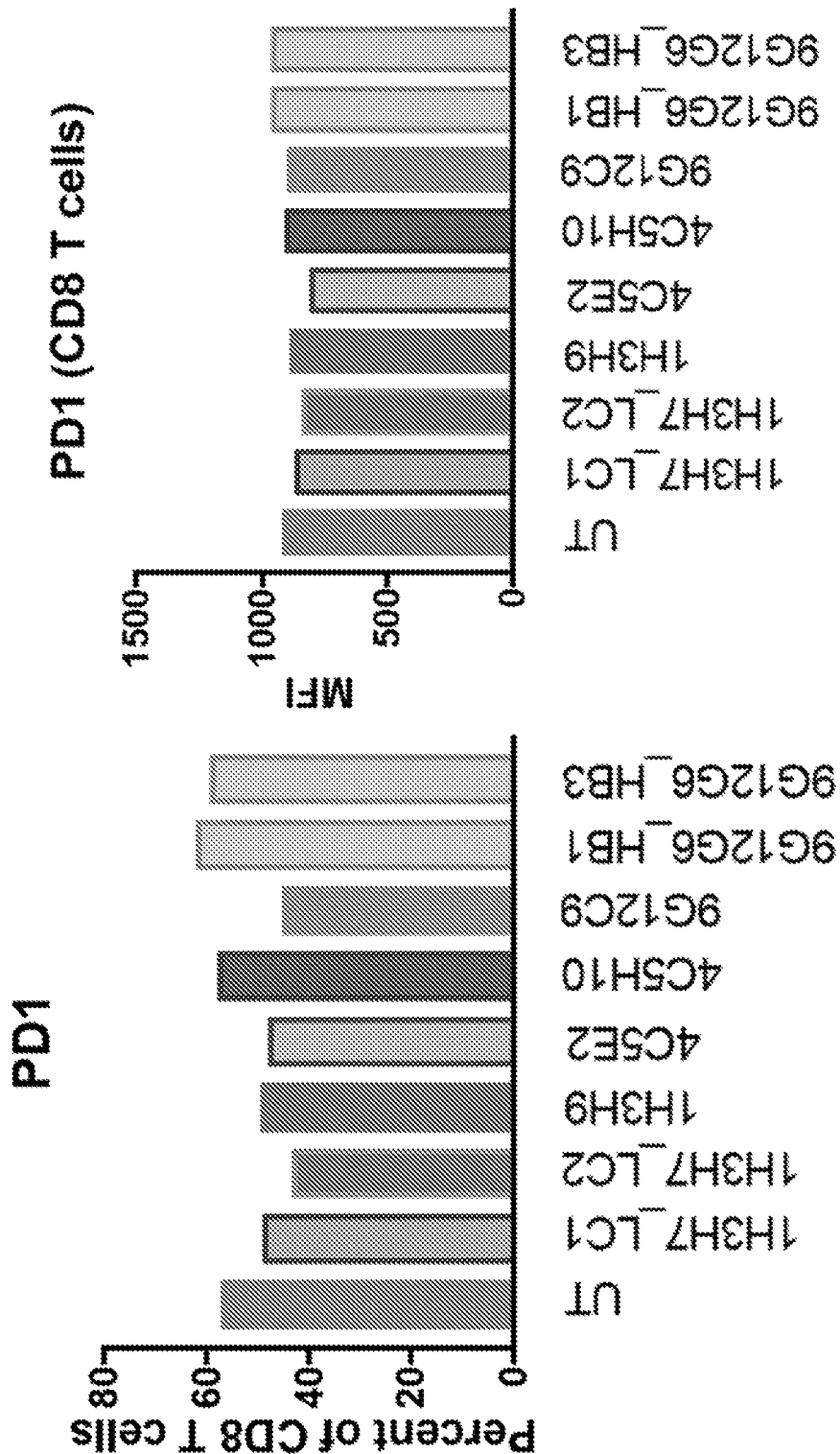

FIG. 4 contains a plot depicting clones that were positive with ELISA and selected for IgH/IgL cloning. Clone 1H3 D1 is negative/low for CD99. FIG. 5 contains flow cytometry plots showing secondary screening of 1H3H7, IH3E9, 4C5E2, 4C5H10, 9G12C9, and 9G12G6.

Using Primary screening with iQUe and Secondary screening with iQue and ELISA, hybridomas and clones were selected that produced monoclonal CD99 antibodies. Monoclonal hybridomas from secondary screening are further subcloned and gene rearrangements of Heavy chain and Light chain of the antibody are determined for designing CD99 Chimeric antigen receptor (CAR).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A chimeric antigen receptor (CAR) polypeptide, comprising a CD99 antigen binding domain, a transmembrane domain, an intracellular signaling domain, and a co-stimulatory signaling region, wherein the CD99 antigen binding domain is a single-chain variable fragment (scFv) of an antibody that specifically binds CD99, wherein the scFv comprises a variable heavy (VH) domain having CDR1, CDR2 and CDR3 sequences and a variable light (VL) domain having CDR1, CDR2 and CDR3 sequences, wherein the CDR1 sequence of the VH domain comprises the amino acid sequence SEQ ID NO:1, the CDR2 sequence of the VH domain comprises the amino acid sequence SEQ ID NO:5, and the CDR3 sequence of the VH domain comprises the amino acid sequence SEQ ID NO:8, wherein the CDR1 sequence of the VL comprises the amino acid sequence SEQ ID NO:12, the CDR2 sequence of the VL domain comprises the amino acid sequence SEQ ID NO:16, and the CDR3 sequence of the VL domain comprises the amino acid sequence SEQ ID NO:19; or wherein the CDR1 sequence of the VH domain comprises the amino acid sequence SEQ ID NO:2, the CDR2 sequence of the VH domain comprises the amino acid sequence SEQ ID NO:6, and the CDR3 sequence of the VH domain comprises the amino acid sequence SEQ ID NO:9, wherein the CDR1 sequence of the VL comprises the amino acid sequence SEQ ID NO:13, the CDR2 sequence of the VL domain comprises the amino acid sequence SEQ ID NO:17, and the CDR3 sequence of the VL domain comprises the amino acid sequence SEQ ID NO:20; or wherein the CDR1 sequence of the VH domain comprises the amino acid sequence SEQ ID NO:4, the CDR2 sequence of the VH domain comprises the amino acid sequence SEQ ID NO:7, and the CDR3 sequence of the VH domain comprises the amino acid sequence SEQ ID NO:10, wherein the CDR1 sequence of the VL comprises the amino acid sequence SEQ ID NO:14, the CDR2 sequence of the VL domain comprises the amino acid sequence SEQ ID NO:18, and the CDR3 sequence of the VL domain comprises the amino acid sequence SEQ ID NO:21.

2. The polypeptide of claim 1, wherein the $V_H$ domain comprises the amino acid sequence of SEQ ID NO: 22, and wherein the $V_L$ domain comprises the amino acid sequence of SEQ ID NO: 34, 36 or 37.

3. The polypeptide of claim 2, wherein the scFv comprises an amino acid sequence selected from the group consisting of SEQ ID NOs: 47-49.

4. The polypeptide of claim 1, wherein the $V_H$ domain comprises the amino acid sequence of SEQ ID NO: 24 or 26, and wherein the $V_L$ domain comprises the amino acid sequence of SEQ ID NO: 38.

5. The polypeptide of claim 4, wherein the scFv comprises an amino acid sequence selected from the group consisting of SEQ ID NOs: 56 and 62.

6. The polypeptide of claim 1, wherein the $V^H$ domain comprises the amino acid sequence of SEQ ID NO: 28, and wherein the $V^L$ domain comprises the amino acid sequence of SEQ ID NO: 42.

7. The polypeptide of claim 6, wherein the scFv comprises the amino acid sequence of SEQ ID NO: 69.

8. The polypeptide of claim 1, wherein the intracellular signaling domain comprises of CD3 zeta (CD3ζ) signaling domain.

9. The polypeptide of claim 1, wherein the co-stimulatory signaling region comprises the cytoplasmic domain of a co-stimulatory molecule selected from the group consisting of CD27, CD28, 4-1 BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

10. The polypeptide of claim 1, wherein the CAR polypeptide is defined by the formula:

SP—CD99—HG—TM—CSR—ISD; or

SP—CD99—HG—TM—ISD—CSR wherein "SP" represents a signal peptide,
wherein "CD99" represents a CD99 antigen binding domain,
wherein "HG" represents an optional hinge domain,
wherein "TM" represents a transmembrane domain,
wherein "CSR" represents a co-stimulatory signaling region,
wherein "ISD" represents an intracellular signaling domain, and
wherein "-" represents a bivalent linker.

11. An isolated nucleic acid sequence encoding the polypeptide of claim 1.

12. A vector comprising the isolated nucleic acid sequence of claim 11.

13. A cell comprising the vector of claim 12.

14. The cell of claim 13, wherein the cell is selected from the group consisting of an αβT cell, a γδT cell, a Natural Killer (NK) cell, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, a regulatory T cell, or any combination thereof.

15. The cell of claim 14, wherein the cell exhibits an anti-tumor immunity when the antigen binding domain of the CAR polypeptide binds to CD99.

16. A cell comprising the chimeric antigen receptor (CAR) polypeptide of claim 1.

17. The cell of claim 16, wherein the cell is an autologous or allogeneic Epstein-Barr.

* * * * *